United States Patent
Adaikkan et al.

(10) Patent No.: US 10,960,225 B2
(45) Date of Patent: Mar. 30, 2021

(54) SYSTEMS AND METHODS FOR PREVENTING, MITIGATING, AND/OR TREATING DEMENTIA VIA VISUAL STIMULATION THAT BINDS HIGHER ORDER BRAIN REGIONS, REDUCES NEURODEGENERATION AND NEUROINFLAMMATION, AND IMPROVES COGNITIVE FUNCTION

(71) Applicant: Massachusetts Institute of Technology, Cambridge, MA (US)

(72) Inventors: Chinnakkaruppan Adaikkan, Somerville, MA (US); Li-Huei Tsai, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/156,833

(22) Filed: Oct. 10, 2018

(65) Prior Publication Data

US 2019/0126062 A1     May 2, 2019

Related U.S. Application Data

(63) Continuation-in-part of application No. 16/135,938, filed on Sep. 19, 2018.
(Continued)

(51) Int. Cl.
*A61N 5/06* (2006.01)
*A61N 5/10* (2006.01)

(52) U.S. Cl.
CPC ......... *A61N 5/0622* (2013.01); *A61N 5/0618* (2013.01); *A61N 5/1001* (2013.01);
(Continued)

(58) Field of Classification Search
CPC .. A61N 5/0622; A61N 5/0618; A61N 5/1001; A61N 2005/0626; A61N 2005/0652
(Continued)

(56) References Cited

U.S. PATENT DOCUMENTS

| 4,449,047 A | * | 5/1984 | Monroe | G01V 5/025 |
| | | | | 250/253 |
| 4,456,910 A | * | 6/1984 | Dimassimo | G09G 3/18 |
| | | | | 345/208 |

(Continued)

FOREIGN PATENT DOCUMENTS

| EP | 0911398 A3 | 4/1999 |
| EP | 2489402 A2 | 8/2012 |

(Continued)

OTHER PUBLICATIONS

"40hz Light Therapy addressing Alzheimer's news!" Indiegogo https://www.indiegogo.com/projects/40hz-light-therapy-addressing-alzheimer-s-news#/, https://www.indiegogo.com, Internet Archive Wayback Machine earliest Internet archived date Oct. 29, 2017, 6 pages.

(Continued)

*Primary Examiner* — Carl H Layno
*Assistant Examiner* — Michael J Lau
(74) *Attorney, Agent, or Firm* — Smith Baluch LLP

(57) ABSTRACT

Devices, systems, and methods for treating dementia or Alzheimer's disease in a subject in need thereof. In one example, chronic visual stimuli having a frequency of about 30 Hz to about 50 Hz, and more specifically about 40 Hz, are non-invasively delivered to the subject to entrain gamma oscillations in multiple brain regions of the subject, including the prefrontal cortex (PFC) and the hippocampus. The entrained gamma oscillations modulate neuronal activity across multiple brain regions (e.g., facilitate functional bind- (Continued)

ing of neural networks at low gamma frequencies) to induce various neuroprotective effects (e.g., amelioration of amyloid plaques and tau hyper-phosphorylation) and reduce neurodegeneration. Neuronal activity mediated by the chronic visual stimuli reduces an immune response in microglia and ameliorates aberrantly modified genes and proteins involved in membrane trafficking, intracellular transport, synaptic function, neuroinflammation and DNA damage response. Behavior modification including enhanced learning and memory is observed.

51 Claims, 109 Drawing Sheets
(51 of 109 Drawing Sheet(s) Filed in Color)

Related U.S. Application Data

(60) Provisional application No. 62/570,929, filed on Oct. 11, 2017, provisional application No. 62/570,250, filed on Oct. 10, 2017.

(52) U.S. Cl.
CPC ............. *A61N 2005/0626* (2013.01); *A61N 2005/0652* (2013.01)

(58) Field of Classification Search
USPC .................................................. 607/88
See application file for complete search history.

(56) References Cited

U.S. PATENT DOCUMENTS

| | | | | |
|---|---|---|---|---|
| 5,151,687 A * | 9/1992 | Younger | ............... | G11B 23/44 345/157 |
| 5,659,287 A * | 8/1997 | Donati | ............... | G08B 7/06 315/292 |
| 5,934,967 A | 8/1999 | Brown et al. | | |
| 6,071,229 A | 6/2000 | Rubins | | |
| 6,113,537 A * | 9/2000 | Castano | ............... | A61B 5/14532 128/897 |
| 6,167,298 A | 12/2000 | Levin | | |
| 6,206,537 B1 * | 3/2001 | Hauck | ............... | F21S 10/02 362/102 |
| 6,234,953 B1 | 5/2001 | Thomas et al. | | |
| 6,443,977 B1 * | 9/2002 | Jaillet | ............... | A61M 21/00 600/27 |
| 6,539,263 B1 | 3/2003 | Schiff et al. | | |
| 6,733,490 B1 * | 5/2004 | Falsini | ............... | A61F 9/00821 128/898 |
| 7,010,356 B2 | 3/2006 | Jog et al. | | |
| 7,361,074 B1 * | 4/2008 | Perlman; Douglas M | ............... | A63H 5/00 362/192 |
| 7,446,785 B1 * | 11/2008 | Hewlett | ............... | G09G 3/2033 345/691 |
| 7,645,226 B2 * | 1/2010 | Shealy | ............... | A61M 21/00 600/27 |
| 7,715,910 B2 | 5/2010 | Hargrove et al. | | |
| 7,748,846 B2 * | 7/2010 | Todd | ............... | A61B 3/0091 351/211 |
| 7,769,439 B2 | 8/2010 | Vesely et al. | | |
| 8,083,392 B2 * | 12/2011 | Chien | ............... | F21S 4/28 362/641 |
| 8,121,694 B2 | 2/2012 | Molnar et al. | | |
| 8,267,851 B1 | 9/2012 | Kroll | | |
| 8,280,502 B2 | 10/2012 | Hargrove et al. | | |
| 8,380,314 B2 | 2/2013 | Panken et al. | | |
| 8,423,144 B2 | 4/2013 | Tass et al. | | |
| 8,543,219 B2 | 9/2013 | Tass | | |
| 8,577,470 B2 | 11/2013 | Assaf et al. | | |
| 8,579,793 B1 * | 11/2013 | Honeycutt | ............ | A61M 21/00 600/26 |
| 8,591,392 B2 | 11/2013 | Baror et al. | | |
| 8,636,640 B2 | 1/2014 | Chang | | |
| 8,700,167 B2 | 4/2014 | Sabel | | |
| 8,892,207 B2 | 11/2014 | Nelson et al. | | |
| 8,894,696 B2 * | 11/2014 | Hurst | ............ | H05B 37/02 607/88 |
| 8,914,119 B2 | 12/2014 | Wu et al. | | |
| 8,932,218 B1 | 1/2015 | Thompson | | |
| 8,942,809 B2 | 1/2015 | Assaf et al. | | |
| 9,119,583 B2 | 9/2015 | Tass | | |
| 9,272,118 B1 | 3/2016 | Acton | | |
| 9,302,069 B2 | 4/2016 | Tass et al. | | |
| 10,159,816 B2 | 12/2018 | Tsai et al. | | |
| 10,265,497 B2 | 4/2019 | Tsai et al. | | |
| 10,682,490 B2 | 6/2020 | Tsai et al. | | |
| 2004/0097841 A1 * | 5/2004 | Saveliev | ............ | A61H 9/0078 601/15 |
| 2005/0070977 A1 * | 3/2005 | Molina | ............ | A61N 5/0616 607/88 |
| 2005/0234286 A1 * | 10/2005 | Riehl | ............ | A61N 2/02 600/9 |
| 2006/0173510 A1 * | 8/2006 | Besio | ............ | A61N 1/36025 607/45 |
| 2006/0263332 A1 | 11/2006 | Li et al. | | |
| 2007/0218994 A1 * | 9/2007 | Goto | ............ | G06F 3/033 463/36 |
| 2007/0225773 A1 | 9/2007 | Shen et al. | | |
| 2008/0227139 A1 | 9/2008 | Deisseroth et al. | | |
| 2009/0005837 A1 * | 1/2009 | Olmstead | ............ | A61N 5/0618 607/88 |
| 2009/0023977 A1 * | 1/2009 | Sperling | ............ | A61M 21/00 600/27 |
| 2009/0093403 A1 * | 4/2009 | Zhang | ............ | A01K 67/0333 514/8.1 |
| 2009/0153800 A1 | 6/2009 | Bassi et al. | | |
| 2009/0237563 A1 * | 9/2009 | Doser | ............ | G09G 5/00 348/579 |
| 2009/0312624 A1 | 12/2009 | Berridge et al. | | |
| 2010/0013402 A1 * | 1/2010 | Chaffai | ............ | H05B 45/10 315/291 |
| 2010/0109541 A1 * | 5/2010 | Roberts | ............ | H05B 45/22 315/224 |
| 2010/0190129 A1 * | 7/2010 | Paz | ............ | A61C 1/088 433/29 |
| 2010/0274329 A1 * | 10/2010 | Bradley | ............ | A61N 1/328 607/90 |
| 2011/0118534 A1 * | 5/2011 | Baror | ............ | A61N 1/36025 600/12 |
| 2011/0122396 A1 * | 5/2011 | Ivaldi | ............ | G01N 21/3103 356/51 |
| 2011/0152967 A1 | 6/2011 | Simon et al. | | |
| 2012/0065709 A1 | 3/2012 | Dunning et al. | | |
| 2012/0271374 A1 | 10/2012 | Nelson et al. | | |
| 2012/0289869 A1 * | 11/2012 | Tyler | ............ | A61B 5/04008 601/2 |
| 2013/0066392 A1 * | 3/2013 | Simon | ............ | A61N 2/006 607/45 |
| 2013/0253338 A1 * | 9/2013 | Kang | ............ | A61B 5/0071 600/477 |
| 2013/0317569 A1 * | 11/2013 | Deisseroth | ............ | A61N 5/0618 607/88 |
| 2013/0328490 A1 * | 12/2013 | Chen | ............ | H05B 47/185 315/185 R |
| 2014/0135680 A1 | 5/2014 | Peyman | | |
| 2014/0324138 A1 * | 10/2014 | Wentz | ............ | A61N 5/0622 607/92 |
| 2014/0330335 A1 * | 11/2014 | Errico | ............ | A61B 5/4893 607/45 |
| 2014/0336514 A1 * | 11/2014 | Peyman | ............ | A61N 5/062 600/473 |
| 2015/0002025 A1 * | 1/2015 | Maricic | ............ | H05B 45/10 315/151 |
| 2015/0157604 A1 * | 6/2015 | Morozova | ............ | A61K 47/32 514/415 |
| 2015/0196762 A1 | 7/2015 | Amurthur et al. | | |

(56) References Cited

U.S. PATENT DOCUMENTS

| | | | |
|---|---|---|---|
| 2015/0342495 A1* | 12/2015 | Davis | A61B 3/14 |
| | | | 351/221 |
| 2016/0091758 A1* | 3/2016 | Yoneyama | G02F 1/133603 |
| | | | 349/69 |
| 2016/0235980 A1 | 8/2016 | Berman et al. | |
| 2017/0082255 A1* | 3/2017 | Bentley | F21S 10/043 |
| 2017/0143934 A1 | 5/2017 | Tsai et al. | |
| 2017/0143966 A1* | 5/2017 | Reymers | A61B 5/4064 |
| 2017/0151436 A1* | 6/2017 | Flaherty | A61N 5/0622 |
| 2018/0206737 A1* | 7/2018 | Colman | A61M 16/0833 |
| 2018/0236262 A1* | 8/2018 | Morries | A61K 31/135 |
| 2018/0277377 A1* | 9/2018 | Eto | H01L 22/26 |
| 2018/0286188 A1* | 10/2018 | Von Novak | B60Q 1/50 |
| 2019/0076670 A1 | 3/2019 | Vyshedskiy | |
| 2019/0105509 A1* | 4/2019 | Tsai | A61N 5/0618 |
| 2019/0126056 A1* | 5/2019 | Vlădila Bogdan | A61N 2/02 |
| 2019/0126062 A1* | 5/2019 | Adaikkan | A61N 5/1001 |
| 2019/0215926 A1* | 7/2019 | Lay | F21V 23/0464 |
| 2019/0240443 A1 | 8/2019 | Tsai et al. | |
| 2019/0254775 A1* | 8/2019 | Gregg, II | A61C 19/004 |

FOREIGN PATENT DOCUMENTS

| | | | |
|---|---|---|---|
| JP | 2014071825 A | | 4/2014 |
| JP | 2015519096 A | | 7/2015 |
| WO | 0184141 A1 | | 11/2001 |
| WO | 2008041129 A2 | | 4/2008 |
| WO | 2013152348 A1 | | 10/2013 |
| WO | 2014179331 A2 | | 11/2014 |
| WO | 2017091698 A1 | | 6/2017 |

OTHER PUBLICATIONS

"Brainsway: Deep TMS Therapy," Brainsway (2014): http://www.brainsway.com/us.

"Good Vibrations Can Help Alzheimer's Patients," Awakening from Alzheimer's http://www.awakeningfromalzheimers.com/good-vibrations-can-help-alzheimers-patients/, Internet Archive Wayback Machine earliest Internet archived date Nov. 2, 2016, 8 pages.

"PSIO Manual," PSiO http://www.psioplanet.com/download/manuals/manuel-psio-1.1-EN.pdf, http://www.psoplanet.com/, Internet Archive Wayback Machine earliest Internet archived date Mar. 2, 2013, 16 pages.

Aronov, D. et al., "Engagement of neural circuits underlying 2D spatial navigation in a rodent virtual reality system," Neuron, vol. 84 (Oct. 2014): 442-456.

Barton, A. "Sound vibration treatment may boost brain activity in Alzheimer's patients," The Globe and Mail (2016): http://www.theglobeandmail.com/life/health-and-fitness/health/sound-vibration-treatment-may-boost-brain-activity-in-alzheimers-patients/article29771676/.

Bartos, M. et al., "Synaptic mechanisms of synchronized gamma oscillations in inhibitory interneuron networks," Nature Reviews Neuroscience, vol. 8 (Jan. 2007): 45-56.

Basar, E. et al., "Delay of cognitive gamma responses in Alzheimer's disease," NeuroImage: Clinical, vol. 11 (2016): 106-115.

Bero, A. et al., "Neuronal activity regulates the regional vulnerability to amyloid-β deposition," Nature Neuroscience, vol. 14 (May 2011): 750-756.

Boissonneault, V. et al., "Powerful beneficial effects of macrophage colony-stimulating factor on beta-amyloid deposition and cognitive impairment in Alzheimer's disease," Brain, vol. 132 (Apr. 2009): 1078-1092.

Bragin, A. et al., "Gamma (40-100 Hz) oscillation in the hippocampus of the behaving rat," Journal of Neuroscience, vol. 15 (Jan. 1995): 47-60.

Busche, M. et al., "Decreased amyloid-β and increased neuronal hyperactivity by immunotherapy in Alzheimer's models," Nature Neuroscience, vol. 18 (Dec. 2015): 1725-1727.

Buzsaki et al., "Mechanisms of Gamma Oscillations," Rev. Neurosci. 35, 203-23 (2012).

Buzsaki, G. "Rhythms of the Brain," Oxford University Press (2006).

Buzsaki, G. "Theta oscillations in the hippocampus," Neuron, vol. 33 (Jan. 2002): 325-340.

Buzsaki, G. et al., "Hippocampal network patterns of activity in the mouse," Neuroscience, vol. 116 (2003): 201-211.

Buzsaki, G. et al., "Scaling brain size, keeping timing: evolutionary preservation of brain rhythms," Neuron, vol. 80 (Oct. 2013): 751-764.

Cardin, J. et al., "Driving fast-spiking cells induces gamma rhythm and controls sensory responses," Nature, vol. 459 (Apr. 2009): 663-667.

Carr, M. et al., "Hippocampal replay in the awake state: a potential substrate for memory consolidation and retrieval," Nature Neuroscience, vol. 14 (Feb. 2011): 147-153.

Carr, M. et al., "Transient slow gamma synchrony underlies hippocampal memory replay," Neuron, vol. 75 (Aug. 2012): 700-713.

Cataldo, A. et al., "Endocytic pathway abnormalities precede amyloid beta deposition in sporadic Alzheimer's disease and Down syndrome: differential effects of APOE genotype and presenilin mutations," American Journal of Pathology, vol. 157 (2000): 277-286.

Chitu, V. et al., "Colony-stimulating factor-1 in immunity and inflammation," Current Opinion in Immunology, vol. 18 (Feb. 2006): 39-48.

Chiu, I. et al., "A neurodegeneration-specific gene-expression signature of acutely isolated microglia from an amyotrophic lateral sclerosis mouse model," Cell Reports, vol. 4 (Jul. 2013): 385-401.

Chung, K. et al., "Structural and molecular interrogation of intact biological systems," Nature, vol. 497 (May 2013): 332-337.

Cirrito, J. et al., "In vivo assessment of brain interstitial fluid with microdialysis reveals plaque-associated changes in amyloid-beta metabolism and half-life," The Journal of Neuroscience, vol. 23 (Oct. 2003): 8844-8853.

Clements-Cortes, A. "Sound Stimulation in Patients With Alzheimer's Disease," Annals of Long-Term Care: Clinical Care and Aging, vol. 23 (May 2015): 10-16.

Colgin, L. et al., "Frequency of gamma oscillations routes flow of information in the hippocampus," Nature, vol. 462 (Nov. 2009): 353-357.

Colgin, L. et al., "Gamma oscillations in the hippocampus," Physiology, vol. 25 (Oct. 2010): 319-329.

Cronk, J. et al., "Methyl-CpG binding protein 2 regulates microglia and macrophage gene expression in response to inflammatory stimuli," Immunity, vol. 42 (Apr. 2015): 679-691.

Crotti, A. et al., "Mutant Huntingtin promotes autonomous microglia activation via myeloid lineage-determining factors," Nature Neuroscience, vol. 17 (Apr. 2014): 513-521.

Das, U. et al., "Activity-induced convergence of App and Bace-1 in acidic microdomains via an endocytosis-dependent pathway," Neuron, vol. 79 (Aug. 2013): 447-460.

Eckhorn, R. et al., "Coherent Oscillations: a Mechanism of Feature Linking in the Visual Cortex," Biological Cybernetics, vol. 60 (1988): 121-130.

Erny, D. et al., "Host microbiota constantly control maturation and function of microglia in the CNS," Nature Neuroscience, vol. 18 (Jun. 2015): 965-977.

Final Office Action dated Jun. 4, 2018 for U.S. Appl. No. 15/360,637, 11 pages.

Fisher Wallace Stimulator http.//www.fisherwallace.com/, Internet Archive Wayback Machine earliest Internet archived date Jul. 13, 2017, 7 pages.

Foster, D. et al., "Reverse replay of behavioural sequences in hippocampal place cells during the awake state," Nature, vol. 440 (Mar. 2006):680-683.

Fries, P. et al., "The gamma cycle," Trends in Neurosciences, vol. 30 (Jul. 2007): 309-316.

Gillepsie, A. et al., "Apolipoprotein E4 Causes Age-Dependent Disruption of Slow Gamma Oscillations during Hippocampal Sharp-Wave Ripples," Neuron, vol. 90 (May 2016): 740-751.

(56) References Cited

OTHER PUBLICATIONS

Gjoneska, E. et al., "Conserved epigenomic signals in mice and humans reveal immune basis of Alzheimer's disease," Nature, vol. 518 (Feb. 2015): 365-369.
Gosselin, D. et al., "Environment drives selection and function of enhancers controlling tissue-specific macrophage identities," Cell, vol. 159 (Dec. 2014): 1327-1340.
Goutagny, R. et al., "Alterations in hippocampal network oscillations and theta-gamma coupling arise before Aβ overproduction in a mouse model of Alzheimer's disease," European Journal of Neuroscience, vol. 37 (Jun. 2013): 1896-1902.
Gray, C. et al., "Chattering cells: superficial pyramidal neurons contributing to the generation of synchronous oscillations in the visual cortex," Science, vol. 274 (Oct. 1996): 109-113.
Gray, C. et al., "Oscillatory responses in cat visual cortex exhibit inter-columnar synchronization which reflects global stimulus properties," Nature, vol. 338 (Mar. 1989): 334-337.
Harvey, C. et al., "Intracellular dynamics of hippocampal place cells during virtual navigation," Nature, vol. 461 (Oct. 2009): 941-946.
Helwig, M. et al., "The neuroendocrine protein 7B2 suppresses the aggregation of neurodegenerative disease-related proteins," The Journal of Biological Chemistry, vol. 288 (Jan. 2013): 1114-1124.
Hen Eka, M. et al., "Innate immune activation in neurodegenerative disease," Nature Reviews Immunology, vol. 14 (Jul. 2014): 463-477.
Hermann, C. et al., "Human Eeg gamma oscillation in neuropsychiatric disorders," Clinical Neurophysiology, vol. 116 (Sep. 2006): 2719-2733.
Hermann, C. et al., "Human EEG responses to 1-100 Hz flicker: resonance phenomena in visual cortex and their potential correlation to cognitive phenomena," Experimental Brain Research, vol. 137 (Apr. 2001): 346-353.
Hsiao, F. et al., "Altered Oscillation and Synchronization of Default-Mode Network Activity in Mild Alzheimer's Disease Compared to Mild Cognitive Impairment: an Electrophysiological Study," PLOS One, vol. 8 (Jul. 2013): 1-10.
Huang, S. et al., "Cell-intrinsic lysosomal lipolysis is essential for alternative activation of macrophages," Nature Immunology, vol. 15 (Sep. 2014): 846-855.
Iliff, J. et al., "A Paravascular Pathway Facilitates CSF Flow Through the Brain Parenchyma and the Clearance of Interstitial Solutes, Including Amyloid β," Science Tranditional Medicine, vol. 4 (Aug. 2012): 147.
International Search Report and Written Opinion in International Patent Application No. PCT/US18/55258 dated Dec. 27, 2018. 16 pages.
International Search Report and Written Opinion issued by the International Searching Authority for Internaltional Application No. PCT/US16/63536, dated Mar. 27, 2017, 19 pages.
Israel, M. et al., "Probing sporadic and familial Alzheimer's disease using induced pluripotent stem cells," Nature, vol. 482 (Jan. 2012): 216-220.
Jeong, J. "EEG dynamics in patients with Alzheimer's disease," Clinical Neurophysiology, vol. 115 (Aug. 2004): 1490-1505.
Koenig, T. et al., "Decreased EEG synchronization in Alzheimer's disease and mild cognitive impairment," Neurobiology of Aging, vol. 26 (Feb. 2005): 165-171.
Kreutzberg, G. "Microglia: a sensor for pathological events in the CNS," Trends in Neurosciences, vol. 19 (Sep. 1996): 312-318.
Kurudenkandy, F. et al., "Amyloid-β-Induced Action Potential Desynchronization and Degradation of Hippocampal Gamma Oscillations is Prevented by Interference with Peptide Conformation Change and Aggregation," The Journal of Neuroscience, vol. 34 (Aug. 2014): 11416-11425.
Leinenga, G. et al., "Scanning ultrasound removes amyloid-βand restores memory in an Alzheimer's disease mouse model," Science Translational Medicine, vol. 7 (Mar. 2015): 278.
Li, F. et al., "Effect of electroacupuncture stimulation of "Baihui" (GV 20) and "Yongquan" (KI 1) on expression of hippocampal amyloid-β and low density lipoprotein receptor-related protein-1 in APP/PS 1 transgenic mice," Zhen Ci Yan Jiu, vol. 40 (Feb. 2015).
Lok, K. et al., "Characterization of the APP/PS1 mouse model of Alzheimer's disease in senescence accelerated background," Neuroscience Letters, vol. 557 (Dec. 2013): 84-89.
Mastrangelo, M. et al., "Detailed immunohistochemical characterization of temporal and spatial progression of Alzheimer's disease-related pathologies in male triple-transgenic mice," BMC Neuroscience, vol. 9 (Aug. 2008): 1-31.
Mind Alive Inc. http://mindalive.com/ Internet Archive Wayback Machine earliest Internet archived date Mar. 2, 2001, 2 pages.
Mind Gear http://Mindlightz.com, Internet Archive Wayback Machine earliest Internet archived date Mar. 1, 2015, 5 pages.
Mind Machines http://www.mindmachines.com/: Internet Archive Wayback Machine earliest Internet archived date Dec. 7, 1998, 4 pages.
Mind Mods http://www.mindmods.com/, Internet Archive Wayback Machine earliest. Internet archived date Mar. 12, 2008, 2 pages.
Mind Place http://mindplace.com/, Internet Archive Wayback Machine earliest Internet archived date Dec. 2, 1998, 4 pages.
Mitrasinovic, O. et al., "Microglial overexpression of the M-CSF receptor augments phagocytosis of opsonized Aβ," Neurobiology of Aging, vol. 24 (Oct. 2003): 807-815.
Neuronix http://neuronixmedical.com, Internet Archive Wayback Machine earliest Internet archived date Nov. 16, 2009, 2 pages.
Neuronix http://neurotronics.eu/, Internet Archive Wayback Machine earliest Internet archived date Sep. 24, 2008, 2 pages.
Oakley, H. et al., "Intraneuronal beta-amyloid aggregates, neurodegeneration, and neuron loss in transgenic mice with five familial Alzheimer's disease mutations: potential factors in amyloid plaque formation," Journal of Neuroscience, vol. 26 (Oct. 2006): 10129-10140.
Ohmi, K. et al., "Defects in the medial entorhinal cortex and dentate gyrus in the mouse model of Sanfilippo syndrome type B," Plos One, vol. 6 (Nov. 2011): 1-10.
Palop, J. et al., "Aberrant excitatory neuronal activity and compensatory remodeling of inhibitory hippocampal circuits in mouse models of Alzheimer's disease," Neuron, vol. 55 (Sep. 2007): 697-711.
Paro Therapeutic Robot http://www.parorobots.com/: Internet Archive Wayback Machine earliest Internet Archived date Dec. 4, 2008, 2 pages.
Pericic, D. et al., "Sex differences in the response to GABA antagonists depend on the route of drug administration," Experimental Brain Research, vol. 115 (Jun. 1997): 187-190.
Raivich, G. et al., "Neuroglial activation repertoire in the injured brain: graded response, molecular mechanisms and cues to physiological function," Brain Research Reviews, vol. 30 (Aug. 1999): 77-105.
Ravassard, P. et al., "Multisensory control of hippocampal spatiotemporal selectivity," Science, vol. 340 (Jun. 2013): 1342-1346.
Sauer et al., "Impaired fast-spiking interneuron function in a genetic mouse modef of deperession," eLIFE, vol. 4., Mar. 5, 2015, pp. 1-20.
Selkoe, D. et al., "The role of APP processing and trafficking pathways in the formation of amyloid beta-protein," Annals of the New York Academy of Sciences (Jan. 1996): 57-64.
Siegle, J. et al., "Enhancement of Encoding and retrieval functions through theta phase-specific manipulation of hippocampus," ELife Sciences Publications (Jul. 2014).
Stam, C. et al., "Generalized synchronization of MEG recordings in Alzheimer's Disease: evidence for involvement of the gamma band," Journal of Clinical Neurophysiology, vol. 19 (Dec. 2002): 562-574.
Subramanian, A. et al., "Gene set enrichment analysis: A knowledge-based approach for interpreting genorne-wide expression profiles," PNAS, vol. 102 (Aug. 2005): 15545-15550.
Sudol, K. et al., "Generating Differentially Targeted Amyloid-β Specific Intrabodies as a Passive Vaccination Strategy for Alzheimer's Disease," Molecular Therapy, vol. 17 (Dec. 2009): 2031-2040.
Thakurela, S. et al., "Dynamics and function of distal regulatory elements during neurogenesis and neuroplasticity," Genome Research, vol. 25 (Sep. 2015): 1309-1324.

(56) References Cited

OTHER PUBLICATIONS

Transparent Corporation https://www.transparentcorp.com/, Internet Archive Wayback Machine earliest Internet archived date Jan. 10, 1998, 3 pages.
Trapnell, C. et al., "Differential gene and transcript expression analysis of RNA-seq experiments with TopHat and Cufflinks," Nature Protocols, vol. 7 (2012): 562-578.
Trapnell, C. et al., "Transcript assembly and quantification by RNA-Seq reveals unannotated transcripts and isoform switching during cell differentiation," Nature Biotechnology, vol. 28 (May 2010): 511-515.
Traub, R. et al., "Analysis of gamma rhythms in the rat hippocampus in vitro and in vivo," the Journal of Physiology, vol. 493 (Jun. 1996): 471-484.
Verret, L. et al., "Inhibitory interneuron deficit links altered network activity and cognitive dysfunction in Alzheimer model," Cell, vol. 149 (Apr. 2012): 708-721.
Wang, Y. et al., "TREM2 lipid sensing sustains the microglial response in an Alzheimer's disease model," Cell, vol. 160 (Mar. 2015): 1061-1071.
Ylinen, A. et al., "Sharp wave-associated high-frequency oscillation (200 Hz) in the intact hippocampus: network and intracellular mechanisms," Journal of Neuroscience, vol. 15 (Jan. 1995): 30-46.
Yoshiyama, Y. et al., "Synapse loss and microglial activation precede tangles in a P301S tauopathy mouse model," Neuron, vol. 53 (Feb. 2007): 337-351.
Yu, H. et al., "Tet3 regulates synaptic transmission and homeostatic plasticity via Dna oxidation and repair," Nature Neuroscience, vol. 18 (Jun. 2015): 836-843.
Zhang, Y. et al., "An RNA-sequencing transcriptome and splicing database of glia, neurons, and vascular cells of the cerebral cortex," Journal of Neuroscience, vol. 34 (Sep. 2014): 11929-11947.
International Search Report and Written Opinion in International Patent Application No. PCT/US2018/051785 dated Jan. 24, 2019, 16 pages.
Berman et al., "Photobiomodulation with near infrared light helmet in a pilot, placebo controlled clinical trial in dementia patients testing memory and cognition." Journal of neurology and neuroscience 8.1 (2017). 15 pages.
Berman et al., Chapter 32—Noninvasive neurotherapeutic treatment of neurodegeneration: integrating photobiomodulation and neurofeedback training in Photobiomodulation in the Brain Low-Level Laser (Light) Therapy in Neurology and Neuroscience 2019, pp. 447-462.
Berman et al., Chapter 4—Photobiomodulation and Other Light Stimulation Procedures in Rhythmic Stimulation Procedures in Neuromodulation 2017, pp. 97-129.
Extended European Search Report in European Patent Application No. 16869248.1 dated Jul. 15, 2019, 7 pages.
Martorell et al., Multi-sensory Gamma Stimulation Ameliorates Alzheimer's-Associated Pathology and Improves Cognition. Cell. Mar. 14, 2019. https://doi.org/10.1016/j.cell.2019.02.014. 39 pages.
Neuro Alpha (Brain PBM). Vielight the Life Light 2019. Accessed at https://vielight.com/devices/vielight-neuro-alpha/ on Aug. 22, 2019. 7 pages.
Quietmind Foundation Launches World's First Clinical Trial of Drug-Free Infrared Light Therapy to Treat Dementia. Global News Wire, Feb. 17, 2011. Accessed at http://www.globenewswire.com/news-release/2011/02/17/1182914/0/en/Quietmind-Foundation-Launches-World-s-First-Clinical-Trial-of-Drug-Free-Infrared-Light-Therapy-to-Treat-Dementia.html on Aug. 22, 2019. 2 pages.
Vielight Neuro Gamma (40hz). QuietMIND Foundation 2019. Accessed at https://www.quietmindfdn.org/store/p5/Vielight_Neuro_Gamma_%2840hz%29_-_20%25_Off_for_Clinical_Trial_Participants.html on Aug. 22, 2019. 3 pages.
Alzheimer's Life Therapy App. Apple Store. Current version 1.5.7 released Aug. 6, 2019, earliest version 1.0.3 released Jan. 17, 2018. Accessed at https://apps.apple.com/us/app/alzheimers-light-therapy/id1327175926. 3 pages.

Notice of Allowance dated Apr. 25, 2018 for U.S. Appl. No. 15/647,157, 5 pages.
Zheng et al., Rhythmic light flicker rescues hippocampal low gamma and protects ischemic neurons by enhancing presynaptic plasticity. Nat Commun. 2020;11(1):3012. Published Jun. 15, 2020. doi:10.1038/s41467-020-16826-0. 16 pages.
Tanaka et al., "Analysis of MEG Auditory 40-Hz Response by Event-Related Coherence." ITEIS 125.6 (2005): 898-903. English Translation 7 pages.
Adaikkan et al., "Gamma entrainment binds higher-order brain regions and offers neuroprotection." Neuron 102.5 (2019): 929-943.
Bebop. Mace Virtual Labs. Accessed at https://www.macevl.com/bebop on Nov. 18, 2020. 4 pages.
Chiu et al., "Nasal administration of mesenchymal stem cells restores cisplatin-induced cognitive impairment and brain damage in mice." Oncotarget 9.85 (2018): 35581. 17 pages.
Clements-Cortes et al., "Short-term effects of rhythmic sensory stimulation in Alzheimer's disease: an exploratory pilot study." Journal of Alzheimer's Disease 52.2 (2016): 651-660.
Geraghty et al., "Loss of adaptive myelination contributes to methotrexate chemotherapy-related cognitive Impairment." Neuron 103.2 (2019): 250-265.
Gibson et al., "Methotrexate chemotherapy induces persistent triglial dysregulation that underlies chemotherapy-related cognitive impairment." Cell 176.1-2 (2019): 43-55.
Hermelink, "Chemotherapy and cognitive function in breast cancer patients: the so-called chemo brain." Journal of the National Cancer Institute Monographs 201551 (2015): 67-69.
Japanese Office Action in Japanese Patent Application No. 2018-525754 dated Nov. 2, 2020, 13 pages.
Khasabova et al., "Pioglitazone, a PPARγ agonist, reduces cisplatin-evoked neuropathic pain by protecting against oxidative stress." Pain 160.3 (2019): 688-701.
Laumet et al., "Cisplatin educates CD8+ T cells to prevent and resolve chemotherapy-induced peripheral neuropathy in mice." Pain 160.6 (2019): 1459. 19 pages.
Leo et al., "Cisplatin-induced neuropathic pain is mediated by upregulation of N-type voltage-gated calcium channels in dorsal root ganglion neurons." Experimental neurology 288 (2017): 62-74.
Martorell et al., "Multi-sensory gamma stimulation ameliorates Alzheimer's-associated pathology and improves ,mgnition." Cell 177.2 (2019): 256-271.
Meyers, "How chemotherapy damages the central nervous system." Journal of biology 7.4 (2008): 11. 3 pages.
Next Wave Physioacoustic Mx therapy chair. Nextwave. Accessed at http://www.nextwaveworldwide.com/products/ physioacoustic-mx-therapy-chair/ on Nov. 18, 2020. 2 pages.
O'Connor et al., "The use of the puzzle box as a means of assessing the efficacy of environmental enrichment." JoVE (Journal of Visualized Experiments) 94 (2014): e52225. 8 pages.
Seibenhener et al., "Use of the open field maze to measure locomotor and anxiety-like behavior in mice." JoVE :Journal of Visualized Experiments) 96 (2015): e52434. 9 pages_.
Smith et al., "The validity of neuropathy and neuropathic pain measures in patients with cancer receiving taxanes and platinums." Oncology nursing forum_ Vol_ 38. No. 2. 2011. 10 pp.
5nailax Massage Mat with Heat. Snailax. Accessed at https://www.amazon.com/Snailax-Massage-Mat-Heat-Relaxation/dp/B07MNZ5Z6P on Nov. 18, 2020_ 10 pages_.
Tanaka et al., "Analysis of Meg Auditory 40-Hz Response by Event-Related Coherence." ITEIS 125.6 (2005): 398-903.
Theragun by Therabody. Accessed at https://www.theragun.comluslen-usl4th-generation-devices/ on Nov. 18, 2020. 26 pp.
Vibration Plate Model VT003F. Vibration Therapeutic. Accessed at https://vibrationtherapeutic.corni_Products-Vibration-PlateNibration-Plate-VT003F.html on Nov. 19, 2020, 17 pages.
Walsh et al., "The open-field test: a critical review." Psychological bulletin 83.3 (1976): 482. 23 pages.

* cited by examiner

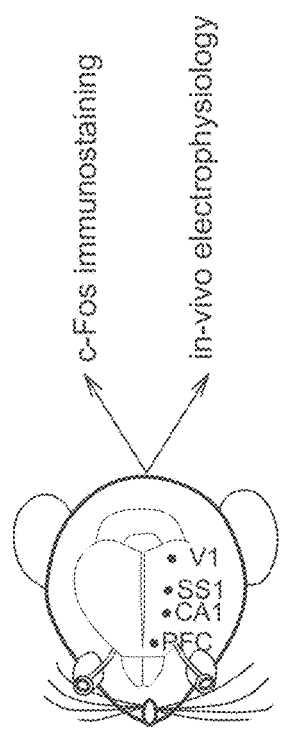
FIG. 1A

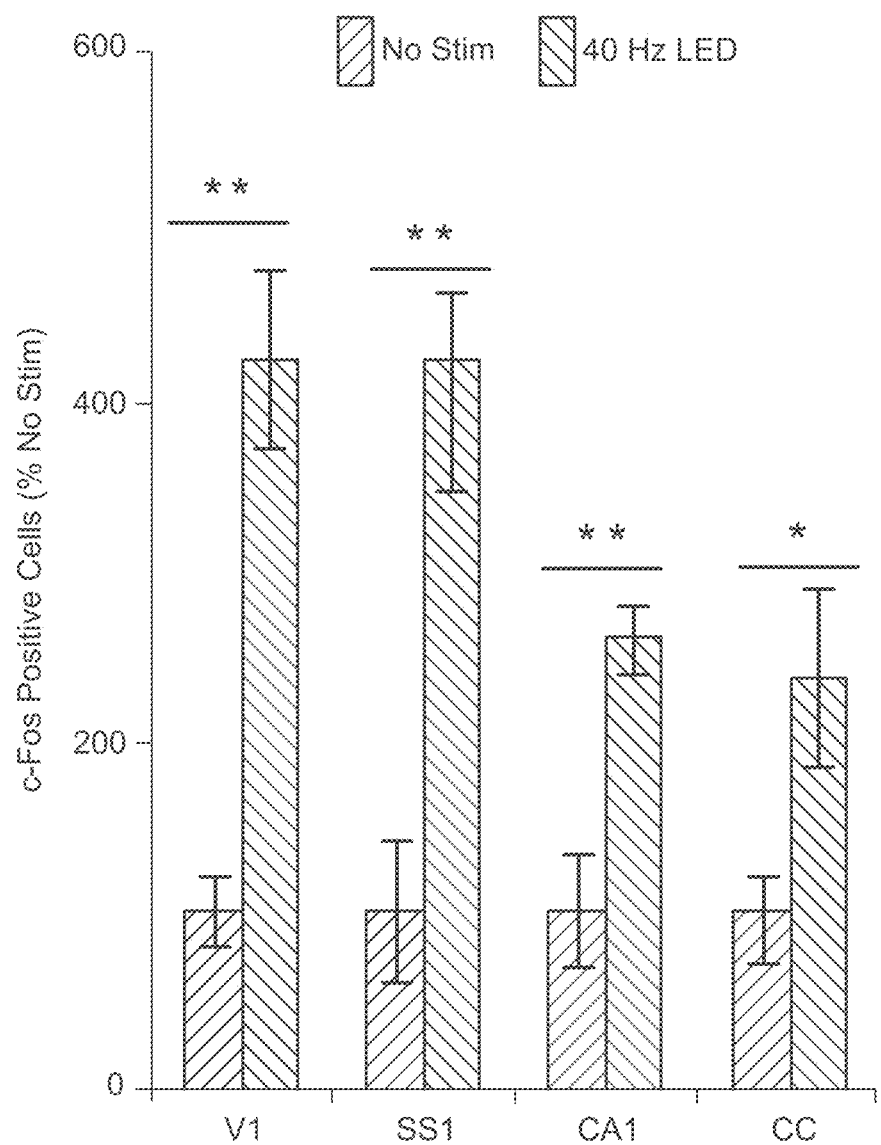
FIG. 1B-Cont'd

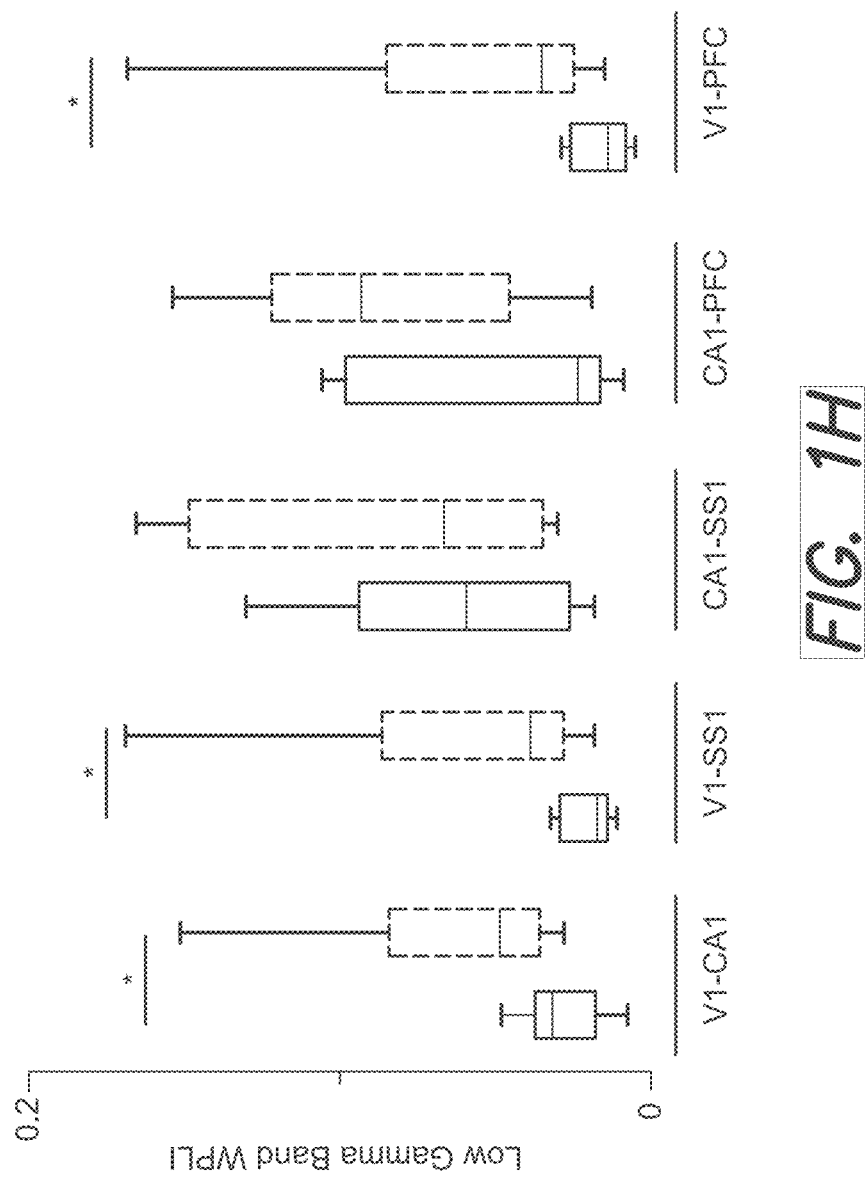

80 Hz LED Light Flicker
(50% Duty Cycle)

on: 6.25 ms   off: 6.25 ms

P301S Tau mice
(7 months old) → No Stim (or) 40Hz LED 1 h/d for 22d → Evaluation for neuroprotection (Immunohistochemistry; Tau protein Ser/Thr phosphoproteomics)

FIG. 3A

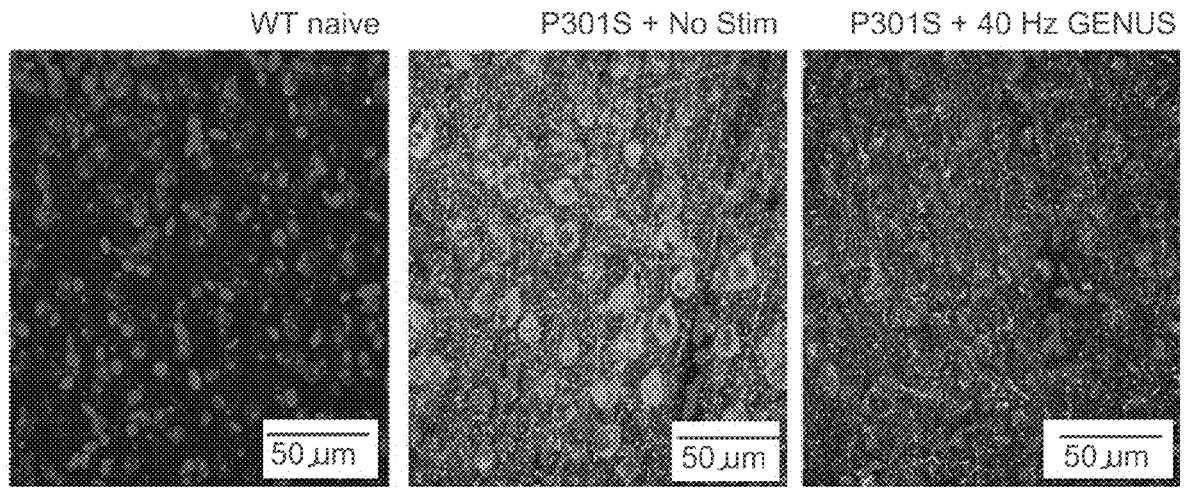
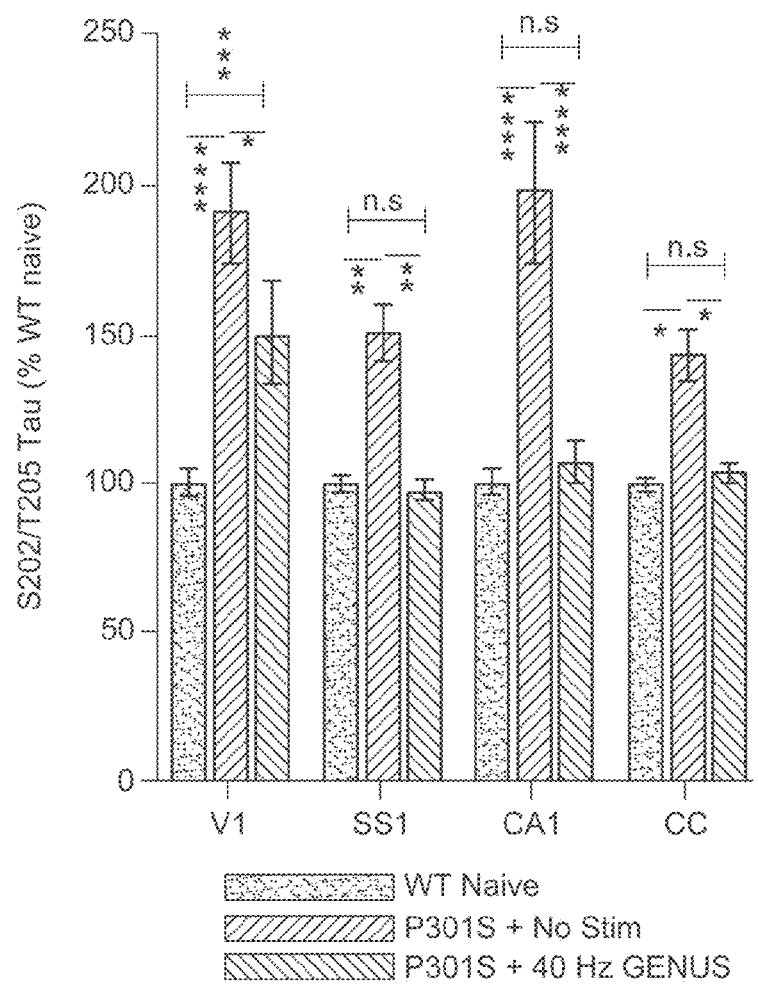
FIG. 3B

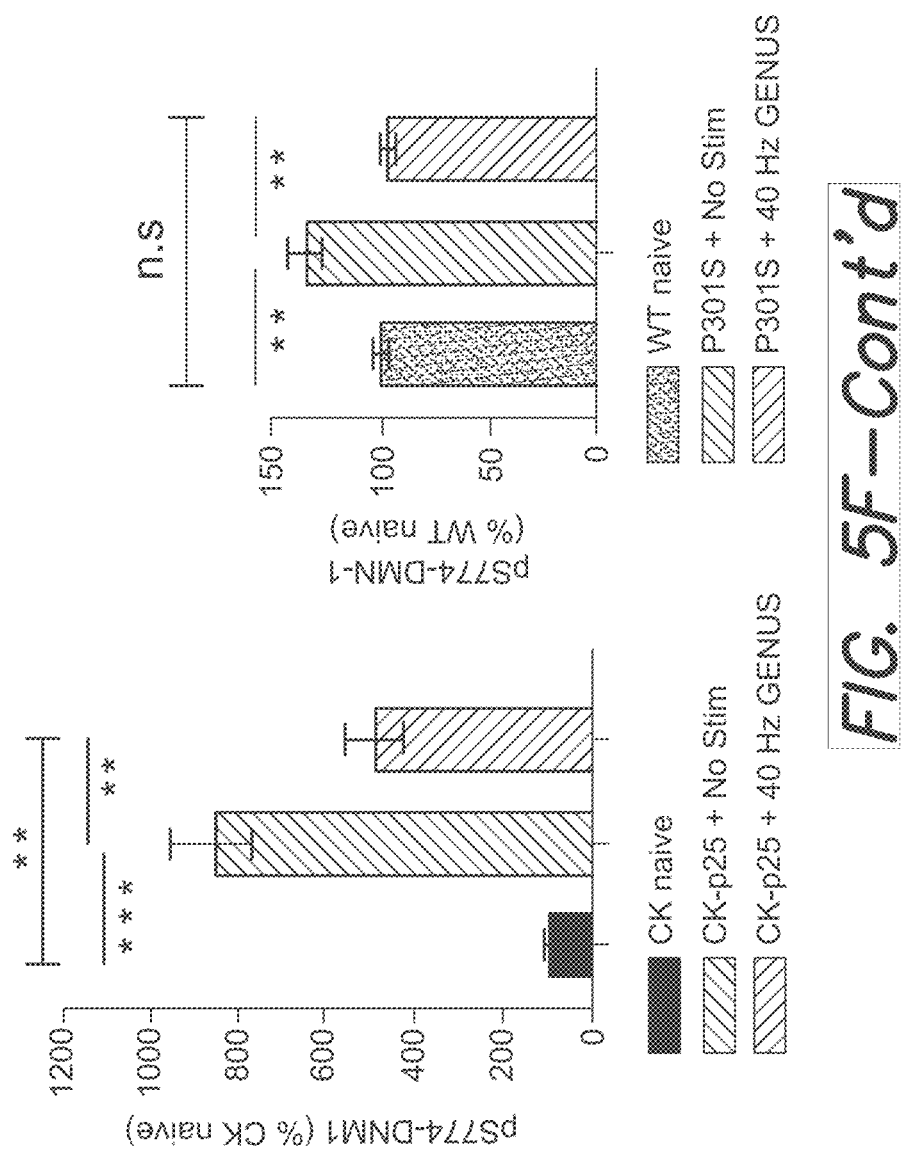
FIG. 5F–Cont'd

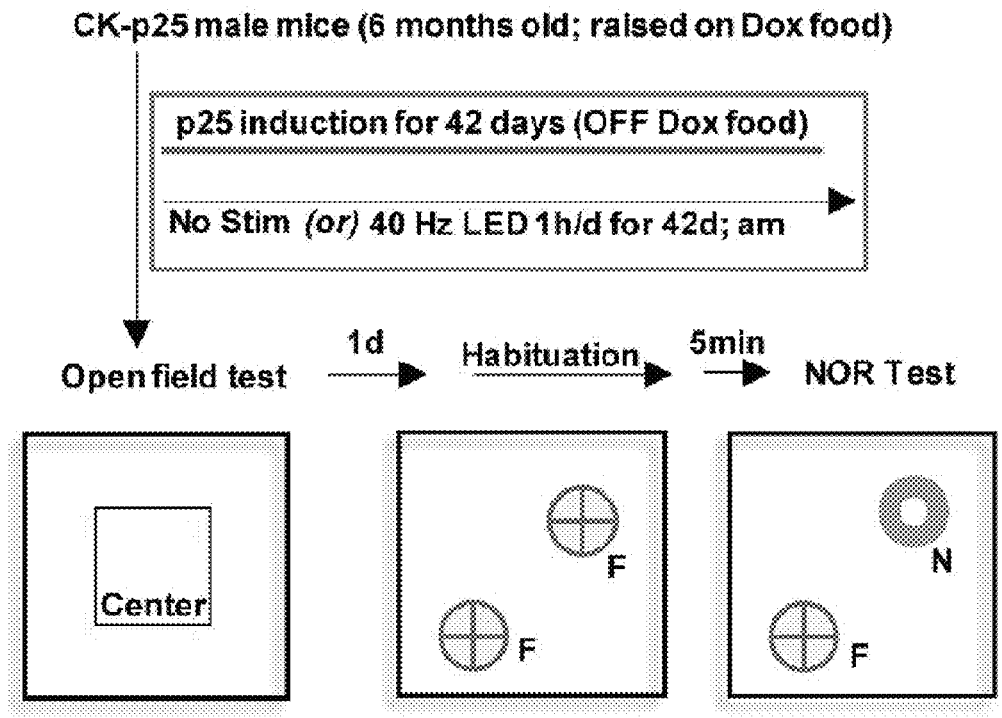
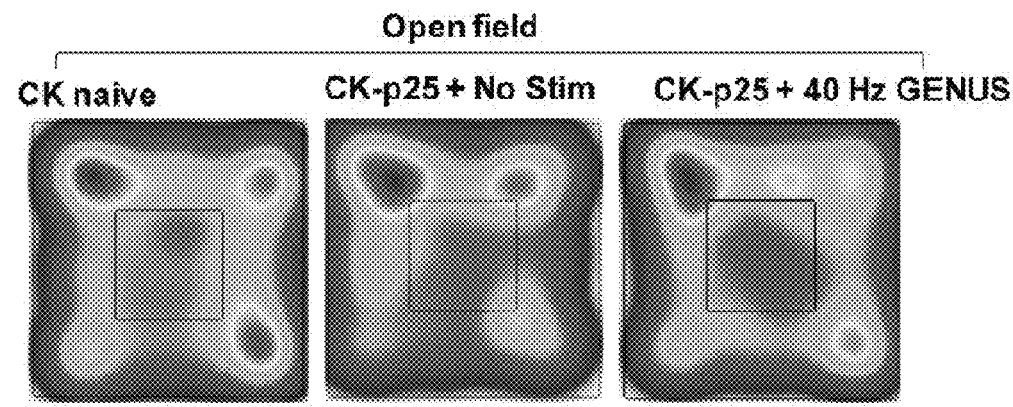
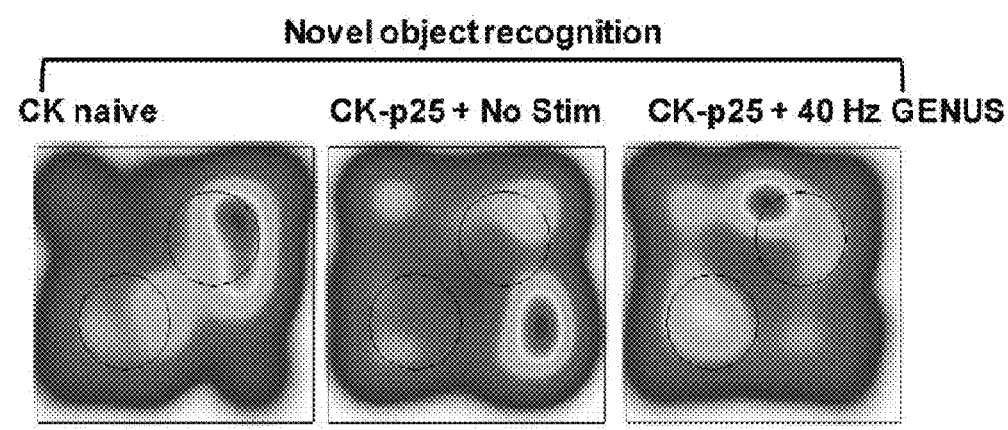
FIG. 6A

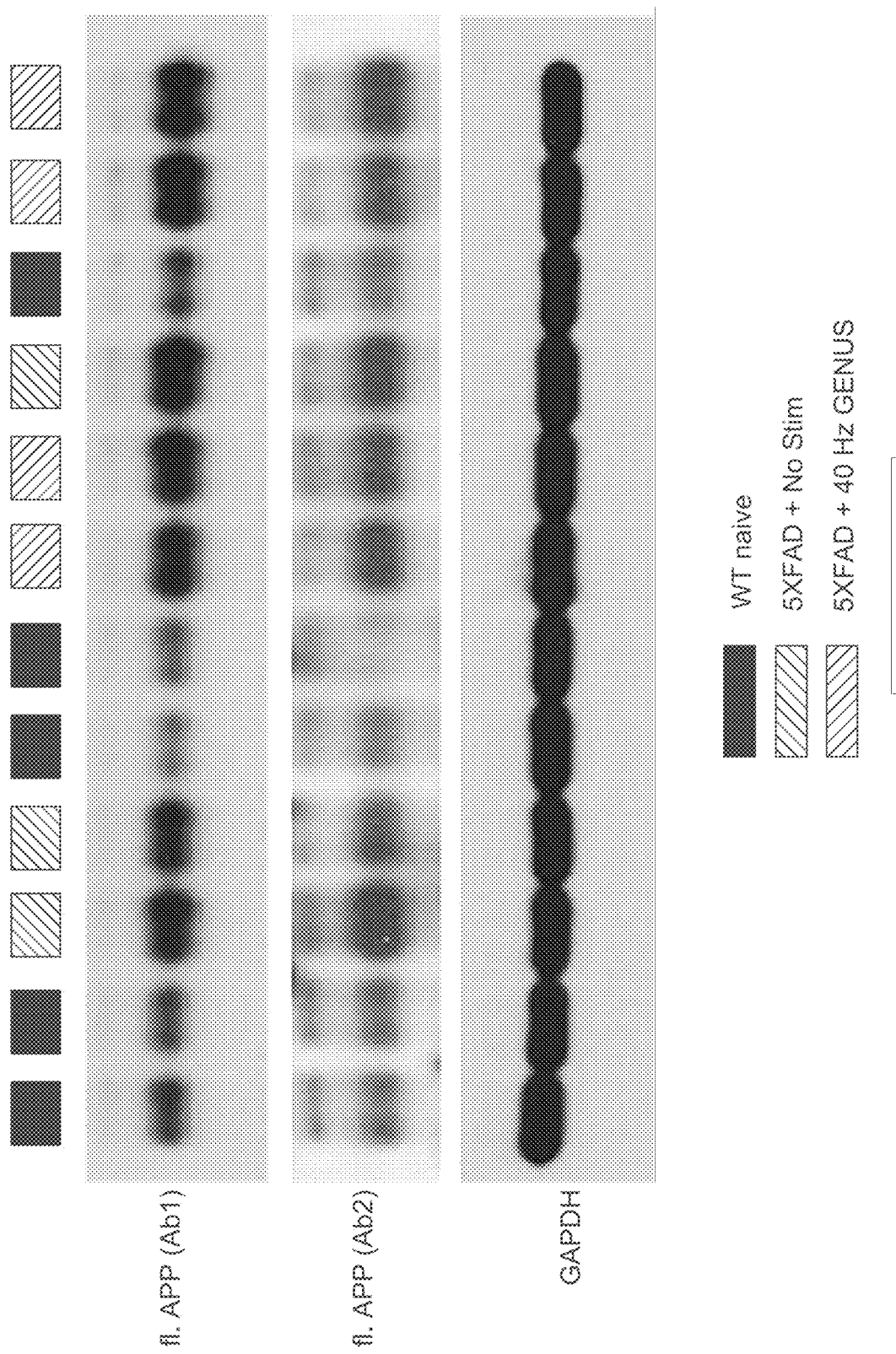

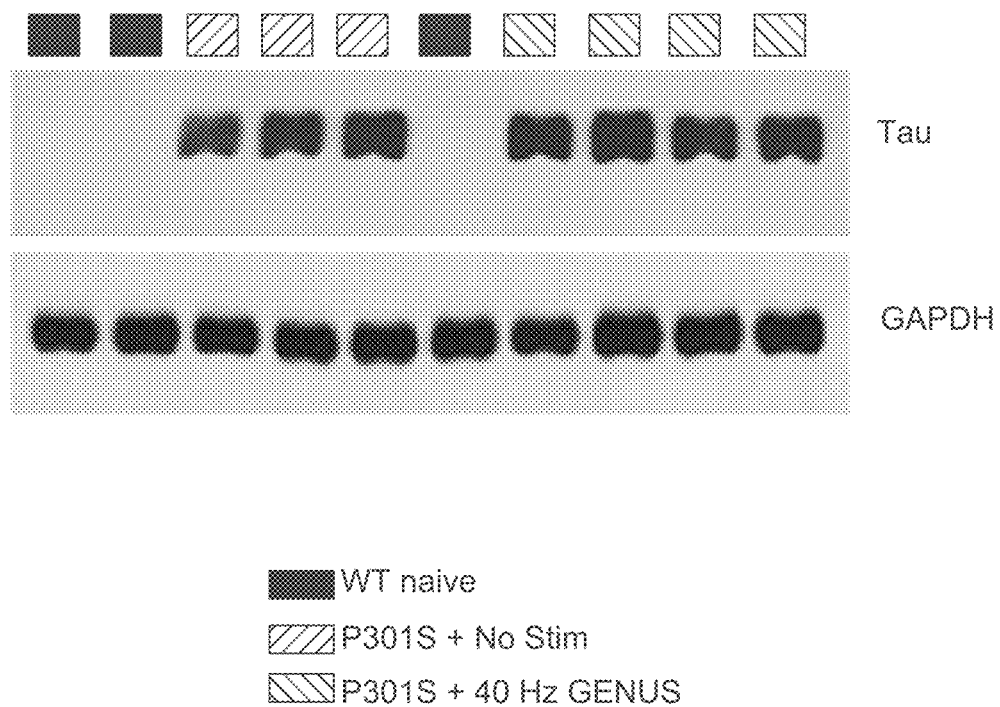
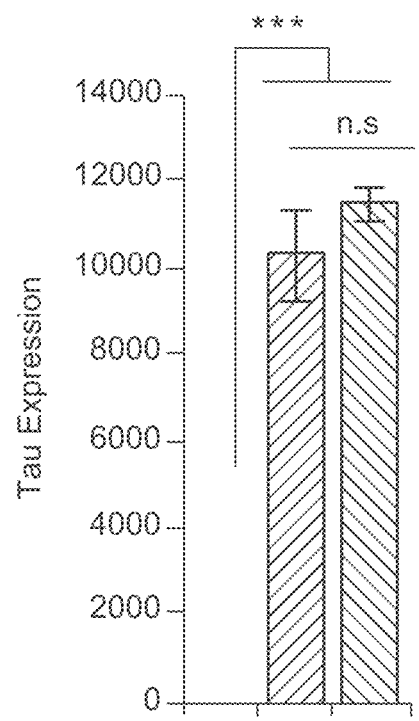
FIG. 9A

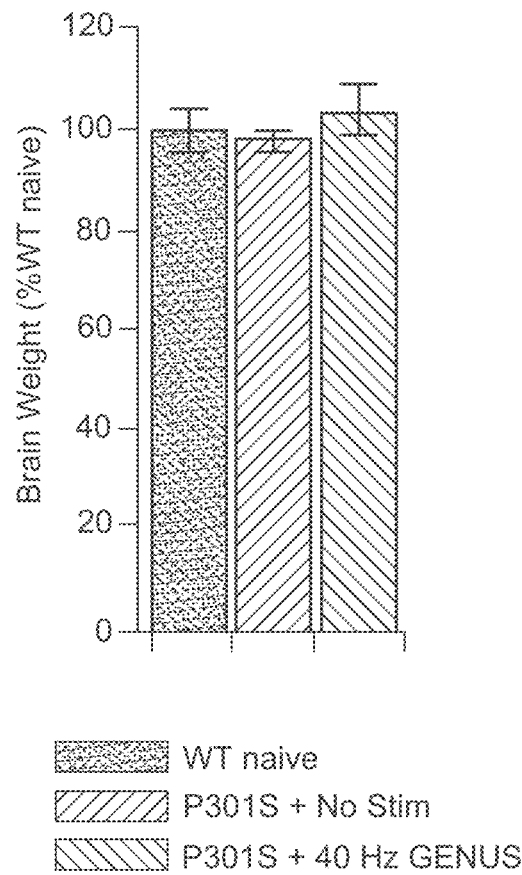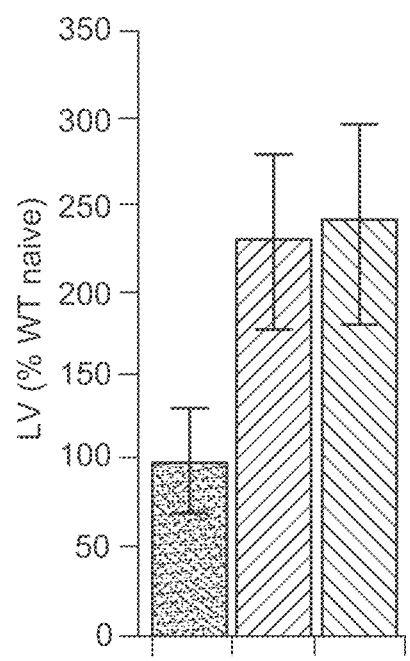
FIG. 9B

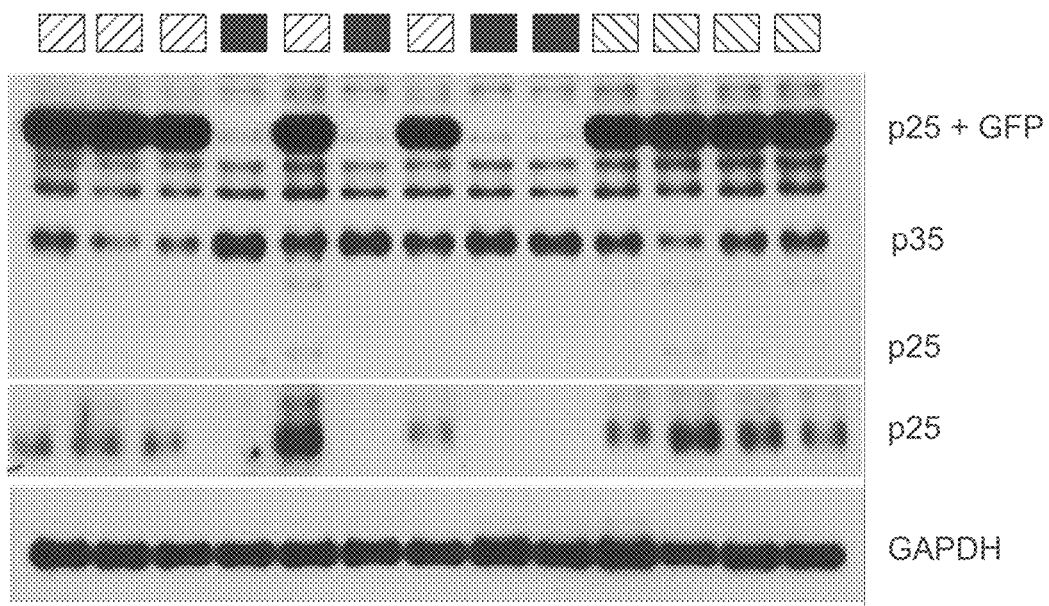
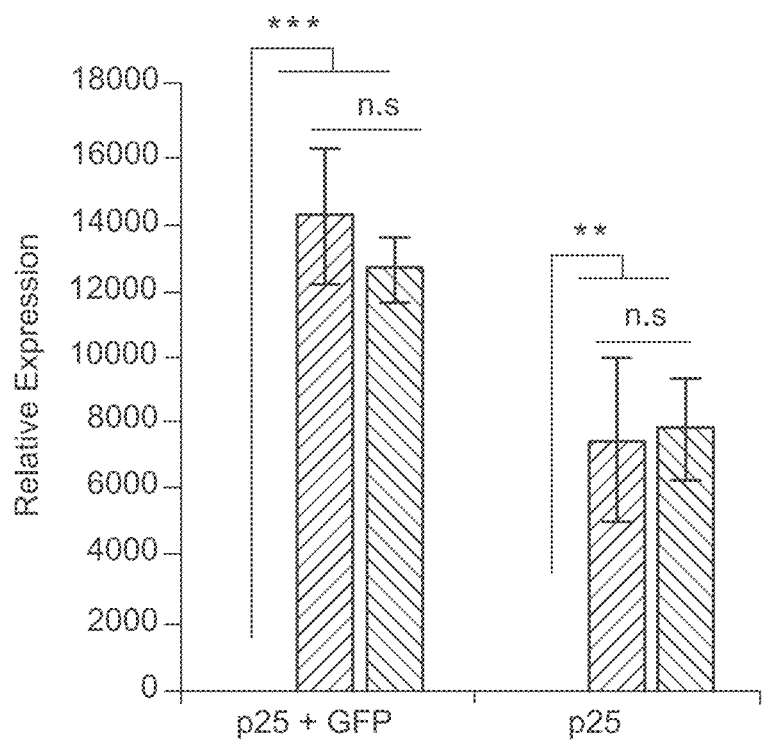
FIG. 9C

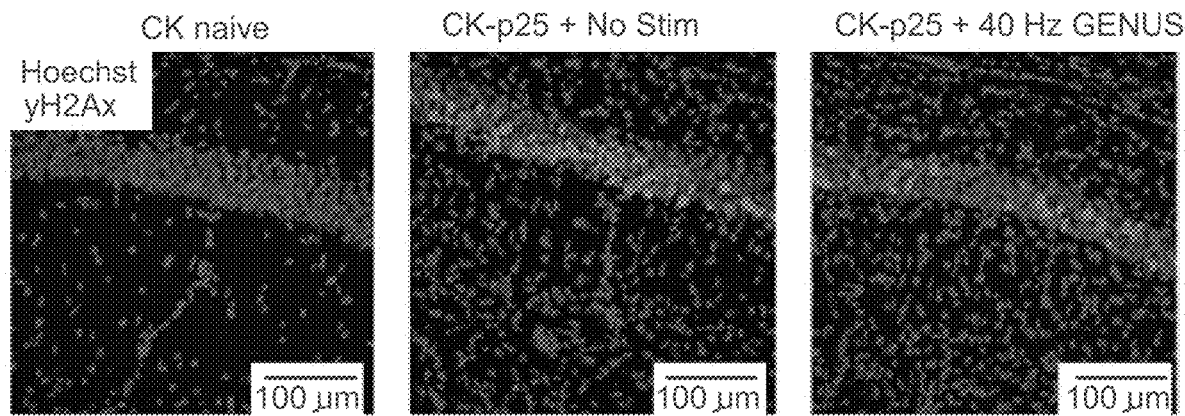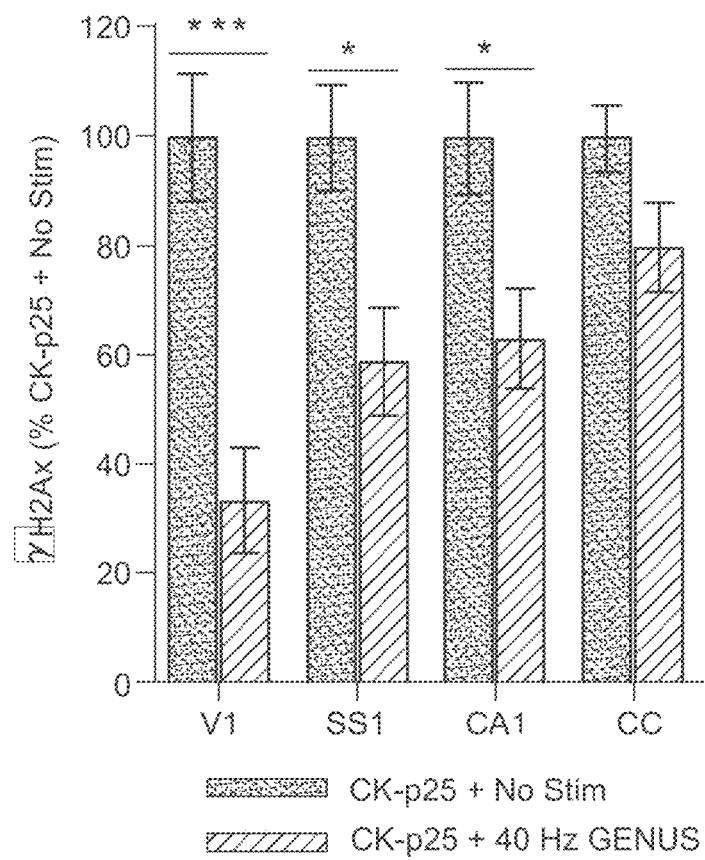
FIG. 9G

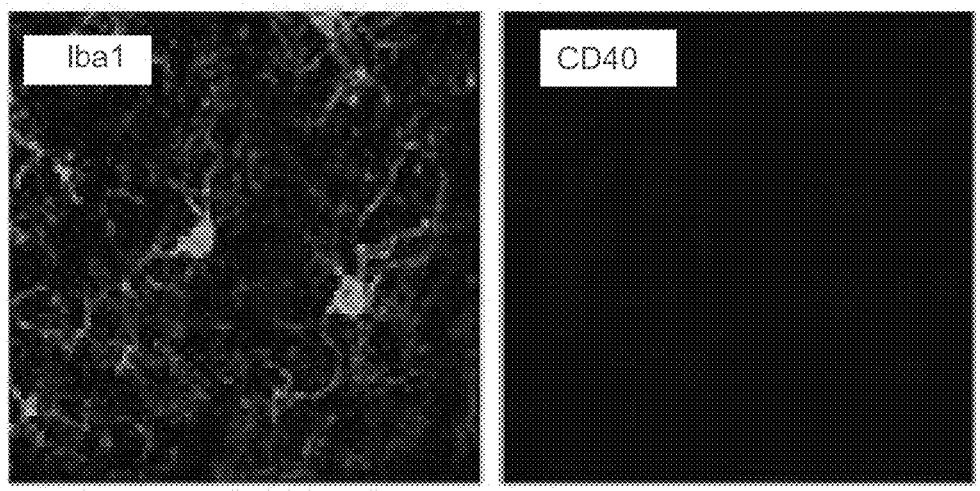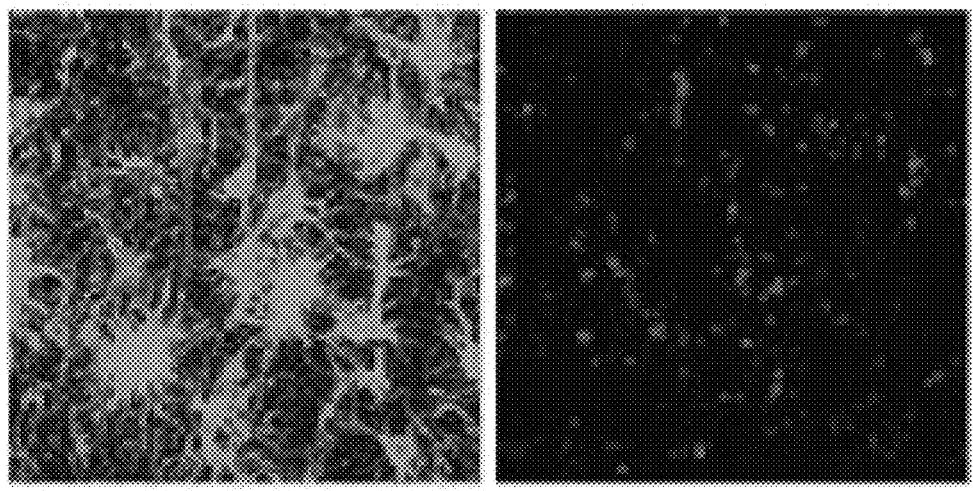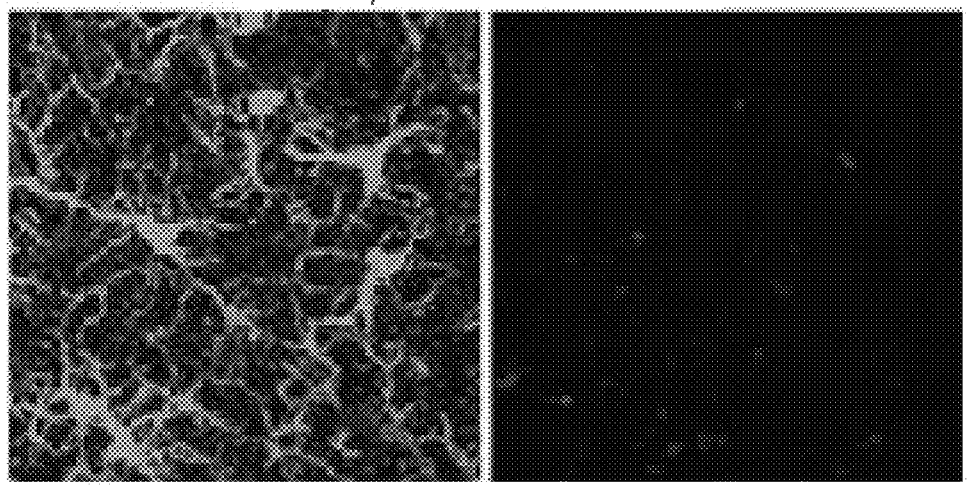
FIG. 10E

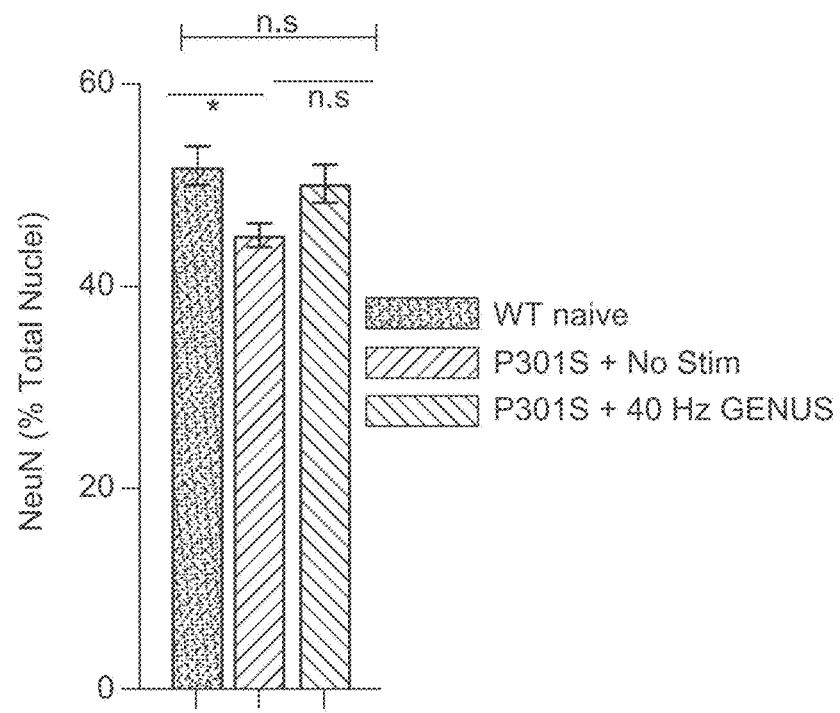
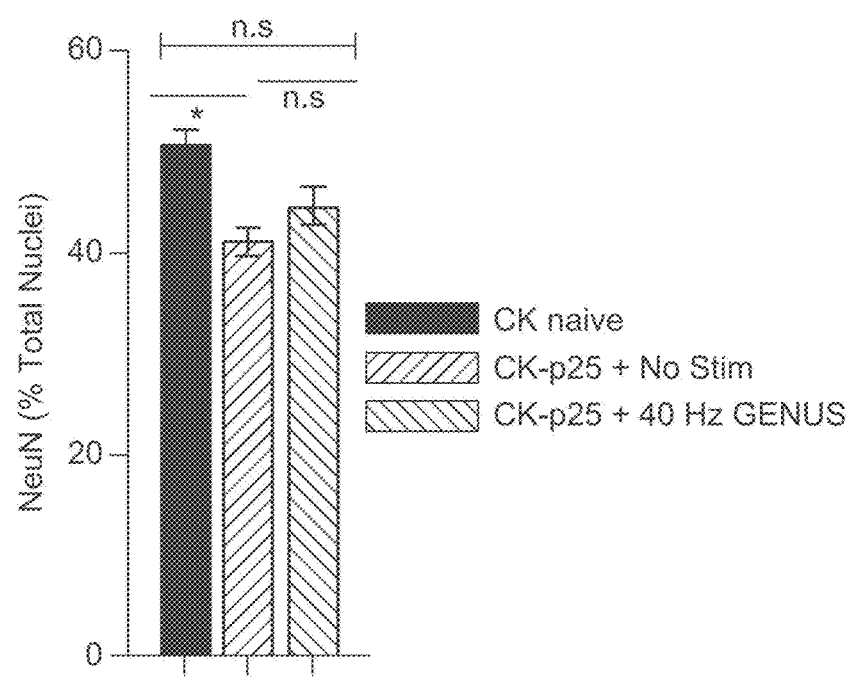
FIG. 10H

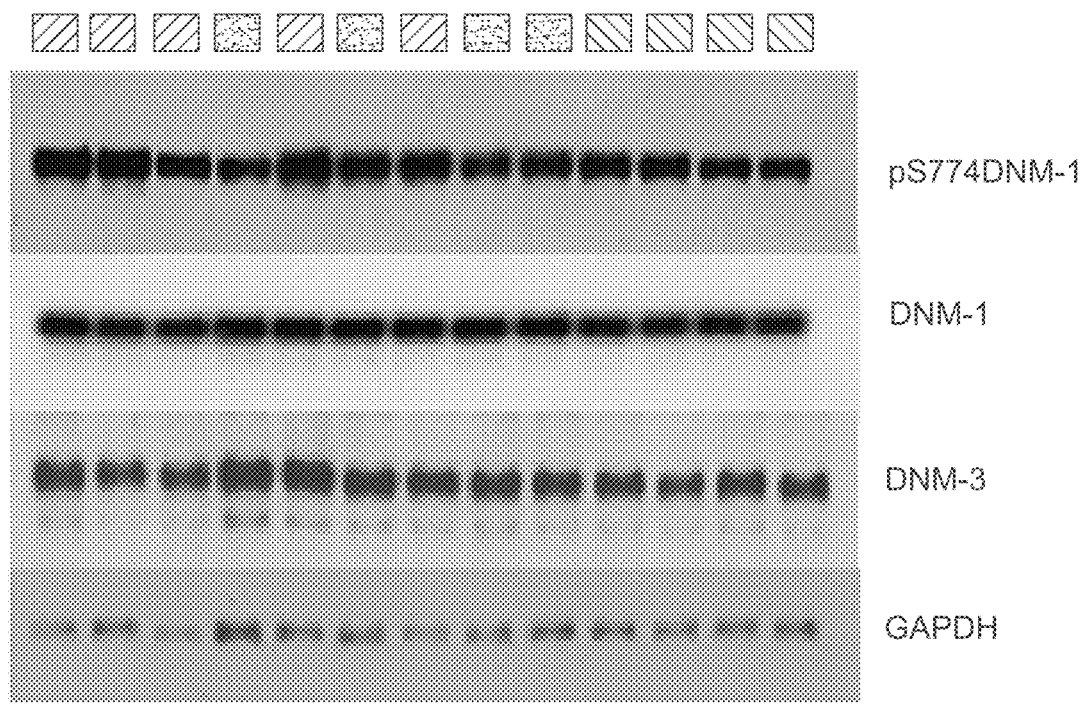
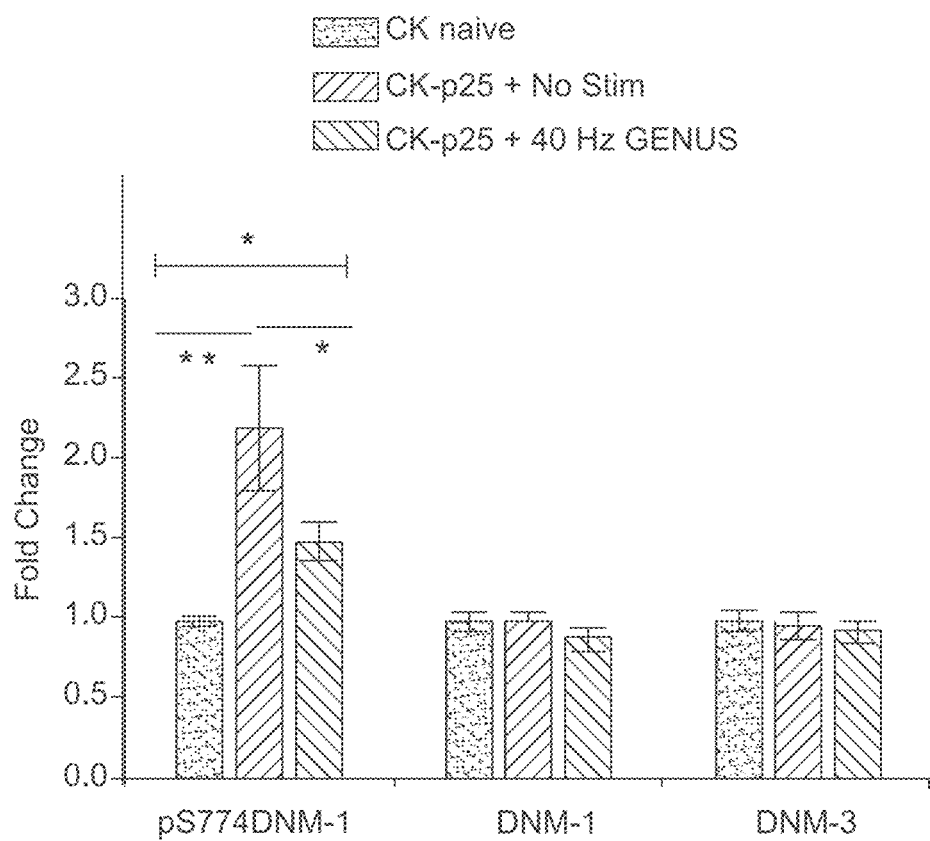
FIG. 10M

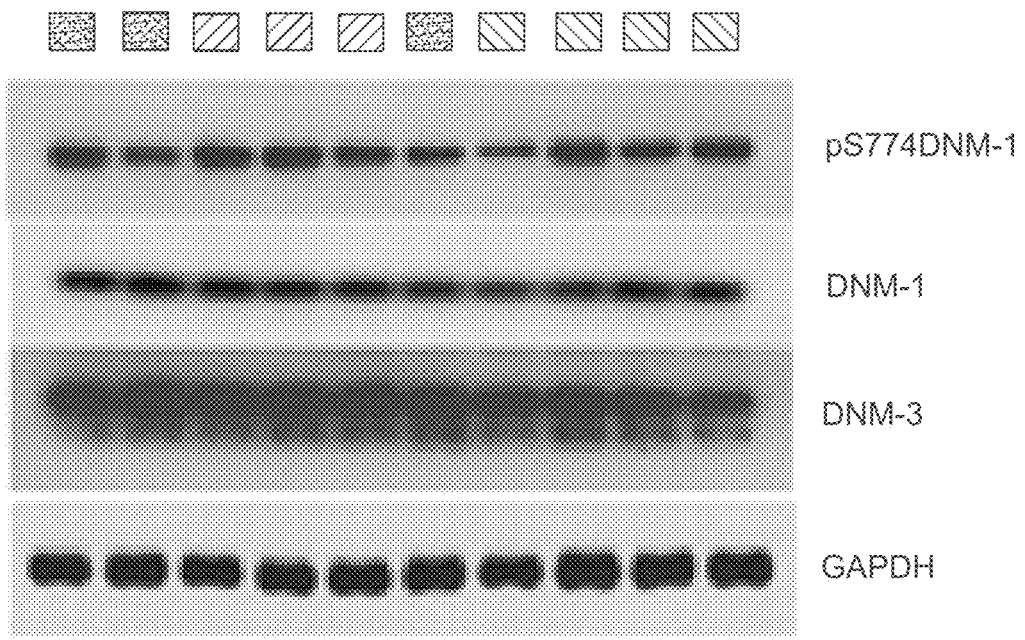
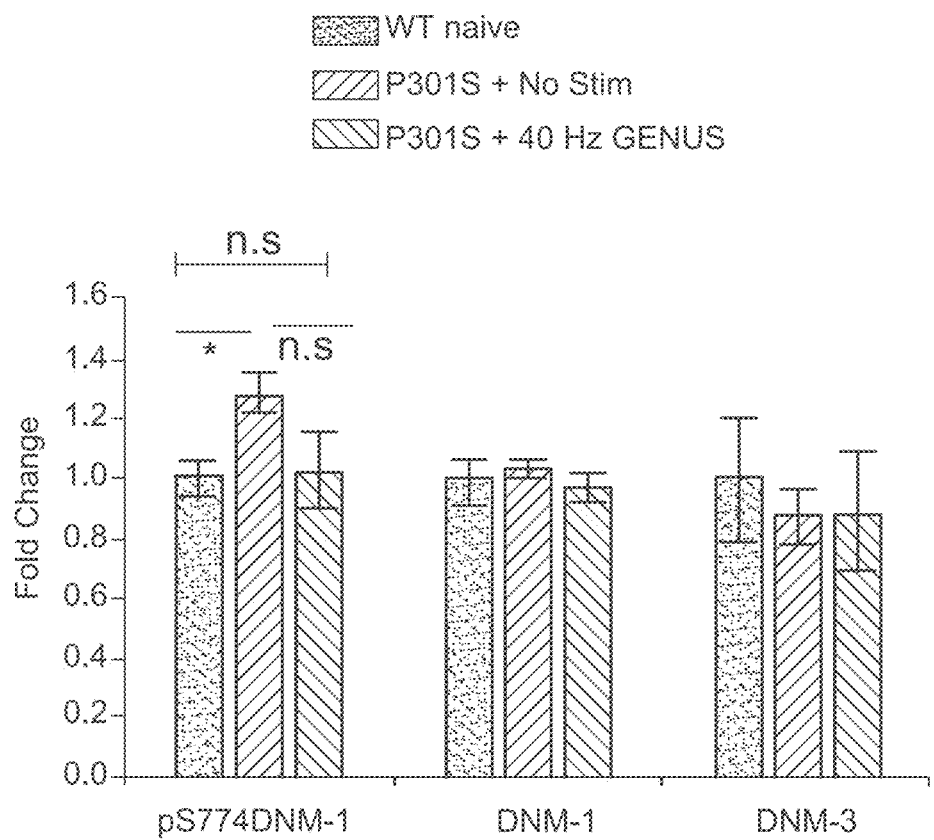
FIG. 10N

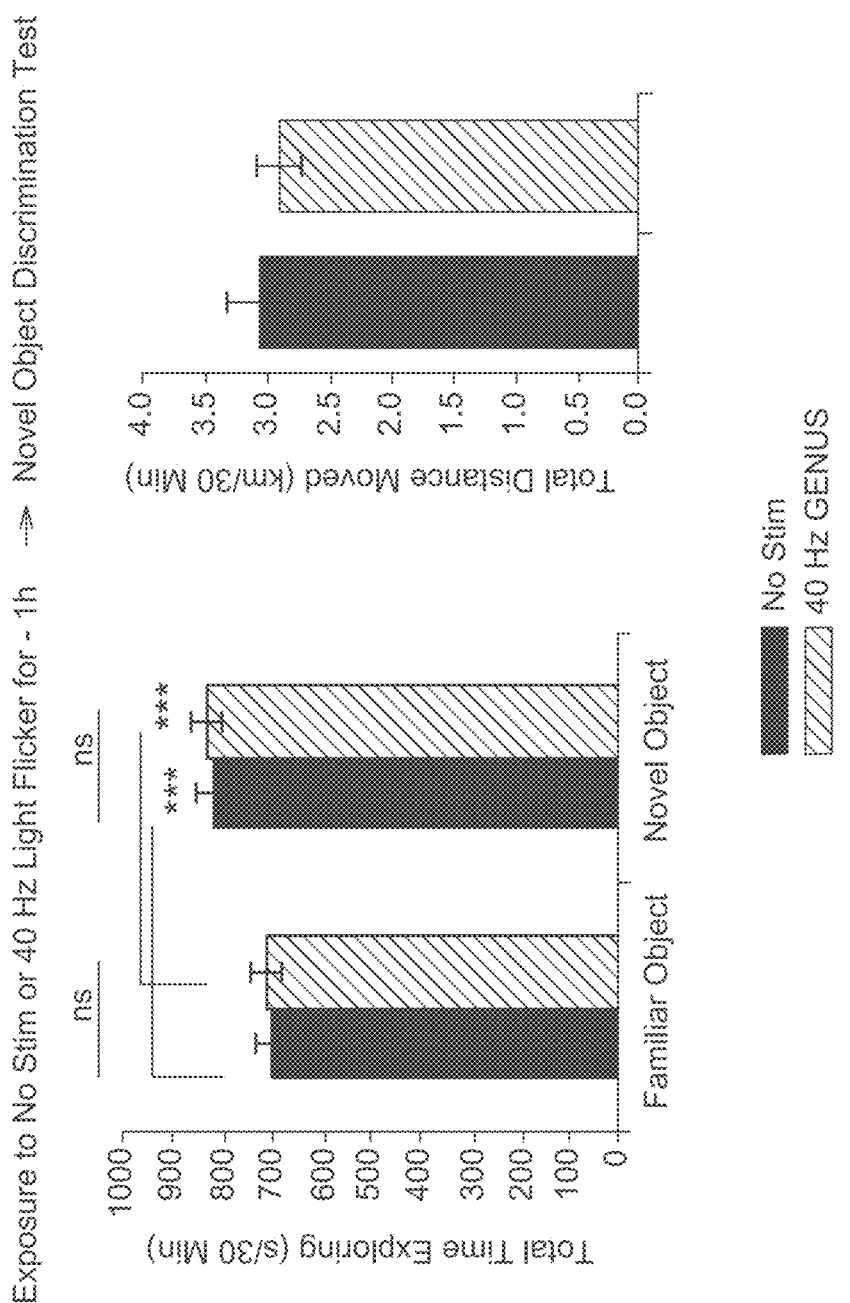
FIG. 11C—Cont'd

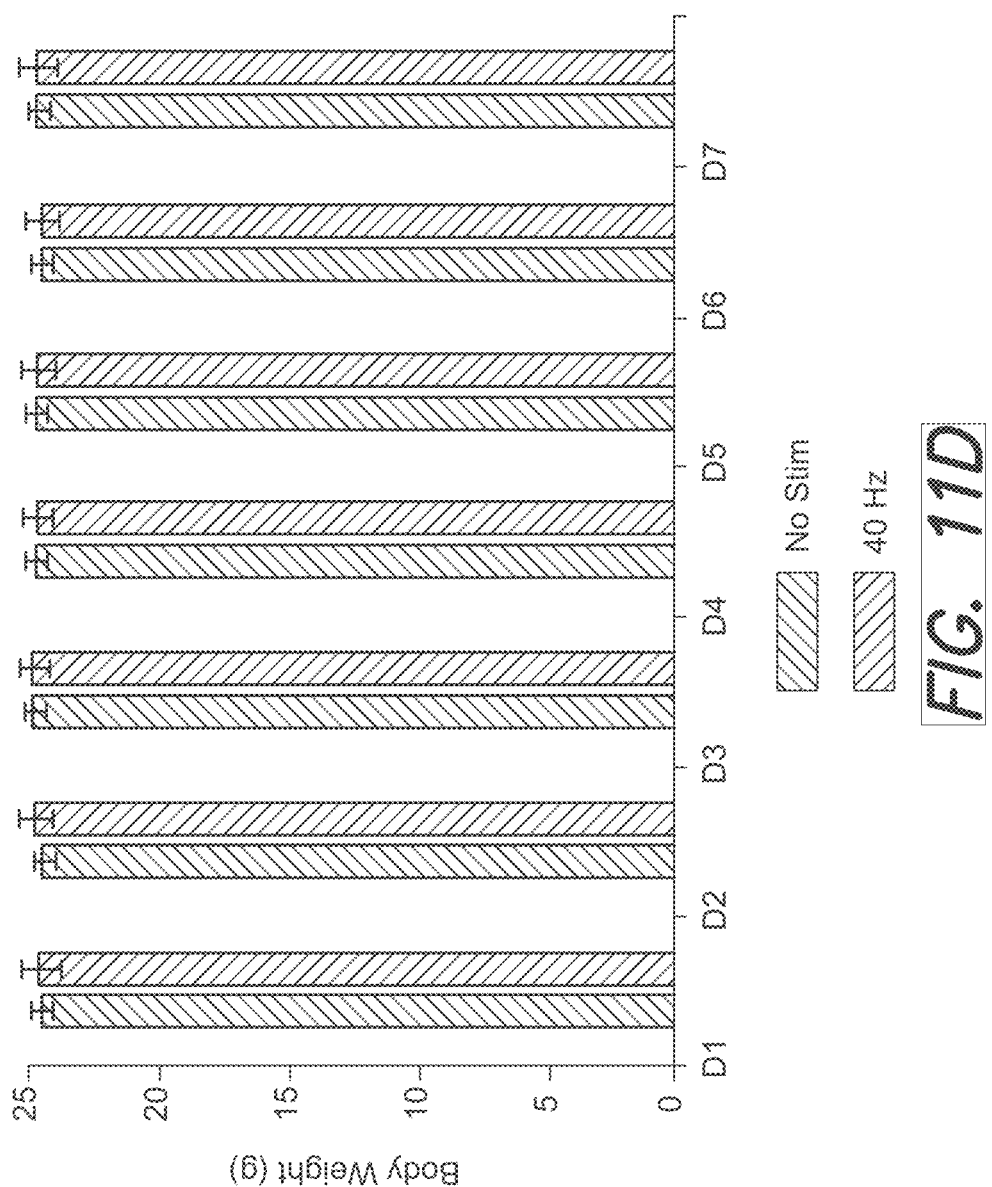

SYSTEMS AND METHODS FOR PREVENTING, MITIGATING, AND/OR TREATING DEMENTIA VIA VISUAL STIMULATION THAT BINDS HIGHER ORDER BRAIN REGIONS, REDUCES NEURODEGENERATION AND NEUROINFLAMMATION, AND IMPROVES COGNITIVE FUNCTION

CROSS-REFERENCES TO RELATED APPLICATIONS

The present application claims a priority benefit to U.S. provisional application Ser. No. 62/570,929, filed on Oct. 11, 2017, and entitled GAMMA ENTRAINMENT BINDS HIGHER ORDER BRAIN REGIONS AND OFFERS NEUROPROTECTION". The present application also claims a priority benefit as a continuation-in-part (CIP) of U.S. non-provisional application Ser. No. 16/135,938, filed on Sep. 19, 2018, entitled "Systems and Methods for Preventing, Mitigating, and/or Treating Dementia," which in turn claims a priority benefit to U.S. provisional application Serial No. 62/570,250, filed on Oct. 10, 2017, and entitled "NEUROPROTECTIVE EFFECTS OF COMBINED SENSORY STIMULATION". Each of the aforementioned application is incorporated by reference herein in its entirety.

GOVERNMENT SUPPORT STATEMENT

This invention was made with U.S. Government support under Grant No. RF1 AG054321 awarded by the U.S. National Institutes of Health. The U.S. Government has certain rights in the invention.

BACKGROUND

Dementia, including Alzheimer's disease (AD), is a devastating disease of the brain characterized by the deterioration of brain and cognitive functions (Canter et al., 2016; Palop and Mucke, 2016). Multiple factors contribute to the pathogenesis of AD including amyloid-β deposition, hyperphosphorylated tau accumulation, microglia- and astrocyte-mediated inflammation, and the loss of neurons and synapses (Ballatore et al., 2007; Huang and Mucke, 2012; Jacobsen et al., 2006; Meyer-Luehmann et al., 2008; Oakley et al., 2006; Ulland et al., 2017; Yoshiyama et al., 2007).

More recent studies have increasingly examined the physiological aspects of AD pathologies, such as neuronal hyper-excitability, interneuron dysfunction, shifted inhibition/excitation balance, epileptic discharges, and altered network oscillations (Canter et al., 2016; Holth et al., 2017; Hsia et al., 1999; Palop and Mucke, 2010; Palop and Mucke, 2016; Verret et al., 2012). These findings are consistent with the network abnormalities observed in human AD (Guillon et al., 2017; Koenig et al., 2005; Ribary et al., 1991; Stam et al., 2002). Recent studies in AD mouse models have highlighted that these changes occur at the presymptomatic stage (Gillespie et al., 2016; Iaccarino et al., 2016). Changes in neural activity have been previously shown to impact AD pathology, such as amyloid-β and tau accumulation, in several mouse models (Bero et al., 2011; Wu et al., 2016; Yamada et al., 2014). Given these observations, multiple approaches have been employed to investigate whether manipulating neuronal oscillations can be effective in ameliorating AD pathology (Iaccarino et al., 2016; Martinez-Losa et al., 2018; Verret et al., 2012).

In particular, oscillations in the gamma frequency band (~30-90 Hz) have been found to be reduced in multiple AD mouse models including hAPP-J20, ApoE4, 5XFAD, but also notably in human AD patients (Gillespie et al., 2016; Guillon et al., 2017; Iaccarino et al., 2016; Koenig et al., 2005; Ribary et al., 1991; Stam et al., 2002; Verret et al., 2012). Given this, several recent studies have targeted gamma oscillations and their findings suggest that this might represent a promising strategy to alleviate AD pathology.

In one previous approach, increasing gamma oscillations through expression of the voltage-gated sodium channel subunit Nav1.1 in parvalbumin-positive (PV+) interneurons, or with brain transplants of Nav1.1 over-expressing interneuron progenitors, alleviated gamma deficits and reduced both epileptiform activity and cognitive decline in hAPP-J20 mice (Martinez-Losa et al., 2018; Verret et al., 2012).

In a second approach, optogenetic activation of PV+ interneurons at 40 Hz, which has been shown to induce robust gamma frequency oscillations (Cardin et al., 2009; Sohal et al., 2009), was found to reduce amyloid load and enhance morphological transformation of microglia in 5XFAD mice (Iaccarino et al., 2016). This non-invasive approach of using 40 Hz visual stimulation was similarly effective in decreasing amyloid load and altering microglia in the visual cortex of 5XFAD mice (Iaccarino et al., 2016). However, in this previous study, amyloid levels in the visual cortex returned to baseline 24 hours after acute visual stimulation for one hour. This earlier study found, however, that extending one hour of visual stimulation to one hour per day for seven days reduced not only amyloid levels (soluble and insoluble forms of Aβ1-40 and Aβ1-42), but also plaque pathology in the visual cortex in 6 month old 5XFAD mice (Iaccarino et al., 2016). Moreover, visual stimulation impacted multiple cell types, including neurons and microglia, to reduce the production and enhance clearance of Aβ, respectively in 5XFAD mice.

SUMMARY

As disclosed in U.S. patent application Ser. No. 15/360, 637, filed on Nov. 23, 2016, and entitled "SYSTEMS AND METHODS FOR PREVENTING, MITIGATING, AND/ OR TREATING DEMENTIA" (hereby incoroporated herein by reference in its entirety), inducing synchronized gamma oscillations in the brain via visual (as well as auditory and/or haptic) stimulus results in reduced amyloid load and morphological changes in some brain regions. The Inventors have recognized and appreciated, however, that there remains a need for systems and methods of treating dementia and Alzheimer's disease that address circuit-wide disease affecting multiple brain centers significantly responsible for learning and memory and other higher-order brain functions.

In the present disclosure, inventive methods and apparatus for entraining gamma oscillations in the brain of a subject via chronic non-invasive visual stimuli, referred to herein as "Gamma ENtrainment Using Sensory visual stimuli" (GENUS), has been demonstrated to extend beyond the visual cortex to multiple other brain regions (e.g., the hippocampus, somatosensory and prefrontal cortices), while also enhancing low gamma coherence across these multiple brain regions. Furthermore, chronic GENUS reduced neurodegeneration in 5XFAD, P301S and CK-p25 mice, with the neuroprotective effect evident across multiple brain regions. Collected data highlights how GENUS mediated modulation of neuronal activity across brain regions can influence genes and proteins involved in intracellular transport and synaptic functions in degenerating neurons. These results establish a connection between GENUS driven gamma oscillation, functional binding of neural networks across multiple brain areas, neuroprotection and behavioral performance in a subject.

In sum, one inventive implementation is directed to method for treating dementia or Alzheimer's disease in a subject in need thereof, the method comprising: A) non-invasively delivering chronic visual stimuli having a frequency of about 30 Hz to about 50 Hz to the subject to entrain synchronized gamma oscillations in multiple brain regions of the subject including at least the prefrontal cortex (PFC) and the hippocampus of the subject.

Another inventive implementation is directed to a method for treating dementia or Alzheimer's disease in a subject in need thereof, the method comprising: A) non-invasively delivering chronic visual stimuli having a frequency of about 30 Hz to about 50 Hz to the subject to entrain synchronized gamma oscillations in multiple brain regions of the subject and ameliorate aberrantly modified genes and proteins in degenerating neurons in multiple brain regions of the subject.

Another inventive implementation is directed to a method for treating dementia or Alzheimer's disease in a subject in need thereof, the method comprising: A) non-invasively delivering chronic visual stimuli having a frequency of about 30 Hz to about 50 Hz to the subject to concurrently entrain synchronized gamma oscillations in multiple brain regions of the subject to significantly increase gamma coherence having the frequency between 30 Hz to 50 Hz between the multiple brain regions of the subject.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally see, e.g., like features (e.g., functionally similar and/or structurally similar elements).

FIGS. 1A through 1J illustrate that visual stimulation entrains gamma oscillations in multiple brain regions of a subject beyond the visual cortex, according to the inventive concepts disclosed.

FIGS. 3A through 3J illustrate that chronic visual stimulation ameliorates Alzheimer's Disease-associated pathology and significantly reduces or prevents neurodegeneration in a subject, according to the inventive concepts disclosed.

FIGS. 6A through 6I illustrate that chronic visual stimulation modifies behavior in multiple subject models of Alzheimer's Disease, according to the inventive concepts disclosed.

FIGS. 7A through 7I illustrate that chronic visual stimulation entrains gamma oscillations beyond visual cortex in mouse models of neurodegeneration, according to the inventive concepts disclosed.

FIGS. 8A through 8I illustrate that chronic visual stimulation reduces AD-associated pathology in 5XFAD mice beyond visual cortex, according to the inventive concepts disclosed.

FIGS. 9A through 9G illustrate that chronic visual stimulation ameliorates AD-associated pathology in P301S and CK-p25 mice, according to the inventive concepts disclosed.

FIGS. 11A through 11J illustrate behavioral characterization of the effect on a subject of acute and chronic visual stimulation according to the inventive concepts disclosed.

DETAILED DESCRIPTION

Figure 1B:
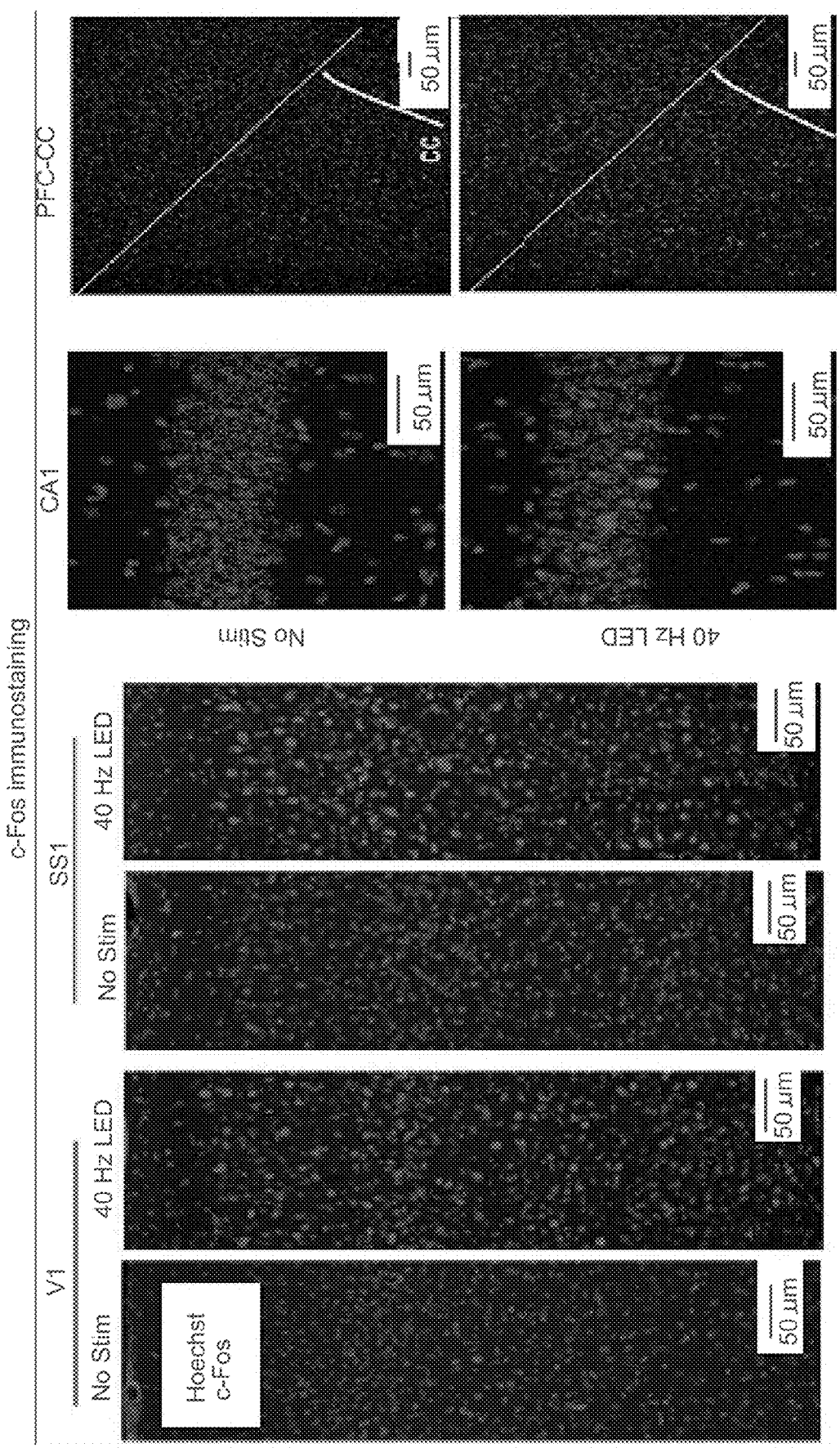

Following below are more detailed descriptions of various concepts related to, and implementations of, systems and methods for preventing, mitigating, and/or treating dementia via visual stimulation that binds higher order brain regions, reduces neurodegeneration and neuroinflammation, and improves cognitive function. It should be appreciated that various concepts introduced above and discussed in greater detail below may be implemented in numerous ways. Examples of specific implementations and applications are provided primarily for illustrative purposes to enable those skilled in the art to practice the implementations and alternatives apparent to those skilled in the art.

The figures and example implementations described below are not meant to limit the scope of the present implementations to a single embodiment. Other implementations are possible by way of interchange of some or all of the described or illustrated elements. Moreover, where certain elements of the disclosed example implementations may be partially or fully implemented using known components, in some instances only those portions of such known components that are necessary for an understanding of the present implementations are described, and detailed descriptions of other portions of such known components are omitted so as not to obscure the present implementations.

In this disclosure, we demonstrate that inventive techniques involving treatment of a subject with chronic non-invasive visual stimuli, referred to herein as "Gamma ENtrainment Using Sensory visual stimuli" (GENUS), addresses symptoms related to dementia, including Alzheimer's Disease (AD), and impacts AD pathology in brain regions beyond the visual cortex. In illustrative examples, we verified the effects of chronic visual GENUS in multiple mouse models of neurodegeneration, including Tau P301S, CK-p25, and older 5XFAD mice. We observed that chronic visual GENUS entrains gamma oscillations in multiple brain regions (including higher order brain areas) and induces functional binding at low gamma frequencies across these brain regions. Across the several neurodegenerative disease mouse models that we tested, we found that chronic visual GENUS ameliorated multiple AD-associated pathologies including amyloid plaques, tau hyper-phosphorylation and brain atrophy, preventing neuronal and synaptic density loss in multiple higher order brain regions. Transcriptomic and proteomic profiling demonstrated that genes and proteins involved in membrane trafficking, intracellular transport and synaptic function that are aberrantly modified in degenerating neurons in P301S and CK-p25 mice are improved or repaired with chronic GENUS and the immune response in microglia is reduced. In view of these widespread neuroprotective effects, we further investigated the effects of chronic daily GENUS on cognitive function and demonstrate improved performance in behavioral tasks in multiple mouse models of AD. Together, our results highlight the neuroprotective efficacy of visual GENUS in treating a subject for dementia, including AD.

As will be described in detail below, several studies were conducted to assess the impact on multiple brain regions of chronic visual stimuli. The visual stimuli generally had a frequency of about 30 Hz to 50 Hz, with particular attention paid to a frequency at or about 40 Hz for the visual stimuli. In some examples, a light-emitting diode (LED)-based device was employed to deliver the visual stimuli, and the LED-based device was driven with a square wave current pattern having a duty cycle of 50%. It should be appreciated, however, that various types of devices may be employed (other than LED-based devices) to effectively deliver the visual stimuli at various frequencies within the ranges noted herein. Additionally, waveforms other than square wave forms, as well as duty cycles other than 50%, may be employed to effectively generate the visual stimuli at various frequencies within the ranges noted herein.

Additionally, various treatment protocols were employed in the several studies described herein, including subject exposure times to visual stimuli of 1 hour per day, and subject exposure periods of 7 days, 22 days (about 3 weeks) and 42 days (about 6 weeks). It should be appreciated, however, that other subject exposure times and subject exposure periods may be employed to deliver visual stimuli at various frequencies within the ranges noted herein and effectively treat dementia, including Alzheimer's Disease. For example, exposure times of greater than 1 hour per day (e.g., delivered in multiple 1 hour increments, shorter increments, or longer increments), and/or exposure periods of less than three weeks, between three weeks and six weeks, and greater than six weeks, may be employed in different combinations and permuations to effectively treat dementia, including Alzheimer's Disease.

Below we first provide a summary of the experiments and respective observations, followed by additional details of experimental protocol to illustrate the efficacy of visual GENUS on treating a subject for dementia, including Alzheimer's Disease.

Visual GENUS Affects Higher Order Brain Areas

We first aimed to determine if 40 Hz visual stimulation could regulate neuronal activity in brain areas beyond the visual cortex, or if it was confined to visual cortex, by performing c-Fos immunohistochemical staining as a marker of neuronal activation in wild-type C57B1/6J mice (FIG. 1A). A custom-made LED device was employed to deliver visual stimuli at specific frequencies with a 50% duty cycle (e.g., lights on for 12.5 ms and lights off for 12.5 ms for 40 Hz stimulation) (Iaccarino et al., 2016; Singer et al., in press). Mice were habituated to their environment for 3 days and then exposed to 1 hour of 40 Hz visual stimulation. They were then returned to their home cage for 1 h before they were sacrificed and the brain tissue collected, sectioned, and labeled with c-Fos antibody. We found that 40 Hz visual stimulation resulted in a significant increase in c-Fos positive neurons in visual cortex (V1) (FIG. 1A-1B), and also noted significant increases in somatosensory cortex (SS1), hippocampal area CA1, and cingulate cortex (CC) area of the prefrontal cortex (FIG. 1A-1B).

Figure 7A:
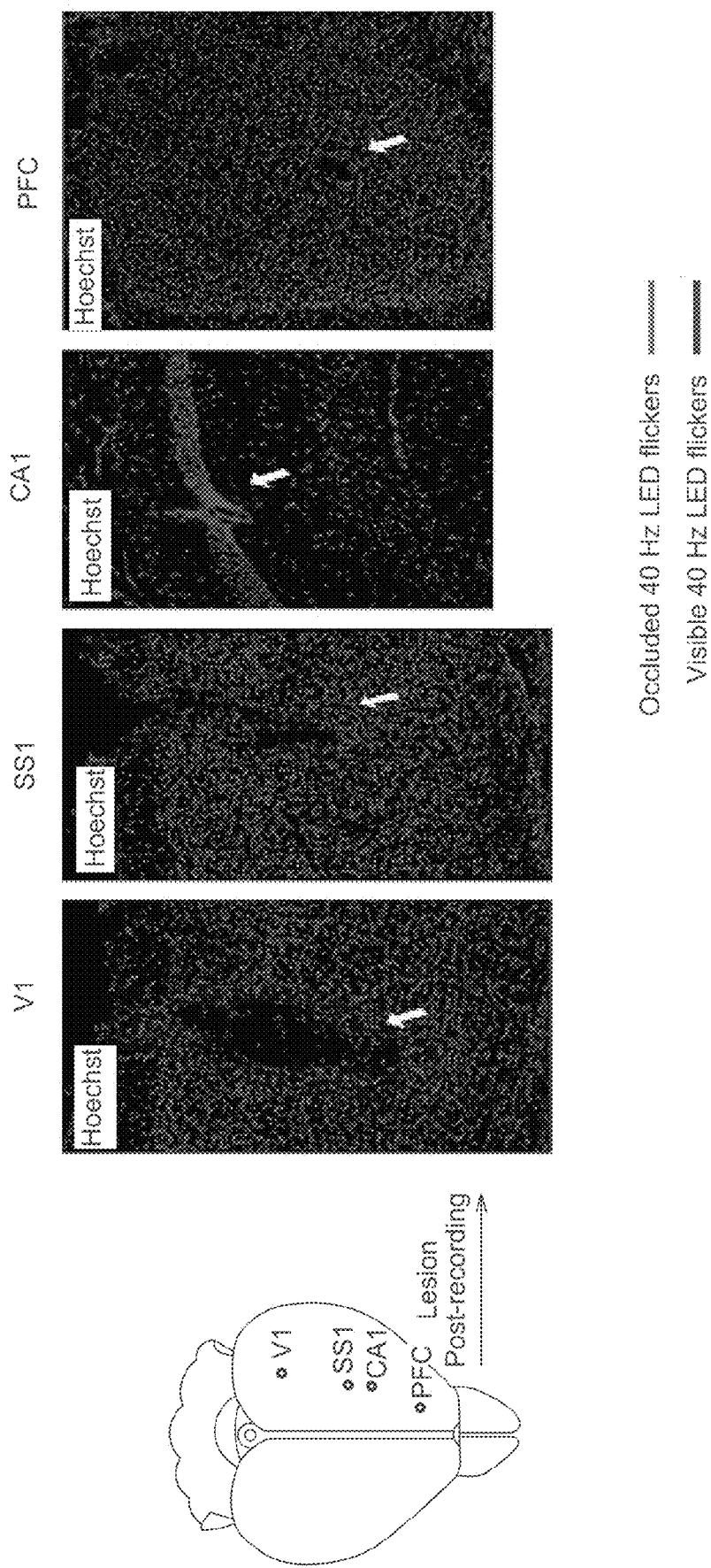

To understand how 40 Hz visual stimulation might alter ongoing neural activity in these brain areas, we implanted C57B1/6J mice with a custom-made microdrive (tungsten wire electrode; see methods for details) to record local field potentials (LFP) concurrently from V1, SS1, CA1, and the cingulate area of the prefrontal cortex (PFC) in freely behaving mice. Mice were confined to a small GENUS box (8×8 inches) to reduce exploratory behavior and local field potentials (LFP) were recorded simultaneously from V1, SS1, CA1, and prefrontal cortex (PFC) as they were exposed to 40 Hz visual stimulation that was initially occluded and then unblocked for 10 min each (FIG. 1A, FIG. 7A). Acute 40 Hz visual stimulation significantly increased the power of low gamma oscillations around 35-45 Hz, with the peak frequency at 40 Hz in V1 (FIG. 1C-1D) and a small but significant increase in CA1 (FIG. 1C-1D), consistent with previous findings in head-restrained mice (Iaccarino et al., 2016). Small but significant increases in gamma power were also observed in SS1 and PFC (FIG. 1C-1D), in agreement with the increase in c-Fos positive cells we observed across these regions (FIG. 1B).

To assess if these visual-stimulation-induced oscillations were capable of entraining neuronal firing in brain regions downstream of visual cortex, we implanted a cohort of C57B1/6J mice with tetrodes targeted to hippocampal area CA1 to record single unit activity. At baseline conditions where the light was occluded, CA1 pyramidal cells showed strong phase-locking to low gamma (~35-45 Hz) with preferential discharging at the peak, consistent with previous reports (Bragin et al., 1995; Middleton and McHugh, 2016) (FIG. 1E). Visual stimulation at 40 Hz, while not altering the preferred phase, induced more robust phase locking of individual neurons, quantified as an increased mean resultant length (MRL; between stimulation-occluded and 40 Hz visual stimulation, P=0.01) across the population (FIG. 1F), indicating that gamma frequency visual stimulation acts to drive populations of hippocampal neurons in a more temporally organized manner.

Figure 7B:
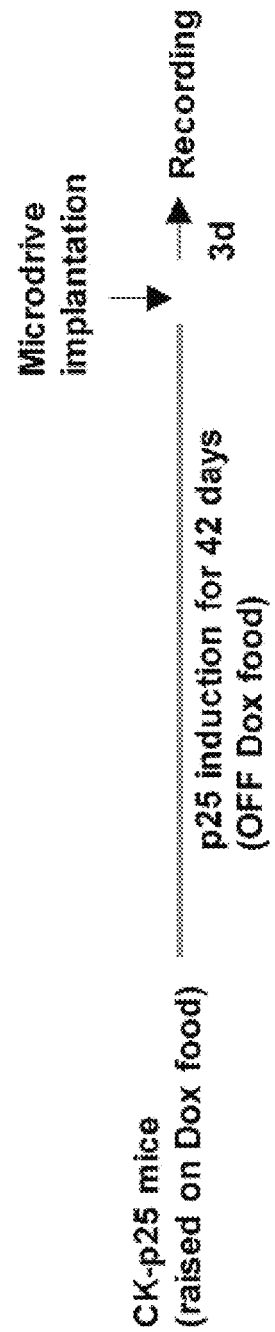
Figure 7C:
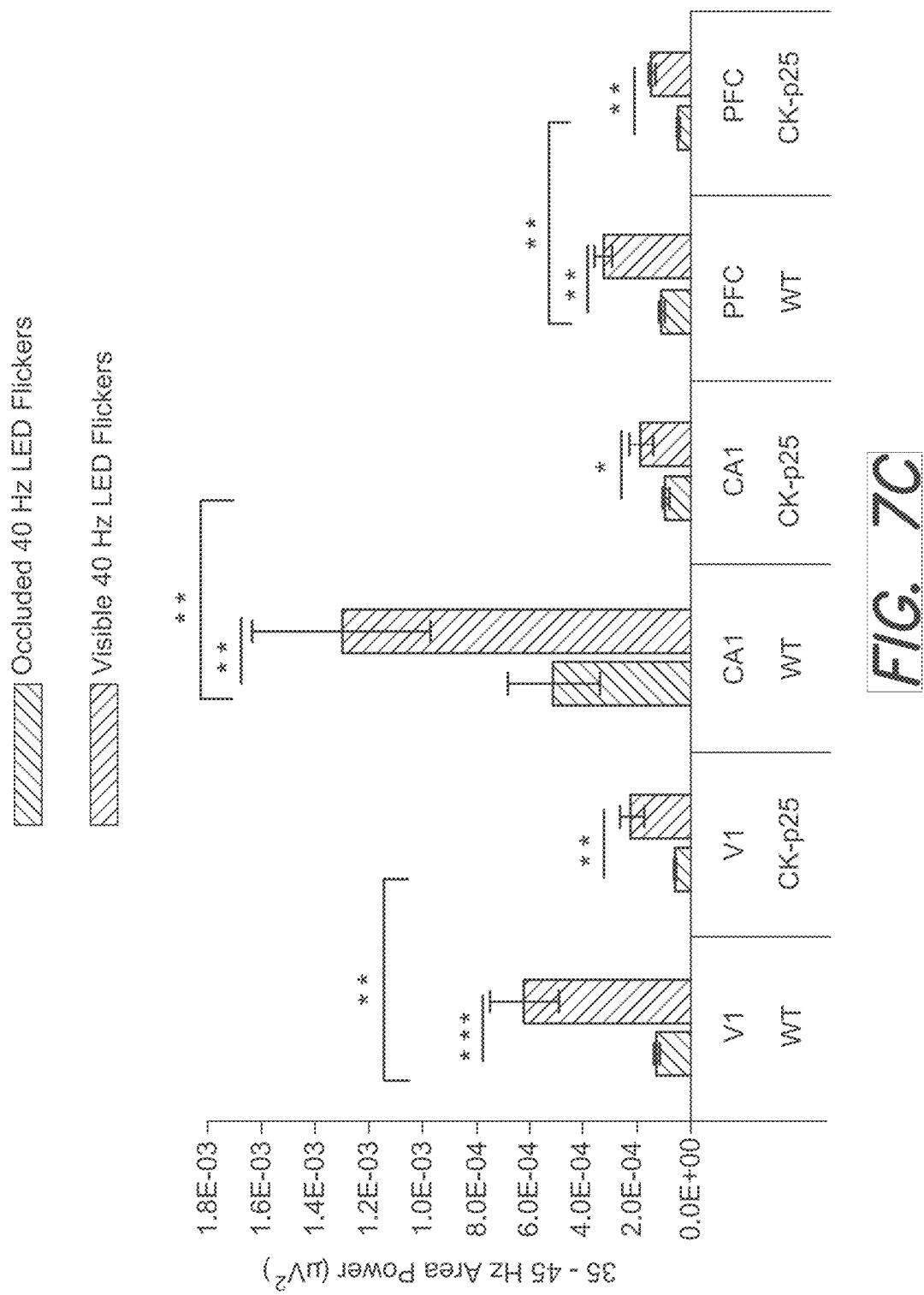
Figure 7D:
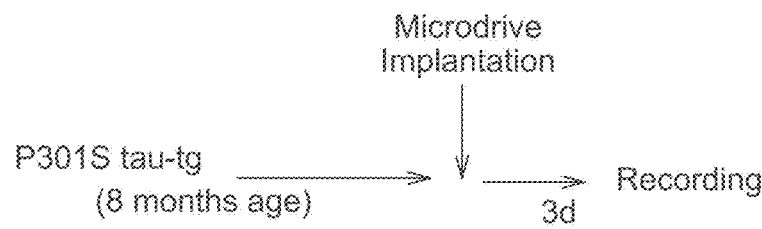
Figure 7E:
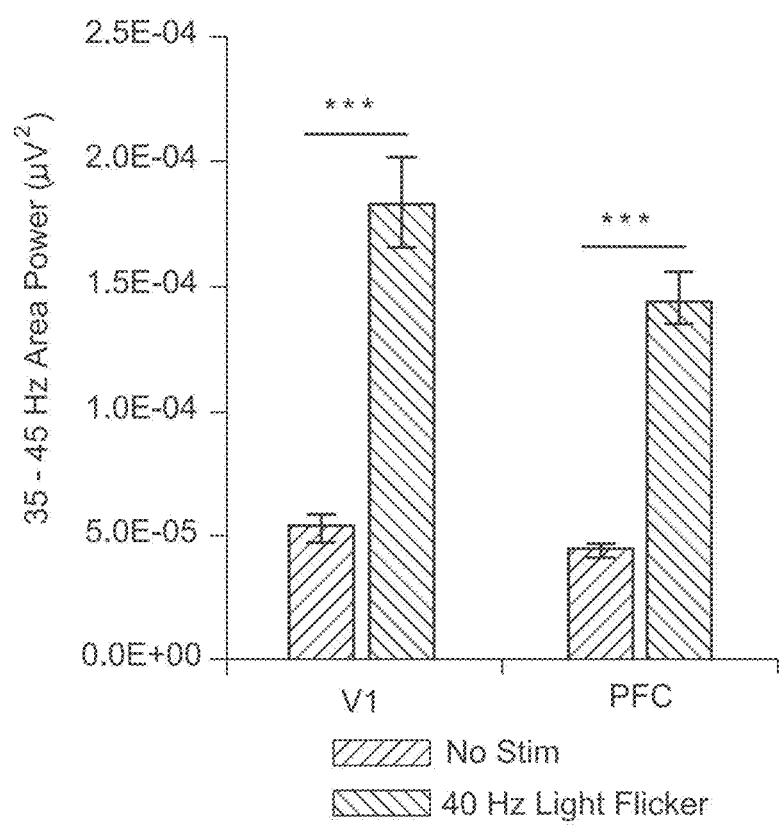

To test the applicability of GENUS to compromised neuronal systems, we used several mouse models of neurodegeneration to verify if we could induce gamma oscillations with visual stimulation, as observed in C57B1/6J animals. We utilized the CK-p25 mouse line, in which the expression of the Cdk5 activator p25 is driven by the excitatory neuron-specific CaMKIIα promoter in an inducible manner (CaMKIIα promoter-tTAxTetO-p25+GFP) (Cruz et al., 2003). Following withdrawal of doxycycline from the diet, CK-p25 exhibit progressive neuronal and synaptic loss with cognitive impairment, which is severe by 6 weeks of p25 induction (Cruz et al., 2003). Consistent with these findings, at 6 weeks post-induction, in vivo LFP recordings from CK-p25 mice showed considerably reduced gamma spectral power at 35-45 Hz compared with control mice in V1, CA1, and PFC (FIG. 7B-7C). Despite these changes, 40 Hz visual stimulation was still able to significantly enhance gamma oscillations in V1, CA1, and PFC (FIG. 7C). We further examined Tau P301S mice, which express high levels of humanized mutant microtubule-associated protein tau and have tau aggregates that are associated with frontotemporal dementia as early as 5 months of age (Yoshiyama et al., 2007). 8 months old P301S mice, at which age they have synaptic and neuronal loss and cognitive deficits, exhibited enhanced gamma power upon 40 Hz visual stimulation in V1 and PFC (FIG. 7D-7E). These results indicate that GENUS is sufficient to entrain gamma oscillations in AD mice independent of the specific mode of neuronal compromise in these mice.

Figure 7F:
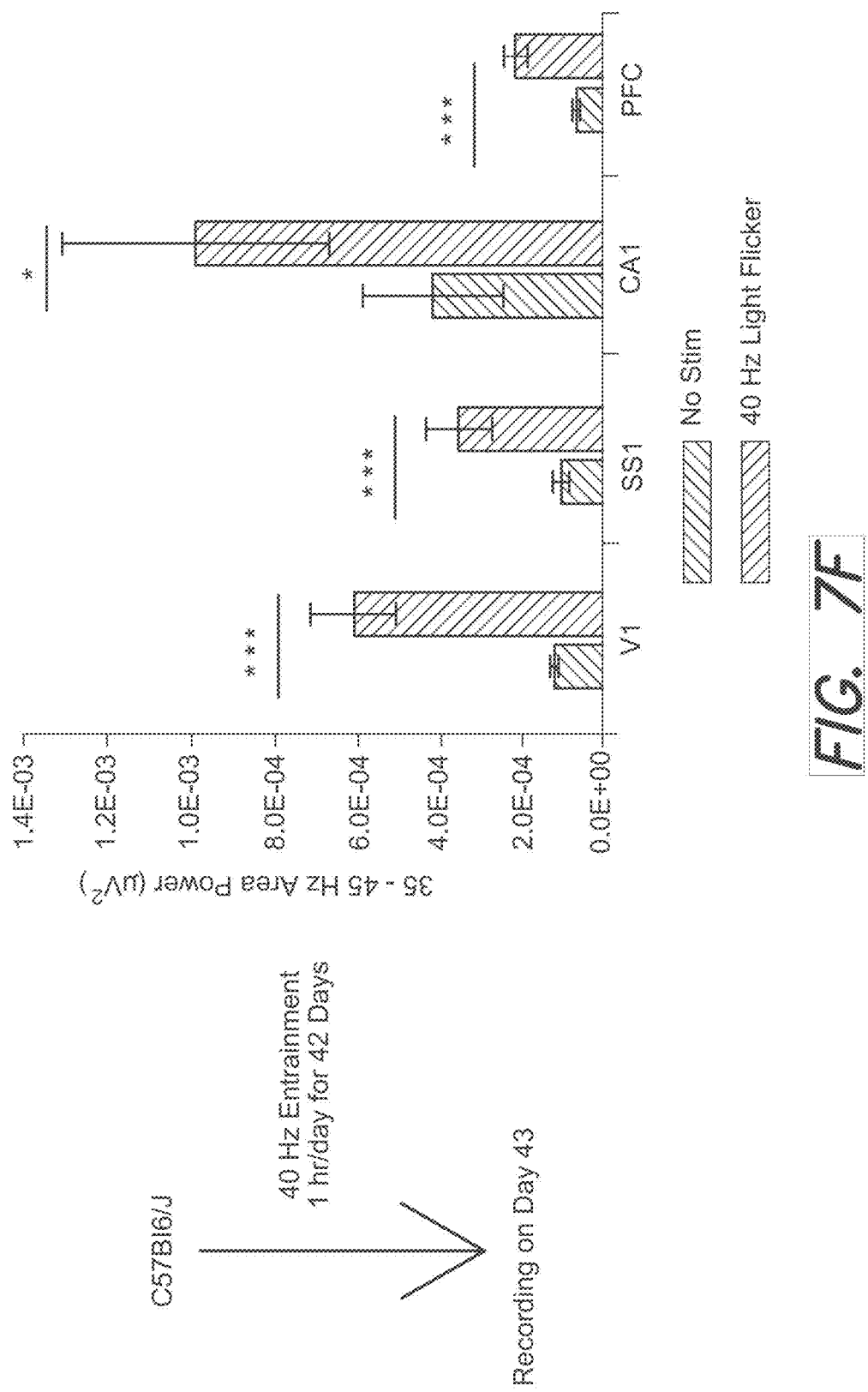
Figure 7G:
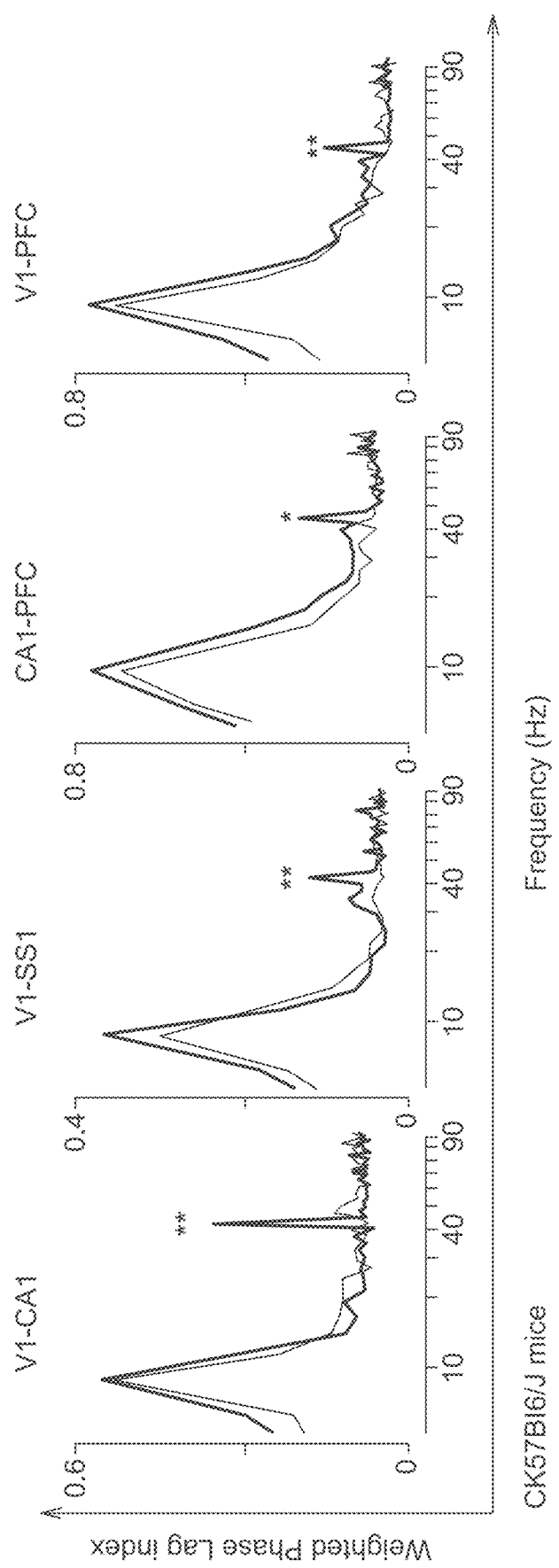
Figure 7H:
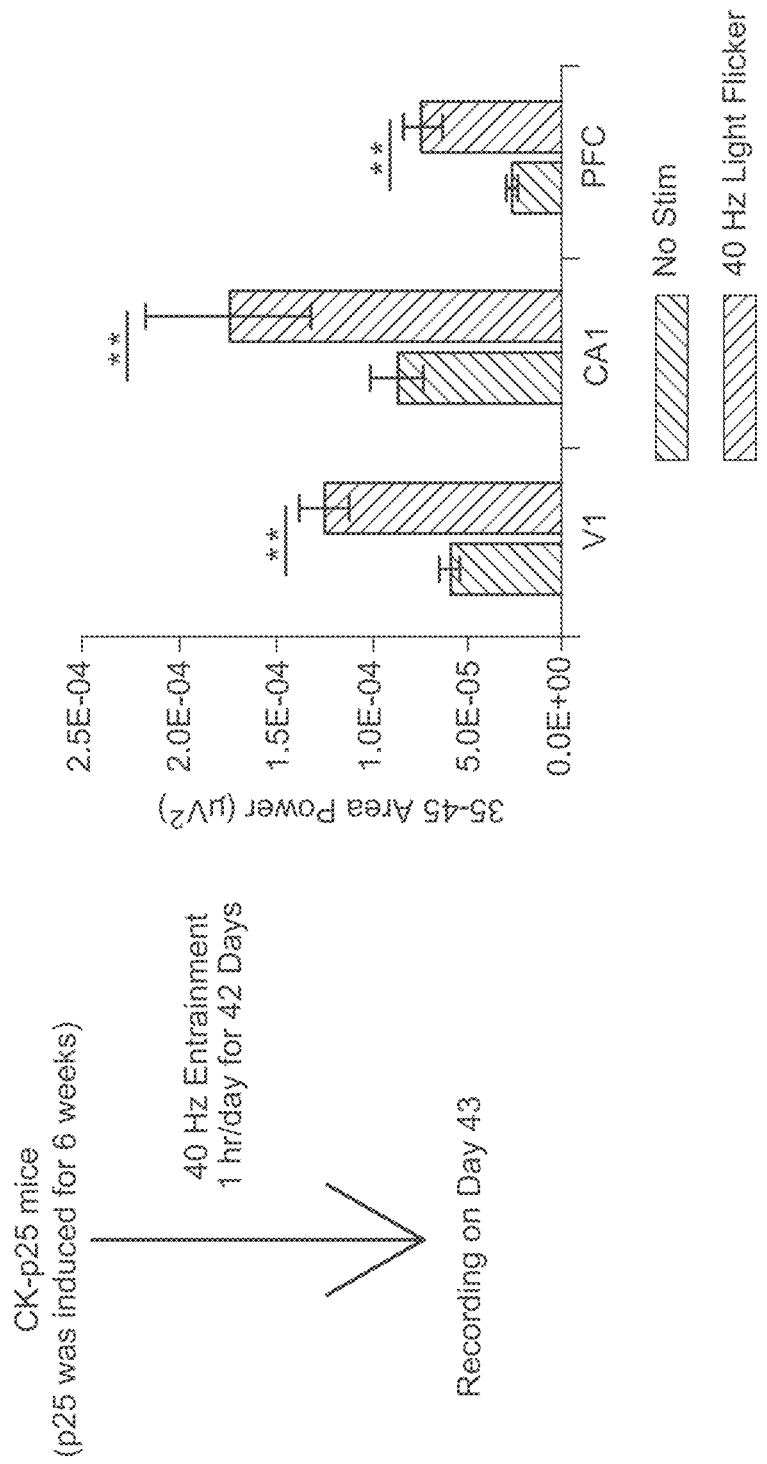
Figure 71:
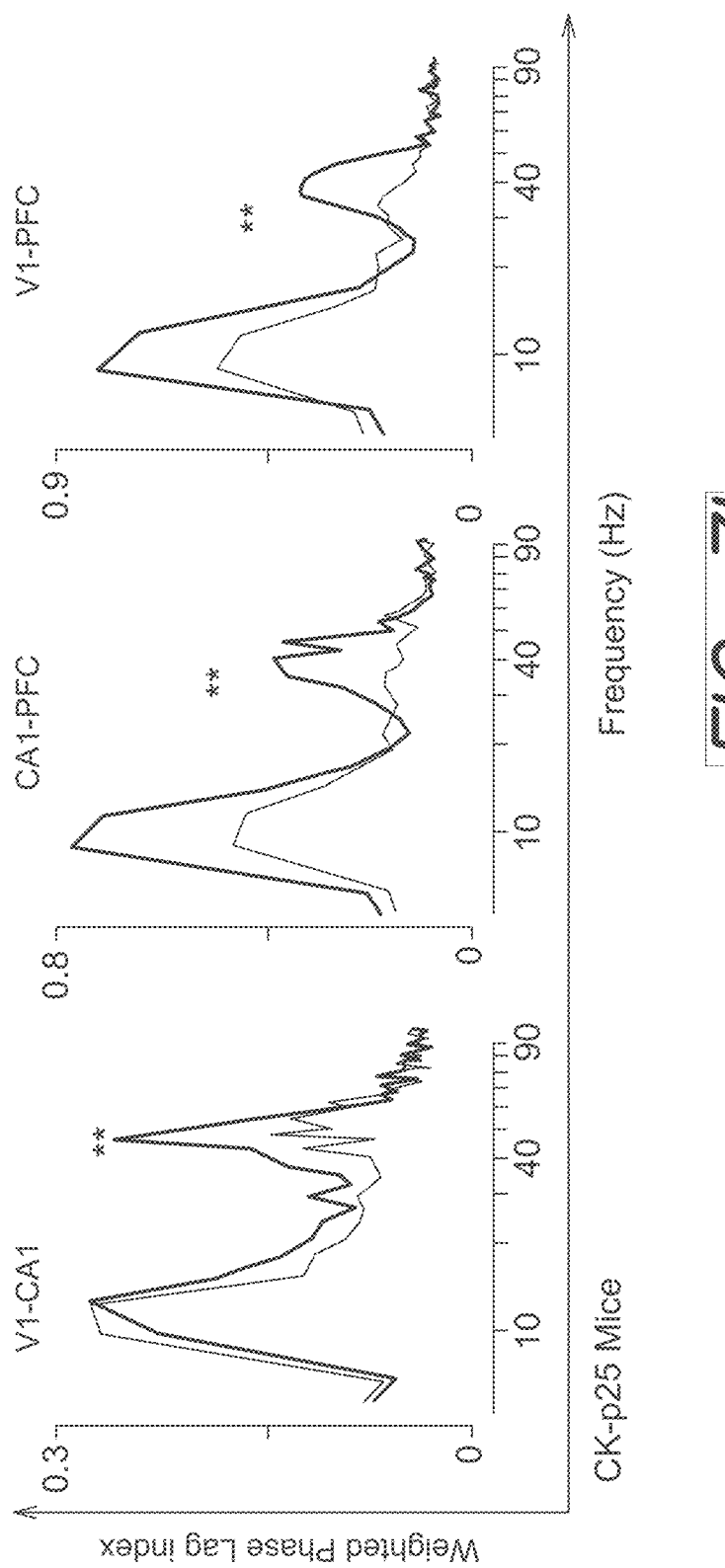

To ensure multiple exposures to the visual stimulation were still able to entrain gamma oscillations even after prolonged time periods, we employed a chronic GENUS protocol whereby C57B1/6J and p25-induced CK-p25 mice were exposed to 40 Hz visual stimulation for 42 days (1 h/day) (FIG. 7F, 7H). On day 43, LFPs recorded from V1, SS1, CA1, and PFC showed a significantly enhanced 40 Hz gamma power across all regions in the C57B1/6J mice, consistent with a single trial acute GENUS application (FIG. 7F). In a similar manner, CK-p25 mice on day 43 (now 85 days post-p25 induction) also resulted in increased low gamma power in V1, CA1, and PFC (FIG. 7H). These results, together with the c-Fos immunostaining data, indicate that both acute and chronic 40 Hz visual stimulation recruit not only visual cortex, but also other higher order cortices including CA1, SS1 and PFC.

Since 40 Hz visual stimulation (both acute and chronic) concurrently enhances 40 Hz power across V1, SS1, CA1, and PFC, we also demonstrated that GENUS acts to coordinate neuronal activity between the visual cortex and these other higher order brain structures. We calculated coherence across these brain regions during 40 Hz visual stimulation with and without the light occluded using the weighted phase lag index (WPLI) method, which minimizes potential contamination through volume conduction (Vinck et al., 2011). We analyzed LFP in C57B1/6J mice across electrode pairs located in V1-CA1, V1-SS1, V1-PFC, CA1-SS1 and CA1-PFC. Average velocity was not significantly different in periods during 40 Hz visual stimulation with versus without the light occluded, negating any potential differences in locomotor activity. Acute 40 Hz visual stimulation significantly increased 30-50 Hz low gamma coherence between visual cortex and other brain areas examined (compared with occluded light periods), specifically between V1-CA1, V1-SS1 & V1-PFC (FIG. 1G, 1H).

To assess the long-term impact of chronic GENUS on coordinated neuronal oscillations across wider brain structures, we applied WPLI analysis to the LFP collected from V1, SS1, CA1, and PFC in C57B1/6J and p25-induced CK-p25 mice that were exposed for 1 h/day to visual stimulation for 42 days. We observed a significant increase in 30-50 Hz low gamma WPLI between V1 and CA1 (FIG. 7G), as well as between V1-SS1, V1-PFC, and CA1-PFC during 40 Hz visual stimulation compared to light occluded conditions (FIG. 7G). Similarly, after chronic GENUS, CK-p25 mice also exhibited significant increase in 30-50 Hz low gamma WPLI between V1-CA1, CA1-PFC and V1-PFC compared to light occluded conditions (FIG. 7I). As a whole, these data suggest that 40 Hz visual stimulation enhances local (40 Hz entrainment) as well as coordinated inter-areal neural oscillatory activities (30-50 Hz low gamma WPLI) in multiple higher order cortices in mice. However, it is important to establish if the changes we observed are specific to low gamma frequency stimulation. To test this, we exposed C57B1/6J mice to 80 Hz visual stimulation, delivered with a 50% duty cycle to ensure mice received a similar light intensity and duration of exposure as in our 40 Hz stimulation experiments (FIG. 1I). We observed no significant changes in 80 Hz spectral power in visual cortex (where we observed the biggest increase in power with 40 Hz GENUS) during 80 Hz visual stimulation compared to pre-stimulation period (FIG. 1I, 1J).

Chronic GENUS Ameliorates Amyloid Plaques Beyond the Visual Cortex

Figure 1I:
Figure 1J:
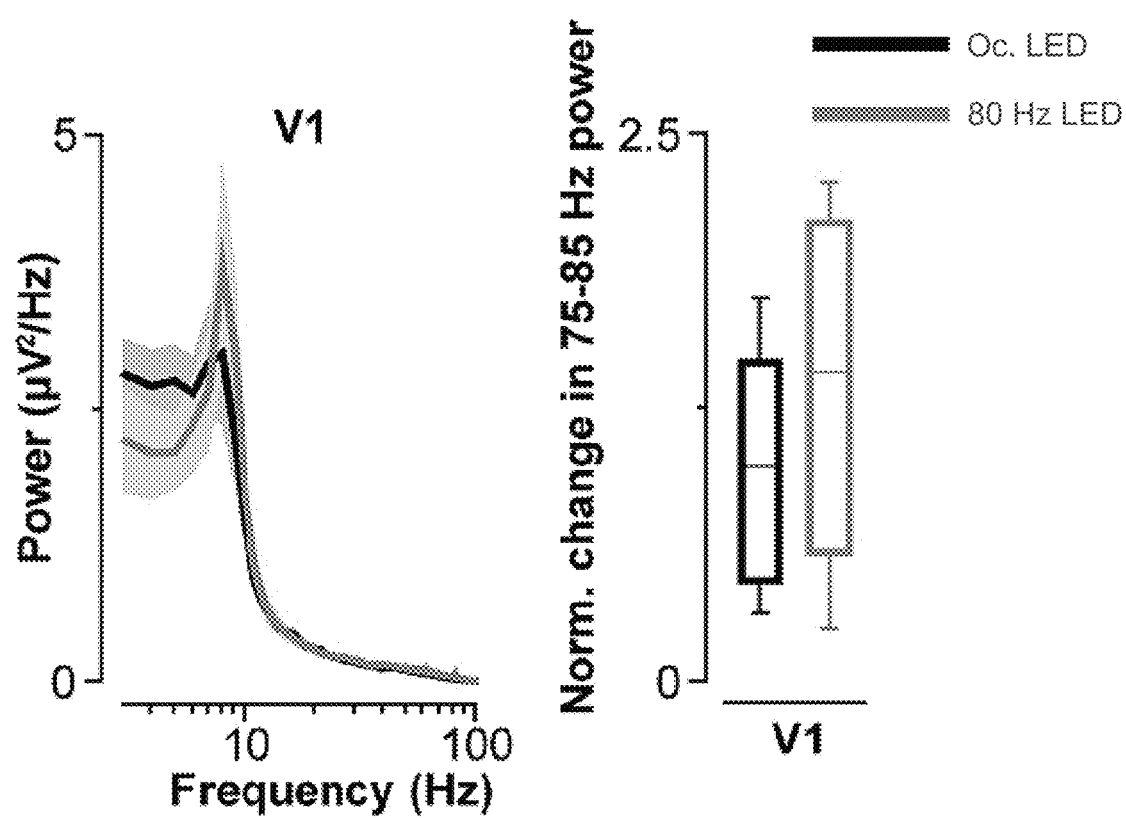
Figure 2A:
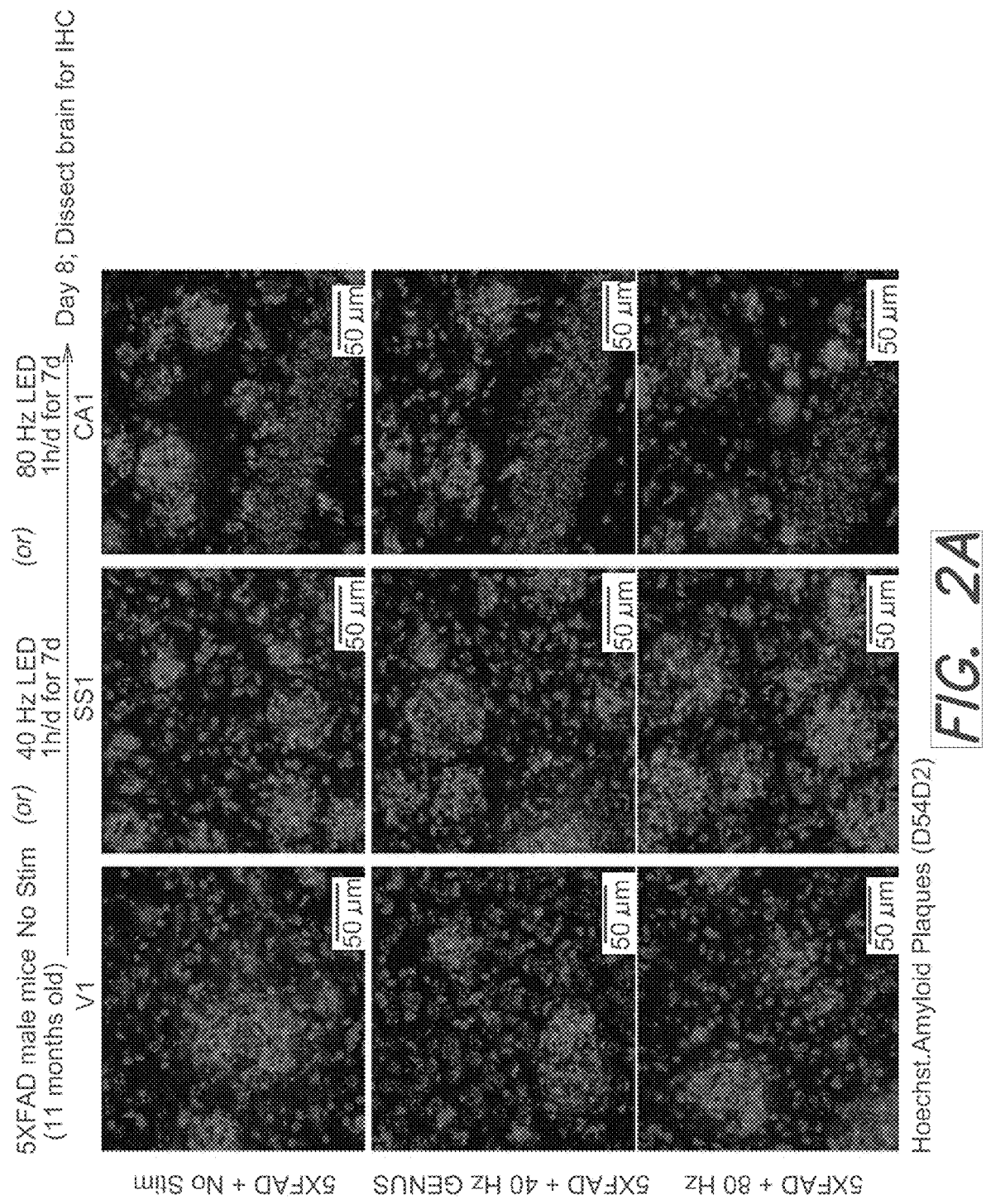
FIGS. 2A through 2F illustrate that chronic 40 Hz (but not 80 Hz) visual flicker stimulation reduces amyloid plaques beyond visual cortex in the subject, according to the inventive concepts disclosed.
Figure 2B:
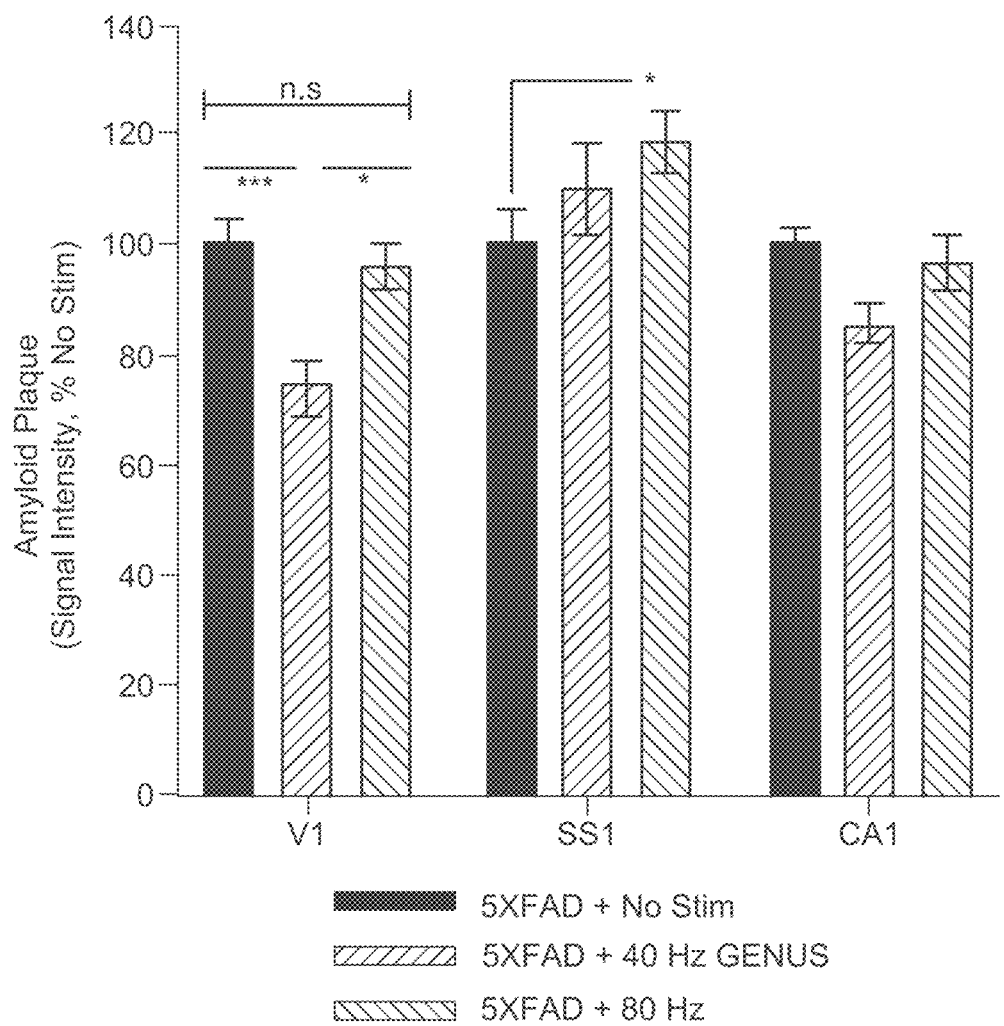

Iaccarino et al. (2016) demonstrated that acute visual GENUS reduced amyloid levels in V1 in young pre-symptomatic 5XFAD mice, whereas 7 days of visual GENUS not only reduced amyloid levels, but also ameliorated amyloid plaques in 6-month old 5XFAD mice with more advanced pathology. We thus aimed to investigate whether 7 days of 40 Hz visual stimulation could affect amyloid plaque pathology in V1—but also CA1, SS1, and PFC—in 11-month old 5XFAD mice. Toward this aim, we introduced the mice into GENUS stimulation cages (FIG. 8A), subjected them to either 40 Hz or 80 Hz visual stimulation (which deliver a similar amount of light as 40 Hz but did not entrain gamma oscillations in V1 (FIG. 1I, 1J), for 1 h/day for 7 days and examined amyloid plaque load (FIG. 2A). After 7 days of 40 Hz visual stimulation, we saw reductions of amyloid plaques in visual cortex (FIG. 2A, 2B), but no differences observed in neither SS1 nor CA1 compared to non-stimulated mice (FIG. 2A, 2B). In agreement with the LFP analysis, 5XFAD mice with 80 Hz visual stimulation showed no change in amyloid plaque load in neither V1 nor CA1, and a modest increase in SS1 (FIG. 2A, 2B). These results show that reduction of amyloid plaques after 7 days of visual GENUS is restricted to V1 and is specific to 40 Hz visual stimulation.

Figure 2C:
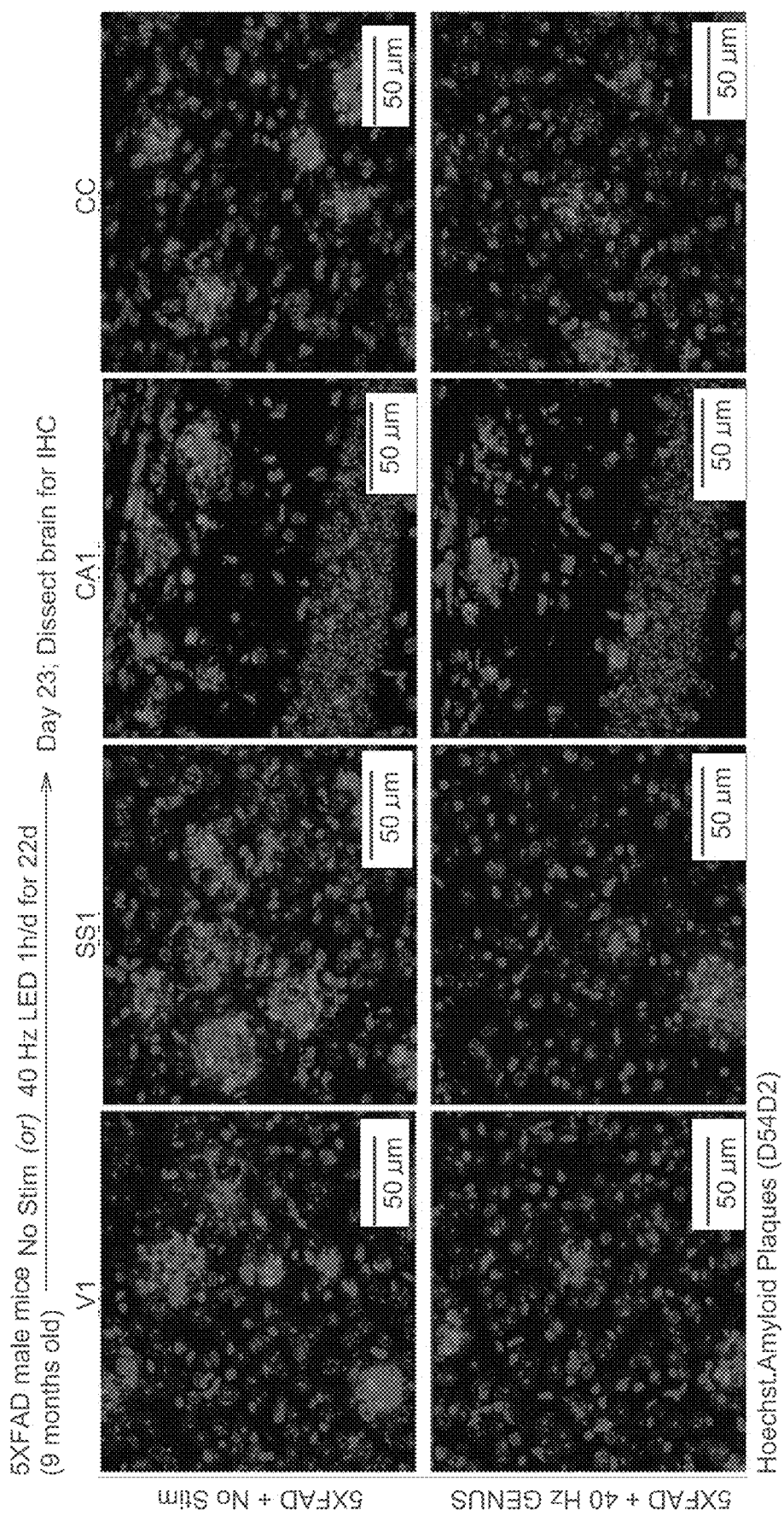

We next extended the GENUS protocol to 22 days, starting with 5XFAD mice at 9 months old, and quantified amyloid plaques when the mice were around 10 months old (FIG. 2C). We found that 22 days of GENUS significantly decreased the intensity and number of amyloid plaques in V1 (FIG. 2C, 2D, and FIG. 8B-8D), consistent with the reduction of amyloid plaques following 7 days of GENUS in 6-month old 5XFAD (Iaccarino et al., 2016) and in 11-month old 5XFAD mice (FIG. 2A, 2B). Importantly, 22 days of GENUS was sufficient to also reduce plaque intensity and number in SS1, CA1, and CC area of prefrontal cortex (FIG. 2D, FIG. 8B-8D). This effect was again specific to 40 Hz stimulation, as 22 days of 80 Hz stimulation did not alter amyloid plaques in V1, SS1, nor CA1 in the 5XFAD mice when compared with non-stimulated 5XFAD mice (FIG. 2E, 2F).

We chose to apply long-term GENUS starting at 9 months of age in 5XFAD mice as previous studies have shown that the progressive loss of neurons and synaptic markers begins around 9-months of age in the 5XFAD model (Oakley et al., 2006). Consistent with these studies, we observed significant reductions in neuronal counts in both CA1 and CC in 10-month old 5XFAD mice, compared with age-matched wild-types littermates (FIG. 8C, 8E). In contrast, 5XFAD mice receiving 22 days of GENUS, in addition to a reduced amyloid load (FIG. 2C, 2D and FIG. 8B-8D), showed significantly reduced neuronal loss compared with non-stimulated mice (FIG. 8E). Similarly, while we observed a significant loss of bassoon (a synaptic marker protein) puncta in CA1 and CC in non-stimulated 5XFAD mice, chronic GENUS for 22 days reduced synaptic loss (FIG. 8F, 8G). The reduced neurodegeneration and amyloid pathology after chronic GENUS was not the result of altered APP transgene expression, as we detected no difference in the expression of full length APP protein in mice that received GENUS versus non-stimulated controls (FIG. 8H, 8I). These results demonstrate that chronic visual GENUS leads to a reduction of amyloid plaque load, and reduced loss of neurons and synapses, in multiple brain regions in 5XFAD mice.

Chronic GENUS Reduces Neurodegeneration

Figure 3C:
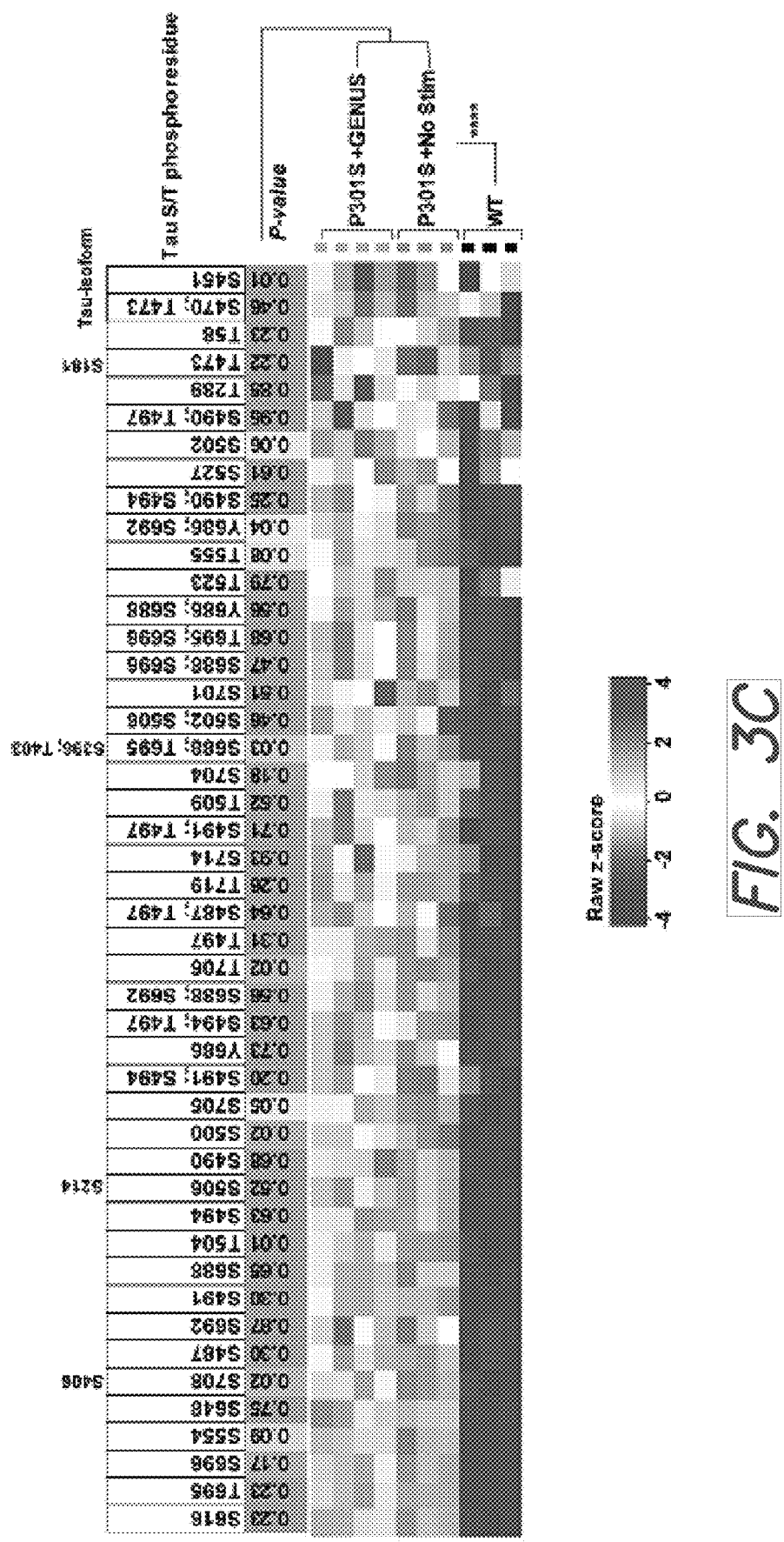

To further explore the potential for chronic GENUS in impacting disease pathology and reducing neuronal loss, as seen in the 5XFAD mice (FIG. 8C, 8E), we next examined Tau P301S and CK-p25 mouse models of neurodegeneration. At 8 months of age, Tau P301S mice exhibit marked neuropathologies (Yoshiyama et al., 2007). We therefore took a cohort of Tau P301S mice, and subjected them to either no stimulation or GENUS 1 h/day for 22 days starting at 7 months old and examined their tau phosphorylation levels and tau associated pathology at around 8 months of age (FIG. 3A-3E, and FIG. 9A, 9B). We observed higher phosphorylation of tau at S202/T205 residues in V1, SS1, CA1 and CC in Tau P301S mice compared with wild-type naïve littermates (WT naïve) (FIG. 3A, 3B). However, Tau P301S mice receiving chronic GENUS had significantly reduced S202/T205 tau phosphorylation compared to non-stimulated P301S mice (FIG. 3A, 3B). In both AD and in P301S mice, tau protein becomes hyper-phosphorylated at multiple residues (Hanger yet al., 2007; Wang et al., 2013; Foidl and Humpel, 2018; Kimura et al., 2018), and therefore utilized a non-biased Ser/Thr (S/T) phosphoproteomics approach to examine the extent to which GENUS stimulation can influence tau phosphorylation. We identified 46 S/T residues that were hyper-phosphorylated and a single residue (S451) that was dephosphorylated in Tau P301S mice compared to WT naïve littermates (FIG. 3C). Our analysis also revealed that chronic GENUS reduced phosphorylation in the tau protein at 6 S/T sites and increased phosphorylation at S451, indicating that GENUS impacts tau phosphorylation on multiple sites (FIG. 3C).

Figure 3D:
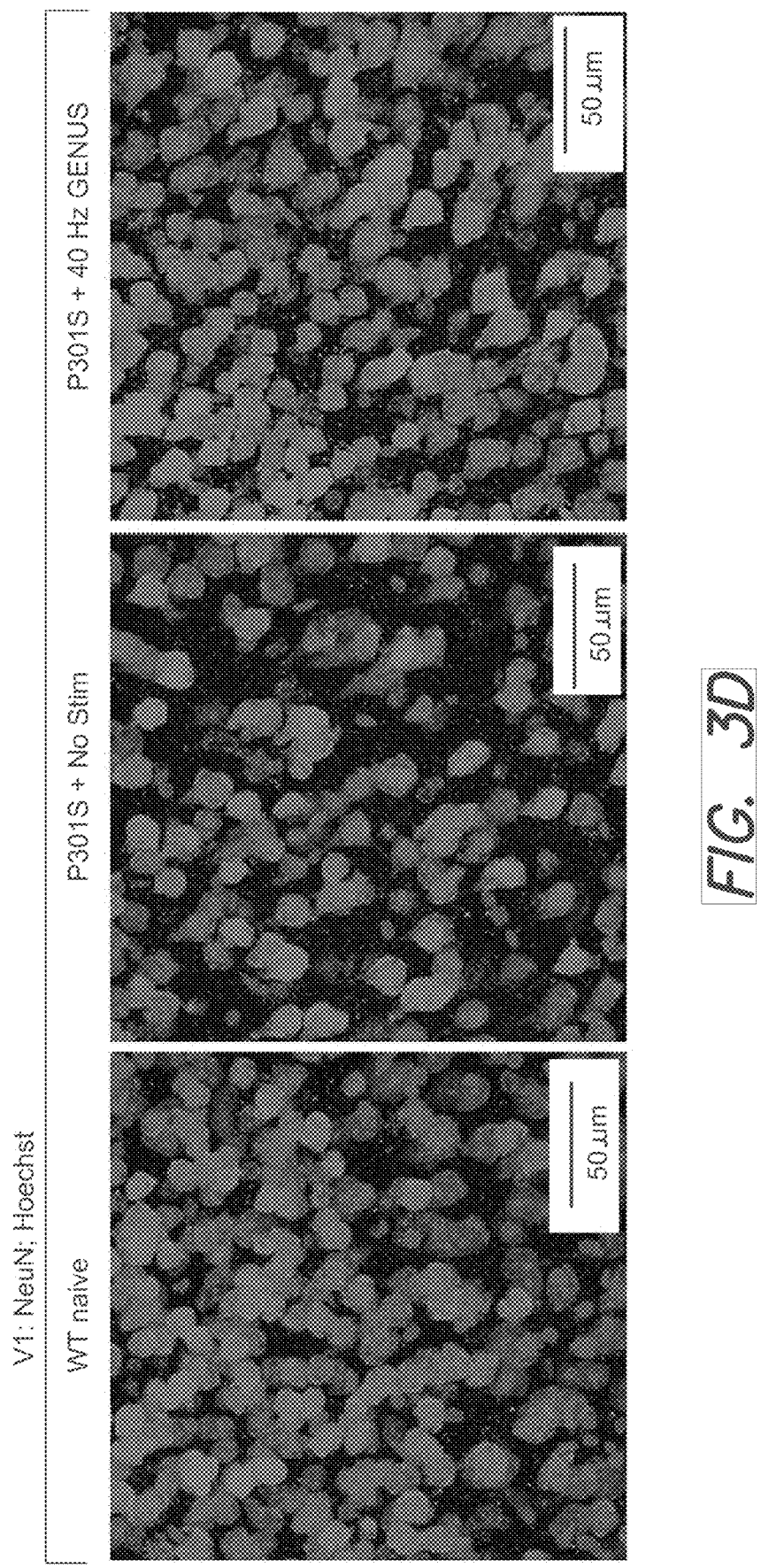
Figure 3E:
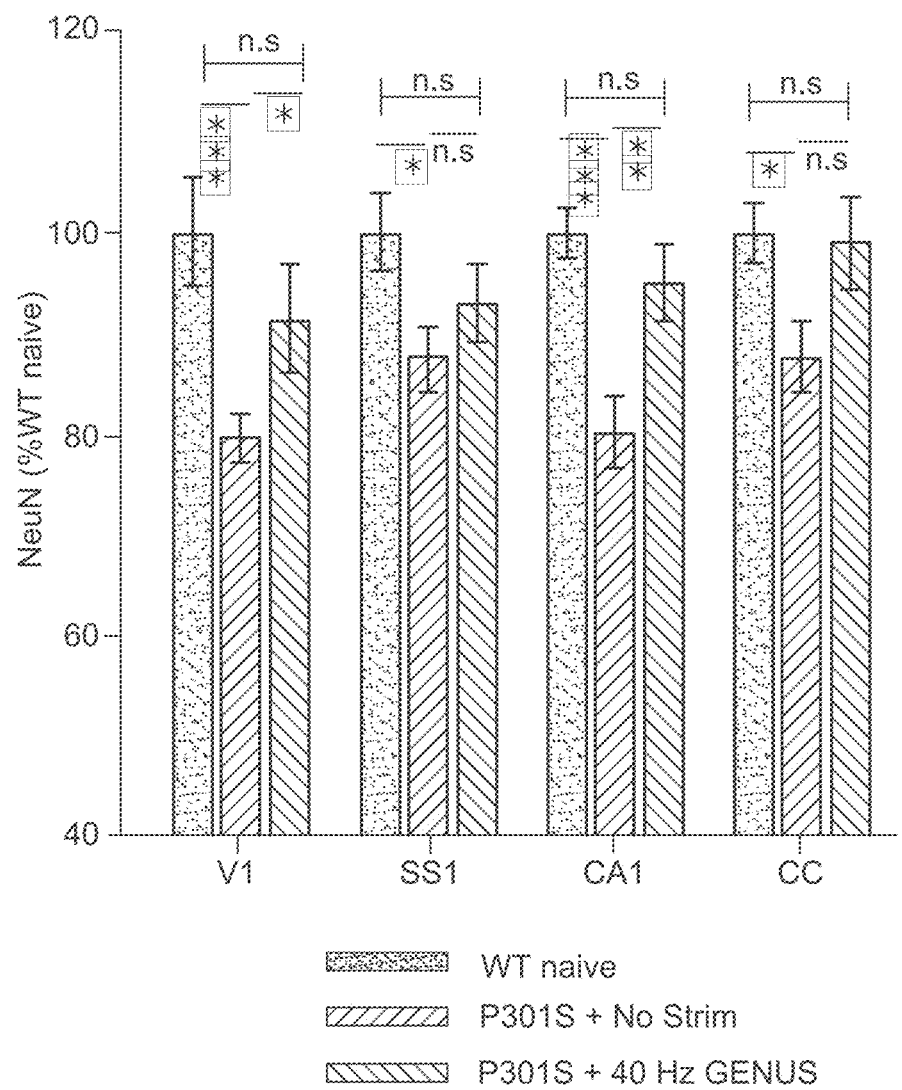

We next characterized neuronal loss in the Tau P301S mice, and as previously reported, they displayed a significant reduction in neuron numbers in V1, CA1, SS1, and CC as quantified by the number of NeuN positive cells (FIG. 3D, 3E). Tau P301S mice that received GENUS from 7-months of age (the time point when neuronal loss begins) for 22 days, showed significantly reduced neuronal loss in all brain areas we examined compared to non-stimulated controls (FIG. 3D, 3E). We next examined brain weight and lateral ventricle size and observed no difference between WT non-stimulated and GENUS stimulated P301S mice (FIG. 9B).

Figure 3F:
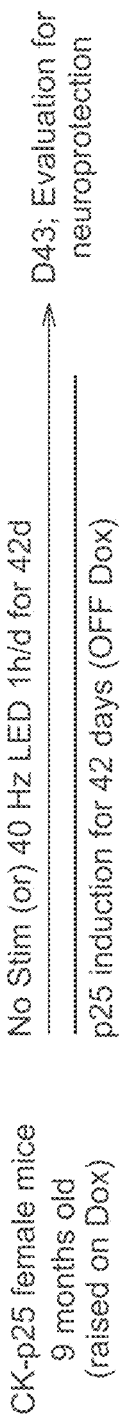
Figure 3G:
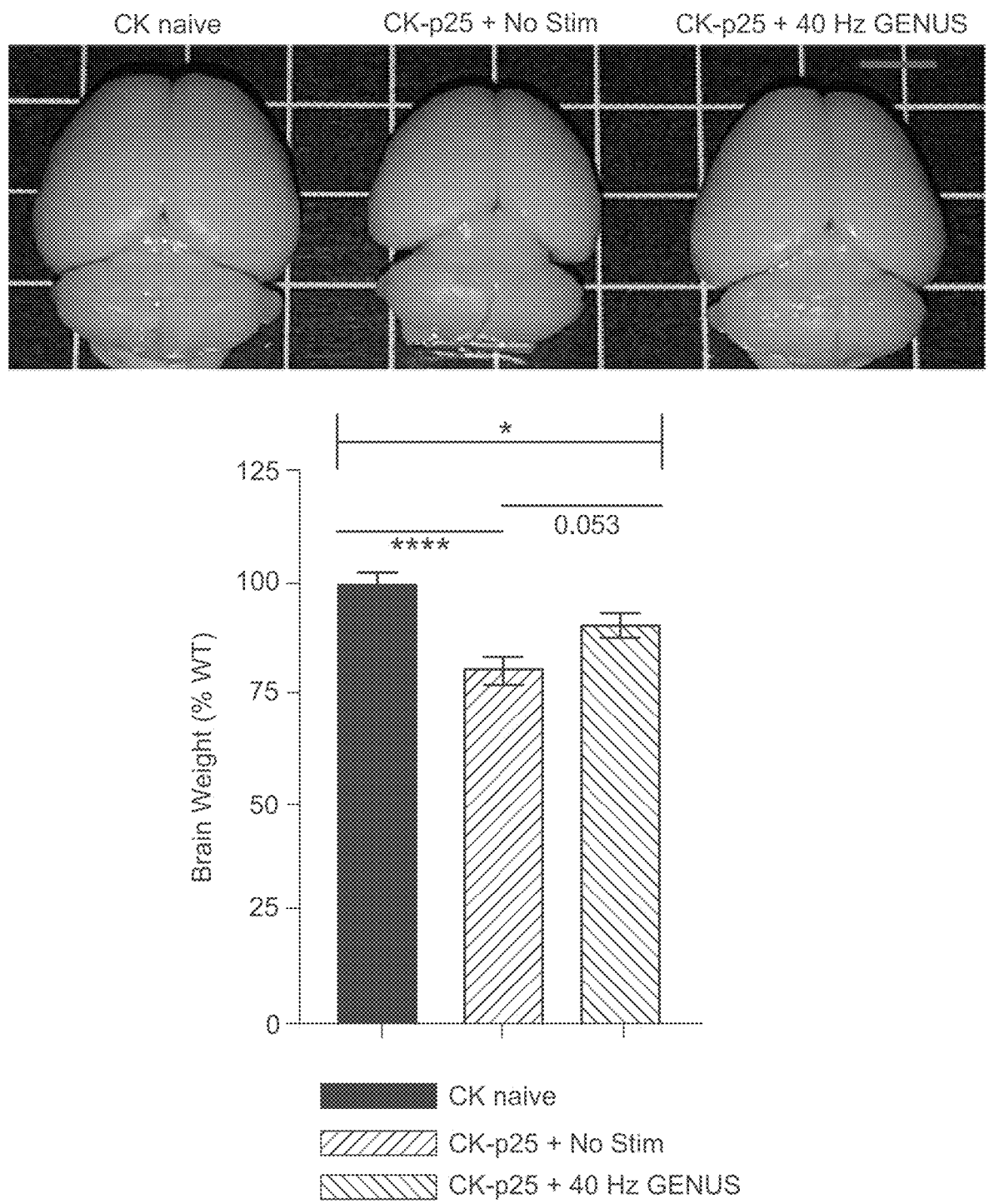
Figure 3H:
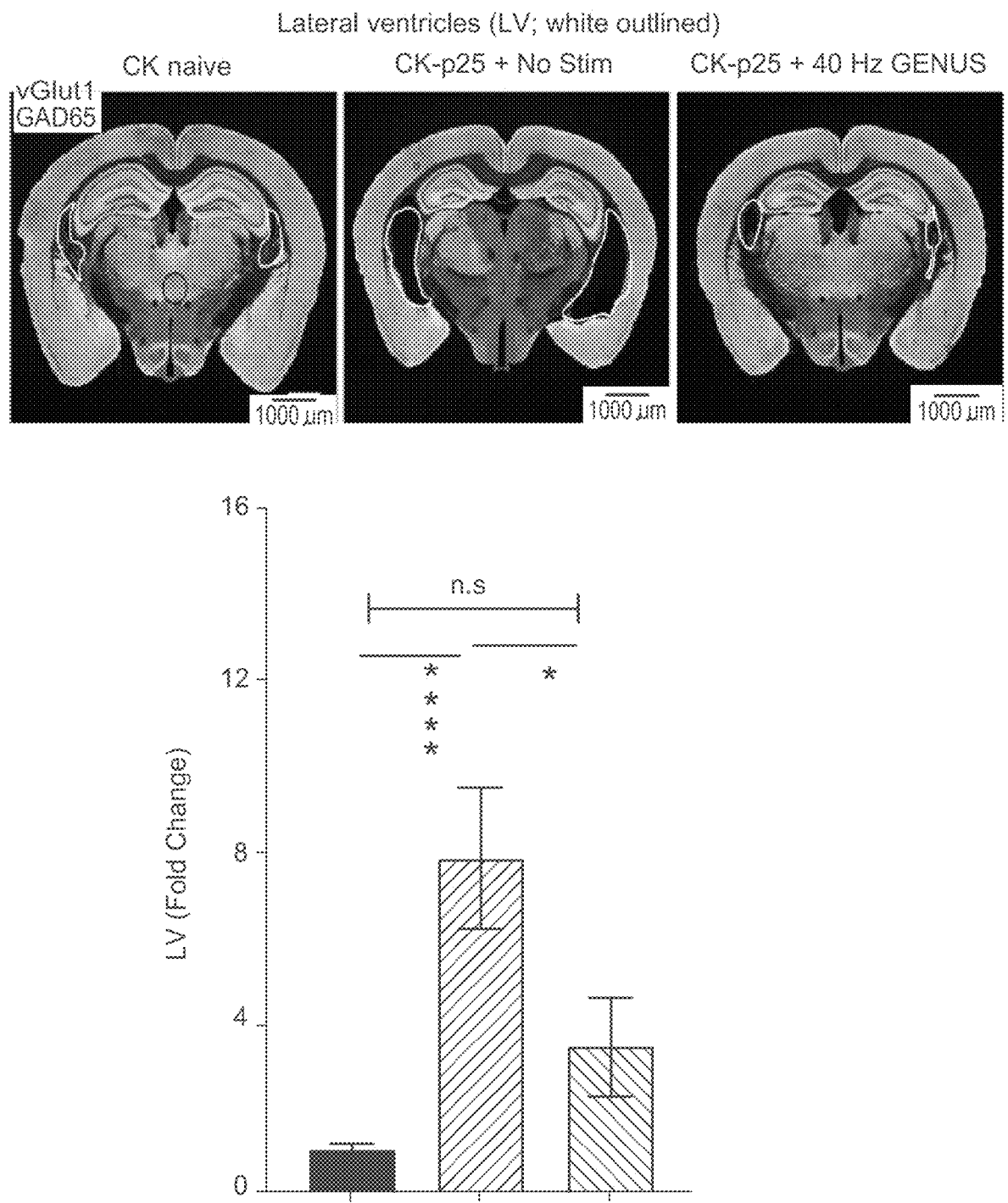
Figure 3I:
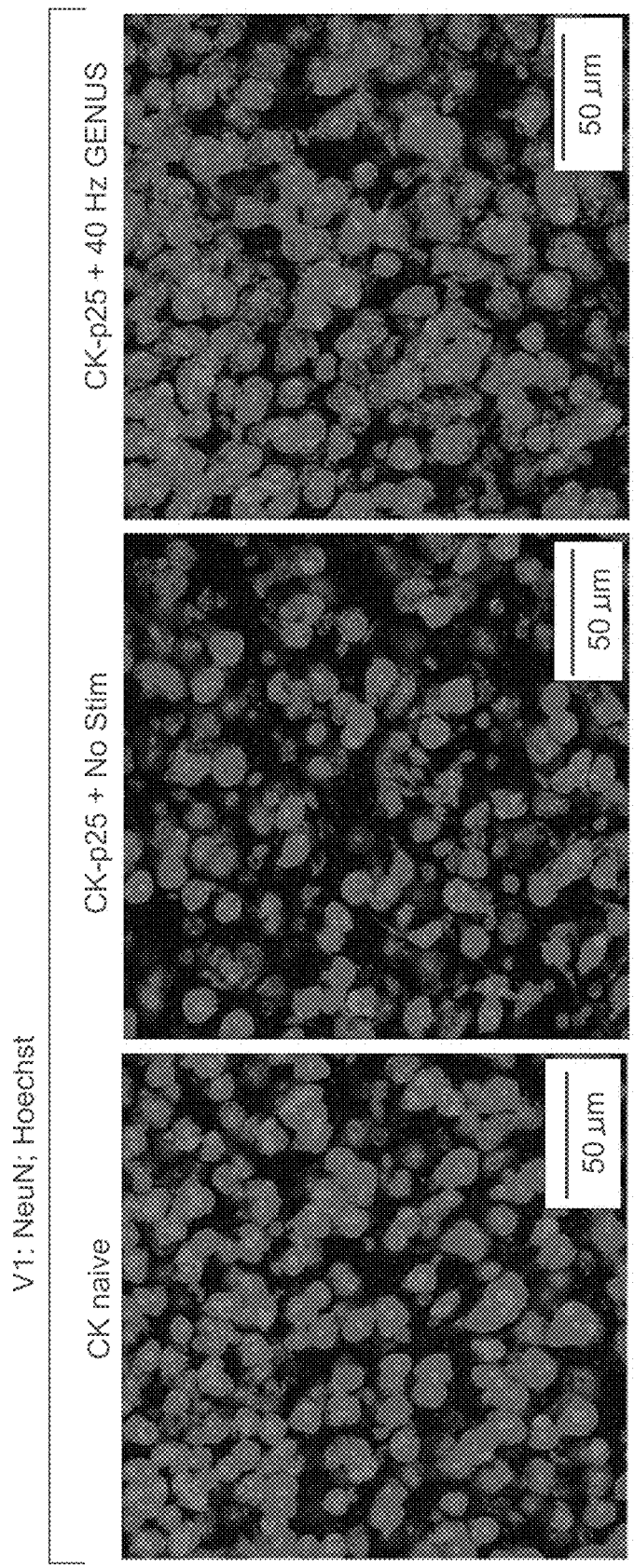
Figure 3J:
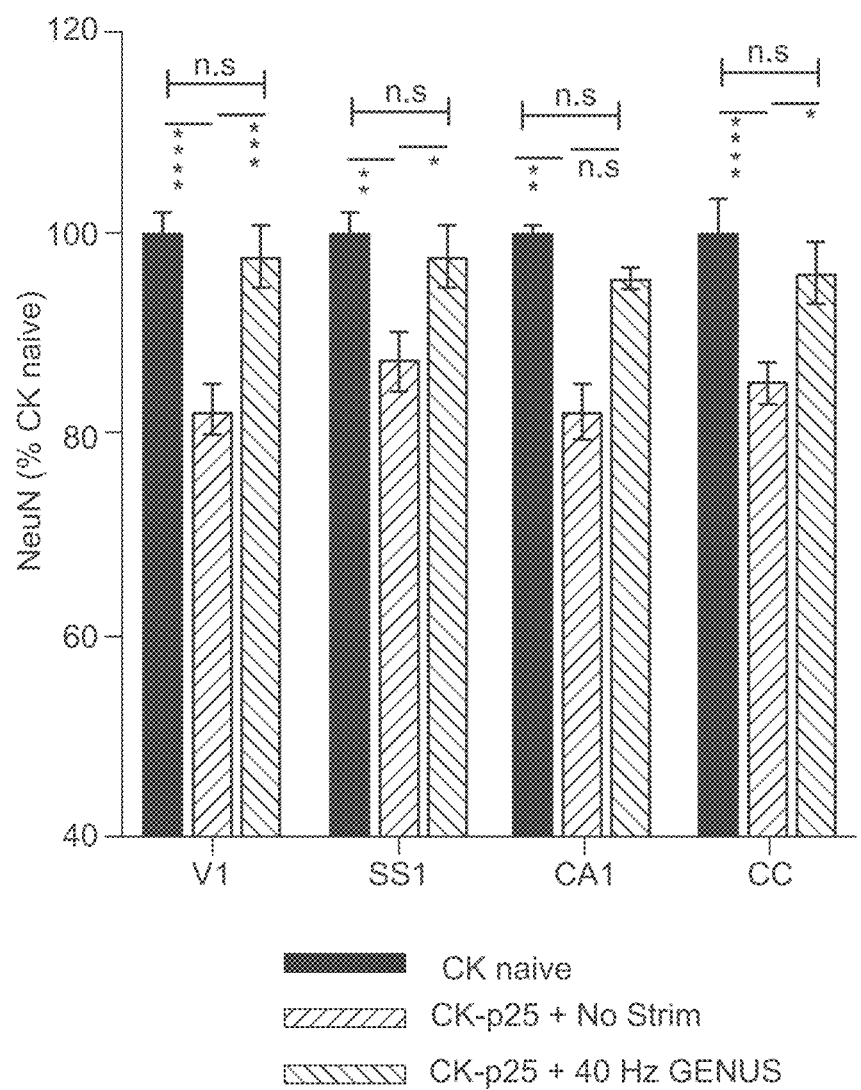
Figure 9D:
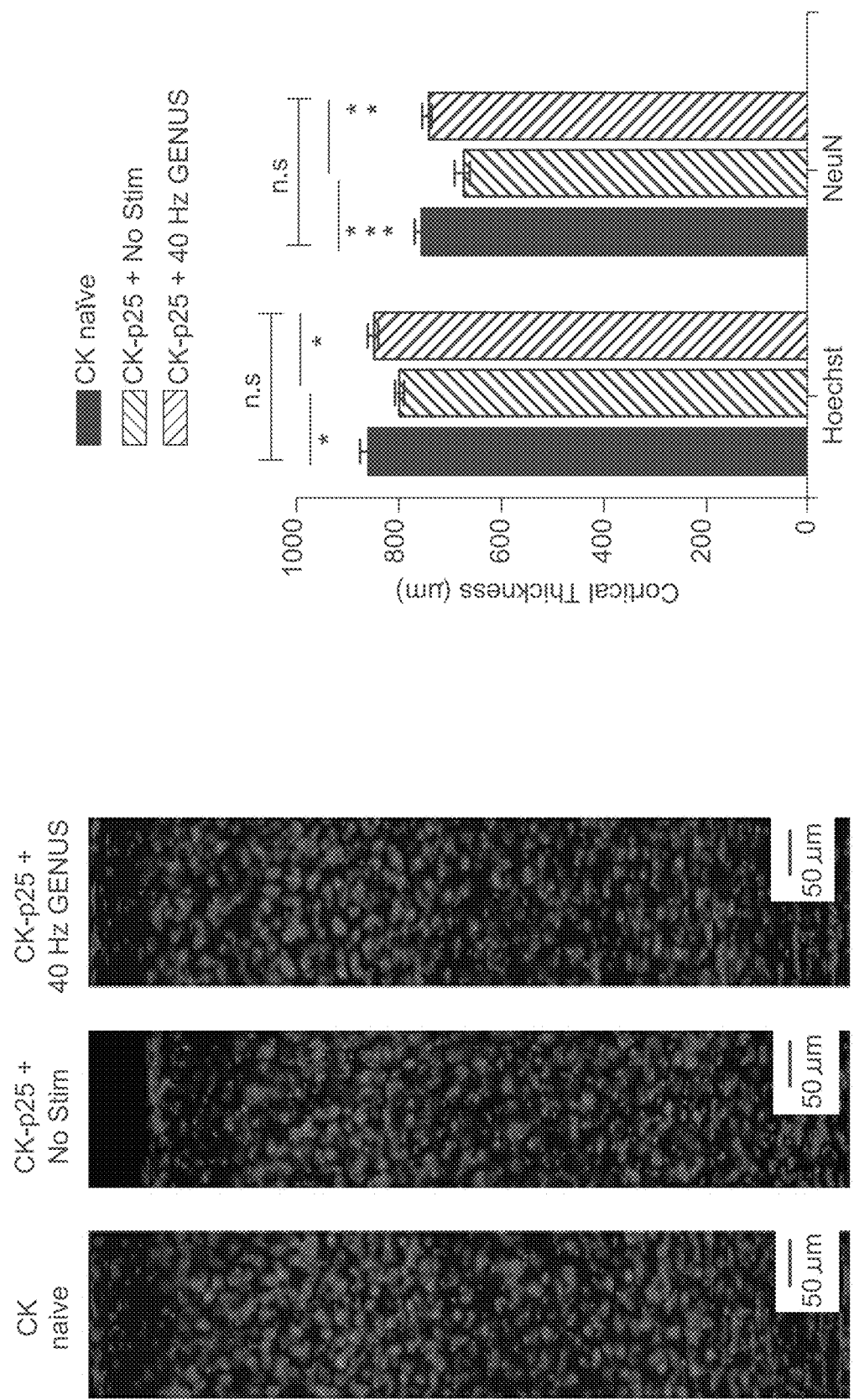
Figure 9E:
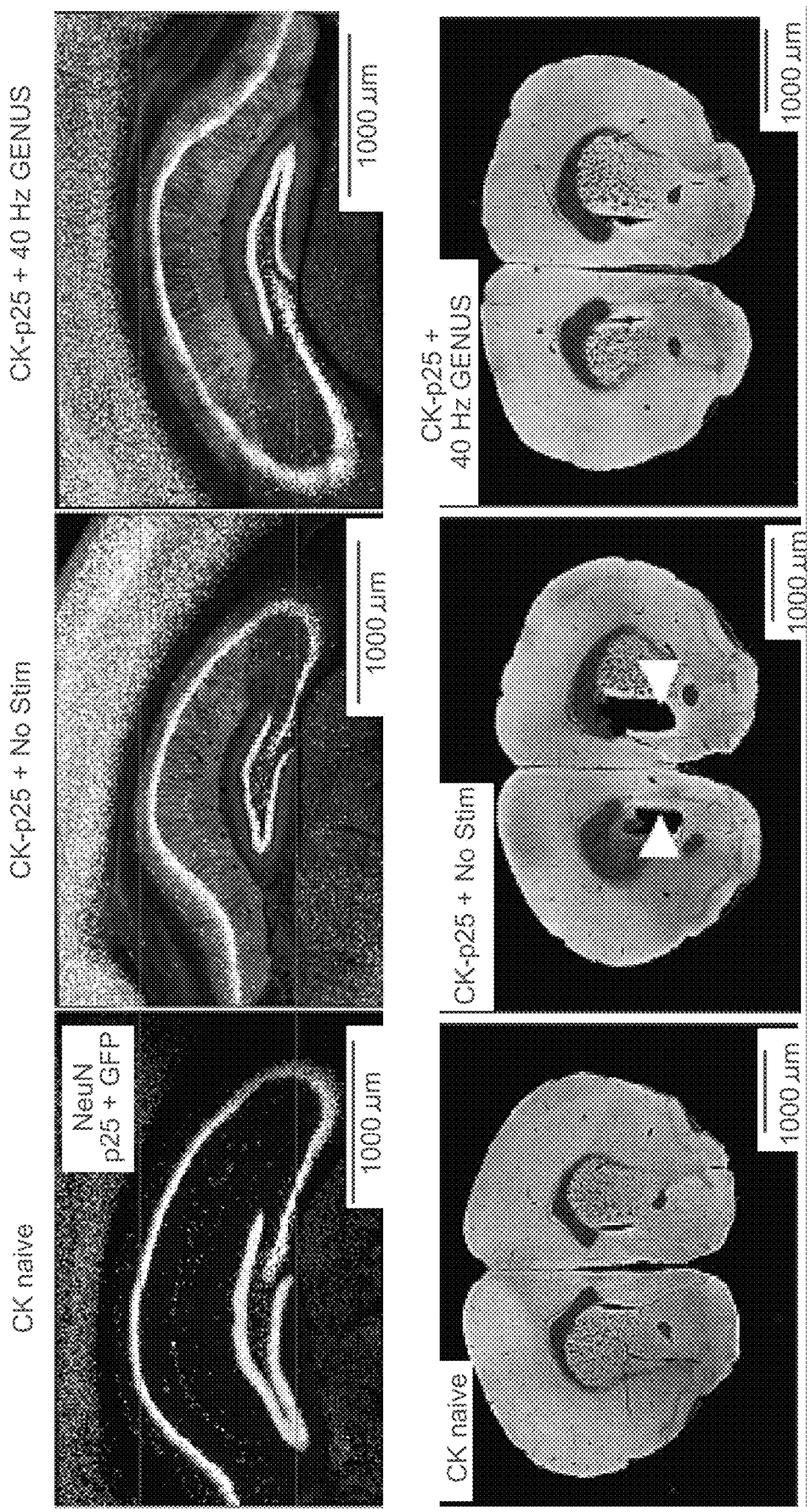
Figure 9F:
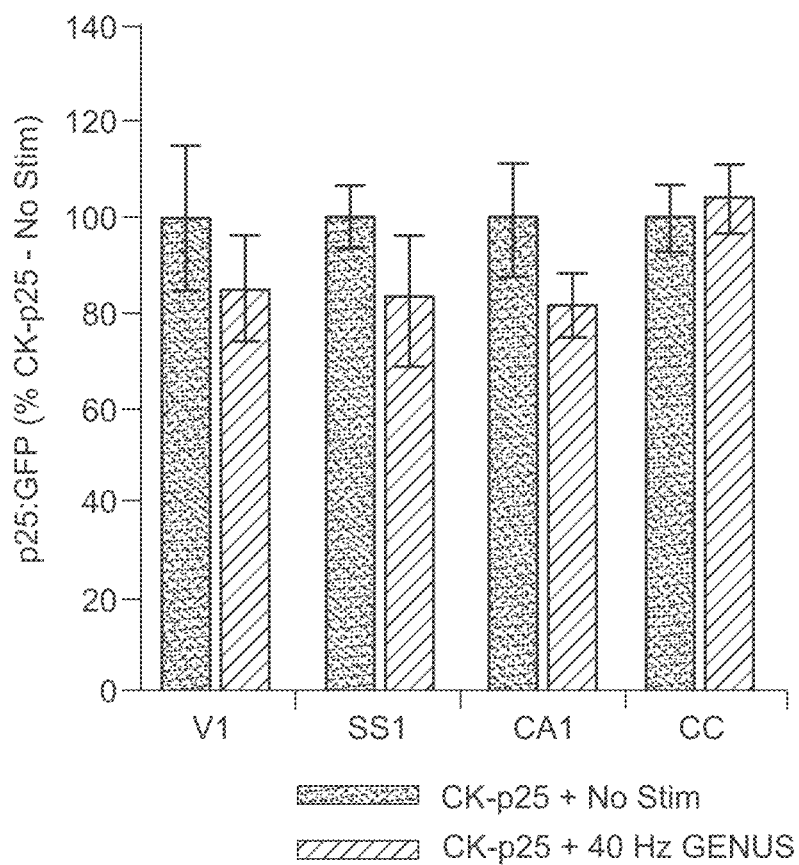

We next turned to the CK-p25 model as they show AD-like pathological features, such as brain atrophy, cortical shrinkage, and aberrant ventricle expansion following 6 weeks of p25 induction (Cruz et al., 2003). To examine the extent to which chronic GENUS might ameliorate these abnormalities we simultaneously induced p25 in CK-p25 mice for 6 weeks whilst also exposing them daily to 1 h of GENUS (FIG. 3F). Non-stimulated CK-p25 mice showed significantly reduced brain weight and cortical thickness compared to CK naïve littermates (CaMKIIα promoter-tTA; Cruz et al., 2003) (FIG. 3G). Chronic GENUS during p25 induction significantly reduced cortical thinning but did not significantly alter brain weight compared to non-stimulated CK-p25 mice (FIG. 3G, and FIG. 9D). In both human AD and the CK-p25 transgenic model, cortical shrinkage is tightly correlated with ventricle expansion (Cruz et al., 2003), and we also observed a profound reduction in ventricle expansion in CK-p25 mice that received chronic GENUS (FIG. 3H, and FIG. 9E). Moreover, CK-p25 mice with chronic GENUS during p25 induction also had significantly less neuronal loss in V1, SS1, CA1, and CC area of the PFC compared with non-stimulated controls (FIG. 3I, 3J). It has been previously reported that DNA damage in the form of double strand breaks (DSBs) represent an early marker for neurodegeneration in the CK-p25 mice (Kim et al., 2008). In agreement with both this finding and our GENUS-mediated reductions in neuronal death, we also observed significantly reduced DSBs as analyzed by the number of γH2AX-positive cells, a well-established marker of DSBs, in V1, SS1, and CA1 (FIG. 9G). These neuroprotective effects of chronic GENUS were not induced by altering transgene expressions in the mutants, since total tau and p25 expression (in P301S and CK-p25 mice, respectively) was not different between GENUS and non-stimulated groups (FIG. 9A, 9C, 9F). Together, these observations establish that chronic GENUS is neuroprotective in P301S and CK-p25 mouse models with severe neurodegeneration.

Chronic GENUS Reduces Inflammatory Response

Figure 4A:
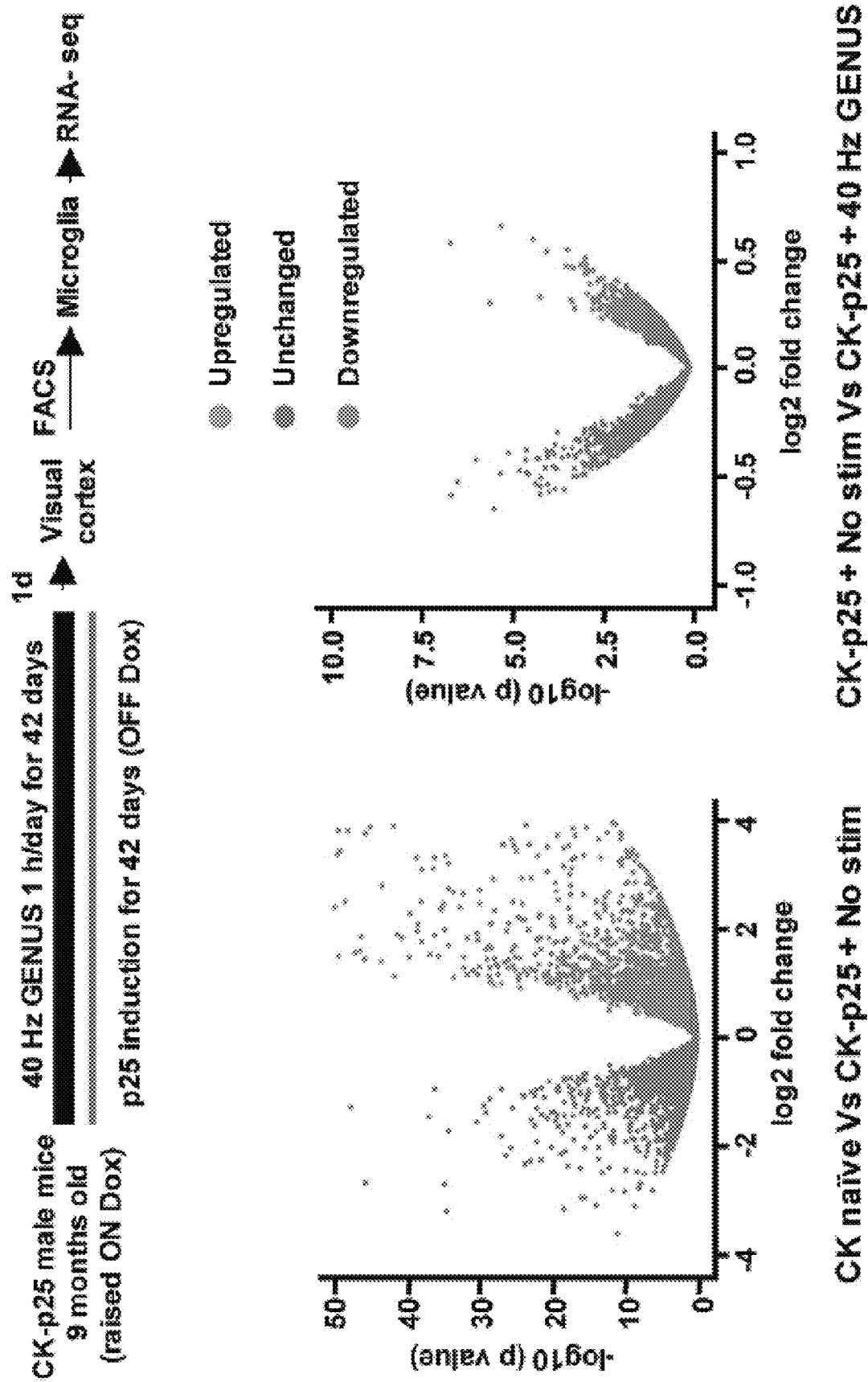
FIGS. 4A through 4Q illustrate that chronic visual stimulation reduces inflammatory response in microglia of a subject, according to the inventive concepts disclosed.
Figure 10A:
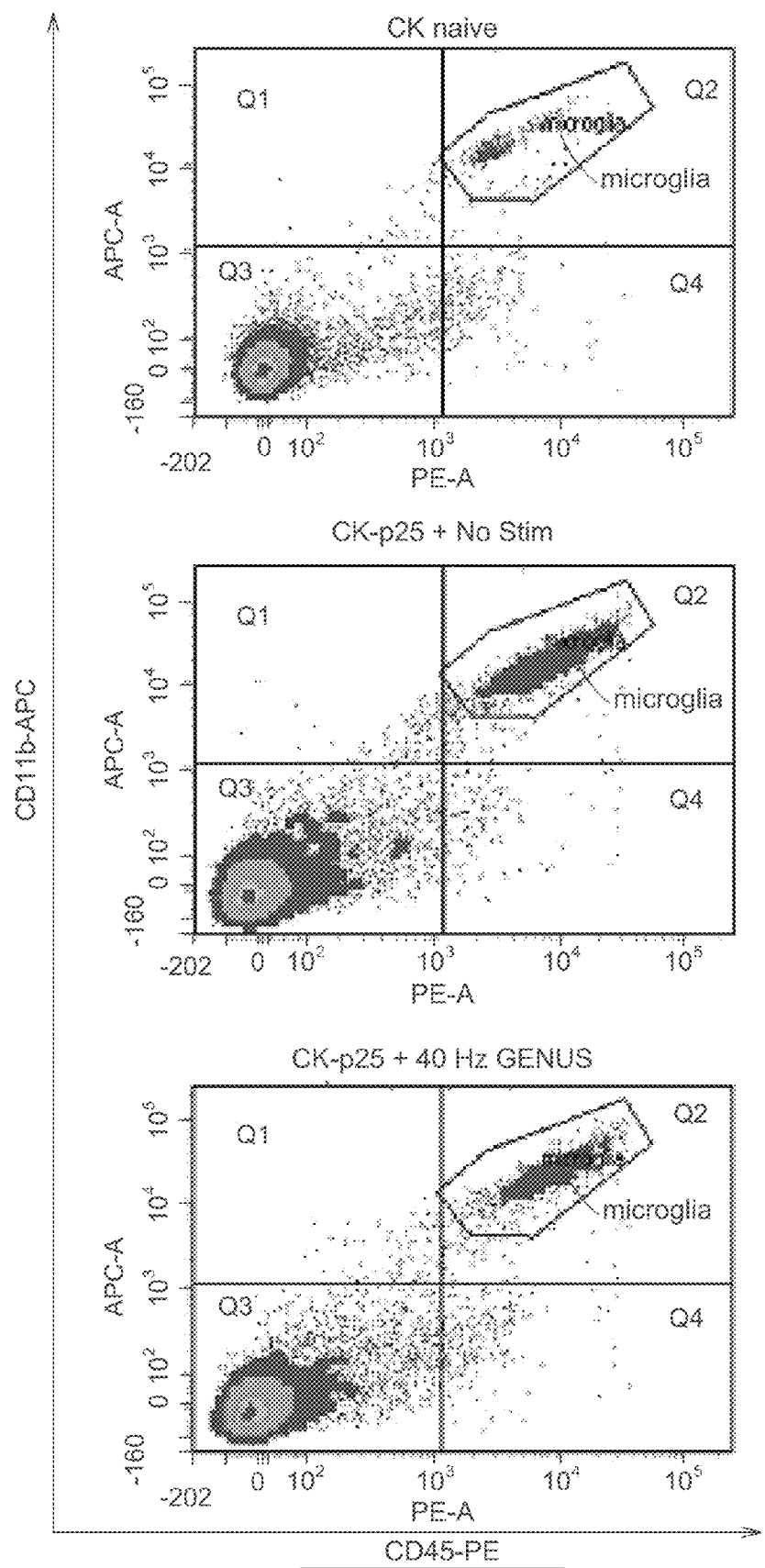
FIGS. 10A through 10N illustrate that chronic visual stimulation modifies microglia, improves intracellular transport and synaptic transmission in neurons, according to the inventive concepts disclosed.
Figure 10B:
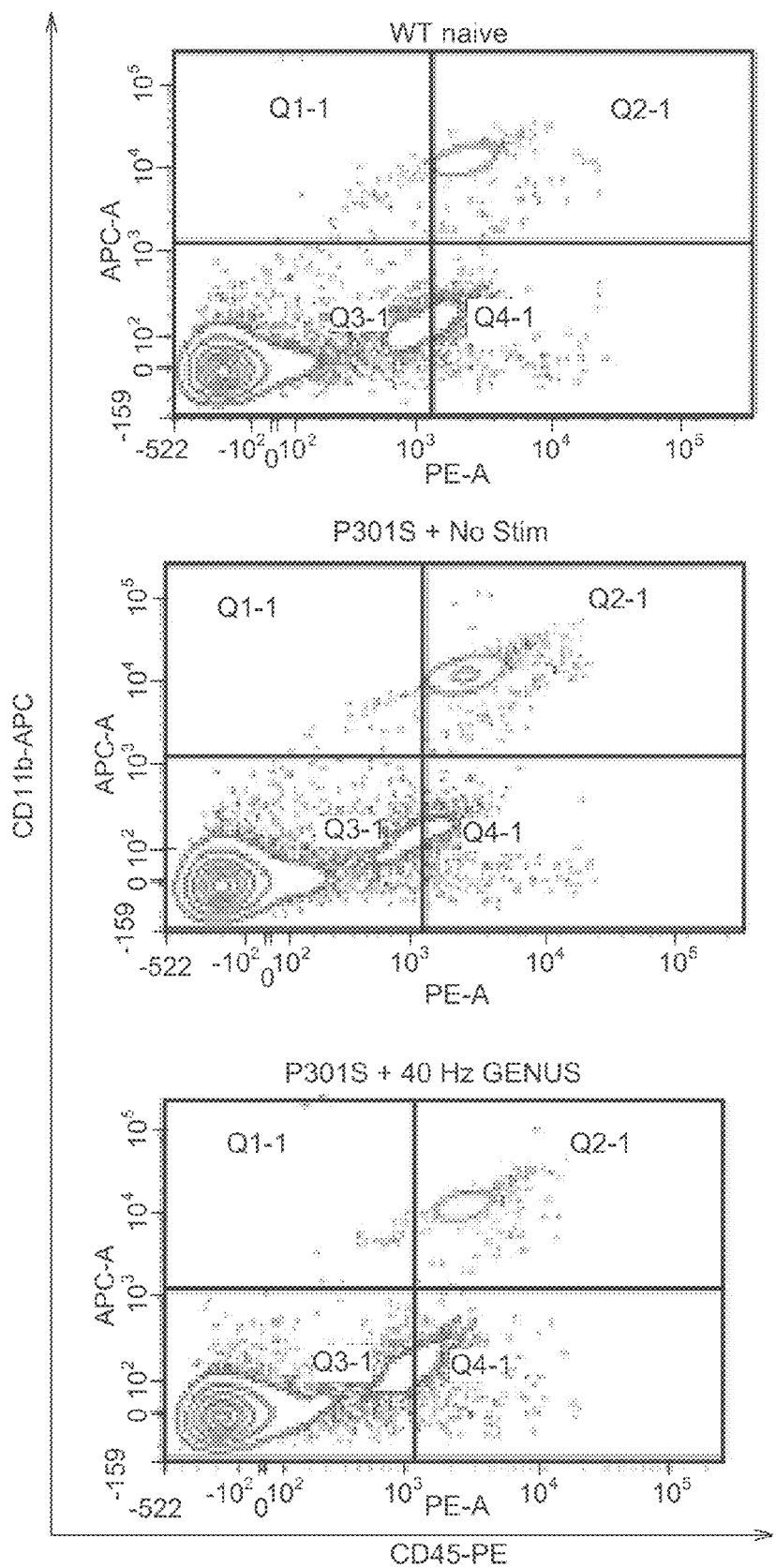

We also demonstrated that the reduced neurodegeneration we observed in Tau P301S and CK-p25 mice following chronic GENUS may be partially mediated by a beneficial microglia response. We performed unbiased RNA sequencing on visual cortex from P301S tau and CK-p25 mice which received GENUS stimulation for 22 days and 42 days respectively, as well as non-stimulated P301S and CK-p25 mice and respective WT controls (FIG. 4A). The visual cortex was dissected out, then enzymatically digested, microglia were identified by CD11b and CD45 immunostaining and then isolated using the fluorescence activated cell sorting (FACS) as described previously (Mathys et al., 2017) (FIG. 10A, 10B). We isolated 35,000 microglia from each mouse, extracted total RNA from each mouse separately and checked the quality of RNA prior to RNA-seq. An average of 28.69 million reads per sample were obtained and of which 89.42 percent were aligned.

Figure 4B:
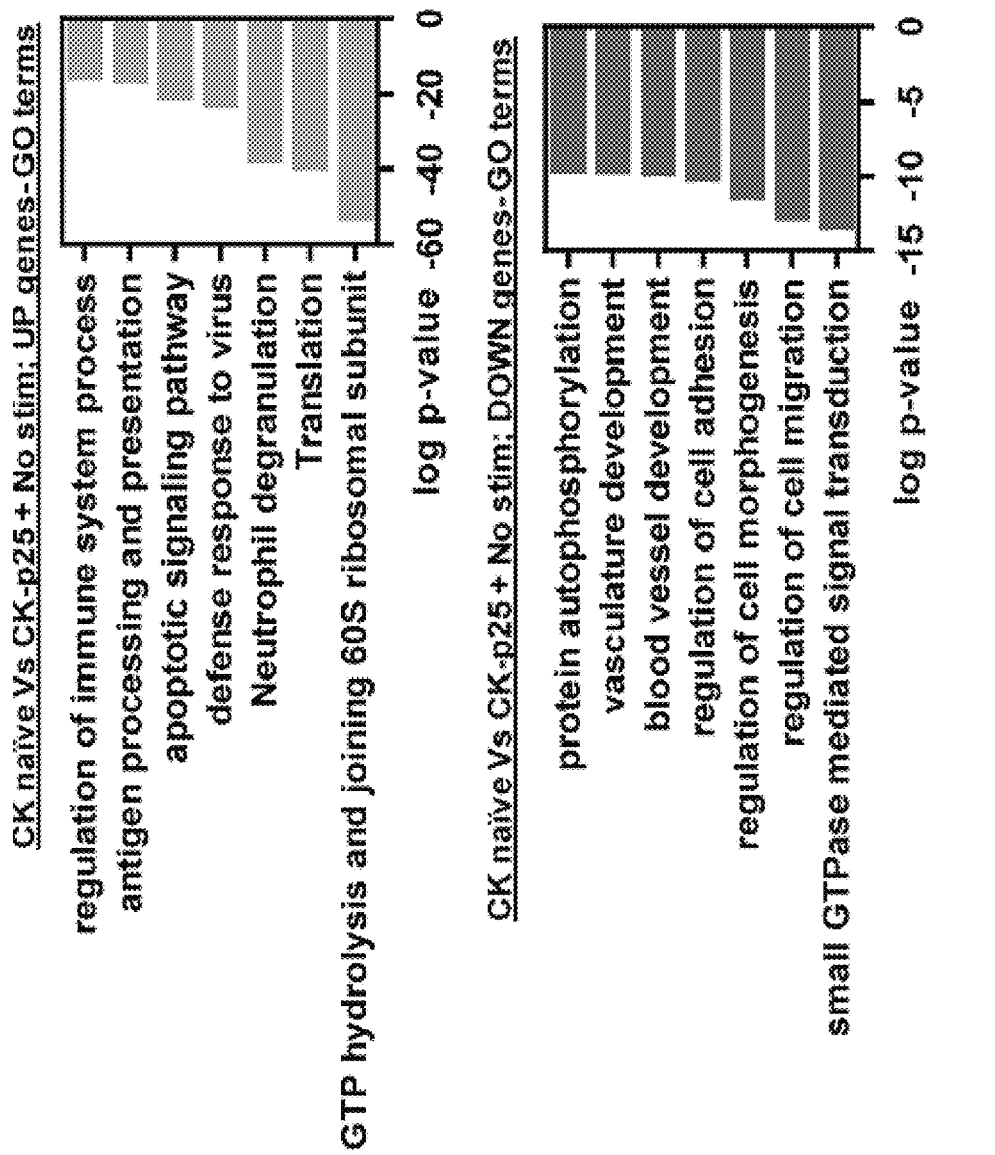
Figure 4C:
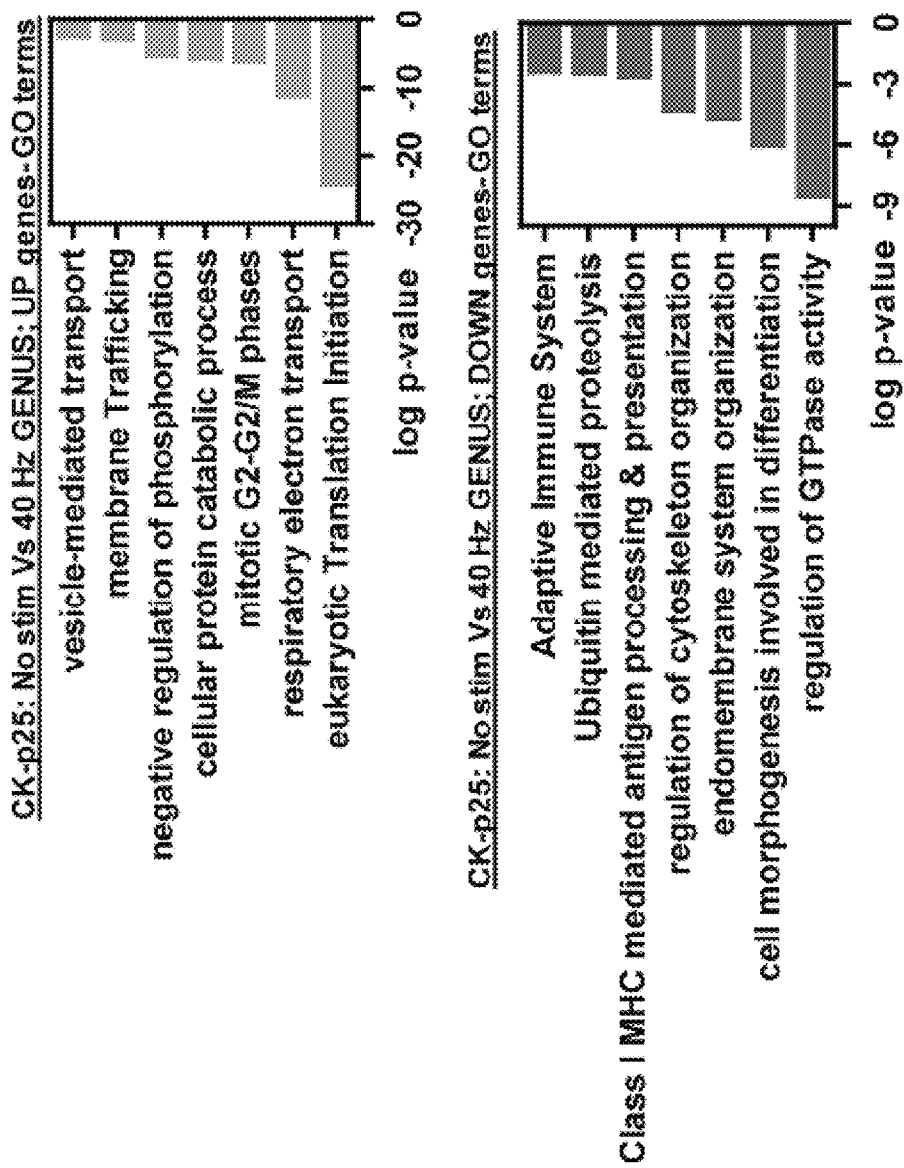

RNA sequencing revealed that microglia derived from non-stimulated CK-p25 mice, had 2333 upregulated genes when compared with CK naïve mice (FIG. 4A). We next performed gene ontology (GO) analysis and observed that the upregulated genes were involved in protein synthesis, ribosomal regulation and immune response (including viral immune-response, antigen presentation and immune response regulation), consistent with a previous report (Mathys et al., 2017) (FIG. 4B). By comparison the 2019 downregulated genes identified were primarily related to cell migration, cell morphogenesis and vasculature development (FIG. 4B). Following chronic GENUS 355 genes were upregulated in CK-p25 mice (compared to non-stimulated CK-p25), and these genes were found be associated with protein synthesis, mitotic cell cycle regulation, membrane trafficking and vesicle mediated transport, whilst the 515 downregulated genes were mostly related to GTPase activity, proteolysis and immune response (including MHC-1 mediated antigen processing presentation and immunoadaptivity) (FIG. 4C). These results indicate that chronic GENUS significantly impacted microglial functions in the CK-p25 mice and rendered them less inflammatory and possibly more capable of phagocytosis, migration and protein degradation.

Figure 10C:
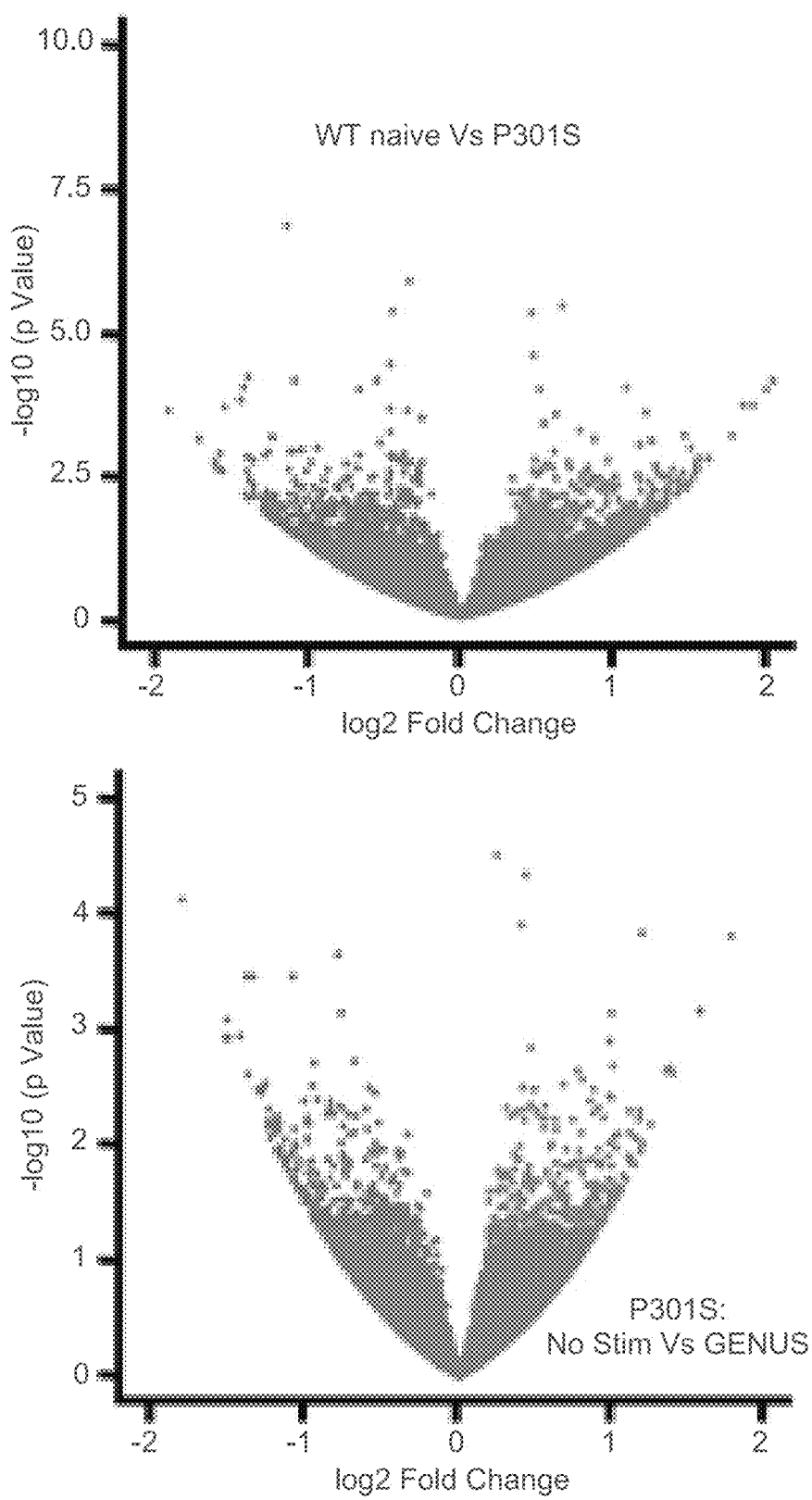
Figure 10D:
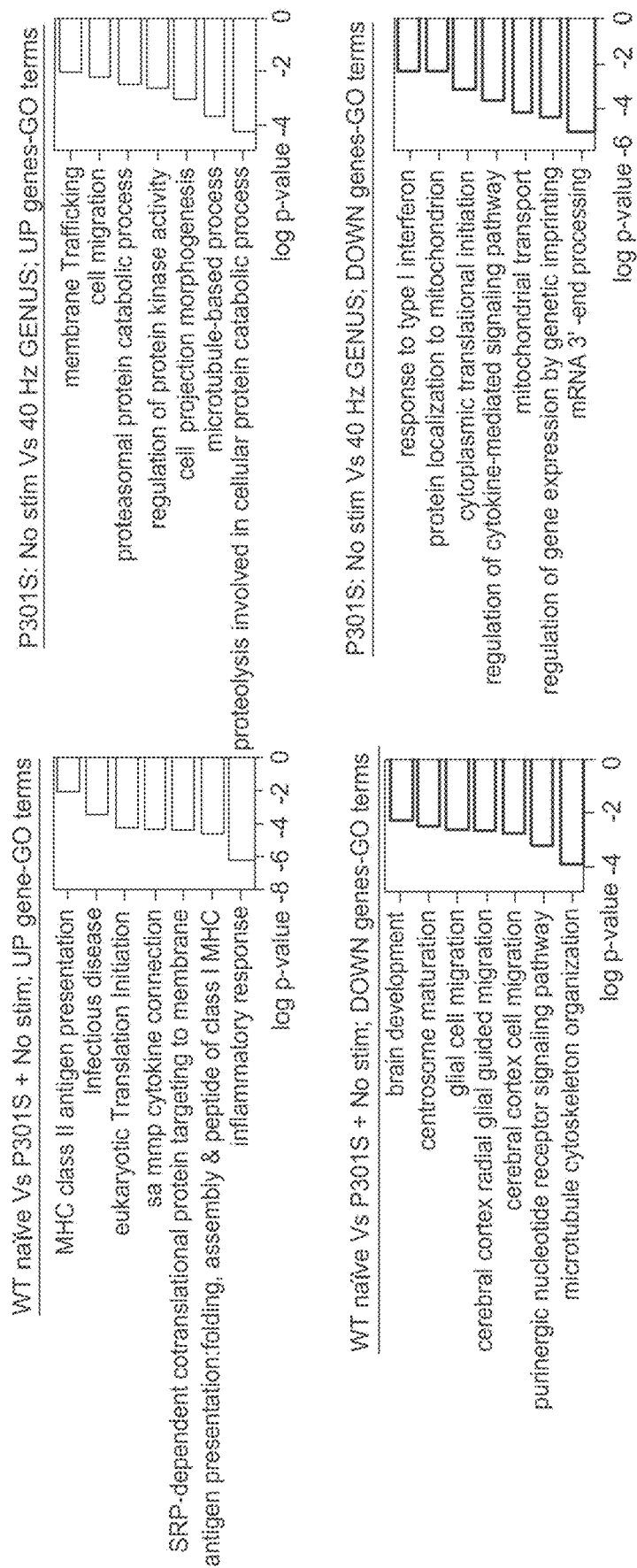

In non-stimulated Tau P301S mice, we found a total of 331 upregulated and 292 downregulated genes relative to their WT naive littermates (FIG. 10C). Gene ontology (GO) analysis associates the upregulated genes with protein synthesis and inflammatory/immune response, whereas the downregulated genes were more related to cytoskeletal organization, cell migration and brain development (FIG. 10D). Microglia obtained from Tau P301S mice after chronic GENUS (22 days) displayed 238 upregulated and 244 downregulated genes compared to non-stimulated Tau P301S mice. Here, upregulated genes were associated with cellular catabolic proteolysis, cell migration, cell morphogenesis and membrane trafficking with downregulated genes involved in gene expression, translation initiation and interferon response (FIG. 10C and FIG. 10D). Therefore, CK-p25 mice with chronic GENUS showed remarkably similar transcriptomic changes as Tau P301S mice with chronic GENUS. Taken together, our microglia-specific transcriptomic analyses indicate that chronic GENUS acts to morphologically transform microglia, enhance protein degradation, and decrease the microglia-mediated immune response, independent of the specific transgenic model (P301S or CK-p25) to produce a disease state.

Figure 4D:
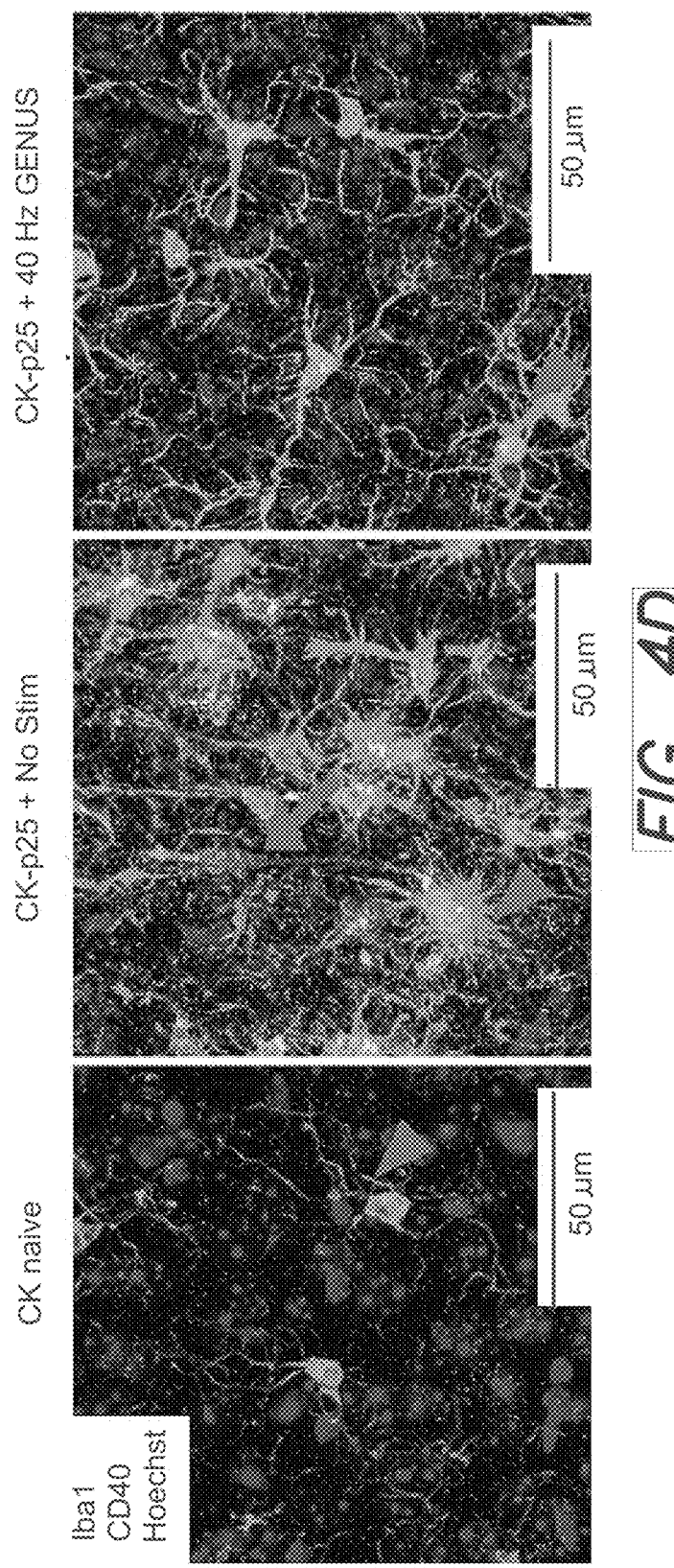

To further validate these findings, we performed immunohistochemical staining using brain slices from CK-p25 and Tau P301S mice after chronic GENUS (CK-p25: 1 h/day for 42 days during p25 induction; Tau P301S: 22 days) as well as from their respective non-stimulated and naïve control groups. The CK-p25 microglial response has been described previously, with an early response characterized by increased proliferation and a late response marked by elevation of MHC class II and interferon pathway (Mathys et al., 2017). We first used the microglia specific marker Iba1 to carry out immunohistochemistry and 3-dimensional rendering, which revealed a significant increase in number and extensive changes in morphology of microglia in V1 of 6-week-induced CK-p25 mice (FIG. 4D-4I and FIG. 10E). Microglia in CK-p25 animals did not show a significant difference in cell soma volume compared to controls on the whole (FIG. 4F), but many displayed a more complex 'bushy' arborization pattern (arrowheads) (FIG. 4D; lower center panel) that has been associated with axonal and terminal synaptic degeneration (Jensen et al., 1994; Jorgensen et al., 1993). We also noted that a large fraction of microglia displayed an elongated rod-like body without polarized processes (arrow) (FIG. 4D, 4I), a phenotype that is known to be present after diffuse brain injury in rats, and in human subjects with traumatic brain injury (Bachstetter et al., 2017; Taylor et al., 2014). In addition, despite reduced processes volume (FIG. 4G), the microglia in CK-p25 were in closer physical proximity to each other compared to CK naïve controls, as analyzed by measuring the minimum distance between microglia (FIG. 4D, 4H). This indicates a loss of their territory and contrasts with resting states where each microglial cell generally has its own region of occupation, with little overlap between neighboring territories (Del Rio-Hortega, 1932; Nimmerjahn et al., 2005).

Figure 4E:
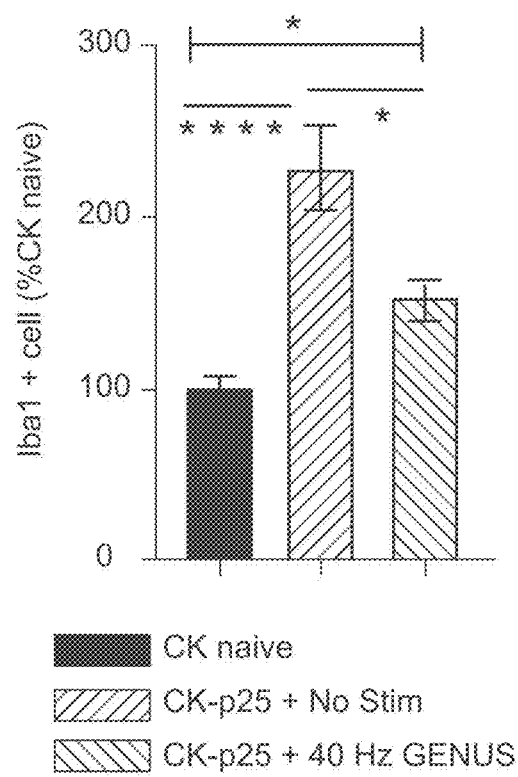

Chronic GENUS resulted in significantly reduced microglia numbers in CK-p25 mice compared to non-stimulated mice, although it remained higher than in naive CK mice (FIG. 4D, 4E). The total volume of the microglia processes after chronic GENUS revealed less retraction, such that there was no significant difference compared to either CK-p25 and CK naïve groups (FIG. 4G). Importantly, the minimum distance between microglia after chronic GENUS was comparable to that in CK naive animals (FIG. 4D, 4H), suggesting the preservation of microglial territories with chronic GENUS. Finally, there was significantly less increase in the overall volume of rod-microglia in CK-p25 animals with chronic GENUS, although it remained significantly higher than CK naïve groups (FIG. 4I). We next characterized Tau P301S microglia and found that there was a trend towards increased microglia in P301S but it did not reach statistical significance in our Iba1 immunostaining (FIG. 4K, 4L). The total volume of microglia soma was also not different in P301S compared to WT naïve mice (FIG. 4K, 4M). However, the total volume of the microglia processes in Tau P301S mice after chronic GENUS was significantly different from non-stimulated P301S mice and was comparable to WT naïve littermates (FIG. 4K, 4N). These results highlight a range of microglia states in baseline and disease conditions, and overall indicate the effects of chronic GENUS to alleviate disease-associated microglia morphological dysfunction in P301S and CK-p25 mice.

We next examined the GO term for immune response shown to be impacted by chronic GENUS. Immunohistochemistry using an antibody specific to interferon response gene CD40 revealed that it was significantly elevated in CK-p25 mice compared to CK naïve mice (FIG. 4D, 4J), in agreement with previous report (Mathys et al., 2017). Chronic GENUS resulted in significantly reduced CD40 signal intensity in the CK-p25 mice, although it remained significantly higher than in CK naïve controls (FIG. 4D, 4J). We next examined another immune response gene, C1q (classical complement component), that was markedly upregulated in our microglia-specific RNA-seq experiments and has been previously implicated in synaptic loss in an AD mouse model (Hong et al., 2016). Immunohistochemistry for C1q showed elevated signal in V1 of non-stimulated CK-p25 and Tau P301S mice (FIG. 4O, 4P, 4Q), compared to their respective naïve control littermates. Chronic GENUS significantly reduced the increase in C1q in CK-p25 mice, although C1q intensity remained above CK naïve levels (FIG. 4O, 4P). In P301S mice, chronic GENUS attenuated the increase in C1q such that there was no significant difference between WT naïve and P301S mice with no stimulation (FIG. 4O, 4Q). Overall, our immunohistochemistry results consistently indicate that chronic GENUS aids in reducing the immune response of microglia.

Figure 5A:
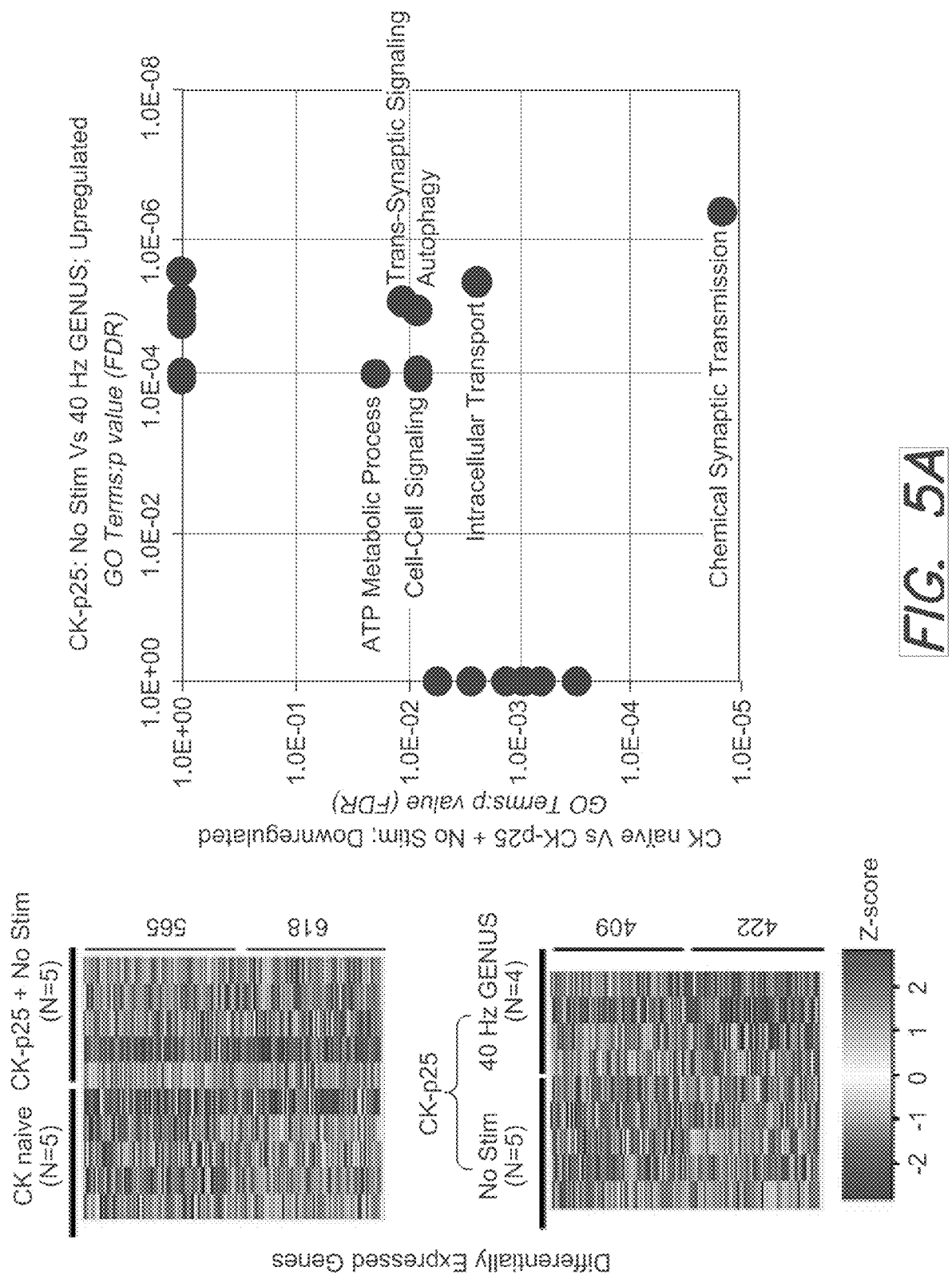
FIGS. 5A through 5I illustrate that chronic visual stimulation modifies synaptic function and intracellular transport in neurons, according to the inventive concepts disclosed.
Figure 5B:
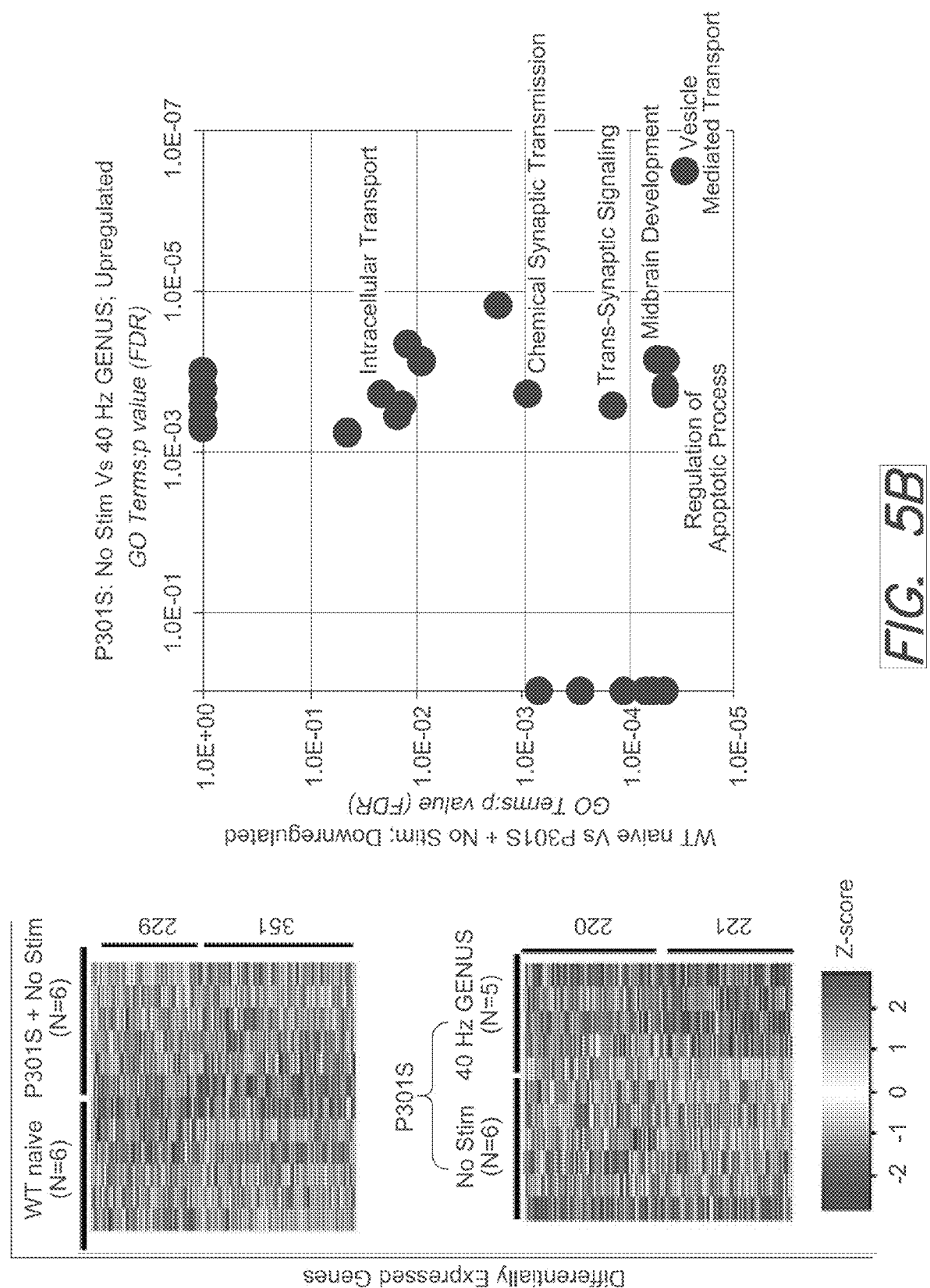
Figure 10F:
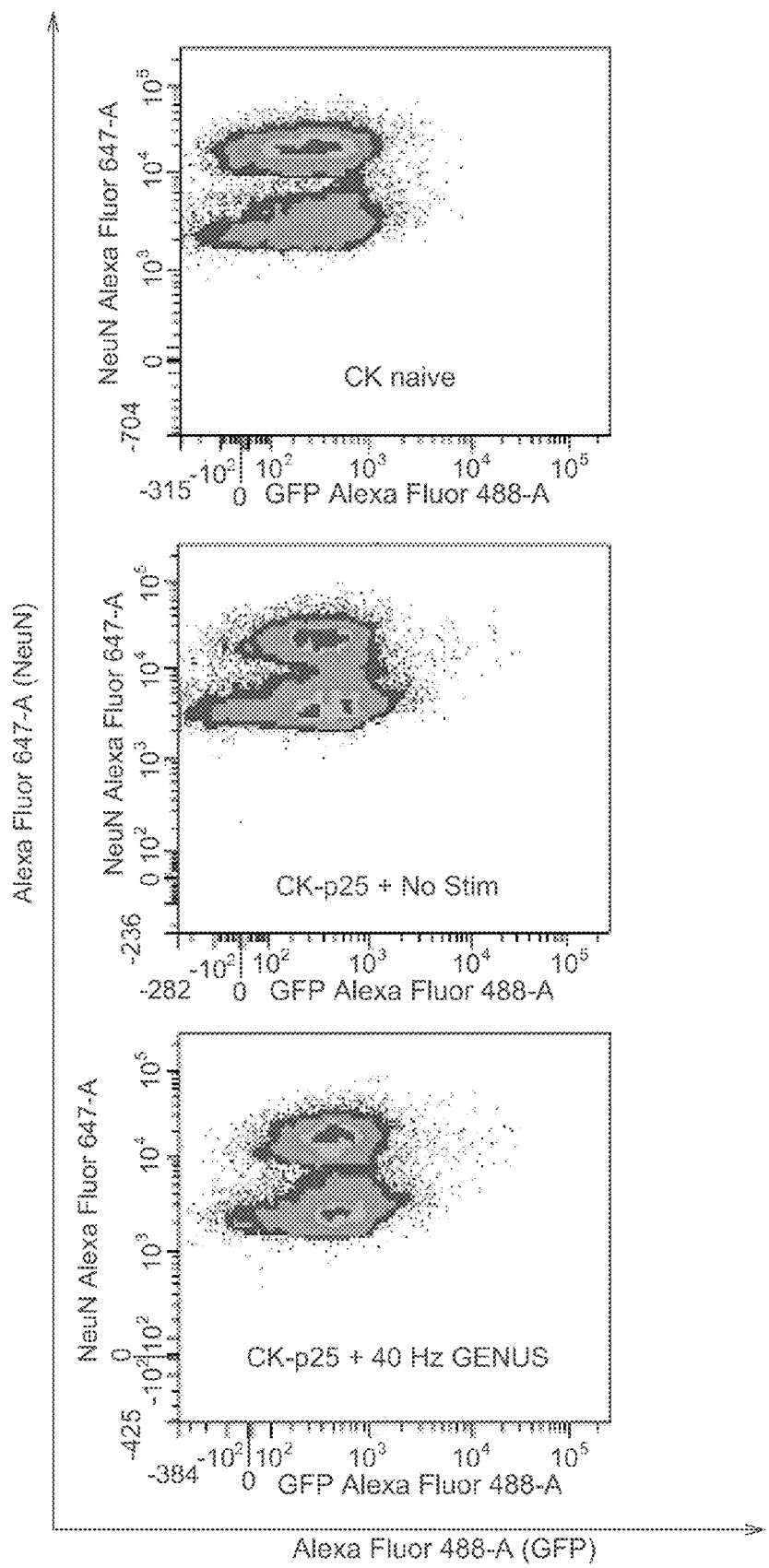

Chronic GENUS Modifies Regulation of Synaptic Transmission and Intracellular Transport in Neurons We next isolated NeuN-positive (NeuN+) neuronal nuclei and performed unbiased RNA-seq analysis to study the effects of chronic GENUS on gene expression in neurons in V1 of CK-p25 mice and Tau P301S (FIG. 5A, 5B and FIG. 10E-10G). Following chronic GENUS (CK-p25: 42 days of p25 induction; Tau P301S: 22 days) visual cortices were harvested from the mice. 100,000 neuronal nuclei were subsequently sorted by FACS into a lysis buffer, after which RNA was extracted and sequenced (FIG. 5A, 5B). In agreement with our findings on brain weight and from quantifying NeuN and cortical thinning using immunohistochemistry (FIG. 3G, 3I and FIG. 9D), we found a significantly reduced percentage of NeuN+ nuclei in non-stimulated CK-p25 mice (81.56±3.29) when compared with naïve CK littermates (100±3.87), which was not evident in the CK-p25 mice with chronic GENUS (88.56±4.49) (FIG. 10F, 10H). Similarly, while the percentage of NeuN+ nuclei in non-stimulated Tau P301S mice was significantly lower (86.11±2.26) than in naive WT littermates (100±3.87), Tau P301S mice with chronic GENUS did not differ from WT mice (96.05±3.99) (FIG. 10G, 10H), consistent with our immunohistochemistry findings (FIG. 3E, 3J). These results demonstrate a reduction in the loss of neuronal nuclei with chronic GENUS in both CK-p25 and Tau P301S neurodegenerative mouse models and point to an overall neuroprotective effect of GENUS.

We next performed RNA-seq from these FACS-sorted neuronal RNAs. An average of 18.09 and 22.79 million reads per sample were obtained, of which 85.23% and 84.45% were aligned from CK-p25 and P301S mice, respectively. Unbiased transcriptomic analysis of NeuN+ nuclei revealed that relatively more genes were downregulated in CK-p25 (618 genes) and Tau P301S (351 genes) than upregulated genes (CK-p25: 565 genes; Tau P301S: 229 genes), compared to their respective control mice (FIG. 5A, 5B). Chronic GENUS resulted in a similar number of upregulated versus downregulated genes in CK-p25 (409 up; 422 down) and Tau P301S (220 up; 221 down), compared to their respective non-stimulated controls (FIG. 5A, 5B).

We subsequently performed GO analysis to examine the biological functions associated with the differentially expressed genes. The neuron-specific downregulated genes in CK-p25 mice after chronic GENUS (618 genes) were involved in chemical synaptic transmission, intracellular transport, autophagy, ATP metabolic process, trans-synaptic signaling, and cell-cell signaling (FIG. 5A). Interestingly, GENUS rescued these biological processes by significantly upregulating genes involved in these processes in neurons in CK-p25 mice (FIG. 5A; right panel). Downregulated genes in Tau P301S (351 genes) were involved in chemical synaptic transmission, trans-synaptic signaling, intracellular transport including vesicle mediated transport, midbrain development and regulation of apoptotic process (FIG. 5B). These same processes—including vesicle mediated transport, intracellular transport, synaptic transmission, midbrain development and regulation of apoptotic process—were all upregulated after chronic GENUS in Tau P301S mice as revealed from the top biological functions associated with the upregulated genes (FIG. 5B, and FIG. 10I). On the other hand, some biological processes were upregulated in both CK-p25 and Tau P301S (compared to naïve controls), including those involved in DNA double strand breaks and DSB repair, in accord with our immunohistochemistry data for γH2AX (FIG. 9G). Importantly, the downregulated genes in CK-p25 and Tau P301S mice after chronic GENUS included those known to be essential for the apoptotic pathway in response to DNA damage, consistent with a shift in neurons towards a less degenerative state. Together, these data suggest that even in two mechanistically distinct mouse models of neurodegeneration (CK-p25 and Tau P301S) the altered patterns of gene modulation converge on similar cellular and biological functions—including downregulation of synaptic function, intracellular transport and apoptotic regulation—ultimately promoting neuronal demise. Importantly, after chronic GENUS many genes involved in rescuing the defects in synaptic transmission, synapse organization and intracellular transport including vesicle mediated transport are upregulated (FIG. 5A, 5B and FIG. 10H).

Figure 5C:
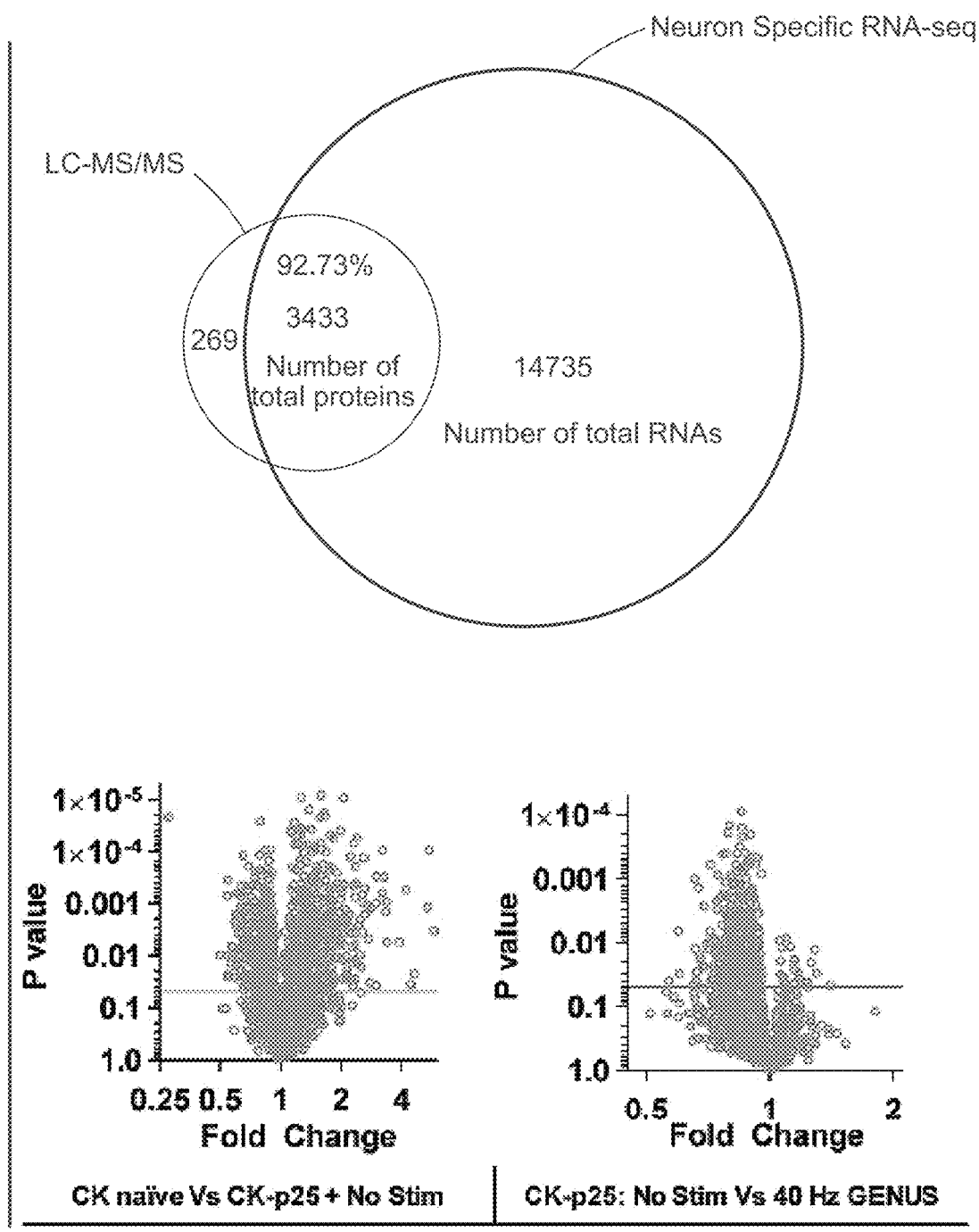
Figure 5D:
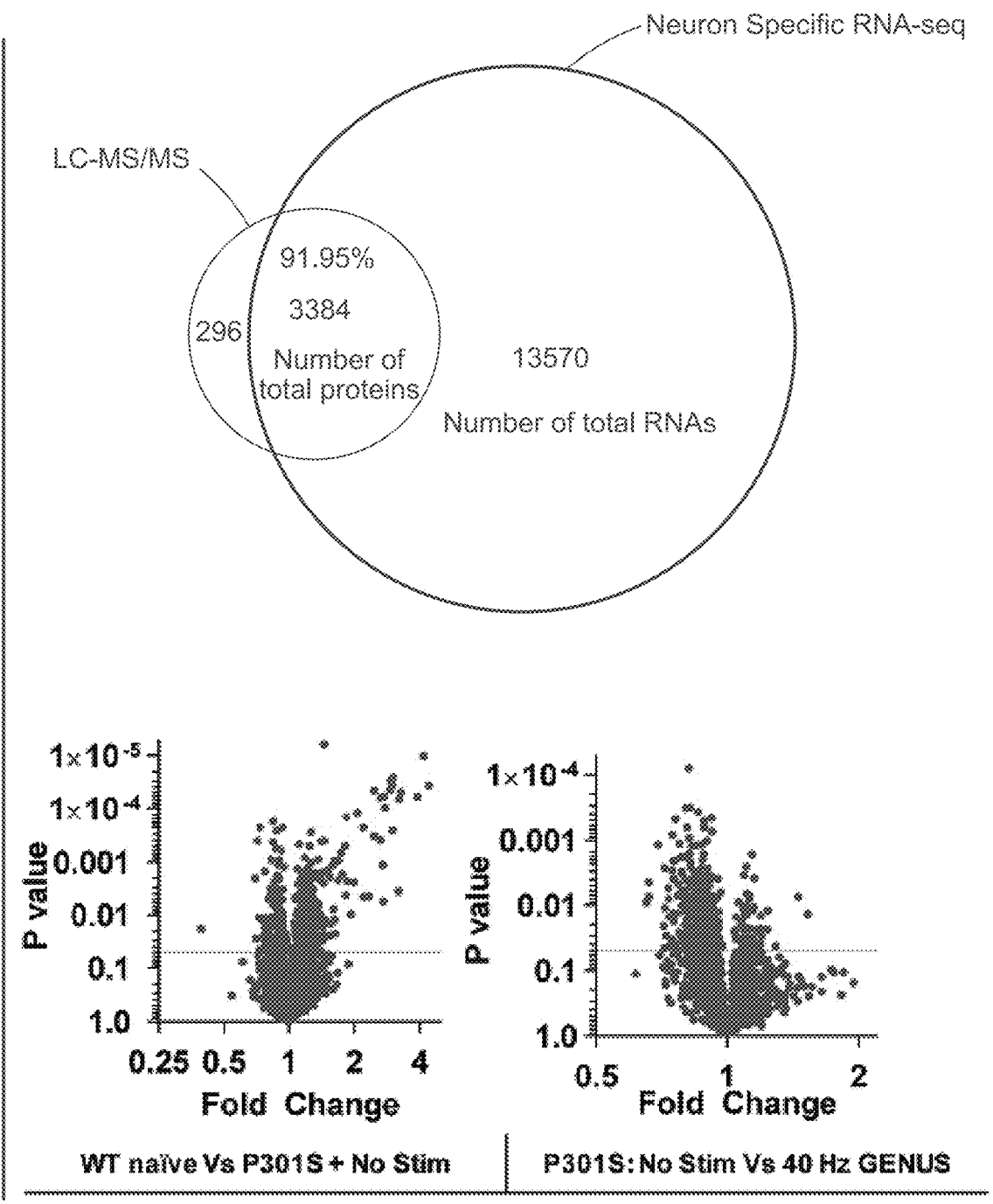

To further characterize and validate these biological processes that are modified by chronic GENUS, we performed unbiased liquid chromatography-tandem mass spectrometry (LC-MS/MS) to probe the differential expression and S/T phosphorylation of proteins in V1 of CK-p25 and Tau P301S mice (FIG. 5C, 5D). We first examined all the proteins identified by mass spectrometry in the combined CK-p25 groups (CK naïve controls, and CK-p25 with and without GENUS) and in the combined Tau P301S groups (WT naïve controls, and P301S with and without GENUS), and compared them to all the RNAs detected from their respective neuron-specific RNA-seq data. We found that 92.75% and 91.95% of the total proteins identified in the combined CK-p25 groups and in the combined Tau P301S groups, respectively, mapped to expressed genes in the neuron-specific RNA-seq data (FIG. 5C, 5D), suggesting that the majority of proteins identified are involved in neuronal function. We next compared differentially S/T-phosphorylated proteins in CK-p25 and Tau P301S mice with their respective naïve control littermates and found that there was an overall increase in S/T-phosphorylated proteins in both CK-p25 and Tau P301S mice (FIG. 5C, 5D; bottom left panels), indicating aberrant modification of functional proteins in both neurodegeneration mouse models. Chronic GENUS resulted in reduced S/T phosphorylation of proteins in both CK-p25 and Tau P301S mice (FIG. 5C, 5D; bottom right panels), compared to their respective controls with no stimulation. Consistent with our neuron-specific gene expression analysis (FIG. 5A, 5B), chronic GENUS modified proteins involved in chemical synaptic transmission, dendrite development, long-term potentiation, regulation of vesicle-mediated transport, vesicle-mediated transport in synapse, and regulation of intracellular transport (FIG. 5E and FIG. 10J-10M), indicating that these processes are altered in degenerating neurons and are improved with chronic GENUS.

Figure 4P:
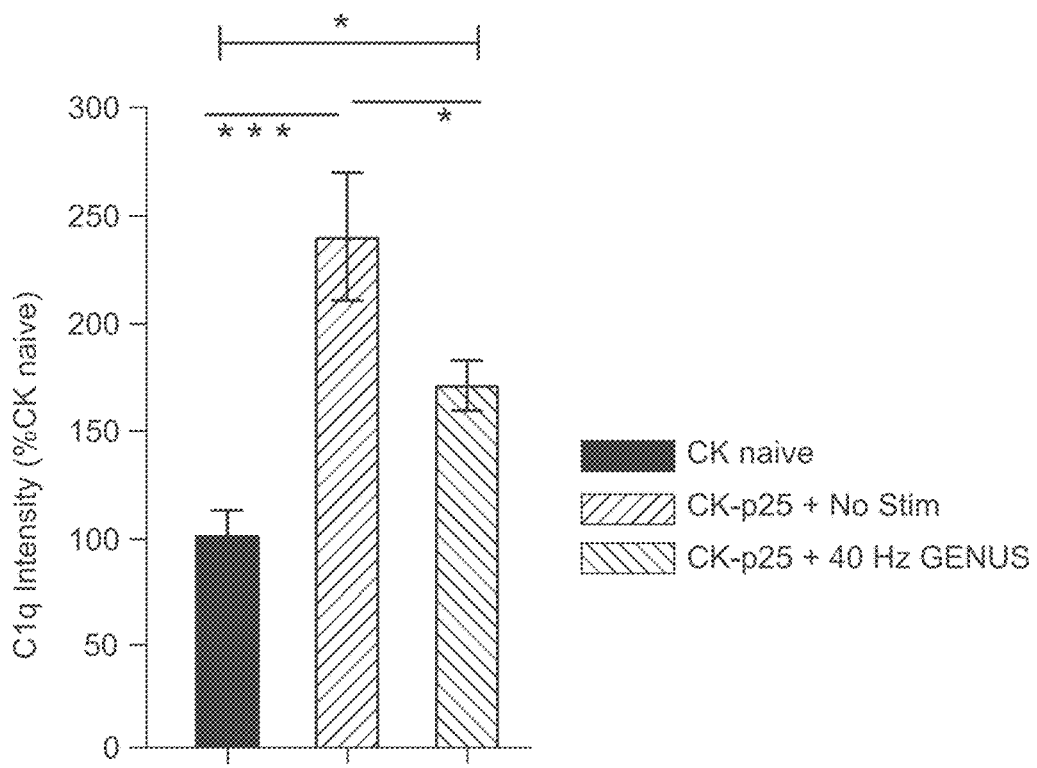
Figure 4Q:
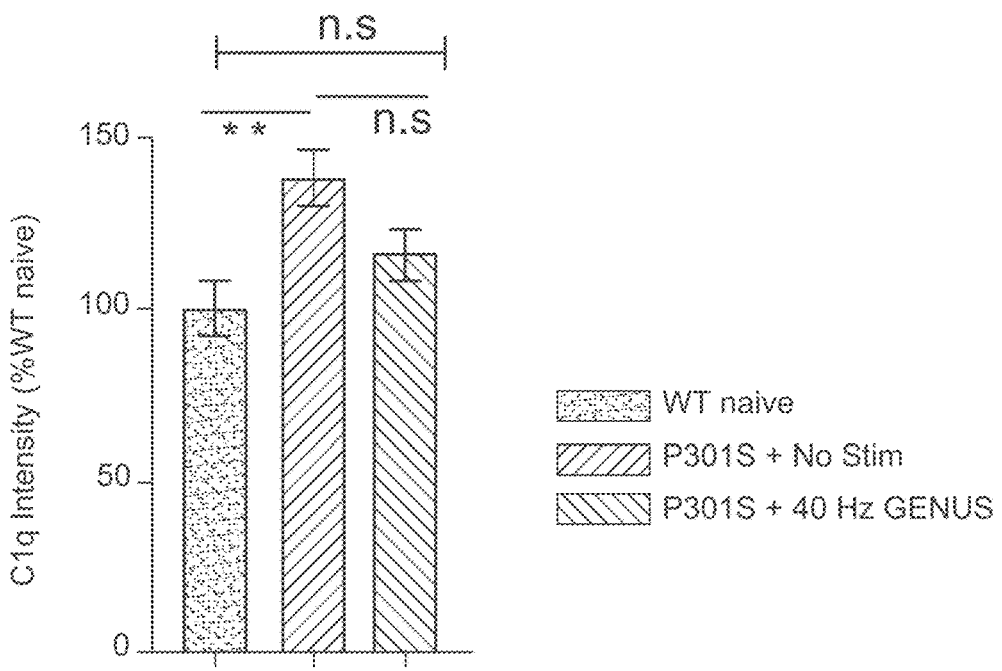
Figure 5E:
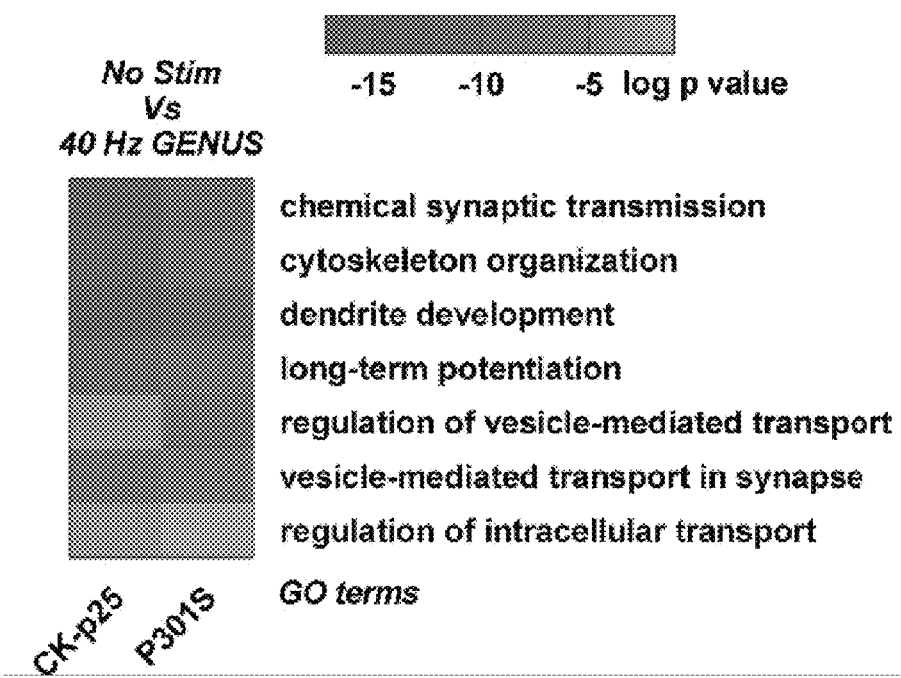
Figure 5F:
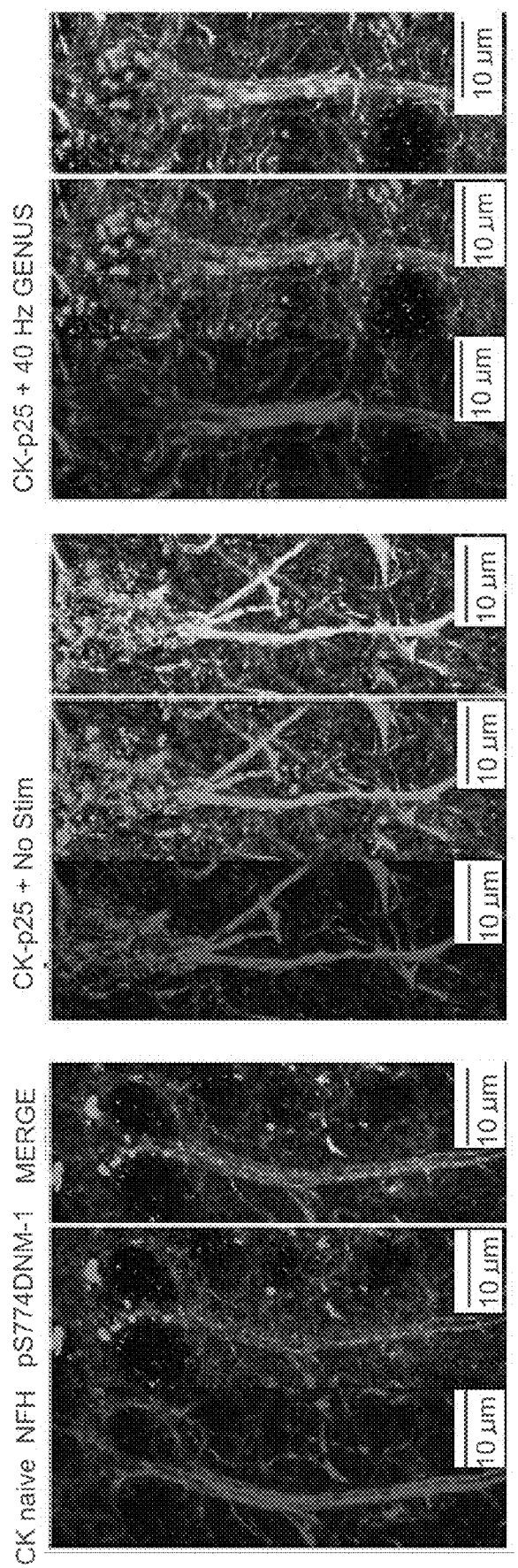
Figure 5G:
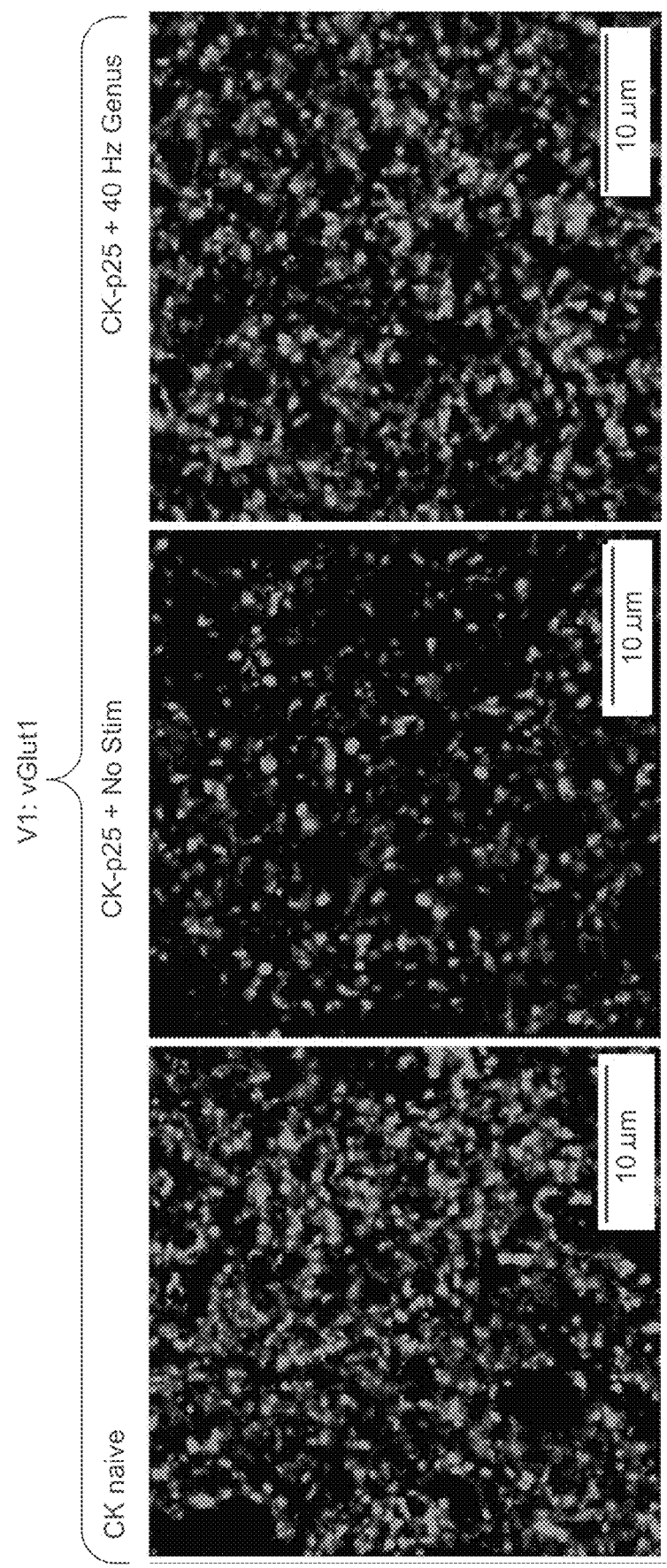
Figure 5H:
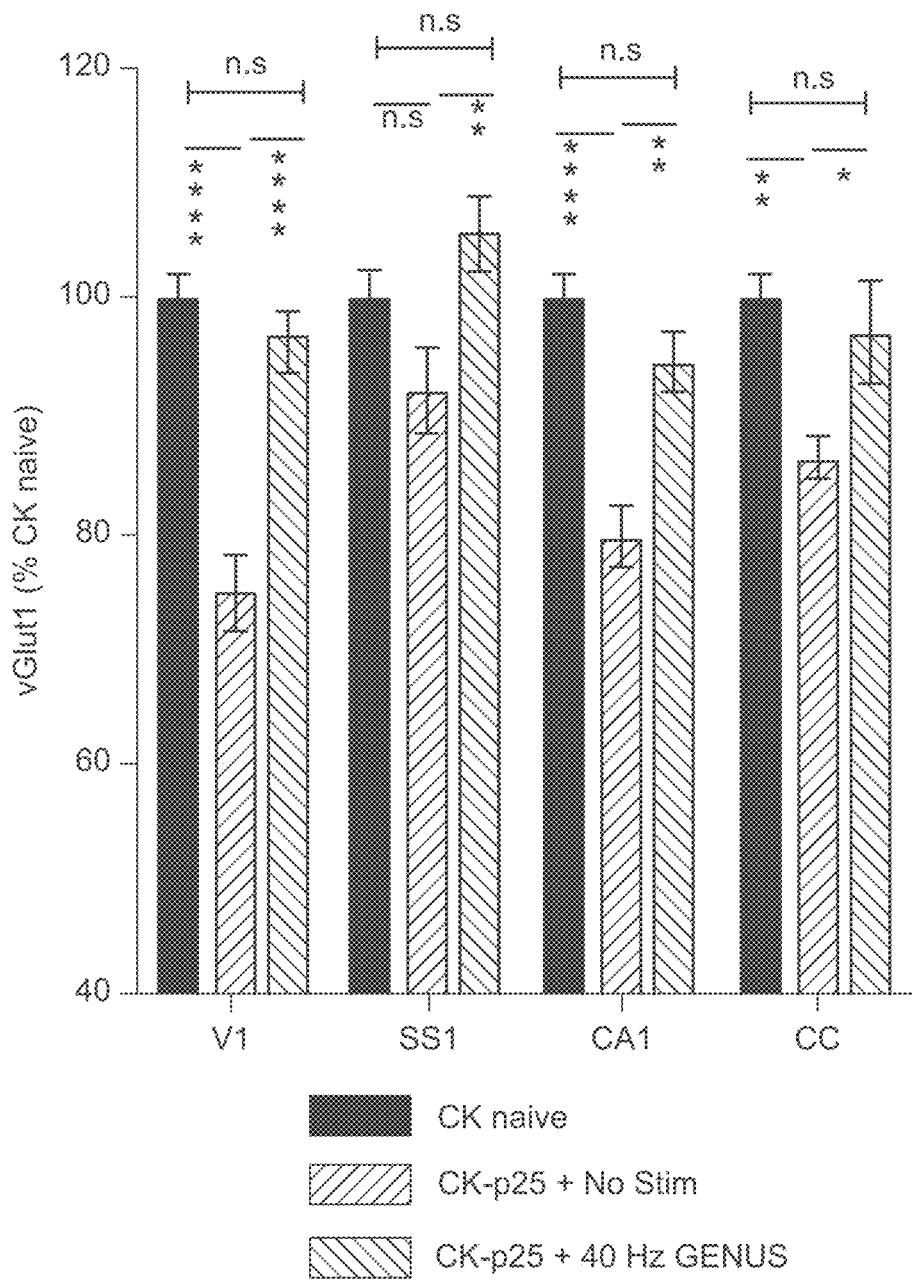
Figure 5I:
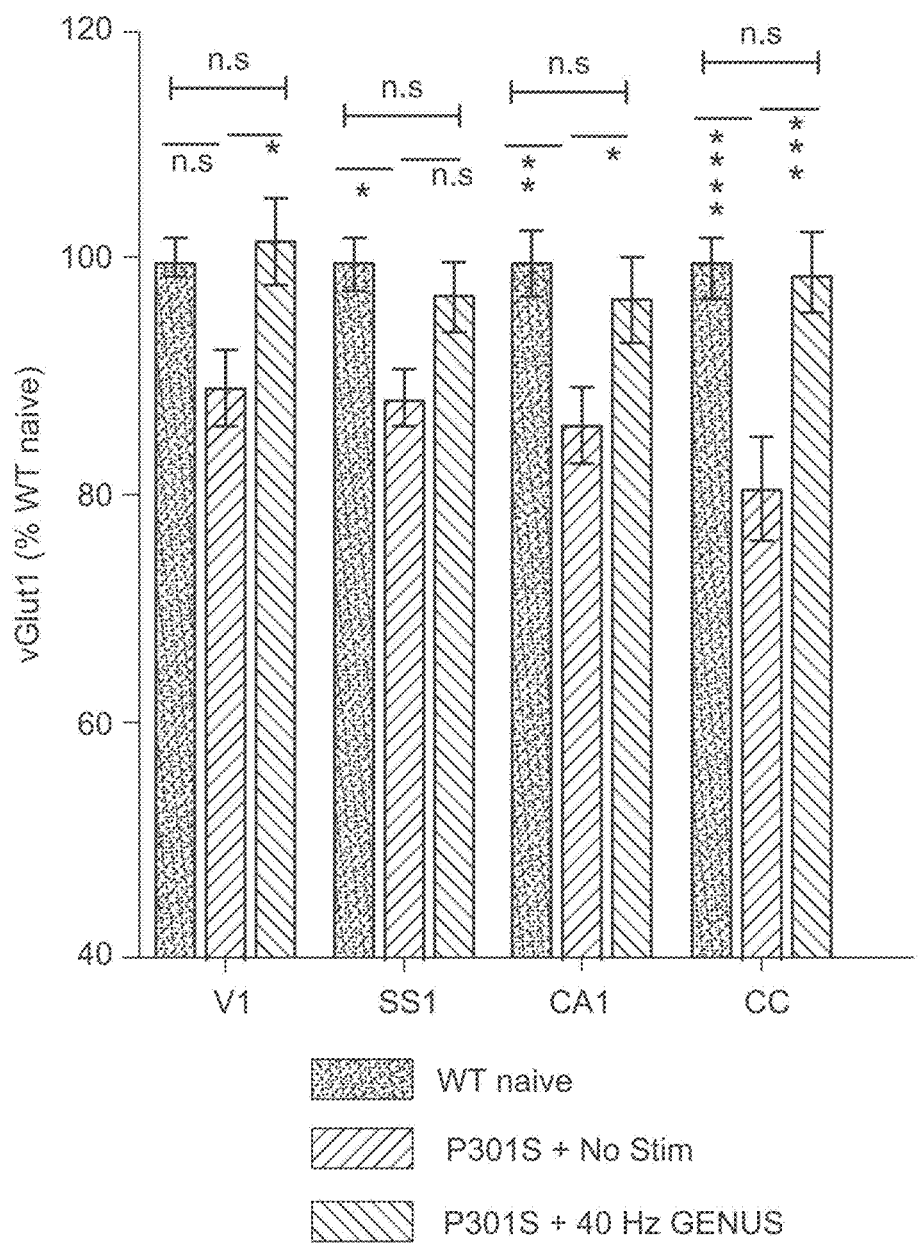

One example protein from our phosphoproteomics analysis implicated in vesicle trafficking, endocytosis, and synaptic transmission is dynamin1 (DNM-1) (Armbruster et al., 2013), which was associated with multiple GO terms in the annotation of differentially S/T-phosphorylated proteins after chronic GENUS in both CK-p25 and Tau P301S (FIG. 5E). Phosphoregulation at Ser774 is required for endocytosis of synaptic vesicles (Clayton et al., 2009), and is one of many residues that was found to be hyper-phosphorylated in CK-p25 and Tau P301S mice and reduced with chronic GENUS. We carried out immunohistochemistry and western blotting and found that DMN-1 Ser774 phosphorylation was significantly increased in CK-p25 and Tau P301 mice and was reduced with chronic GENUS (FIG. 5F and FIG. 10M, 10N). We also carried out immunohistochemistry for vesicular glutamate transporter 1 (vGlut1), another protein that is involved in vesicle and neurotransmitter transport, synaptic transmission, and learning and memory (Balschun et al., 2009). We found that vGlut1 puncta were significantly reduced in CK-p25 mice compared to CK naïve mice (FIG. 5G, 5H), with significantly higher vGlut1 expression in CK-p25 mice after chronic GENUS (compared to non-stimulated controls) not only in V1, but also in SS1, CA1, and the ACC area of PFC (FIG. 5G, 5H). Similarly, the decreased expression of synaptic marker vGlut1 puncta in Tau P301S mice across these brain regions was lessened after chronic GENUS in Tau P301S mice (FIG. 5I). These data are consistent with reduced neuronal (FIG. 3D and 3I) and synaptic loss (FIG. 4O, 4P, 4Q) across these brain regions with chronic GENUS in both neurodegenerative models.

Chronic GENUS Modifies Behavioral Performance

Figure 11A:
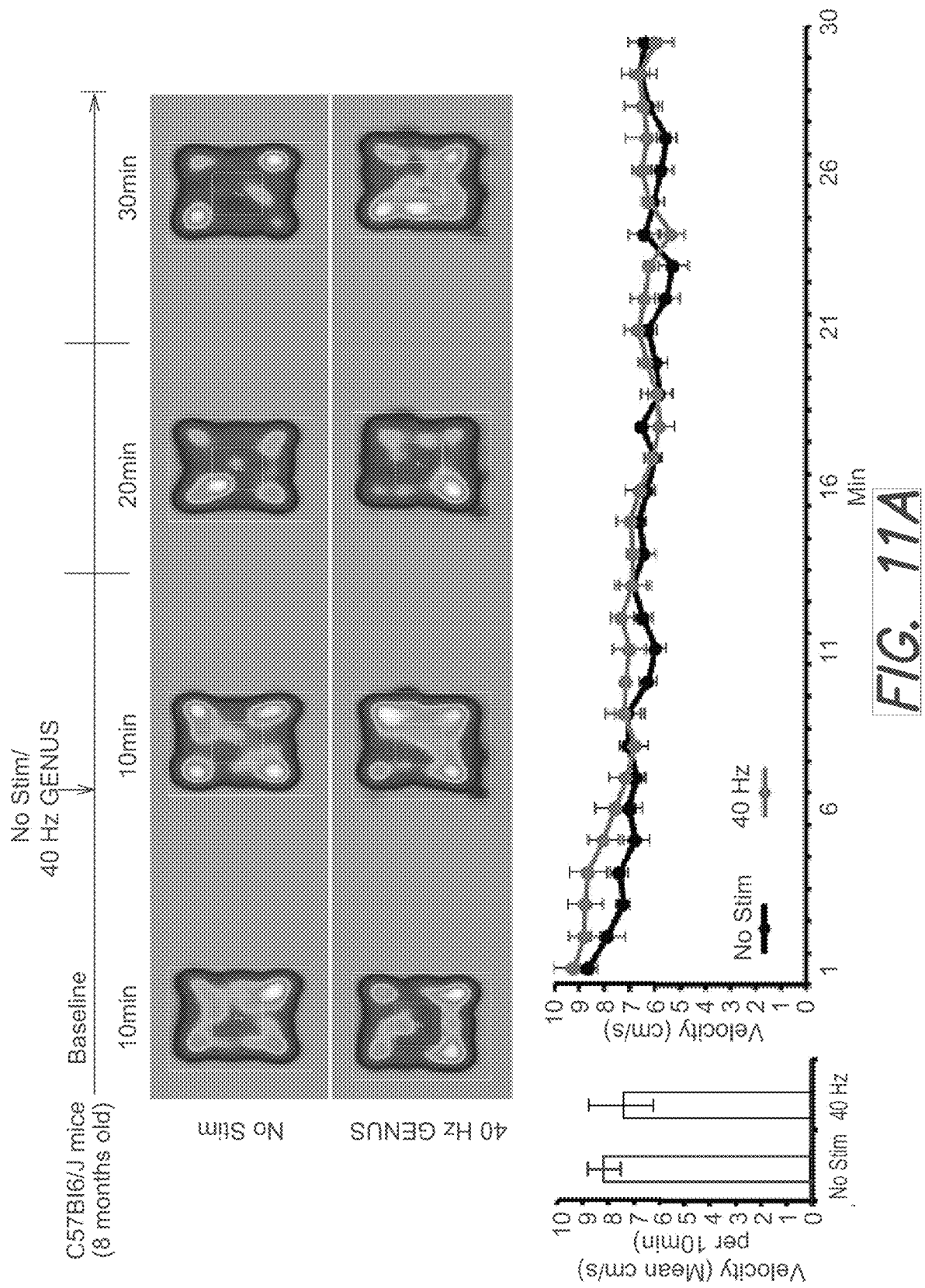
Figure 11B:
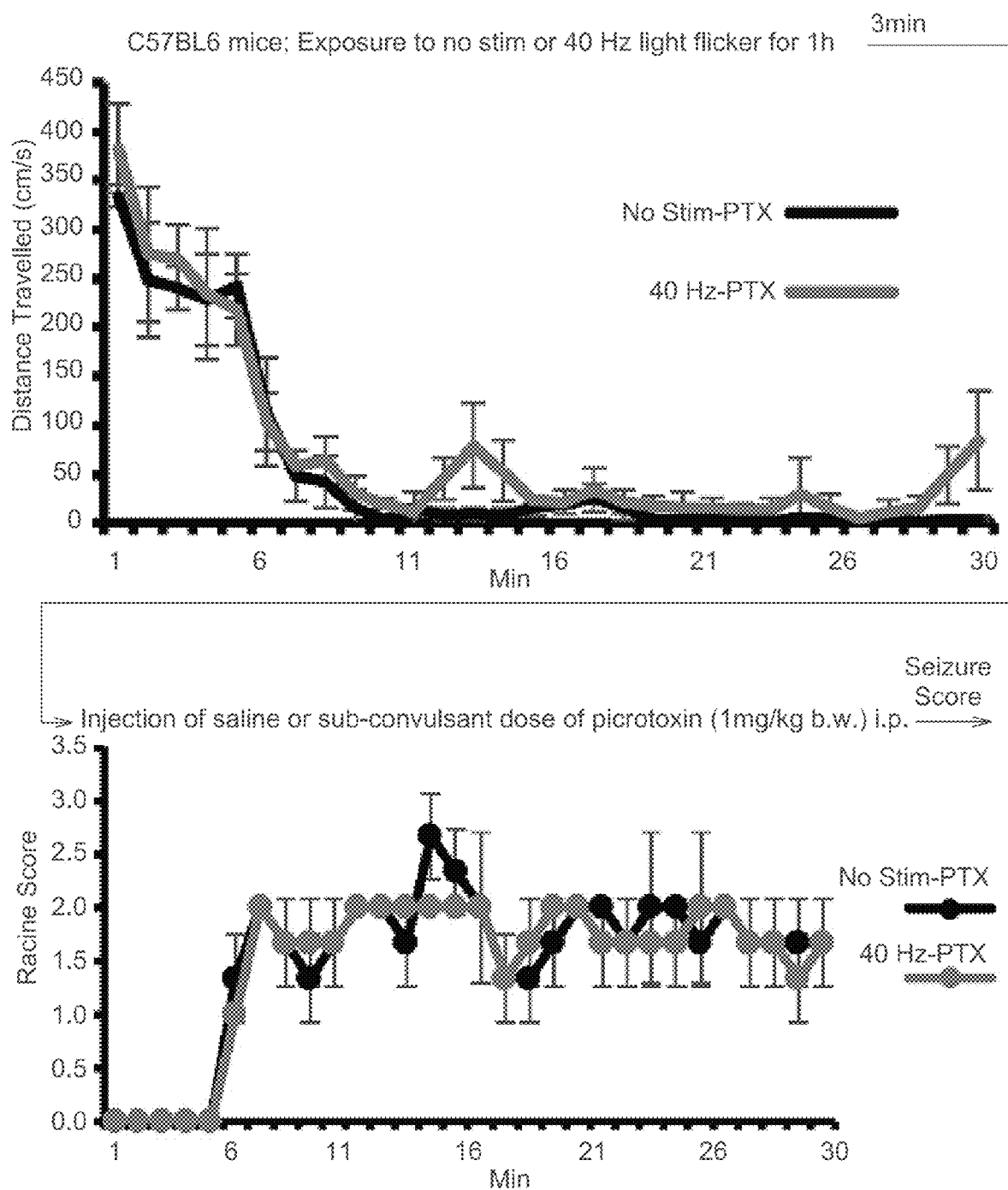
Figure 11C:
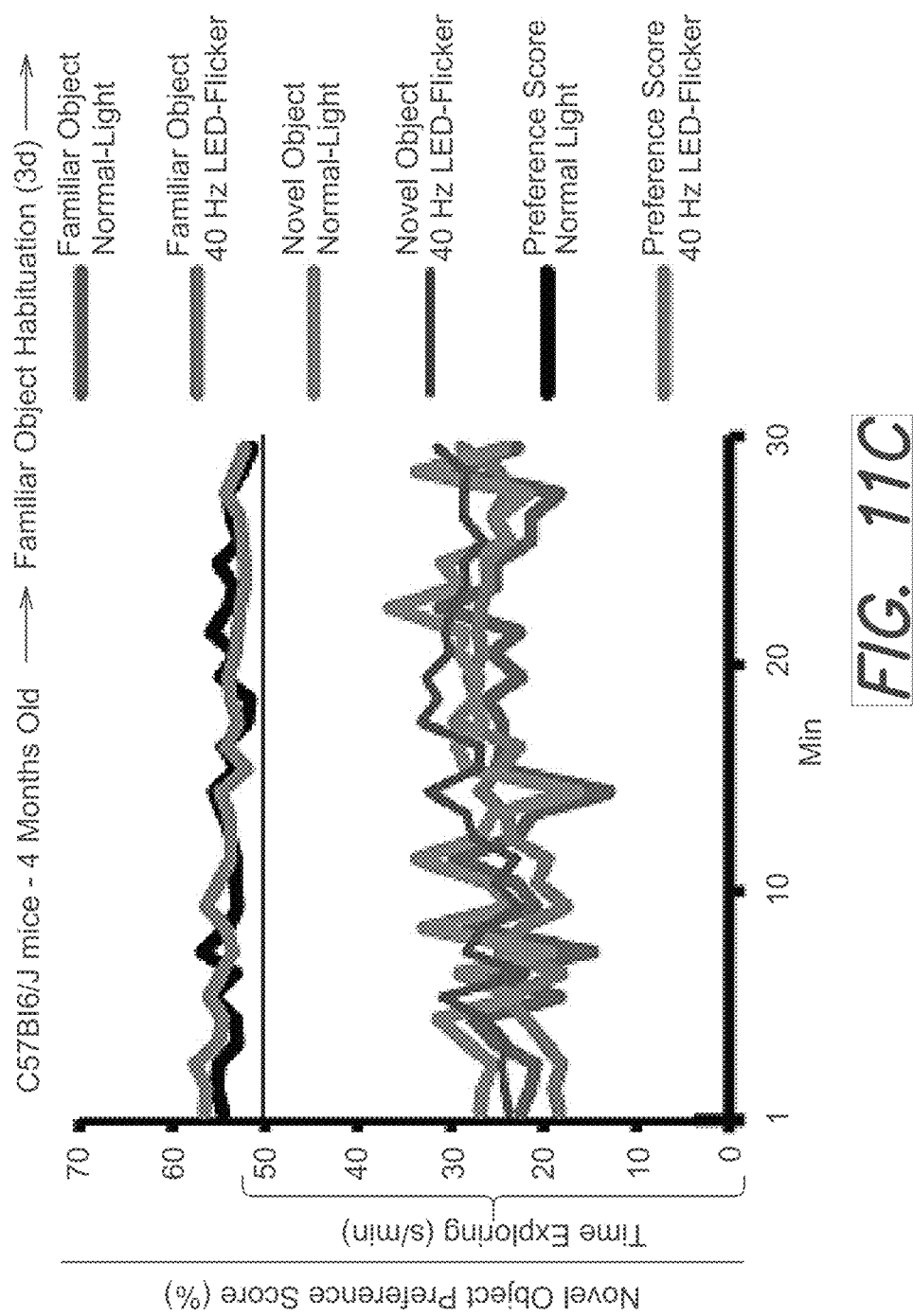
Figure 11E:
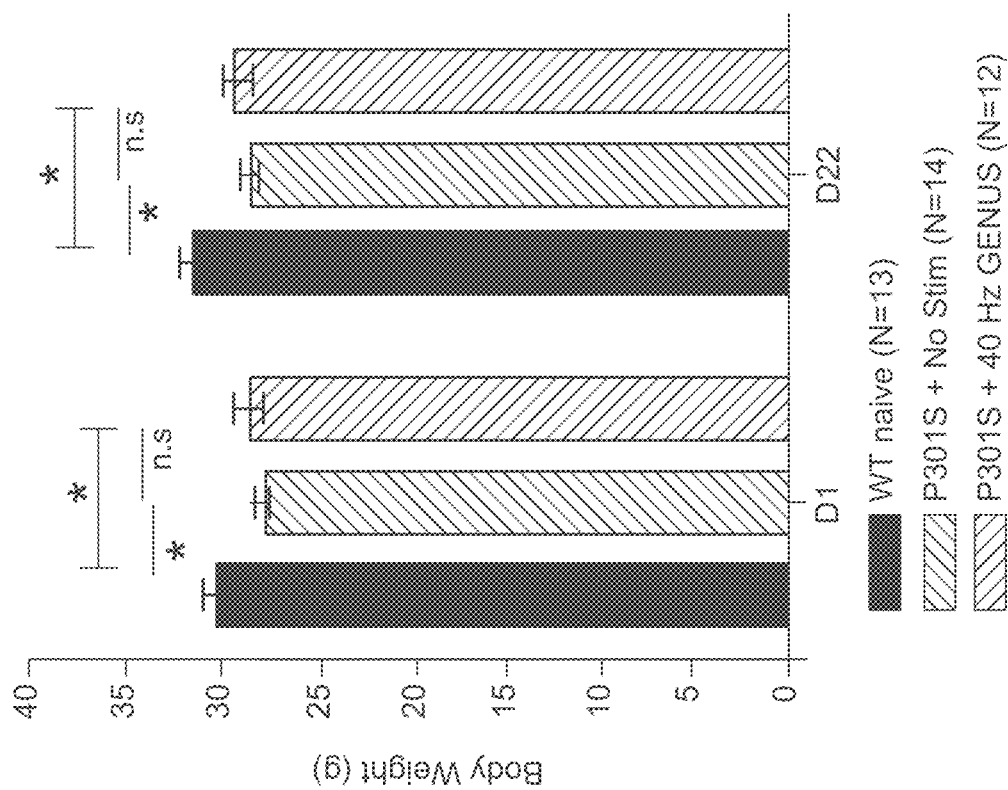
Figure 11F:
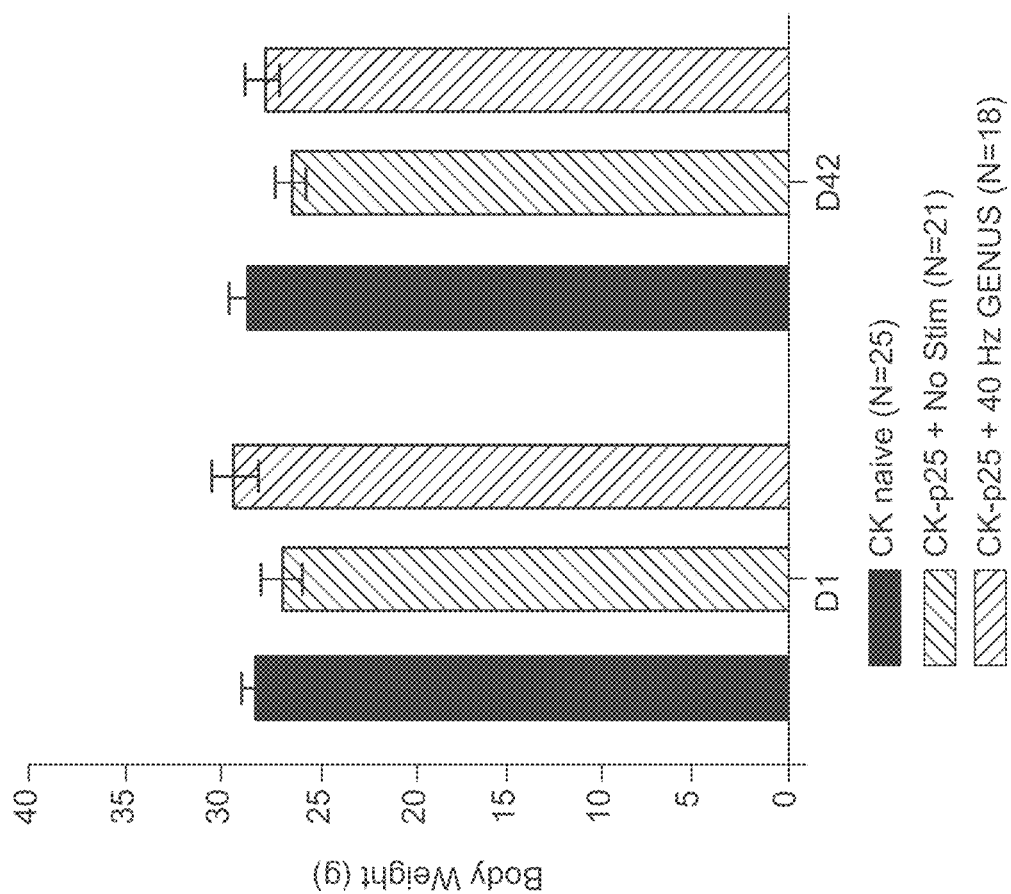

Our results thus far show that GENUS can entrain neural oscillations far beyond V1, including CA1, SS1, and PFC, and reduces AD-associated pathology including amyloid plaques, tau hyperphosphorylation, synaptic loss, and neuronal loss in all of these brain regions in CK-p25 and Tau P301S mice. Our RNA-seq and phosphoproteomic data supports a capacity for chronic GENUS to mitigate some disease-associated deficits in synaptic transmission and intracellular transport that are consistent with preserved synaptic function. We therefore asked if chronic GENUS also improves cognitive function. We first sought to determine if GENUS triggered any systematic behavioral changes that might complicate the interpretation of any cognitive changes. No difference was evident in locomotor activity either during or distance travelled after acute GENUS in C57B1/6J mice (FIG. 11A-11C). Moreover, both seizure susceptibility by picrotoxin and novel object discrimination were not altered (FIG. 11B-11C). Animals of all groups stimulated chronically with GENUS (C57B16: 7 days; CK-p25: 1 h/day for 42 days during p25 induction; Tau P301S: 22 days) had comparable body weights to non-stimulated controls (FIG. 11D-11F). Finally, seven days of GENUS did not affect stress response marker plasma corticosterone in C57B1/6J mice (FIG. 11I).

Figure 6B:
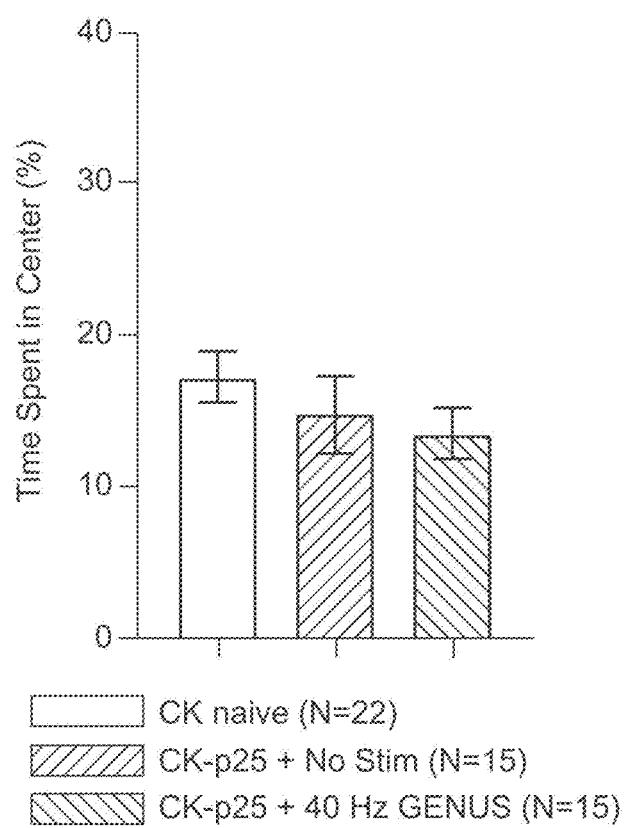

To assess the cognitive benefits of GENUS we focused on learning and memory in the CK-p25 mouse models of AD, after induced p25 expression for 6 weeks while chronically stimulating with GENUS in CK-p25 mice. In the final week mice were exposed to an open field (OF) followed by novel object recognition (NOR) tests (FIG. 6A). Our results indicate that GENUS did not affect anxiety in CK-p25 mice, measured by the time spent in the center of the open field arena (FIG. 6A, 6B), nor did it alter plasma corticosterone levels (FIG. 11I), suggesting that chronic GENUS did not affect anxiety or stress in CK-p25 mice. Interestingly, GENUS stimulated CK-p25 mice, while did not show any difference in locomotor activity, spent significantly more time exploring the novel object compared to familiar object (FIG. 6A, 6C and FIG. 11G), indicating that chronic GENUS improved novel object recognition in CK-p25 mice compared with non-stimulated CK-p25 mice. We next conducted Morris water maze (MWM) test in 6 weeks induced CK-p25 mice during the $6^{th}$ week of GENUS. In the MWM test, compared to CK naïve mice non-stimulated CK-p25 mice displayed impaired spatial learning manifest as higher latencies to find the platform during training (FIG. 6D). Non stimulated CK-p25 mice also exhibited impaired spatial memory as shown by reduced number of platform location visits and less time spent in the target quadrant in the probe test (24 h after the last training day) compared with the CK naïve group (Fischer et al., 2005) (FIG. 6D). These impairments were significantly improved by chronic GENUS and was not the result of altered swimming velocity which remained comparable across groups and across all training days (FIG. 6D, and FIG. 11J).

To establish that this GENUS mediated improvement in behavioral performance was not limited to a single mechanism underlying cognitive impairment but was more generally applicable to AD associated cognitive decline, we tested multiple AD model mice. We subjected 8-month old Tau P301S mice to GENUS for 22 days (1 h/day) and on the third week of stimulation, mice were tested in an OF and NOR task and compared to an age matched non-stimulated group (FIG. 6E). As with CK-p25 mice, GENUS did not alter either time spent in the center of the OF arena (FIG. 6E, 6F), nor plasma corticosterone levels in Tau P301S mice (FIG. 11I), suggesting that chronic GENUS did not alter anxiety like behavior in Tau P301S mice. We next performed novel object recognition test and observed that the WT naïve and GENUS stimulated Tau P301S mice exhibited higher preference for novel object compared to familiar object (FIG. 6G). Similarly, novel object preference was higher in the non-stimulated Tau P301S mice (FIG. 6G).

We next performed MWM test during the third week of GENUS in Tau P301S mice. WT naive and GENUS stimulated Tau P301S mice exhibited significantly increased learning curve in MWM training compared to non-stimulated Tau P301S mice (FIG. 6H and FIG. 11J). Finally, we tested the effectiveness of GENUS on improving behavior in amyloid models of AD. We subjected GENUS stimulated 5XFAD mice (22 days-1 h/day) to MWM test during the third week of training (FIG. 6I). While GENUS stimulated 5XFAD mice exhibited slightly lower learning curve during the first four days of MWM training, they improved over multiple training trials compared to WT littermates, in contrast to the non-stimulated 5XFAD mice which were significantly impaired (FIG. 6I and FIG. 11J). Finally, employing 80 Hz visual stimulation we investigated whether chronic stimulation with other frequency can affect behavior. Similar to in vivo recordings from V1, 5XFAD mice that experienced 80 Hz visual stimulation for 22 days showed no difference compared to non-stimulated 5XFAD controls (quantified as latency to find the platform and target crossings in the probe test) in the MWM (FIG. 12-12C). Together, these results indicate that chronic stimulation specifically at 40 Hz improves the behavioral performance in multiple mouse models of neurodegeneration.

Increasing evidence supports the notion that manipulating neural network oscillations may represent a promising strategy to alleviate pathological changes and behavioral performance deficits associated with neurological disorders (Cho et al., 2015; Iaccarino et al., 2016; Kastanenka et al., 2017; Martinez-Losa et al., 2018; Verret et al., 2012). Here, we demonstrated that chronic daily entrainment of low gamma oscillations via 40 Hz visual stimulation was effective in entraining gamma oscillations, even in conditions of advanced neurodegeneration, to reduce neuropathology in multiple brain regions. The neuroprotective effects of chronic GENUS include a reduction of the microglia-mediated inflammatory response, boosting the expression of genes and proteins that facilitate synaptic transmission and intracellular transport in neurons, and improving behavioral performance.

Chronic Visual GENUS Entrains Low gamma Oscillations and Increases Gamma Coherence Across Brain Regions We previously showed that acute one hour (1 h) of visual stimulation at 40 Hz entrained neural activity to oscillate in the gamma frequency range and reduced AD-related phenotypes in young, presymptomatic 3-month-old 5XFAD mice (Iaccarino et al., 2016). In the present disclosure, we demonstrated that GENUS significantly increased low gamma (~35-45 Hz) oscillatory power in CK-p25 and Tau P301S mouse models with neurodegeneration, across multiple parts of the brain—including visual cortex (V1), hippocampal CA1, somatosensory cortex (SS1), and prefrontal cortex (PFC)—despite the severe AD-like pathologies and loss of neurons. Locomotor activity can be a confounding factor in the detection of gamma oscillations, although we detected no difference in the velocity nor total distance travelled during the recording session between occluded and visible 40 Hz visual stimulation, making it unlikely that the low gamma entrainment we observed during GENUS is related to differences in activity levels. Moreover, analysis of single unit recordings in CA1 showed that GENUS is capable of recruiting neuronal activation in multiple brain regions downstream from V1 (see also Martorell and Paulson et al., accompanying submission) and measures of weighted phase lag index (WPLI), which is less susceptible to volume conductance from uncorrelated noise sources, illustrate that V1, CA1, SS1, and PFC show enhanced low gamma coherence to become more functionally coupled with GENUS. This is significant given that 'communication through coherence (CTC)' has been suggested to be essential for cognitive function (Fries, 2015), and not surprisingly that human AD subjects show defects in inter-cortical area coherence (Stam et al., 2009).

Visual GENUS Confers Broad Neuroprotection Across Multiple Neurodegeneration Mouse Models To determine if chronic application of GENUS could affect pathology in broader brain regions, we focused on visual cortex and other key structures of the default mode network, such as the hippocampus and cingulate part of the prefrontal cortex (PFC), which are highly affected in AD. We first applied GENUS for seven days in older 5XFAD mice and found that, as in Iaccarino et al. (2016), although amyloid plaques were significantly reduced in V1, it failed to alter amyloid levels in the hippocampus (FIG. 2A, 2B).

Thus, we extended the GENUS regime for 3 weeks using relatively older 5XFAD mice (10-month old) that have severe pathology, and show that amyloid plaque load was significantly ameliorated in not only V1, but also in other distributed parts of the brain including SS1, hippocampus and PFC. We applied this extended GENUS regime for the entirety of the 6 weeks of p25 induction in the CK-p25 model, and for 3 weeks in Tau P301S and 5XFAD mice at the age when neuronal loss begins in these respective models. We found significant reductions in their respective pathologies—including, hyper phosphorylated tau, synaptic and neuronal loss, and DNA damage—that was not just restricted to V1, but also evident in CA1, SS1, and CC (cingulate part of the prefrontal cortex) across the CK-p25, Tau P301S, and 5XFAD mouse models. The neuroprotective effects of GENUS to prevent neuronal loss was especially evident in the CK-p25 mouse model that normally exhibits dramatic brain atrophy, cortical volume shrinkage, and corresponding ventricle expansion that is associated with human AD when neurons and their extended processes degenerate. Thus, we demonstrate that GENUS confers broad neuroprotective effects across multiple mouse models with differing pathological features.

Visual GENUS Modifies Synaptic Function, Intracellular Transport, and Behavior

To examine the impact of GENUS at the molecular level, we next turned to unbiased transcriptomic and proteomic analysis. Our data from isolated/purified Tau P301S and CK-p25 neurons demonstrated a marked dysregulation of multiple genes, proteins, and post-translationally modified proteins that regulate synaptic functions, consistent with the altered neuronal excitability and excitatory/inhibitory balance that has been previously reported in these neurodegeneration models (Fischer et al., 2005; Yoshiyama et al., 2007). AD is also known to cause reduced dendritic spine density and it has been shown that increasing spine density in AD mice by either genetic manipulation, pharmacological inhibition of histone deacetylases (HDACs), or optogenetics alleviates cognitive impairments (Fischer et al., 2007; Graff et al., 2012; Roy et al., 2016). Moreover, we found that chronic visual GENUS alleviated these gene expression and protein phosphorylation defects across CK-p25 and Tau P301S models, and immunohistochemical analysis with markers specific to synaptic proteins (vGlut1, bassoon) confirmed synaptic density comparable to respective control mice. These gene expression changes and rescue of synaptic density, together with the enhanced low gamma coherence we see with chronic visual GENUS, suggest that chronic GENUS modifies the plasticity in the visual cortex and the downstream brain regions.

Study of post-mortem human AD samples, AD mice, iPSC models and primary cultured cells have also implicated the disruption of intracellular transport, vesicle trafficking, and endosomal functions in AD (Millecamps and Julien, 2013; Small et al., 2017; Israel et al., 2012; Cataldo et al., 2000). The link between endocytosis and Aβ production is well documented by many studies (Marks and McMahon, 1998; Cirrito et al., 2008; Schobel et a., 2008; Wu and Yao, 2009). Our unbiased transcriptomic and proteomic data show that chronic GENUS invokes changes to these intracellular transport, vesicle trafficking and endocytosis processes at the gene expression and post-translational modification of protein levels. Our findings are consistent with the reduction of enlarged early endosomes in CA1 of young 5XFAD mice following acute optogenetically-driven gamma oscillations (Iaccarino et al., 2016). Moreover, our data show that chronic GENUS reduced the S774 dynamin 1 hyper-phosphorylation, which impacts the role of dynamin in endocytosis (Raimondi et al., 2011; Armbruster et al., 2013), in both P301S and CK-p25 mouse models of neurodegeneration.

Taken together, we show that enhanced neuronal survival by chronic GENUS is most likely aided by the rescue (or "repair") of a wide range of genes and proteins involved in regulating DNA damage response, autophagy, synaptic transmission, intracellular transport, vesicle trafficking and reduced neuroinflammation. Supporting the broad neuroprotective effects of chronic visual GENUS to promote neuronal survival and maintain neuronal function, we find improvements in behavioral performance in multiple mouse models after chronic GENUS, including improved novel object recognition and spatial Morris water maze in CK-p25 mice and enhanced spatial water maze learning and memory in Tau P301S mice and 5XFAD mice. While we observed improved behavioral performance, chronic GENUS did not alter body weights (FIG. 11D-11F), anxiety by open field exploration, nor stress response as assayed by the marker corticosterone, in C57Bl/6J, CK-p25, and P301S mice (FIG. 11A, 11C, 11G-11I). Interestingly, Zhang et al., (2015) demonstrated that while chronic 2 Hz visual stimulation (6 h per day for 4 weeks) improved cognitive performance, it did not alter Aβ1-42 in the cingulate cortex in 3×Tg mice.

Visual GENUS Reduces Neuroinflammation

Inflammatory processes are noted to play a crucial role in AD and in neurodegeneration, and acute GENUS was previously shown to induce a striking morphological activation of microglia (Iaccarino et al., 2016). The specific role of microglia in neurodegeneration is complex (as it can be beneficial or detrimental) and remains to be thoroughly investigated, and recent studies revealed that microglia phenotypes can morph as disease progresses (Mathys et al., 2017; Lee et al., 2018; Ulland et al., 2017; Deczkowska et al., 2018). In the present disclosure, we carried out a detailed morphological analysis with immunohistochemistry and microglia-specific transcriptomic analysis to more closely examine the underlying processes affected by chronic GENUS. We found that, although chronic GENUS modifies microglia morphology, immune response, and catabolic processes across both CK-p25 and Tau P301S mouse models, there is a range of morphological phenotypes.

First, Iba1 immunostaining reveal that in CK-p25 mice microglia are very proliferative (more microglia; consistent with Mathys et al. (2017) and tend to clump together, which are reduced after chronic GENUS. The total volume of the processes of microglia is reduced, with an exception of subset of rod-like microglia whose total soma and primary process volume was higher in non-stimulated CK-p25 mice, with the chronic GENUS reduces these aberrant microglia phenotype. Intriguingly, rod-shaped microglia was recently reported to be present in diffuse brain injured rat brain, and in human subjects with traumatic brain injury (Bachstetter et al., 2017; Taylor et al., 2014). Next, microglia enter a phagocytic state to uptake Aβ in 5XFAD mice, this occurs for several modalities of GENUS (visual, auditory or a combination of both), with morphological changes in microglia correlating with a reduced amyloid plaque count (Iaccarino et al., 2016; Martorell and Paulson et al., accompanying submission). Furthermore, the phagocytic state of microglia is accompanied with an increased protein degradation (protein catabolic processes as identified by GO). The inflammatory response of microglia has recently been investigated in the context of neurodegeneration and AD. Our data suggest that chronic GENUS reduced the inflammatory response of microglia in CK-p25 mice, downregulating genes such as those involved in adaptive immune system and MHC class II, which are known to be upregulated in neurodegeneration (Mathys et al., 2017). Perhaps as a result of this reduced inflammatory response, we see a reduction in a marker of synaptic pruning, C1q (Hong et al., 2016), concurrent with increase in synaptic markers vGlut1 and bassoon which illustrate a preservation of synaptic density with chronic GENUS. It is important to note that in accompanying paper Martorell and Paulson et al., demonstrate astrocytes response, and vasculature changes after chronic auditory GENUS and combined auditory and visual GENUS.

In sum, our data demonstrate that visual GENUS can propagate to multiple regions (SS1, CA1, PFC) in the forebrain and elicit response from multiple cell types (neurons, microglia, astrocytes). Gamma entrainment using visual stimuli represents a non-invasive strategy for providing protective effects and improving cognitive function against neurological disorders. We found that chronic visual GENUS reduced the loss of neurons and synapses, and modified genes and proteins associated with synaptic function that, together, supports the behavioral improvements we observed. The present disclosure demonstrates the neuroprotective effect of chronic visual GENUS in AD mouse models to affect AD pathology in multiple brain regions and behavior, indicating the overall efficacy of GENUS to confer neuroprotection.

DETAILED DESCRIPTIONS OF FIGURES

FIGS. 1A through 1J illustrate that visual stimulation entrains gamma oscillations in multiple brain regions of a subject beyond the visual cortex, according to the inventive concepts disclosed.

Figure 40:
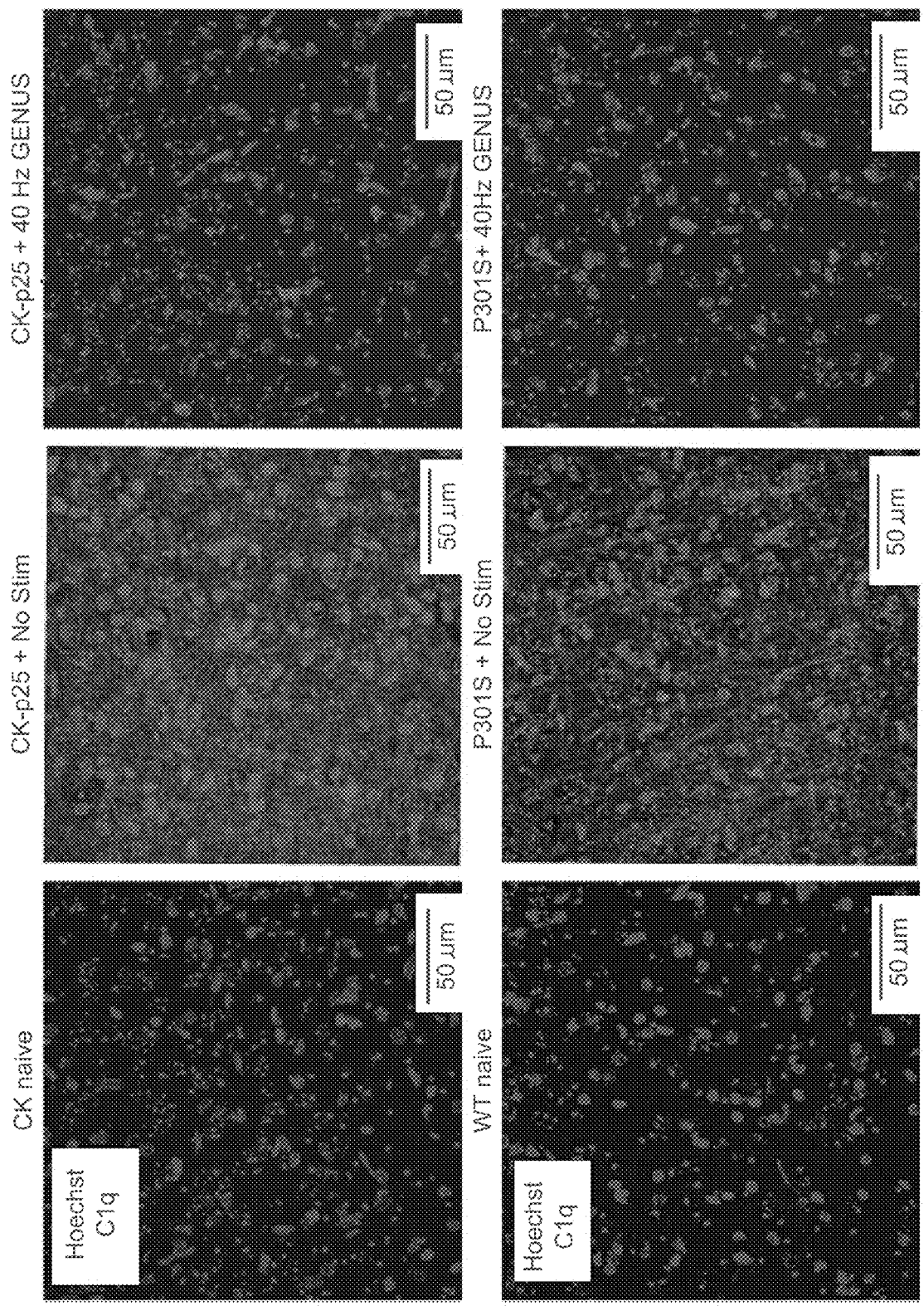

In FIG. 1A, 40 Hz visual stimulation with 50% duty cycle (12.5 ms lights on and 12.5 ms lights off) was delivered using an Arduino system. C57BL/6J mice received either no stimulation or 40 Hz visual stimulation for a 1 h period, after which they were sacrificed and brains stained for c-Fos expression. Microdrives were implanted in a separate cohort for in vivo electrophysiology.

In FIG. 1B, c-Fos expression was quantified in 40 μm thick coronal brain slices to assess neuronal activity. Representative c-Fos immunostaining images. Scale bar represents 50 μm. Right: 40 Hz visual stimulation significantly increased neuronal activity marker c-Fos in the visual cortex (V1; N=4 mice/group. Independent samples t-test, T=−7.110, P=0.002), somatosensory cortex (SS1; T=−5.239, P=0.006), hippocampus (CA1; T=−4.989, P=0.008) and prefrontal cortex (CC; T=−2.938, P=0.01) compared to non-stimulated mice.

Figure 1C:
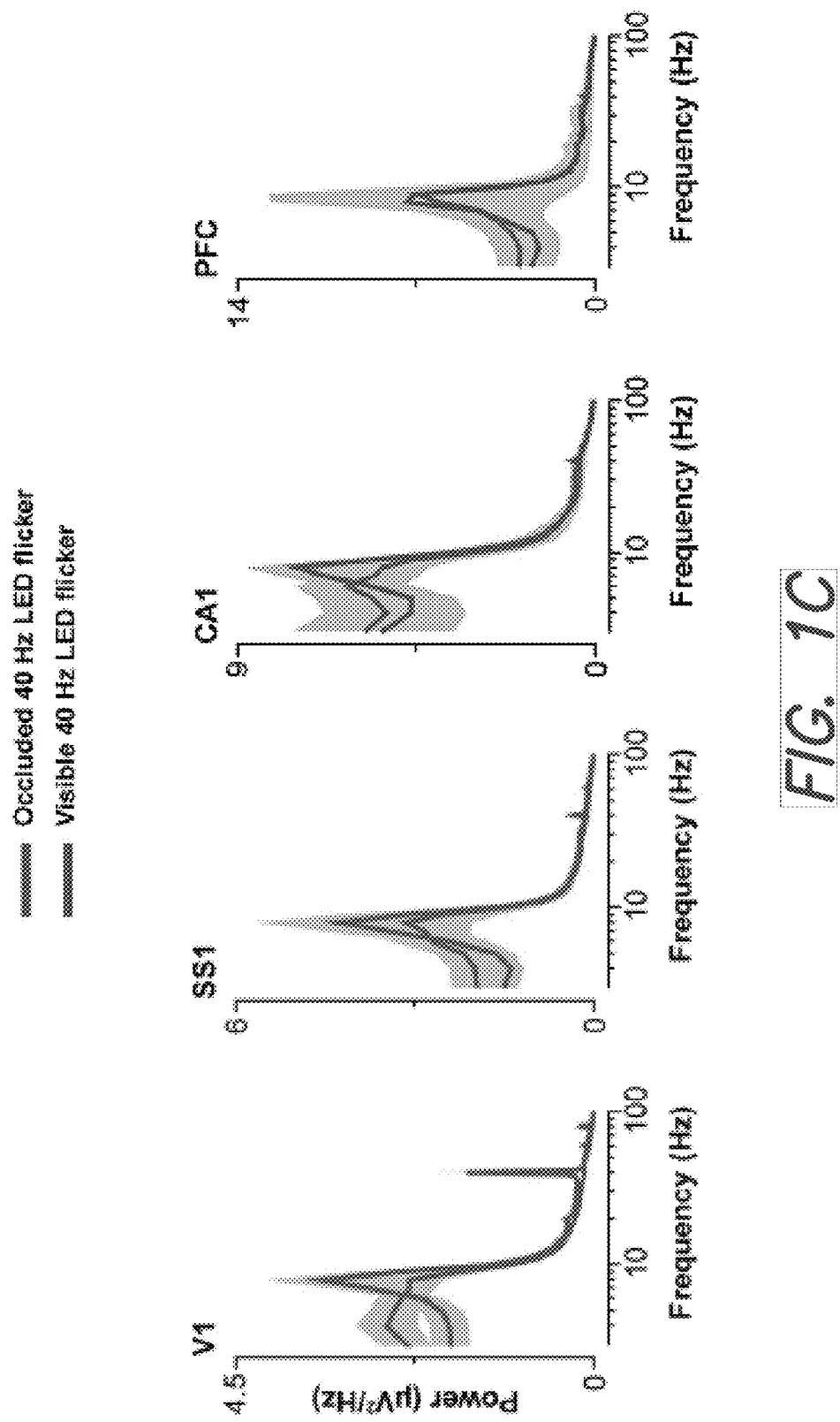

In FIG. 1C, power spectra from C57BL/6J mice LFPs were recorded from V1, SS1, CA1 and PFC. Red line indicates recording during visible 40 Hz visual stimulation presentation, whereas blue line indicates occluded 40 Hz light flicker (LED array was covered to occlude light; see methods; N=7 mice).

Figure 1D:
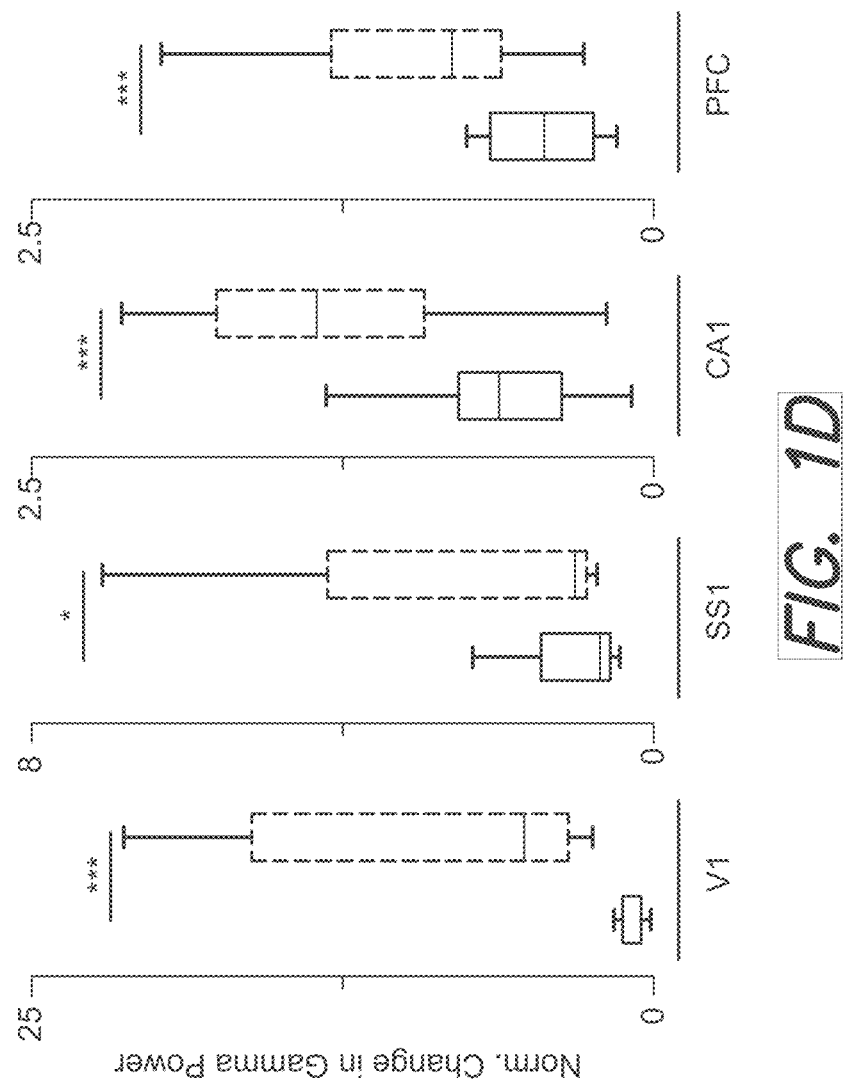
Figure 1E:
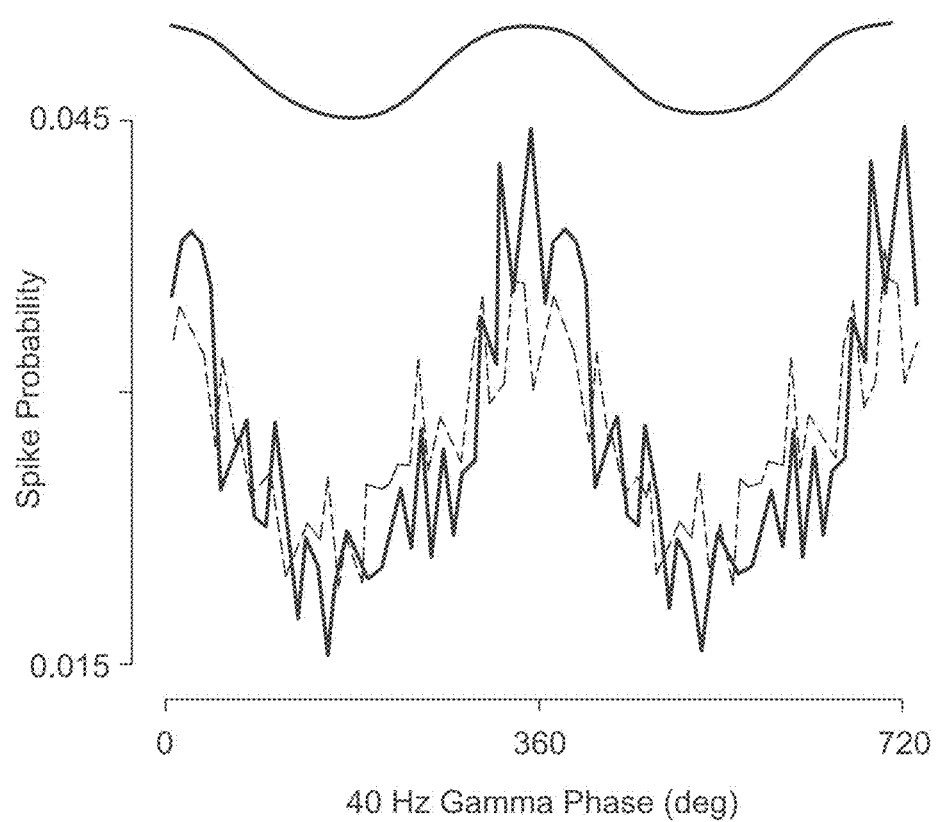

In FIG. 1D, group gamma area power (40±5 Hz) was calculated from FIG. 1C. 40 Hz visual stimulation significantly increased gamma power across V1 (Wilcoxon-Ranksum, $Z=5.9$, $P=3.1\times10^{-9}$), SS1 ($Z=2.4$, $P=0.018$), CA1 ($Z=3.4$, $P=6.9\times10^{-4}$), and PFC ($Z=3.3$, $P=9.2\times10^{-4}$) compared to control condition (LED flicker is occluded).

In FIG. 1E, we implanted custom-made tetrode microdrive in C57BL/6J mice, tetrodes were adjusted to CA1 and single units were isolated. Chart shows the spike probability across 40 Hz phase in light occluded and 40 Hz stimulation periods.

Figure 1F:
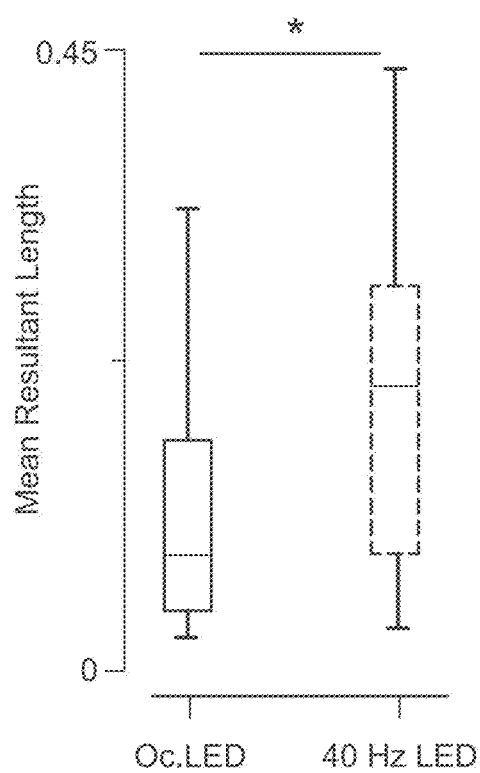
Figure 1G:
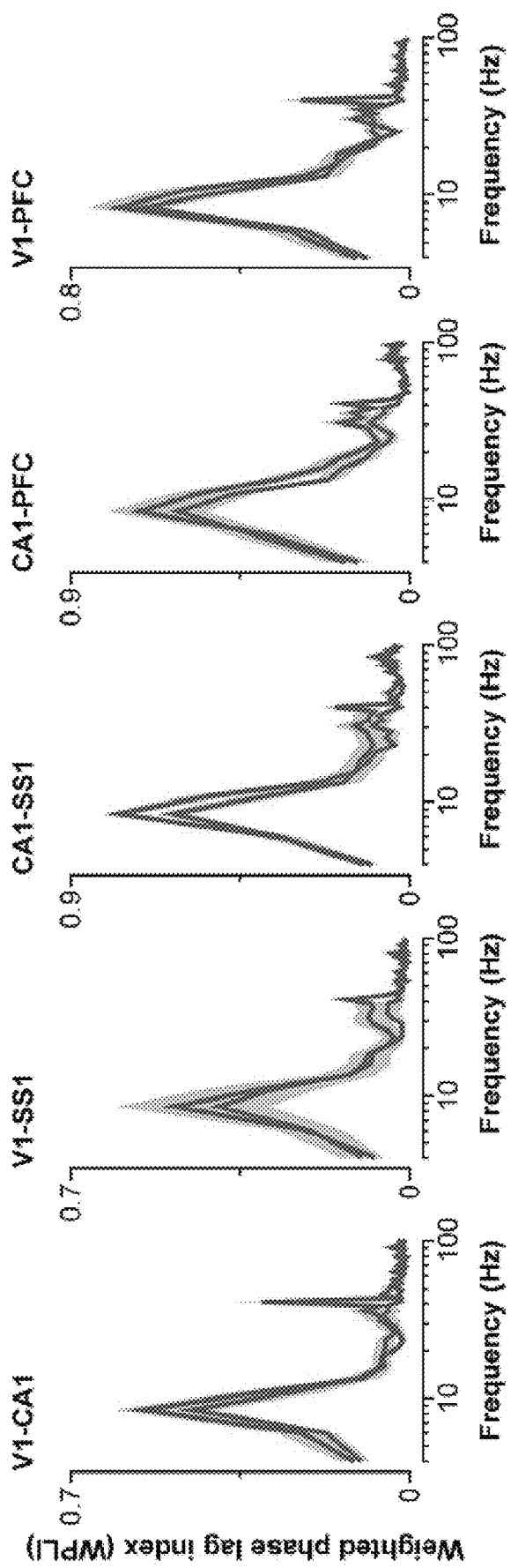

In FIG. 1F, 40 Hz visual stimulation is shown to significantly increase phase locking strength of pyramidal neuronal spikes to local LFP as analyzed by the mean resultant length (MRL) (N=24 cells from 4 mice. Wilcoxon-Ranksum, $Z=2.5$, $P=0.011$) compared to light occluded condition (Oc. LED).

In FIG. 1G, LFP coherence between structures was quantified using the weighted phase lag index method (WPLI; N=7 mice), recording sites are indicated.

In FIG. 1H, group changes in low gamma band (30-50 Hz) WPLI are illustrated, related to FIG. 1G. 40 Hz visual stimulation induced significant increases in coherence between V1-CA1 (Wilcoxon-Ranksum, $Z=2.2$, $P=0.03$), V1-SS1 ($P=0.021$) and V1-PFC ($Z=2.5$, $P=0.014$).

FIG. 1I is a schematic of 80 Hz LED light delivery with 50% duty cycle (6.25 ms lights on and 6.25 ms lights off).

FIG. 1J, on the left, shows power spectra of V1 LFP in C57B1/6J mice subjected to light occluded (Oc. LED) or 80 Hz visual stimulation. On the right, the area power centered on 80 Hz (±5 Hz) was not significantly different with 80 Hz visual stimulation (N=5 mice, Wilcoxon-Ranksum test, $Z=1.2$, $P=0.22$).

FIGS. 2A through 2F illustrate that chronic 40 Hz (but not 80 Hz) visual flicker stimulation reduces amyloid plaques beyond visual cortex in the subject, according to the inventive concepts disclosed.

FIG. 2A shows amyloid plaque load in 5XFAD mice exposed to either no stimulation, 40 Hz or 80 Hz visual stimulation 1 h per day for 7 days, as visualized by immunohistochemistry staining of the D54D2 antibody. Representative images from V1, SS1 and CA1 in each condition, scale bar represents 50 μm.

FIG. 2B illustrates group quantification showing that GENUS 1 h per day for 7 days reduced amyloid plaques in V1, but it did not significantly alter amyloid plaques in SS1 or hippocampal area CA1. 80 Hz visual stimulation exposure did not alter levels of amyloid plaques in V1 or CA1, whereas it significantly increased amyloid plaques in the SS1. N=8 non-stimulated, and 6 mice each from 40 Hz and 80 Hz group. Two-way ANOVA between groups effect $F(2, 51)=5.378$, $P=0.0076$. Bonferroni's post-hoc multiple comparisons, *** $P<0.001$, * $P<0.05$.

FIG. 2C shows representative images of amyloid plaque load in 5XFAD mice exposed to either no stimulation or an extended GENUS protocol of 22 days (1 hour per day). Scale bars represent 50 μm.

Figure 2D:
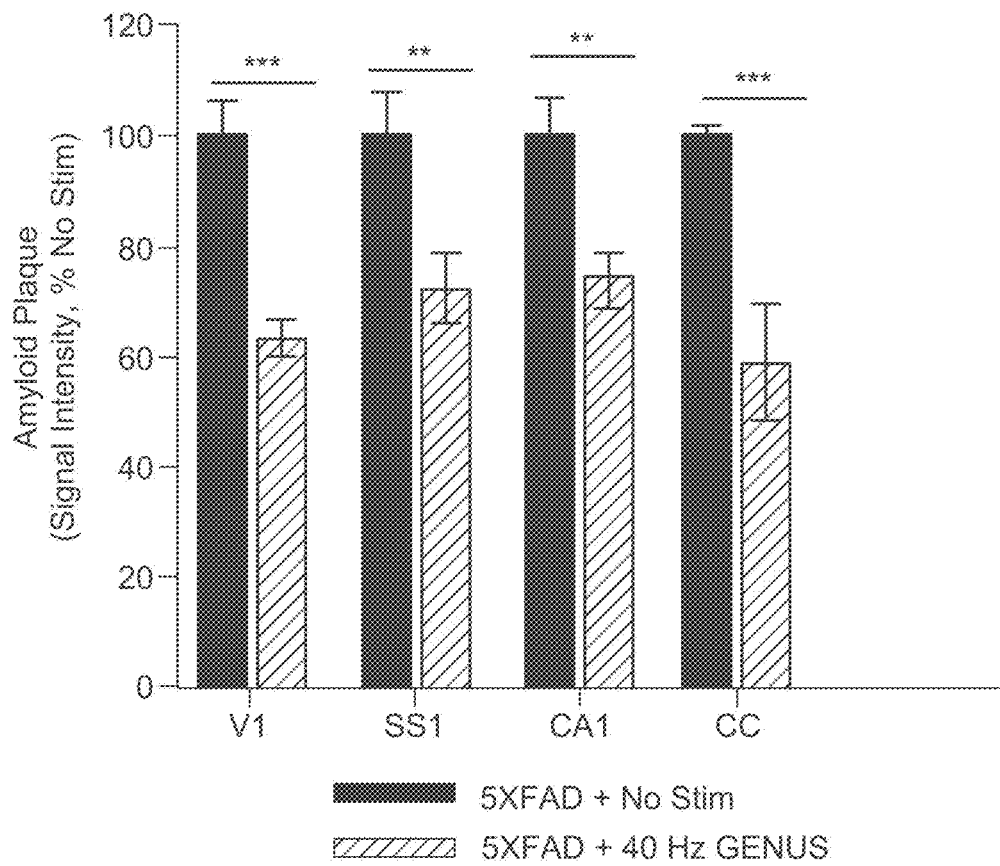
Figure 2E:
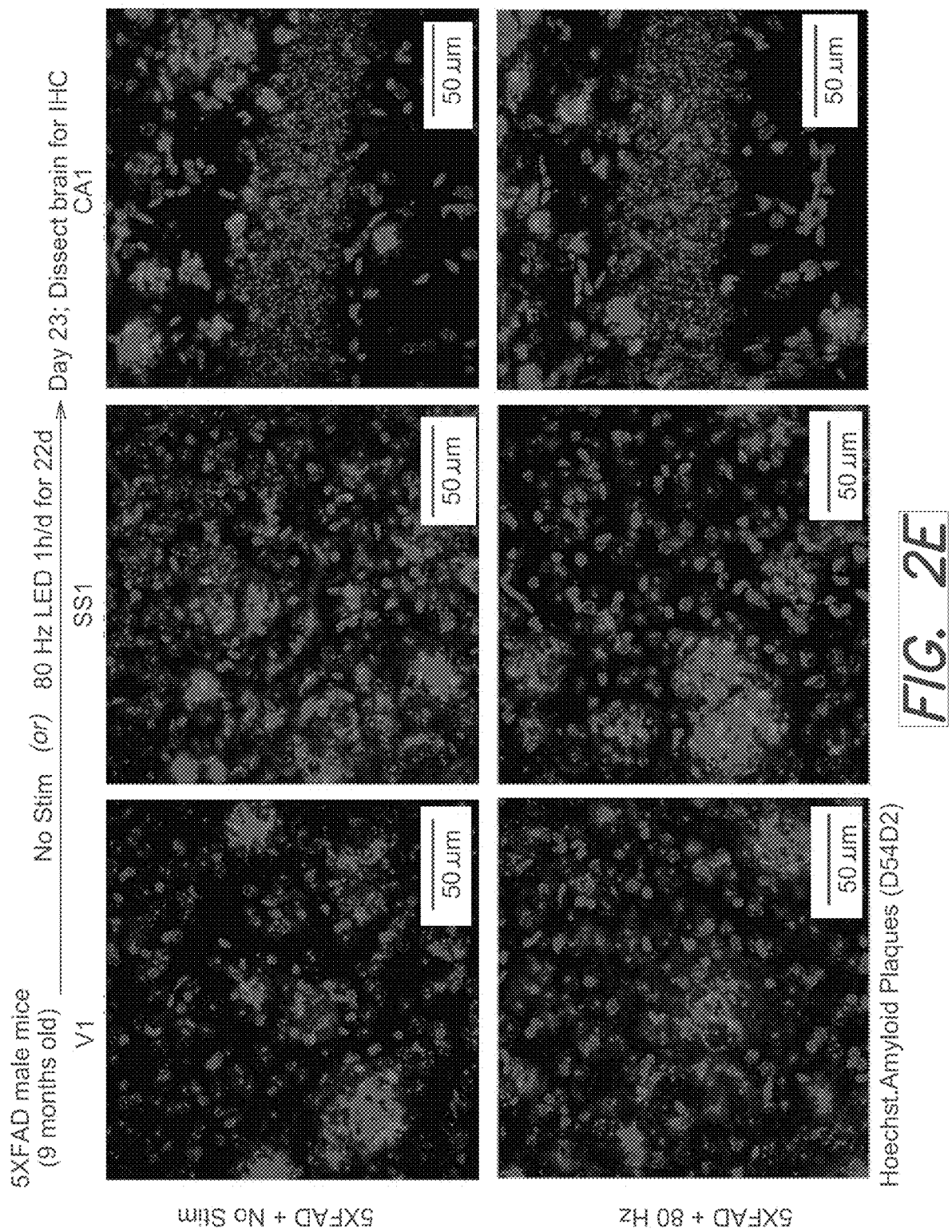
Figure 2F:
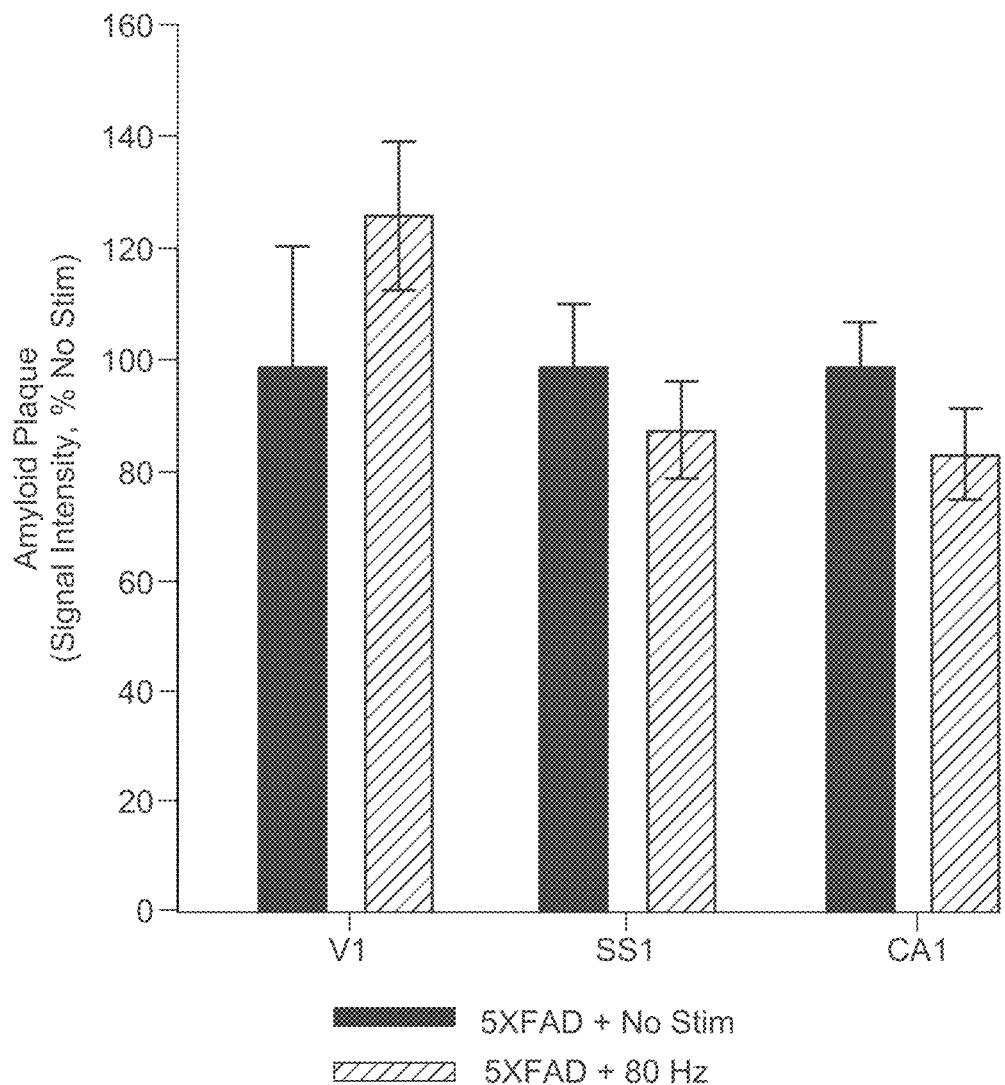

FIG. 2D shows that 22 days of GENUS significantly reduced amyloid plaques in V1, SS1, CA1 and CC. N=6 mice per condition. Two-way ANOVA between groups effect F (1, 40)=51.00, P<0.0001. Bonferroni's multiple comparisons test, * P<0.001,  P≤0.01.

FIG. 2E shows representative images of amyloid plaques in V1, SS1 and CA1 visualized from mice exposed to no stimulation or 80 Hz light flicker for 1 h per day for 22 days, scale bar represents 50 μm.

FIG. 2F is related to FIG. 2E, showing group data quantifying amyloid plaques in V1, SS1 and CA1 N=6 mice per group. No significant differences between groups were found in two-way ANOVA measures F (1, 30)=0.0033, P=0.9565.

FIGS. 3A through 3J illustrate that chronic visual stimulation ameliorates Alzheimer's Disease-associated pathology and significantly reduces or prevents neurodegeneration in a subject, according to the inventive concepts disclosed.

FIG. 3A provides an experiment outline showing that P301S mice were subjected to no stimulation or GENUS for 22 days (1 h per day) followed by immunohistochemical and phosphoproteomics analyses. WT cage littermates that did not undergo stimulation regimen were considered WT naïve mice.

FIG. 3B provides representative images showing S202/T205 phosphorylated tau immunostaining from visual cortex. Scale bar 50 μm. Right: P301S tau mice exhibited higher S202/T205 levels in V1, SS1, CA1 and CC, whereas 22 days of GENUS significantly reduced S202/T205 in all areas examined. N=7 WT naïve, 8 non-stimulated P301S mice and 7 GENUS stimulated P301S mice. Two-way ANOVA between group effect F (2, 76)=45.35, P<0.0001. Post-hoc multiple comparisons with Bonferroni's correction, ** P<0.0001, * P<0.001, ** P<0.01, * P<0.05.

FIG. 3C illustrates phosphoproteomic analysis of Serine/Threonine phosphorylated tau protein from visual cortex. Heat-map displays S/T residues of tau protein that were differentially phosphorylated in P301S compared to WT mice. Two-way ANOVA between groups effect F (2, 322)= 2146, P<0.0001. All phosphopeptides were mapped as described in the methods. All S/T residues of tau shown in the heat-map were statistically significant between WT naïve and non-stimulated P301S. Statistical comparison (P values) between non-stimulated and GENUS stimulated P301S mice for specific residues are shown in the chart. GENUS reduced phosphorylation in the tau protein at 6 S/T sites and increased phosphorylation at S451. Commonly known human tau S/T sites are shown on top.

FIG. 3D shows representative images for the neuronal marker NeuN in visual cortex from WT naïve and P301S mice that underwent no-stimulation or GENUS. Scale bar represents 50 μm.

FIG. 3E shows group data indicating P301S mice showed significant loss of neurons in V1, SS1, CA1 and CC compared to WT naïve mice. GENUS stimulated P301S group showed significantly reduced neurodegeneration. N=same as in FIG. 3B. Two-way ANOVA between groups effect F (2, 76)=19.73, P<0.0001. Post-hoc multiple comparisons with Bonferroni's correction, * P<0.001,  P<0.01, * P<0.05.

FIG. 3F provides and experimental overview showing induction of p25 expression in CK-p25 mice for 42 days. This was accompanied by GENUS for 1 h per day in one experimental group, the non-stimulation control group received room light. CK (CaMK2α-promoterxtTA) cage littermates that did not undergo stimulation regimen were considered CK naïve mice.

FIG. 3G is a photomicrograph showing qualitative differences in brains between CK-naive, non-stimulated and GENUS stimulated CK-p25 mice, 42 days post induction. Right: CK-p25 mice exhibited reduced brain weight (i.e. brain atrophy) compared to CK naïve mice, whereas chronic GENUS partially alleviated brain atrophy in CK-p25 mice. N=13 CK naïve mice, 10 mice each for non-stimulated and GENUS CK-p25 groups. ANOVA F (2, 30)=15.46, P<0.001. Post-hoc multiple comparisons with Bonferroni's correction, **** P<0.0001, * P<0.05.

FIG. 3H provides representative images and size quantification of the lateral ventricles (outlined), scale bar represents 1000 μm. Right: compared to CK naïve mice, CK-p25 mice exhibited aberrant ventricles expansion, which was significantly reduced after chronic GENUS. N=9 CK naïve mice and 6 mice from each of the non-stimulated and GENUS CK-p25 group. ANOVA F (2, 18)=12.36, P<0.001. Post-hoc multiple comparisons with Bonferroni's correction, **** P<0.0001, * P<0.05. See also FIG. 9E.

FIG. 3I provides representative images for the neuronal marker NeuN in visual cortex from CK naïve and CK-p25 mice that underwent no-stimulation or GENUS. Scale bar represents 50 μm.

FIG. 3J shows that CK-p25 mice exhibited severe neuronal loss in V1, SS1, CA1 and CC, whereas chronic GENUS reduced the loss of neurons in CK-p25 mice. N=same as in FIG. 3G. Two-way ANOVA F (2, 72)=31.38, P<0.0001. Post-hoc multiple comparisons with Bonferroni's correction ** P<0.001, * P<0.001, ** P<0.01, * P<0.05.

FIGS. 4A through 4Q illustrate that chronic visual sitmulation reduces inflammatory response in microglia of a subject, according to the inventive concepts disclosed.

FIG. 4A relates to CK-p25 mice that were subjected to no stimulation or GENUS 1 h per day for 42 days. Microglia from visual cortex were then isolated using the fluorescence activated cell sorting (FACS; using a CD11b and CD45 double positive criteria) after which RNA was extracted and sequenced. Differentially expressed genes (DEGs) are shown in volcano plots. Group comparisons are shown to the bottom. Left: DEGs between CK naïve and non-stimulated CK-p25 mice, N=4 mice per group. Right: DEGs between non-stimulated and GENUS CK-p25 mice, N=4 mice group.

FIG. 4B shows selected gene ontology (GO) terms for biological processes associated with the identified DEGs. Top: GO terms associated with the upregulated (UP) genes in non-stimulated CK-p25 mice compared to CK naïve mice. Bottom: GO terms associated with the downregulated (DOWN) in non-stimulated CK-p25 mice compared to CK naïve mice.

FIG. 4C shows selected GO terms associated with DEGs. Top: GO terms associated with the upregulated (UP) genes in GENUS CK-p25 mice compared to non-stimulated CK-p25 mice. Bottom: GO terms associated with the down-regulated (DOWN) in GENUS CK-p25 mice compared to non-stimulated CK-p25 mice.

FIG. 4D provides representative images showing microglia marker Iba1 (green) and CD40 (red) immunostaining from visual cortex. Scale bar 50 μm. N=7 CK naïve mice, 6 mice each for non-stimulated and GENUS groups. Arrow and arrowhead indicate rod-shaped ramified processes and branch volume of microglia processes respectively.

FIG. 4E shows that non-stimulated CK-p25 mice exhibited higher number of Iba1 positive cells compared to CK naïve mice, chronic GENUS significantly reduced Iba1 cell density in CK-p25 mice. ANOVA F (2, 16)=17.79, P<0.0001.

Figure 4F:
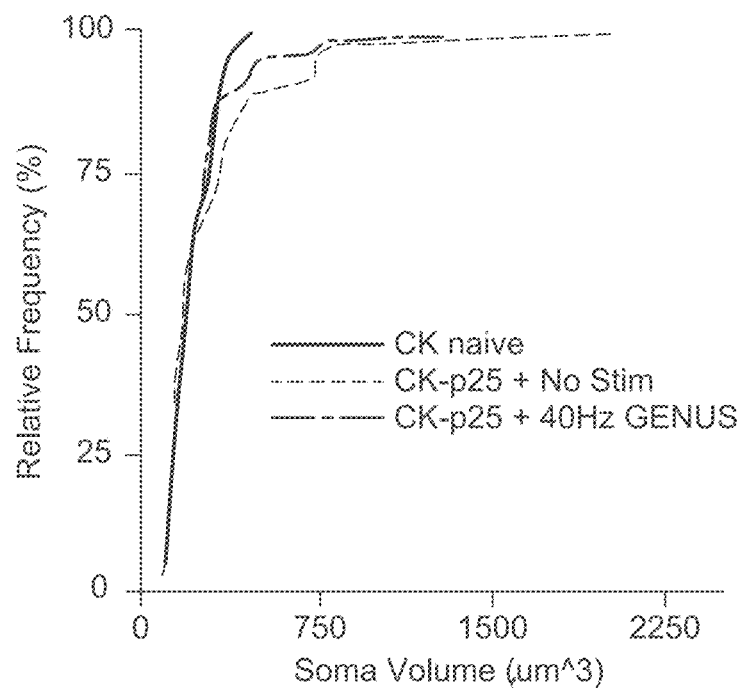
Figure 4G:
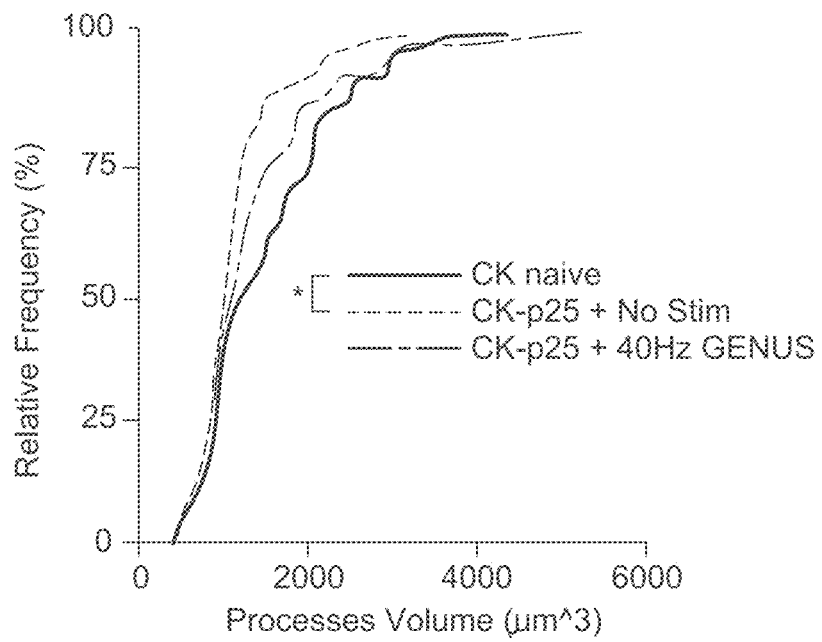
Figure 4H:
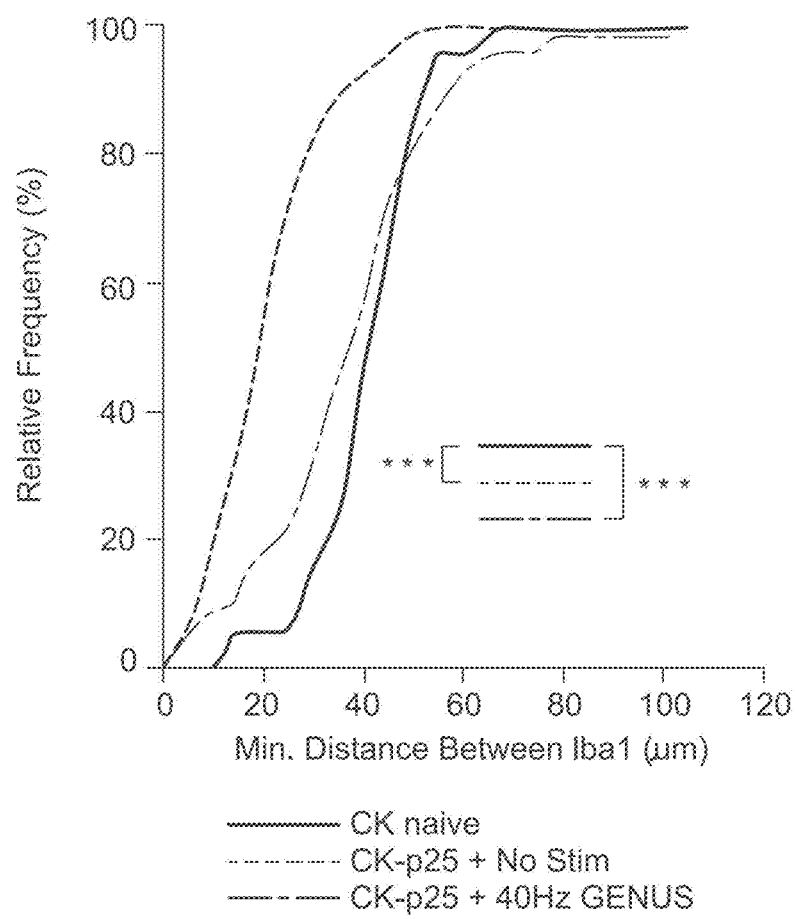
Figure 4I:
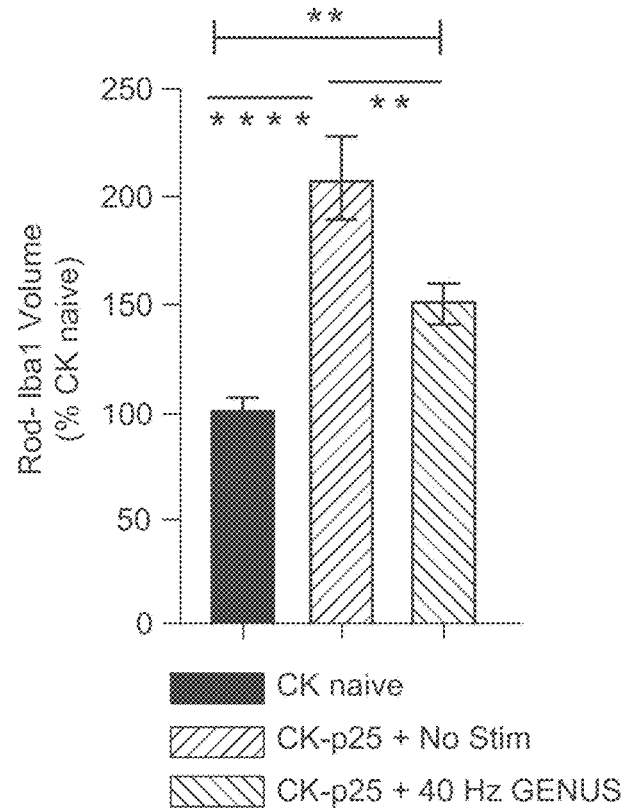
Figure 4J:
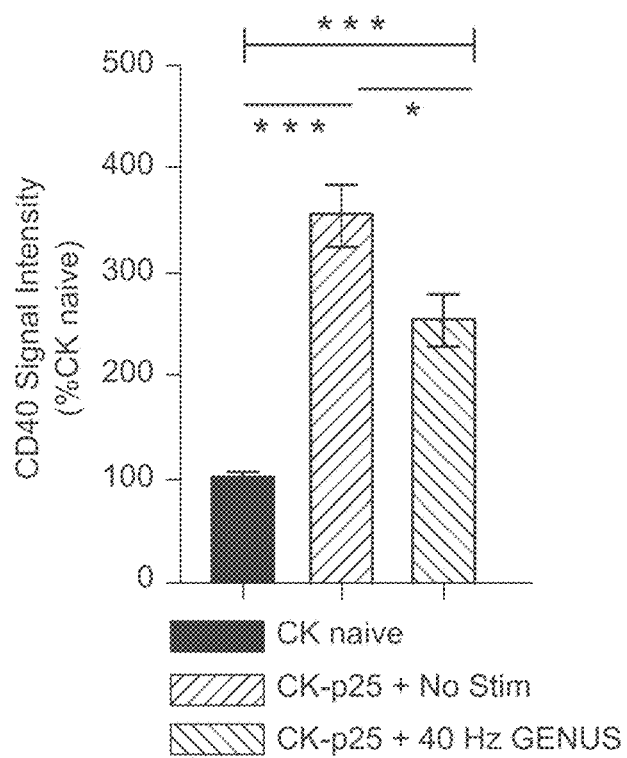
Figure 4K:
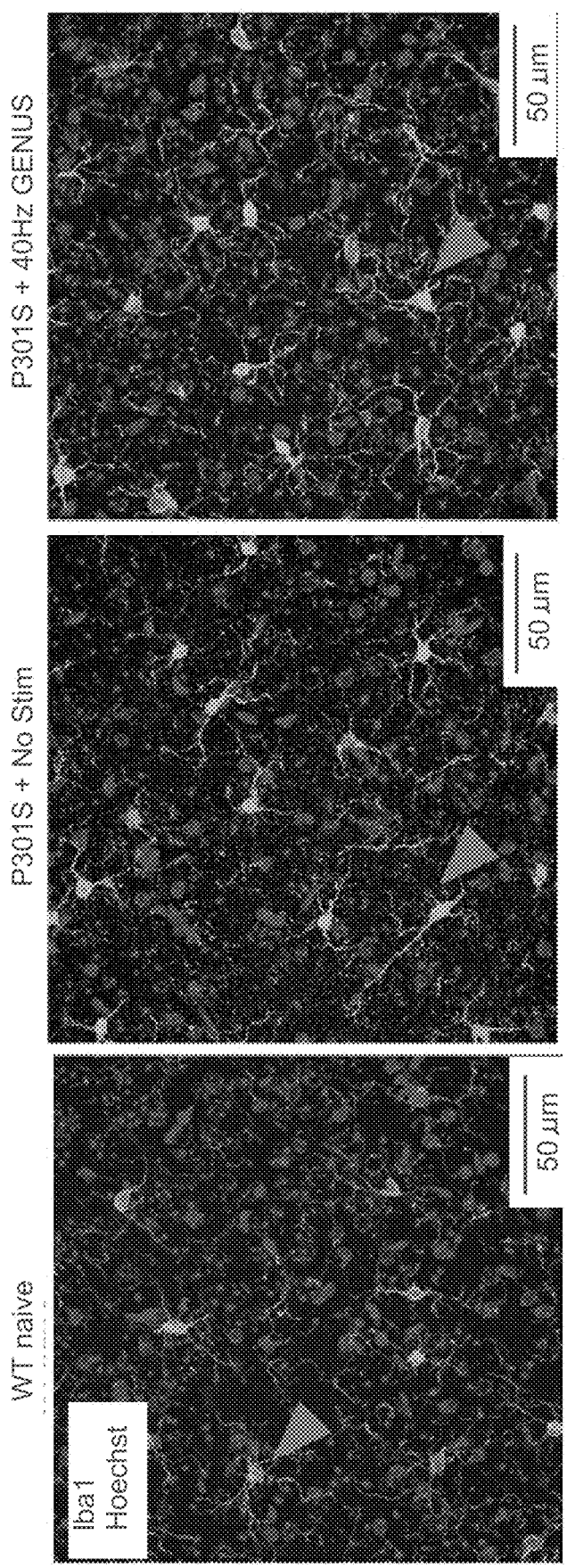
Figure 4L:
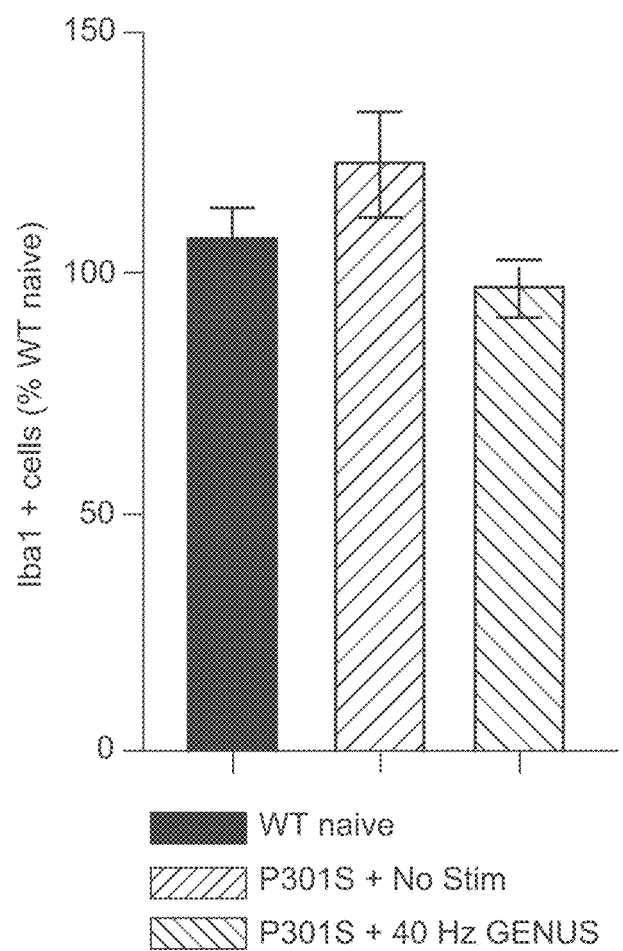
Figure 4M:
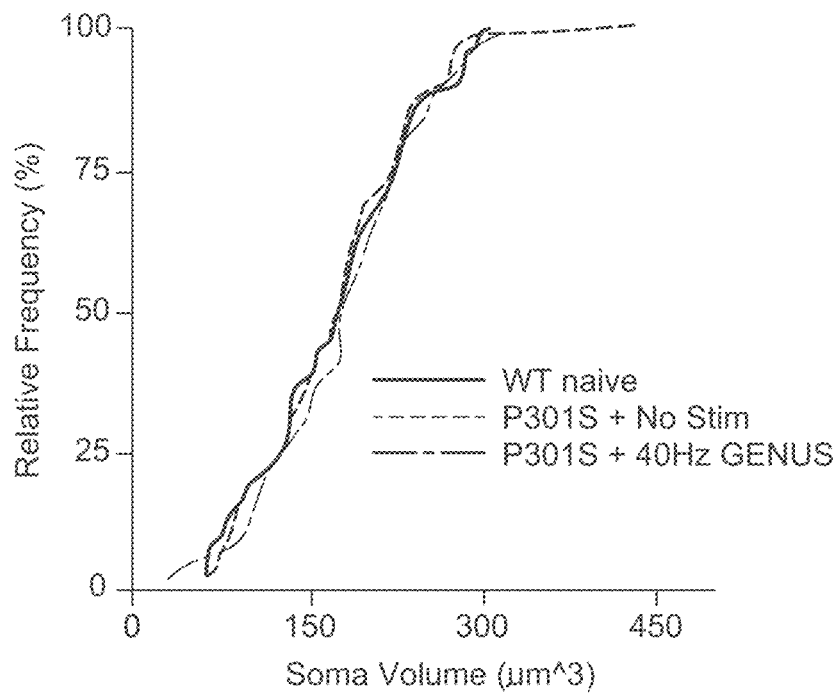
Figure 4N:
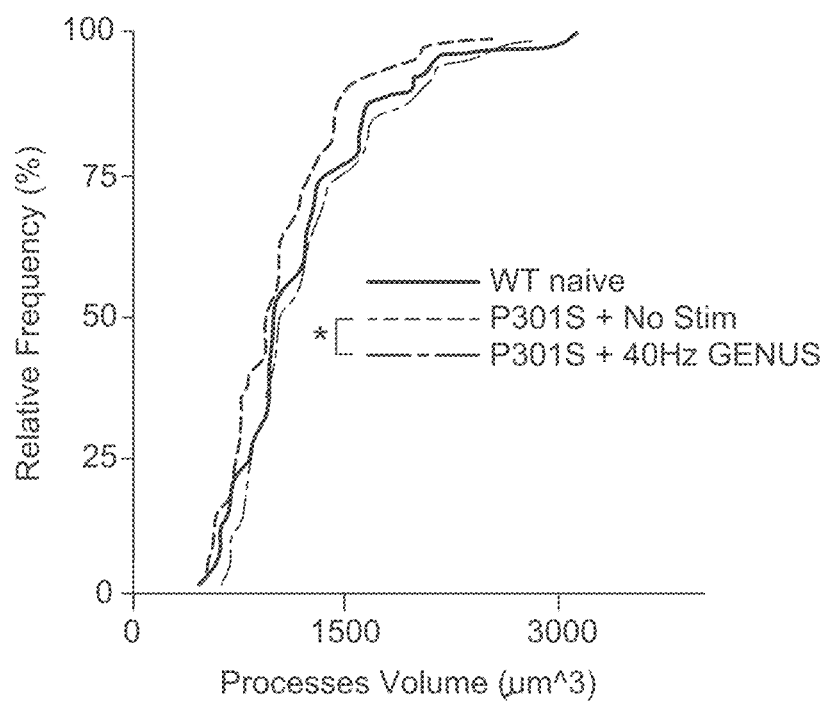

In FIG. 4F, we performed three-dimensional rendering of microglia using Imaris and quantified the volume of soma and processes of microglia. N=73 microglia per group from the same number of mice as in FIG. 4D. The frequency distribution of the volume (size) of microglia soma, which did not show any statistical significance between groups (Kruskal-Wallis test, H=0.3529, P=0.8382).

FIG. 4G shows the overall volume of microglia processes (excluding rod like microglia) was significantly lower in non-stimulated CK-p25 mice compared to CK naïve mice. GENUS stimulated CK-p25 mice did not show difference compared to CK naïve mice (H=9.224, P=0.009).

FIG. 4H illustrates quantification of minimum distance between microglia. N=68 microglia from 9 CK naïve, 131 microglia from 6 non-stimulated and 95 microglia from 6 GENUS CK-p25 mice. Microglia in non-stimulated CK-p25 mice aggregated together compared to CK naïve mice, whereas GENUS significantly reduced microglia aggregation (H=100.1, P<0.0001).

FIG. 4I illustrates quantification of radial primary processes of rod like microglia. N=16 microglia from 9 CK naïve, 19 microglia per group from 6 mice each from non-stimulated and GENUS CK-p25 group. The overall volume of processes of rod like microglia was significantly reduced after GENUS in CK-p25 mice compared to non-stimulated CK-p25 mice. ANOVA F (2, 51)=16.27, P<0.0001.

FIG. 4J shows that non-stimulated CK-p25 mice exhibited higher signal intensity of interferon response protein CD40 compared to CK naïve mice, whereas chronic GENUS significantly reduced CD40 signal in CK-p25 mice. ANOVA F (2, 16)=36.84, P<0.0001.

FIG. 4K provides representative images from visual cortex showing Iba1 in green and nuclear stain Hoechst in blue. Scale bar 50 µm. Arrowhead indicates the complexity of microglia processes.

FIG. 4L illustrates that P301S tau mice showed a trend towards increased total number of Iba1 positive cells but was not statistically significant compared to WT mice. N=7 WT naïve, 8 non-stimulated P301S mice and 7 GENUS mice. ANOVA F(2,19)=2.401, P=0.1190.

FIG. 4M is a frequency distribution chart showing the size of microglia soma. N=7 WT naïve, 8 non-stimulated P301S mice and 7 GENUS mice. A total of 58 microglia per group was analyzed. The overall volume of microglia soma did not differ between groups. Kruskal Wallis test H=0.04269, P=0.9789.

FIG. 4N shows that the volume of the processes of microglia was smaller in P301S tau mice compared to WT mice, whereas GENUS stimulated P301S mice showed similar process length to that of WT mice. Kruskal Wallis test H=7.895, P=0.0193.

FIG. 4O provides representative images showing C1q (classical complement pathway imitating protein) immunostaining from visual cortex. Scale bar 50 µm. Top: N=7 CK naïve mice, 6 mice each for non-stimulated and GENUS stimulated groups. Bottom: N=7 WT naïve, 8 non-stimulated P301S mice and 7 GENUS mice.

FIG. 4P shows that non-stimulated CK-p25 mice exhibited higher C1q signal intensity compared to CK naïve mice, whereas chronic GENUS stimulated CK-p25 mice showed significantly reduced C1q intensity. ANOVA F (2, 16)=13.39, P=0.0004.

FIG. 4Q shows that non-stimulated P301S mice exhibited higher C1q signal intensity compared to WT naïve mice, chronic GENUS did not differ between any groups. ANOVA F (2, 19)=6.887, P=0.005. Post-hoc multiple comparisons with Bonferroni's correction in E, I, J, L, P, Q ** P<0.0001,  P<0.01,* P<0.05, n.s—not significant.

FIGS. 5A through 5I illustrate that chronic visual stimulation modifies synaptic function and intracellular transport in neurons, according to the inventive concepts disclosed.

In FIG. 5A, CK-p25 mice were subjected to no stimulation or GENUS 1 h per day for 42 days. NeuN positive (100,000) nuclei of neurons from visual cortex were isolated using FACS followed by RNA extraction and sequencing. Heat-maps of the DEGs. Number of mice per group is indicated in the heat-maps. Top left: DEGs between CK naïve and non-stimulated CK-p25 mice. Bottom left: DEGs between non-stimulated and GENUS stimulated CK-p25 mice, number of genes is indicated on the right. Right: Chart showing the biological processes associated with the downregulated genes in non-stimulated CK-p25 mice compared to CK naïve mice, and the overlap of the same biological process associated with the upregulated genes after GENUS in CK-p25 mice.

In FIG. 5B, P301S mice were subjected to no stimulation or GENUS stimulation 1 h per day for 22 days. NeuN positive (100,000) nuclei of neurons from visual cortex were isolated using FACS followed by RNA extraction and sequencing. Heat-maps of the differentially expressed genes. Number of mice per group is indicated in the heat-maps. Top left: DEGs between WT naïve and non-stimulated P301S tau mice. Bottom left: DEGs between non-stimulated and GENUS stimulated P301S tau mice, number of genes is indicated on the right. Right: Chart showing the biological processes associated with the downregulated genes in non-stimulated P301S mice compared to CK naïve mice, and the overlap of the same biological process associated with the upregulated genes after GENUS stimulation in P301S mice.

In FIG. 5C, CK-p25 mice were subjected to no stimulation or GENUS for 42 days. Total protein expressions and S/T phosphorylated proteins analysis was performed on visual cortex tissue using TMT 10-plex kit and mass spectrometry. N=3 CK naïve, 3 non-stimulated CK-p25 and 4 GENUS stimulated CK-p25 mice. Top: Venn diagram showing the overlap of total RNAs identified from neuron specific RNA seq (FIG. 5B, above) and total proteins identified from LC-MS/MS. 92.73% of the proteins identified were found to be expressed in neurons. Bottom: Volcano plot of differentially S/T phosphorylated proteins in CK-p25 mice compared to the control littermates (left) and GENUS (right).

In FIG. 5D, P301S tau mice were subjected to no stimulation or GENUS stimulation for 22 days. Total protein expressions and S/T phosphorylated proteins analysis was performed on visual cortex tissue using tandem mass tag (TMT) 10-plex kit (see methods) and mass spectrometry (LC-MS/MS). N=3 WT naïve, 3 non-stimulated P301S and 4 GENUS stimulated P301S mice. Top: Venn diagram showing the overlap of total RNAs identified from neuron specific RNA seq (FIG. 5A, above) and total proteins identified from LC-MS/MS. 91.95% of the proteins identified were found to be expressed in neurons. Bottom: Volcano plots of differentially S/T phosphorylated proteins in P301S tau mice compared to the control littermates (left) and GENUS (right). Phosphorylated proteins with fold change of ±0.2 and adjusted P value of <0.05 were considered statistically significant.

FIG. 5E shows GO terms for the differentially S/T phosphorylated proteins in CK-p25 and P301S tau mice after chronic GENUS.

FIG. 5F shows representative images showing neurofilament heavy chain (NFH, a neuronal marker expressed primarily in axons) and Ser774 phosphorylated dynamin1 immunostaining from visual cortex. NFH was used to label neuronal processes. Scale bar 10 µm. N=7 CK naïve mice, 6 mice each for non-stimulated and GENUS stimulated groups. Middle: CK-p25 mice exhibited significantly higher levels of pS774-DNM1 signal intensity compared to CK naïve, whereas GENUS significantly reduced this aberrant phosphorylation in CK-p25 mice. $F (2, 16)=38.551$, $P<0.0001$. Bonferroni's multiple comparisons test, *$P<0.001$, $P<0.01$. Right: Non-stimulated P301S tau mice exhibited significantly higher levels of pS774-DNM1 signal intensity compared to WT naïve mice, whereas GENUS significantly reduced this aberrant phosphorylation in P301S mice. N=7 WT naïve, 8 non-stimulated P301S mice and 7 GENUS mice. ANOVA $F (2, 19)=18.69$, $P<0.0001$. Post-hoc multiple comparisons with Bonferroni's correction ** $P<0.01$, n.s—not significant.

FIG. 5G shows representative brain slices immunostained for vesicular glutamate transporter 1 (vGlut1) from visual cortex of CK naïve, non-stimulated and GENUS stimulated CK-p25 mice. Scale bar represents 10 µm.

FIG. 5H shows that while the expression of vGlut1 puncta was significantly lower in non-stimulated CK-p25 mice, GENUS stimulated CK-p25 mice exhibited higher levels of vGlut1 puncta compared to non-stimulated CK-p25 mice in V1, SS1, CA1 and CC. N=9 CK naïve mice, and 6 mice each from non-stimulated and GENUS CK-p25 group. Two-way ANOVA between groups effect $F (2, 72)=42.06$, $P<0.0001$. Post-hoc multiple comparisons with Bonferroni's correction ** $P<0.0001$,  $P<0.01$,* $P<0.05$.

FIG. 5I shows that the expression of synaptic puncta vGlut1 was significantly lower in P301S compared to WT naïve mice, GENUS rescued vGlut1 expression in V1, CA1 and CC in P301S. N=7 WT naïve, and 8 non-stimulated P301S mice and 7 GENUS mice. Two-way ANOVA between groups effect $F (2, 76)=23.67$, $P<0.0001$. Post-hoc multiple comparisons with Bonferroni's correction ** $P<0.0001$, * $P<0.001$, ** $P<0.01$,* $P<0.05$.

FIGS. 6A through 6I illustrate that chronic visual stimulation modifies behavior in multiple subject models of Alzheimer's Disease, according to the inventive concepts disclosed.

In FIG. 6A, p25 expression was induced in two groups of CK-p25 mice for 42 days, only one of which received daily GENUS for 1 h (stimulation was performed between 9 am-12 pm). Mice were subjected to open field (OF) and novel object recognition (OR) tests on day 40 (OF) and day 41 (OR) afternoon (3 pm-7 pm). F and N denote familiar and novel objects, respectively. Representative occupancy heat maps from OF and OR sessions are shown. Color level is mapped to the range of location frequencies in the arena or objects: warm color represents higher time and frequency, whereas cold color represents less time in the specified locations.

FIG. 6B shows that chronic visual GENUS did not affect anxiety levels in CK-p25 mice. Time spent in the center of OF arena did cold not differ between CK naïve, non-stimulated and GENUS stimulated CK-p25 mice. ANOVA between groups effect $F (2, 49)=1.198$, $P=0.3104$.

Figure 6C:
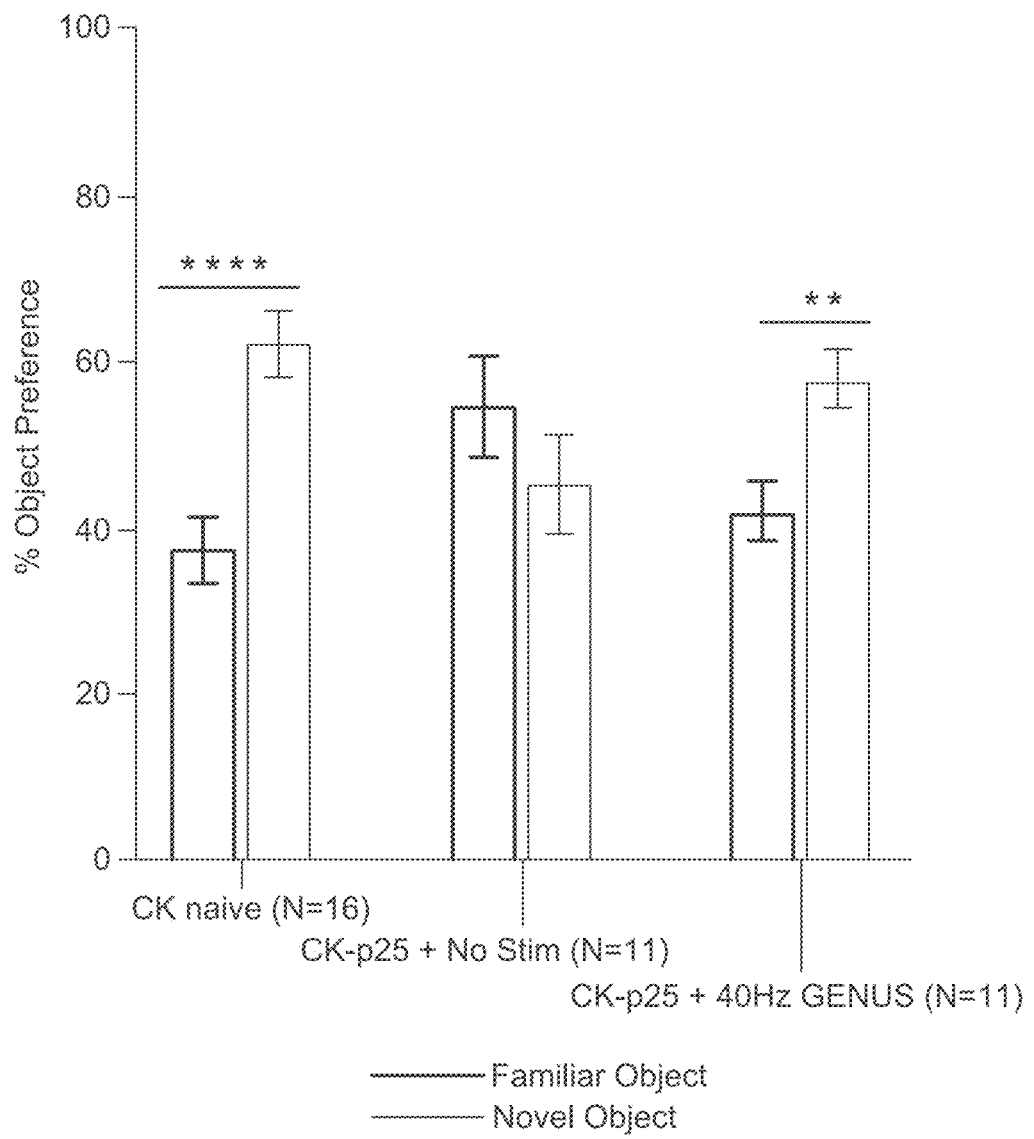
Figure 6D:
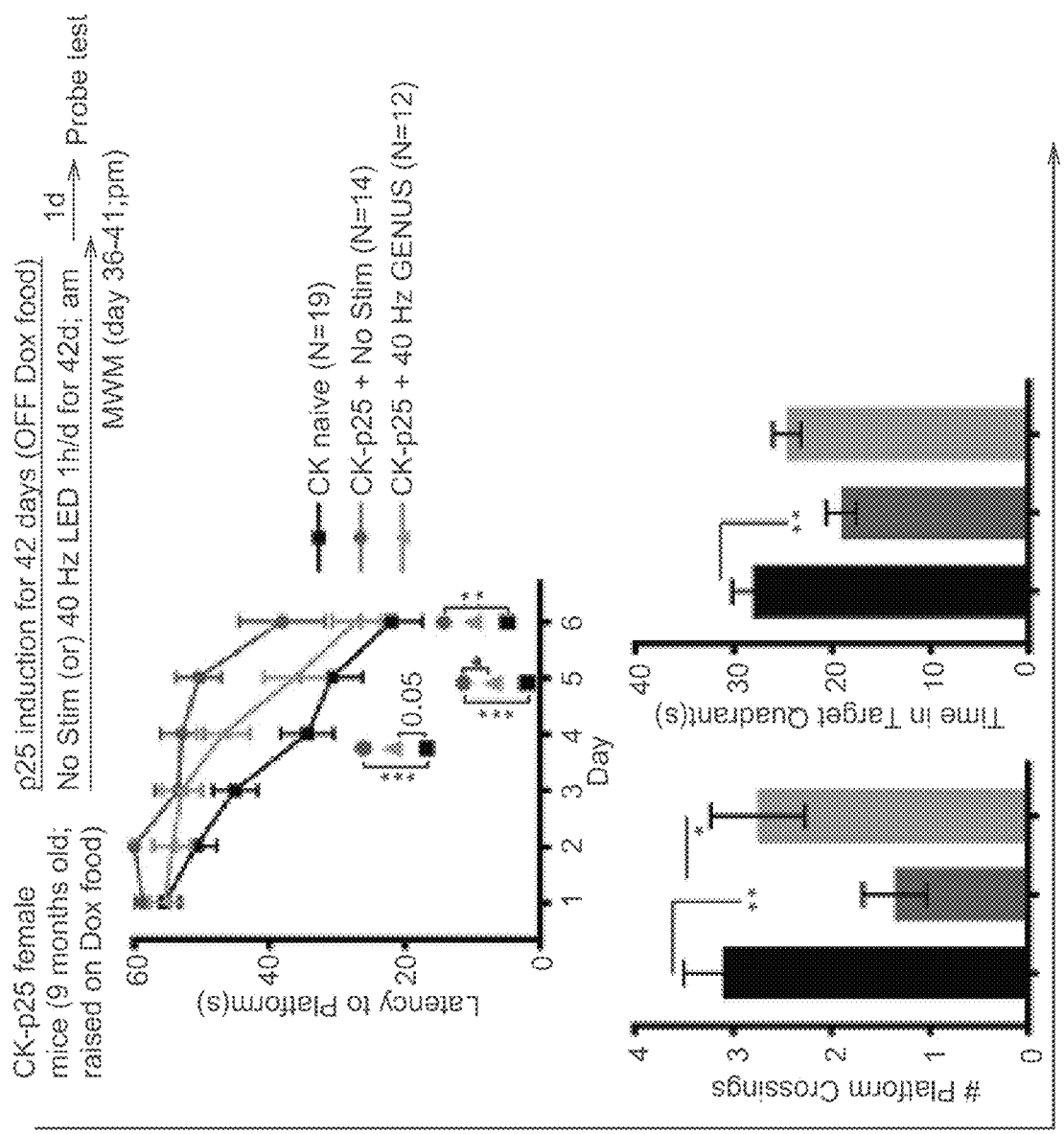
Figure 6E:
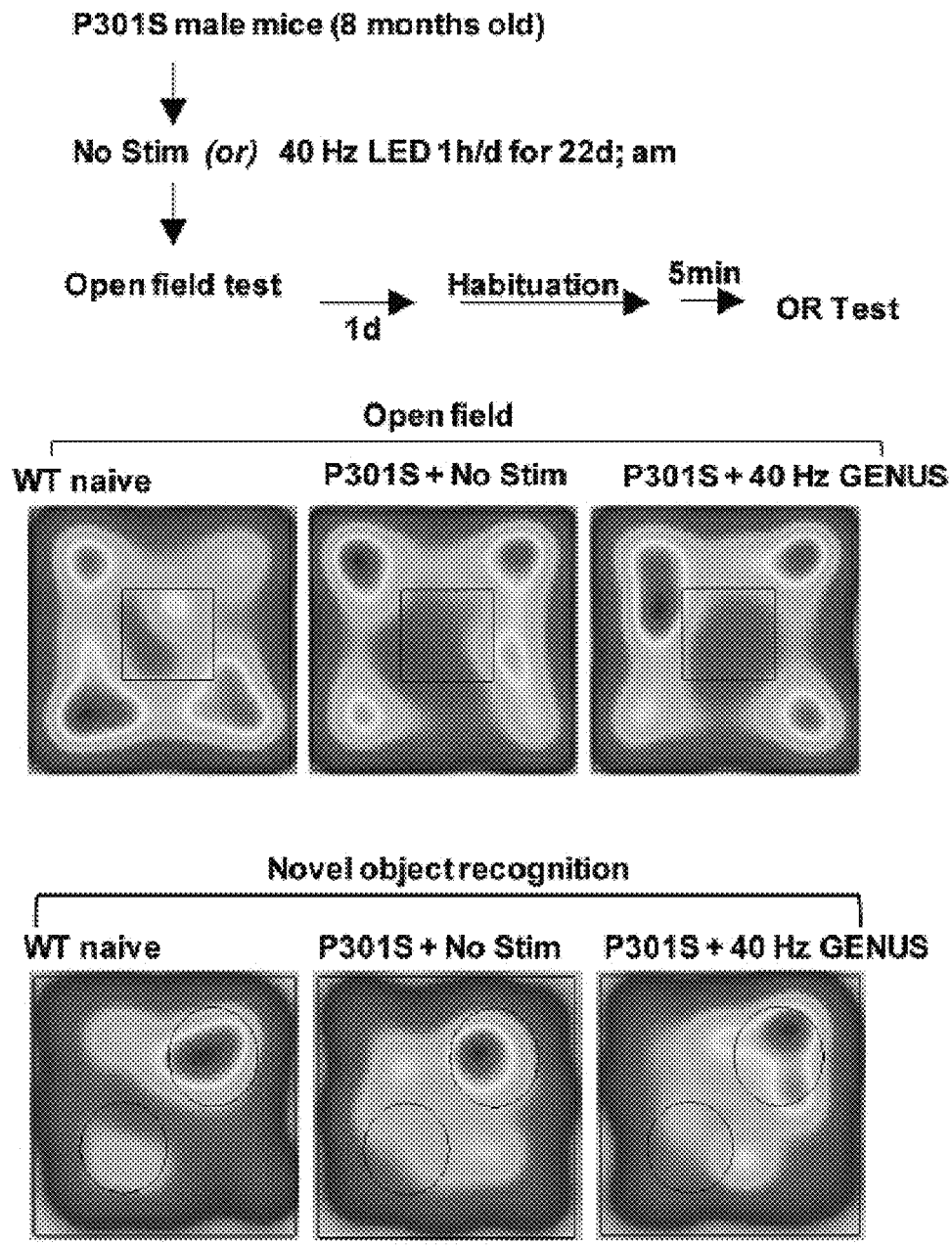

FIG. 6C shows preference for novel objects in CK naïve and GENUS stimulated CK-p25 mice was significantly higher than familiar object, however; non-stimulated CK-p25 mice showed no preference. Two-way ANOVA effects between familiar and novel objects $F (1, 70)=7.742$, $P=0.0069$. T-test; CK naïve, $T=4.421$, $P=0.0001$; CK-p25+No stim, $T=1.108$, $P=0.0946$; CK-p25+GENUS, $T=3.306$, $P=0.0017$.

FIG. 6D shows Morris water maze performance of p25 induced CK-p25 mice with or without GENUS for 42 days (MWM; between day 36 and 41 of p25 induction). Top: Chronic GENUS reduced the latency to find the platform in the training in CK-p25 mice compared to non-stimulated CK-p25 mice. Two-way ANOVA between groups effect $F (2, 252)=18.64$, $P<0.0001$. Bottom: Number of platform crossings in the probe test which was conducted 24 h after the final training session was significantly higher in the GENUS stimulated group compared to non-stimulated CK-p25 mice (left: between groups effect $F (2, 42)=5.277$, $P=0.0090$). Time spent in the target quadrant (right; between groups effect $F (2, 42)=6.35$, $P=0.0039$) was significantly lower in the non-stimulated CK-p25 mice compared to CK naïve mice.

FIG. 6E relates to P301S tau mice exposed to no stimulation or GENUS for 1 h per day for 22 days (9 am-12 pm) then assessed in OF (day 20; 3-7 pm) and OR (day 21) tests. Representative occupancy heat maps from OF and OR sessions are shown.

Figure 6F:
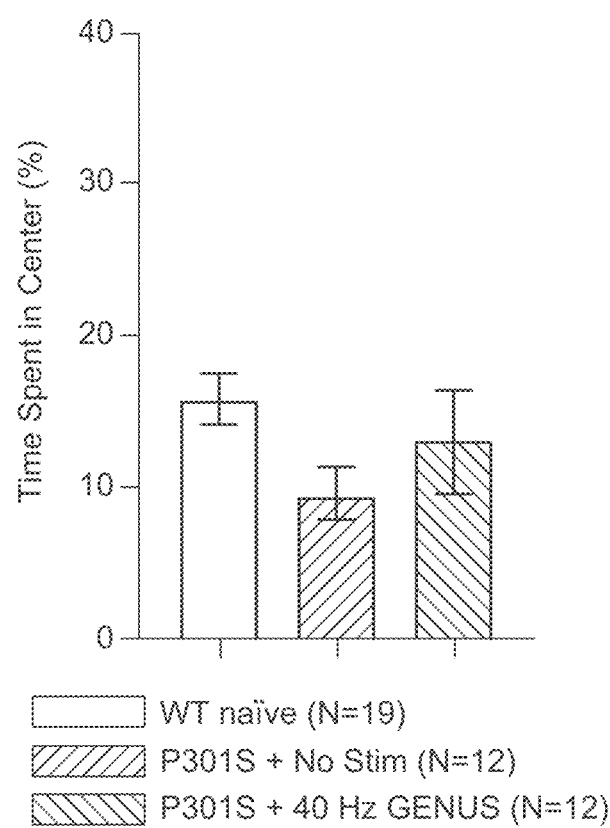
Figure 6G:
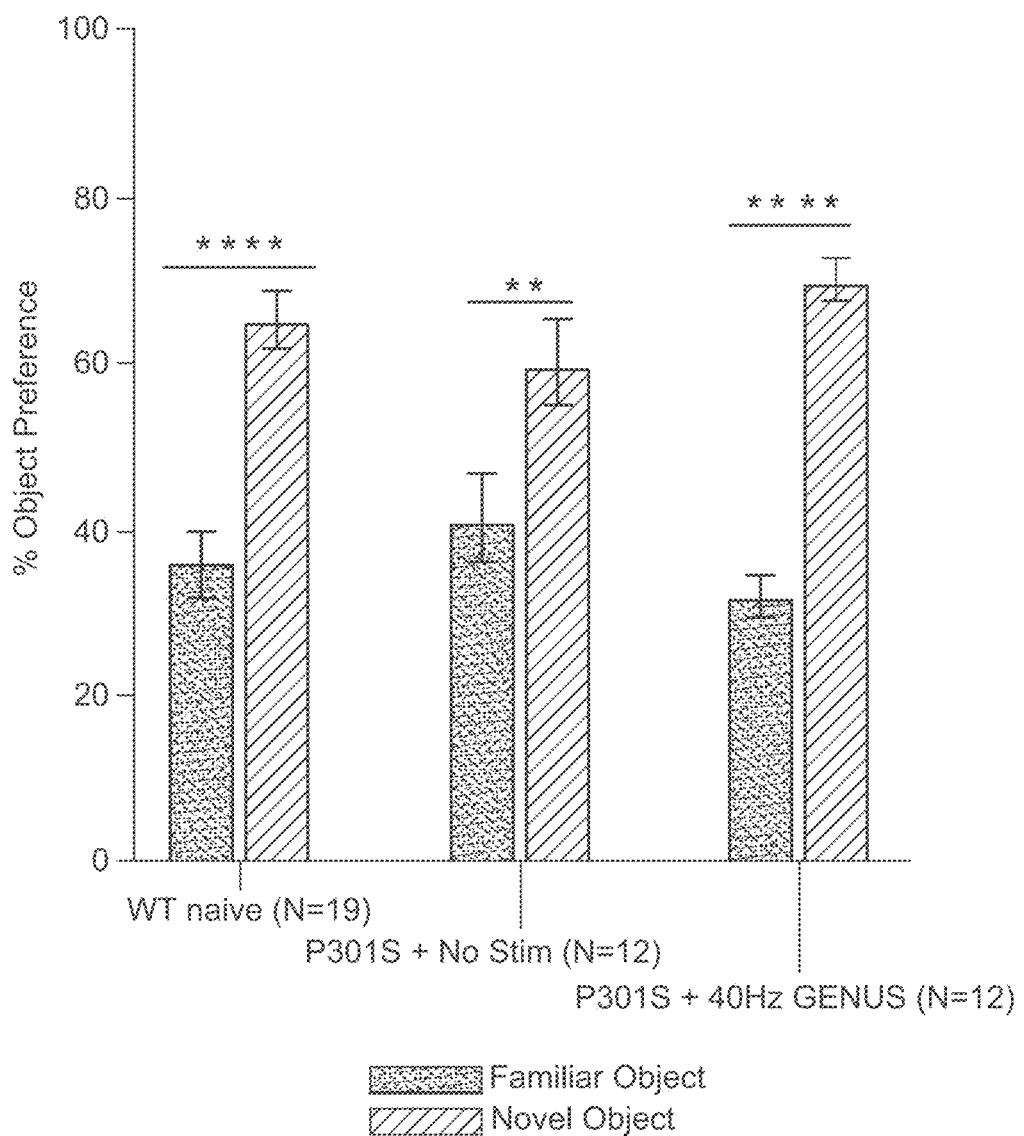
Figure 6H:
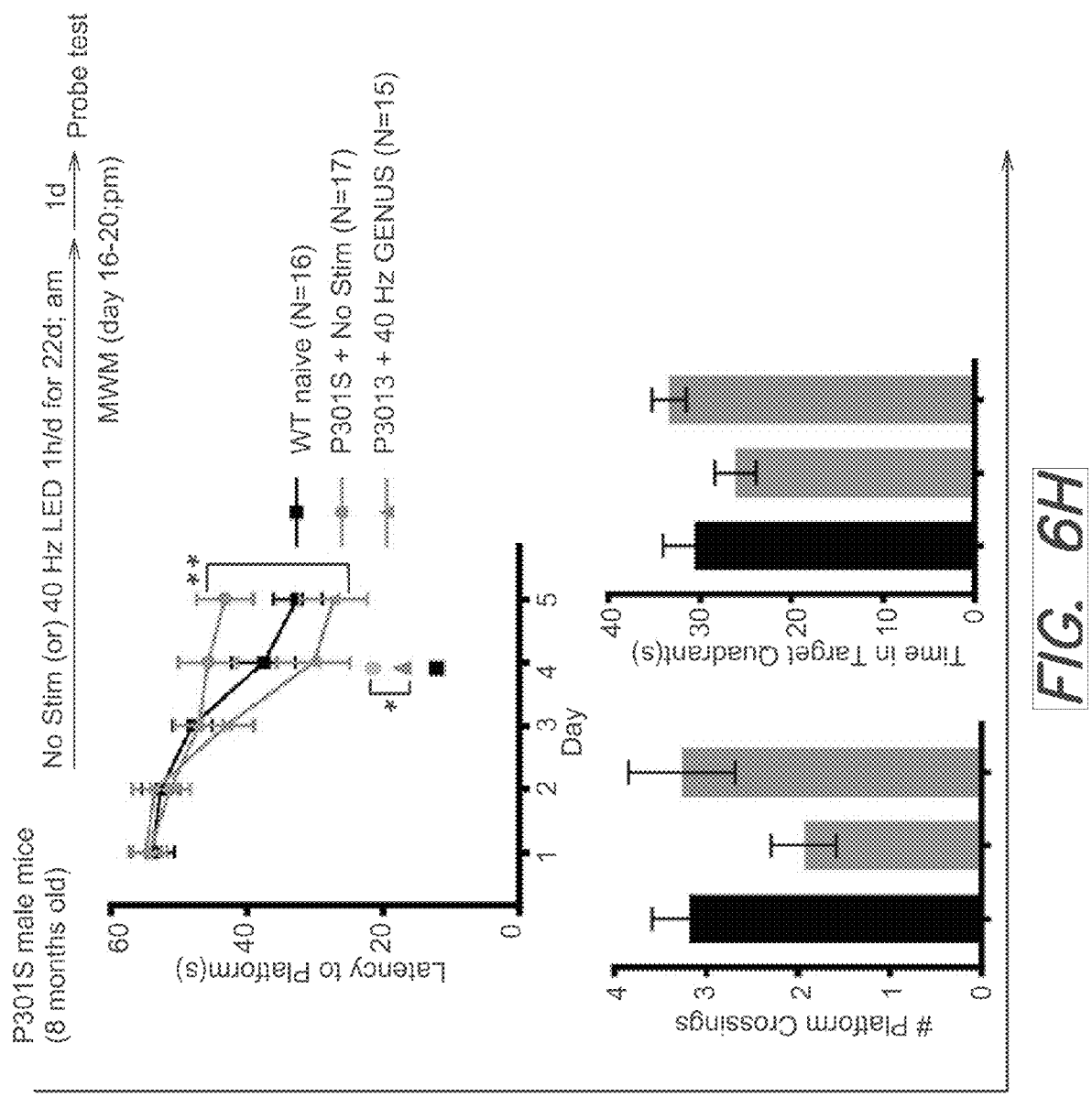
Figure 6I:
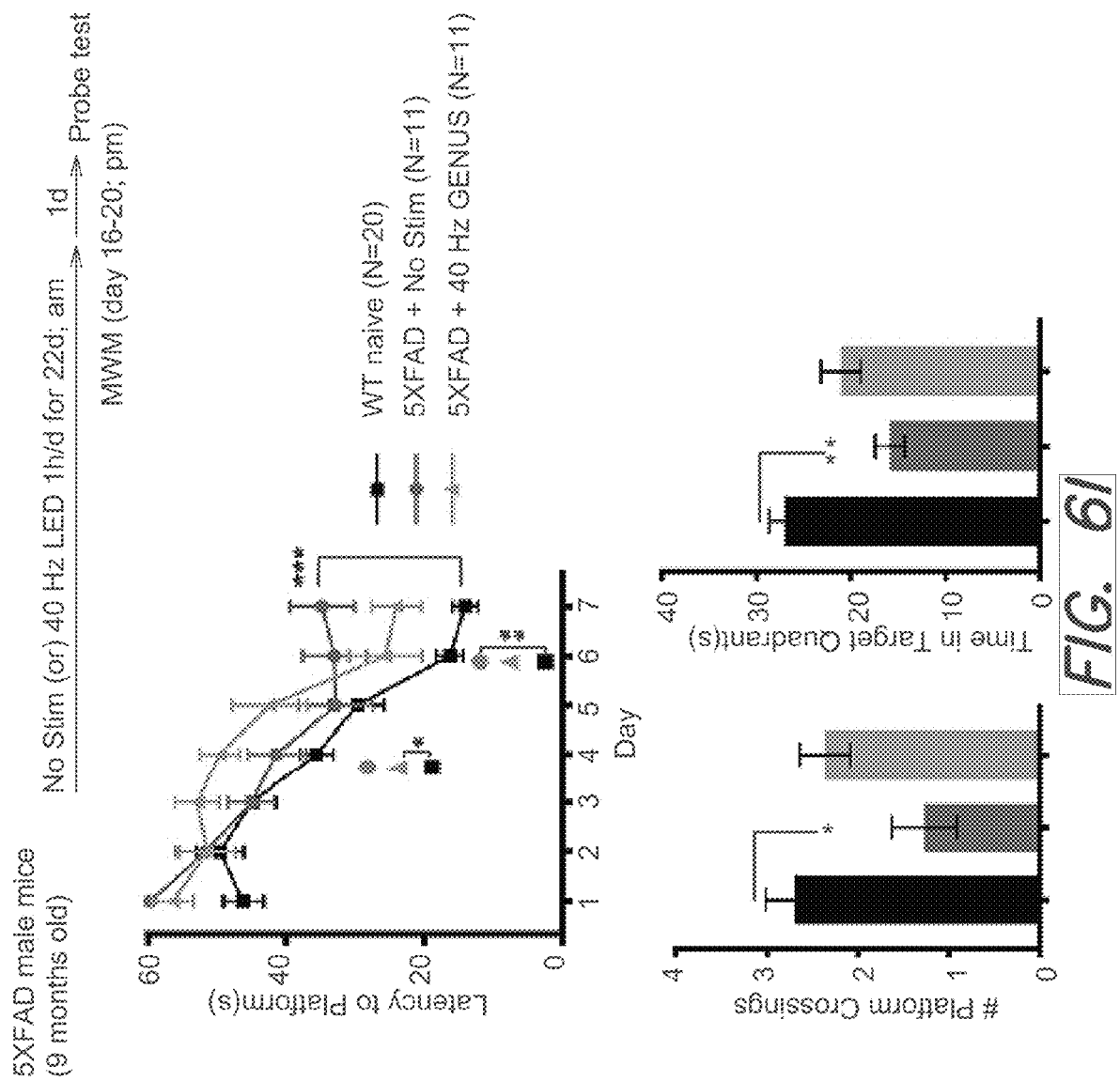

FIG. 6F shows that GENUS did not affect anxiety levels in P301S mice. Time spent in the OF center did not differ between non-stimulated, GENUS stimulated P301S and WT naïve groups (ANOVA $F (2, 36)=1.189$, $P=0.3163$).

FIG. 6G shows that WT, non-stimulated and GENUS stimulated P301S mice all exhibited higher preference for novel objects. Two-way ANOVA effects between familiar and novel objects $F (1, 80)=88.61$, $P<0.0001$. T-test; WT naïve, $T=6.525$, $P<0.00001$; P301S+No stim, $T=2.602$, $P=0.0054$; P301S+GENUS, $T=10.65$, $P<0.00001$.

FIG. 6H shows MWM performance of WT naïve, non-stimulated or GENUS stimulated P301S tau mice. Top: Chronic GENUS reduced the latency to find the platform during the training in P301S mice compared to no-stimulated P301S mice. Two-way ANOVA between groups effect $F (2, 225)=3.782$, $P=0.0242$. Bottom: Number of platform crossings in the probe test (left: $F (2, 45)=2.872$, $P=0.067$) and time in target quadrant in the probe test (right: $F (2, 45)=3.115$, $P=0.054$.

In FIG. 6I, 5XFAD mice with or without GENUS (1 h per day for 22 days) were tested for MWM performance. Left: Latency to find the platform during training. Two-way ANOVA between groups effect $F (2, 273)=16.97$, $P<0.0001$. Number of platform crossings in the probe test (middle: between groups effect $F (2, 39)=4.702$, $P=0.0148$) and time spent in the target quadrant (right: between groups effect $F (2, 39)=7.289$, $P=0.0020$) was significantly lower in non-stimulated CK-p25 mice.

FIGS. 7A through 7I illustrate that chronic visual stimulation entrains gamma oscillations beyond visual cortex in mouse models of neurodegeneration, according to the inventive concepts disclosed.

FIG. 7A shows electrolytic lesions to verify recording sites in mice used for main FIGS. 1C, 1D post-recording. Representative images show the site of recording from V1, SS1, CA1 and PFC.

In FIG. 7B, CDK5 activator p25 was induced in CK-p25 mice for 6 weeks, followed by microdrive implantation and LFP recording.

In FIG. 7C, area powers (35-45 Hz) were significantly lower in CK-p25 mice compared to age matched WT mice in V1, CA1 and PFC (all regions $P<0.01$). 40 Hz visual stimulation increased 40 Hz power in V1 (Wilcoxon-Rank sum; $P=0.0022$), CA1 ($P=0.001$) and PFC ($P=0.002$) during 40 Hz light flicker exposure in 6 weeks induced CK-p25 mice.

In FIG. 7D, microdrives were implanted in 8 month old P301S tau mice.

FIG. 7E shows that significant increases in power (35-45 Hz) were observed during 40 Hz light stimulation in V1 (P=6.01E-05) and PFC (P=4.11E-05).

FIG. 7F relates to C57B16/J mice subjected to no stimulation or GENUS 1 h/day for 42. Right: Significant increases in 35-45 Hz area powers were observed in V1 (Wilcoxon-Ranksum test; P=1.54E-06), SS1 (P=2.88E-04), CA1 (P=0.04) and PFC (P=3.39E-06), during 40 Hz visual stimulation.

In FIG. 7G, C57B16/J mice were subjected to no stimulation or GENUS 1 h/day for 42 days. Mice were subjected to 40 Hz visual stimulation on day 43 and LFPs were collected. Between areas significant increases were observed in 30-50 Hz low gamma coherence (measured as the weighted phase lag index) between V1-CA1 (P=0.002), V1-SS1 (P=0.008), CA1-PFC (P=0.04), V1-PFC (P=0.002), during GENUS. There was no difference in low gamma WPLI between CA1 and SS1 (P=0.18).

In FIG. 7H, p25 was induced in CK-p25 mice for 6 weeks. Six weeks induced CK-p25 mice underwent (from day 43) no stimulation or GENUS 1 h/d for 42 days. Right: Significant increases in low gamma area power (35-45 Hz) were observed in all brain areas studied in CK-p25 mice [V1, P=0.0017), CA1 (P=0.0379), PFC (P=0.0030)] (measured on day 85).

FIG. 7I shows that significant increases were also evident in low gamma coherence between V1-CA1 (P<0.01), CA1-PFC (P<0.01), V1-PFC (P<0.01).

FIGS. 8A through 8I illustrate that chronic visual stimulation reduces AD-associated pathology in 5XFAD mice beyond visual cortex, according to the inventive concepts disclosed.

Figure 8A:
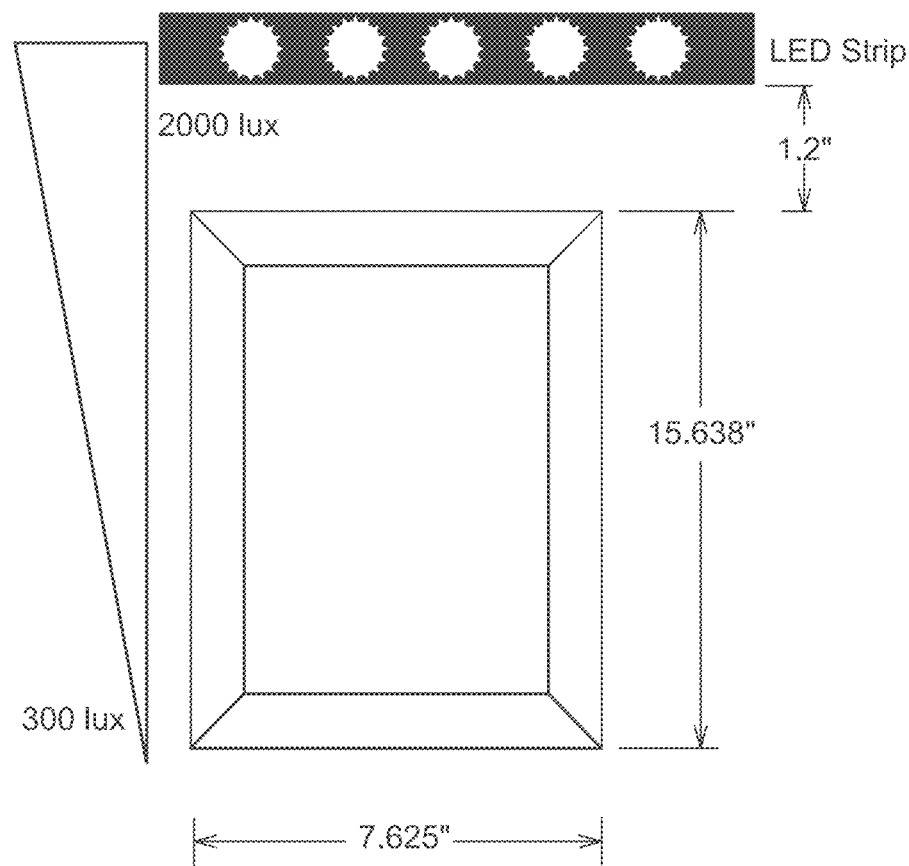

FIG. 8A is a schematic showing the visual flicker stimulation set up. An array of light emitting diodes (LEDs) was present on the open side of the cage and was driven to flicker at a frequency of 40 Hz with a square wave current pattern using an Arduino system. Since mice freely move in the cage (83 in$^2$ total floor area), the light intensity that they received ranges from ~1500 to 300 lux.

Figure 8B:
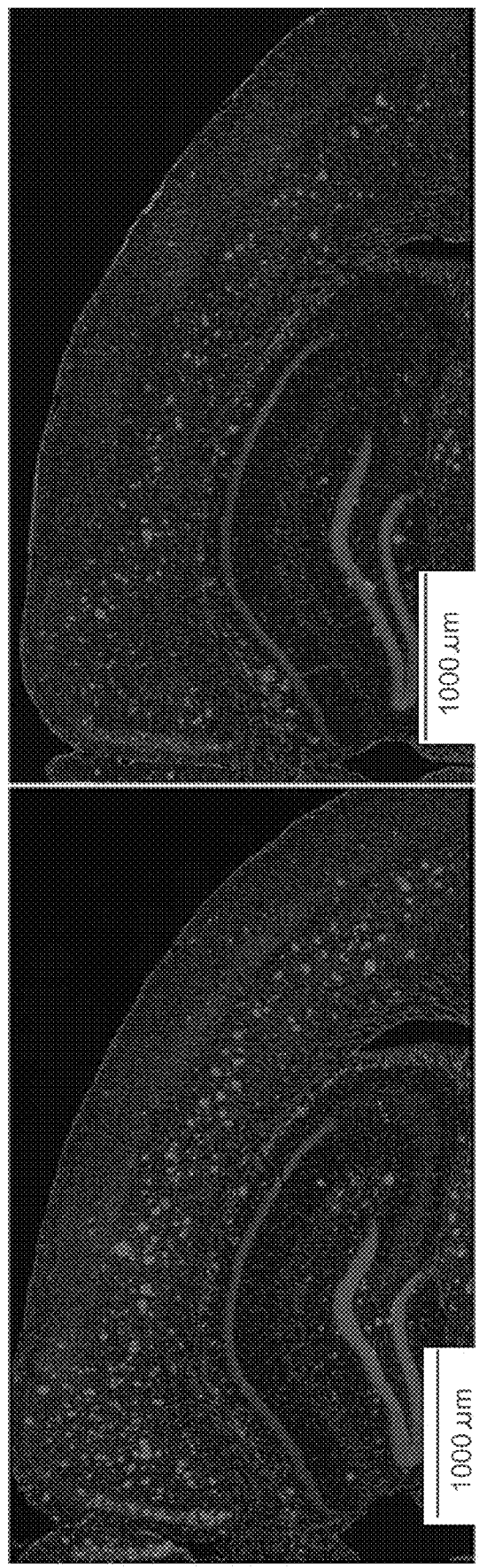
Figure 8C:
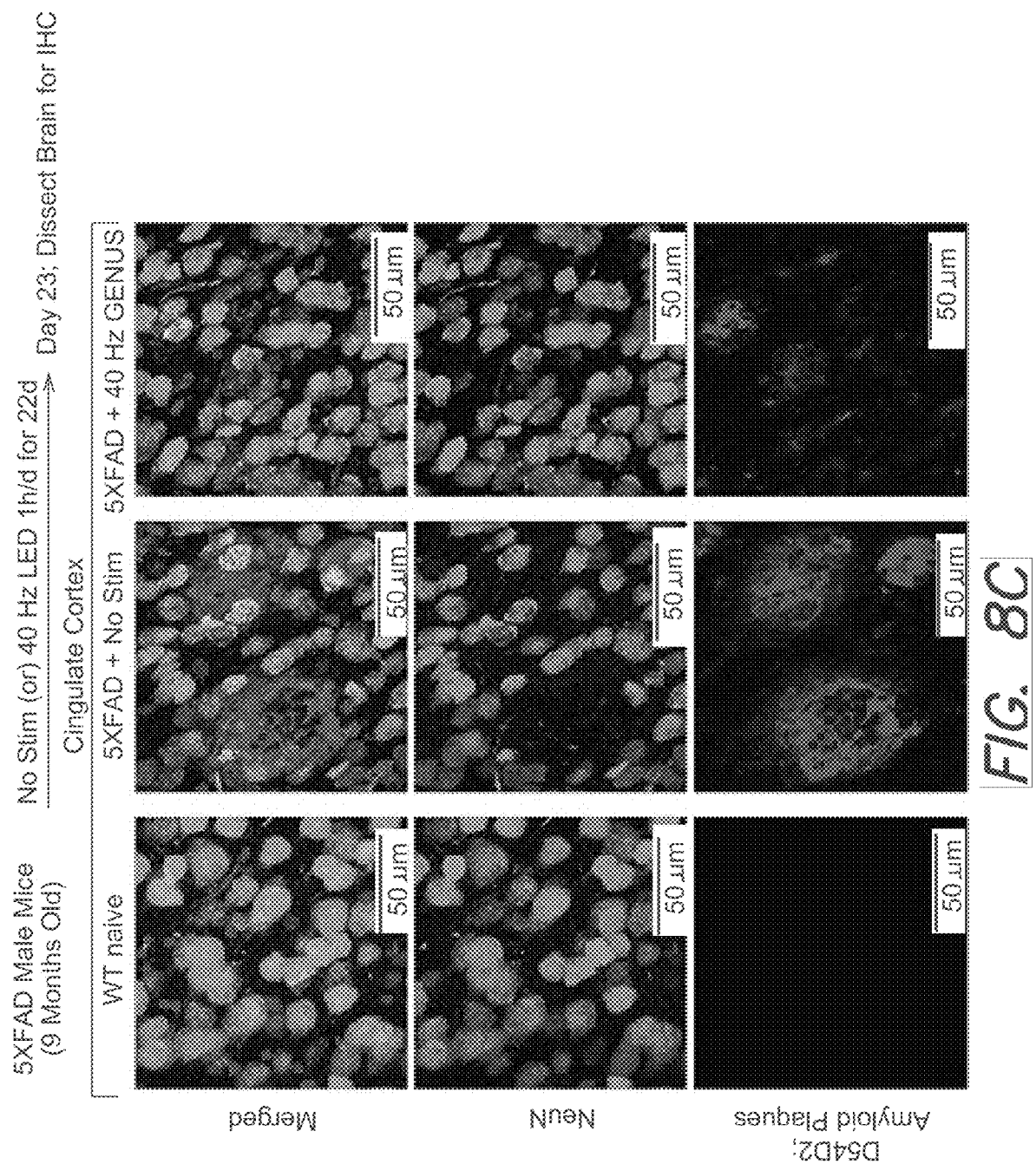

In FIG. 8B, 10 month old 5XFAD mice underwent no stimulation or GENUS 1 h per day for 22 days. Representative images show amyloid plaques in red and nuclear stain Hoechst in blue from slices containing hippocampus and somatosensory cortex. Scale bar 1000 μm. Related to main FIG. 2C-2D.

In FIG. 8C, 10 month old 5XFAD mice underwent no stimulation or GENUS 1 h per day for 22 days. Representative images show amyloid plaques in red, neuronal marker NeuN in green and nuclear stain Hoechst in blue from cingulate cortex. Scale bar 50 μm. Related to main FIG. 2C-2D.

Figure 8D:
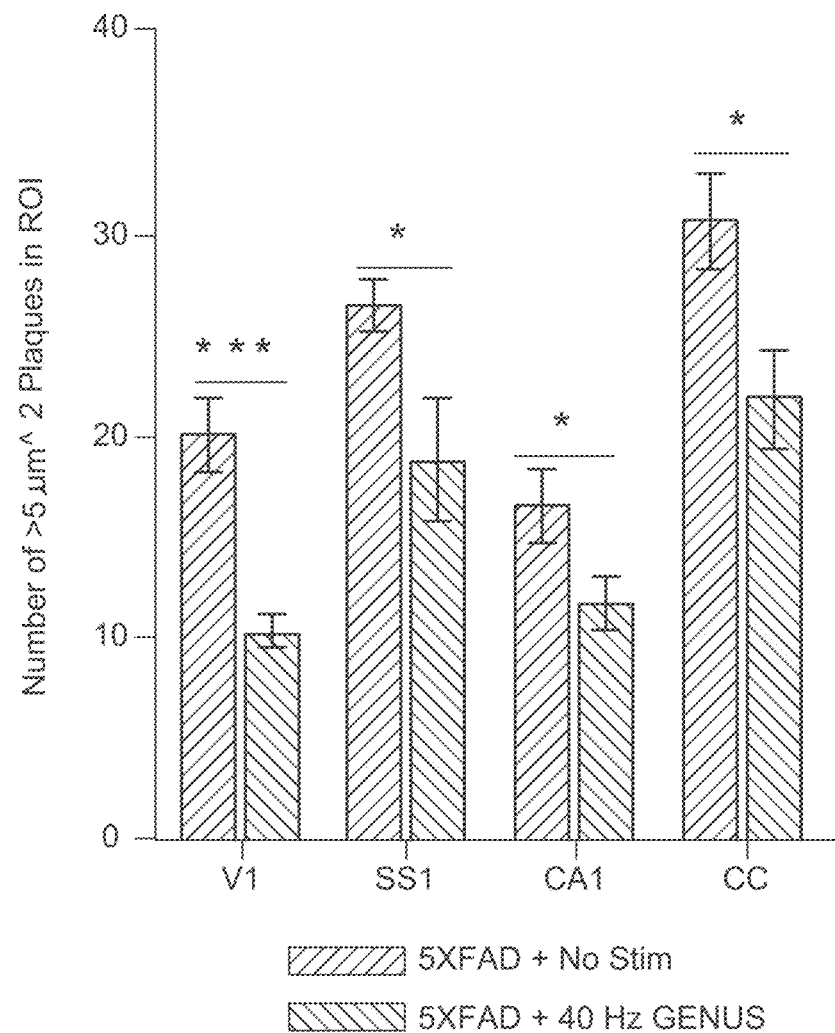
Figure 8E:
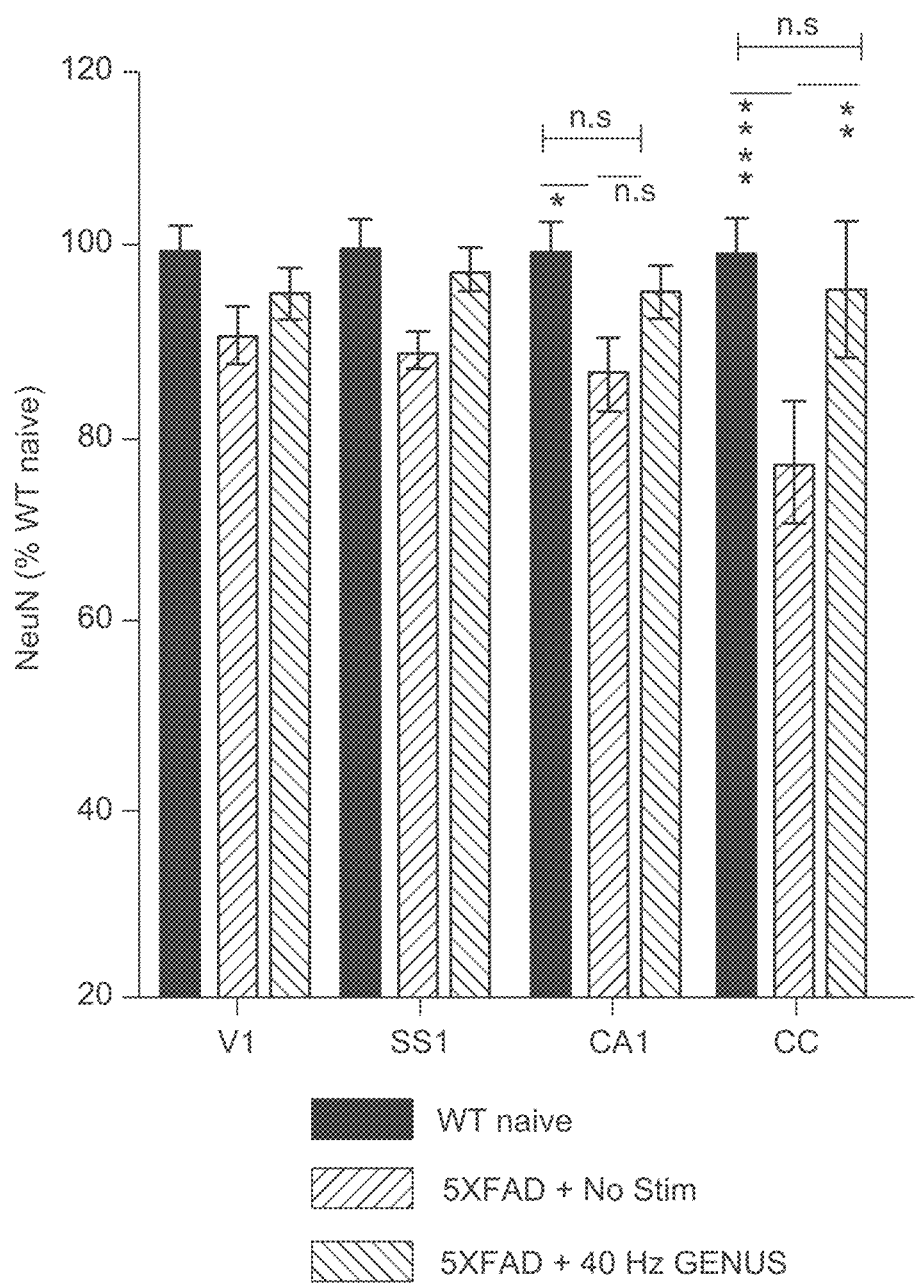
Figure 8F:
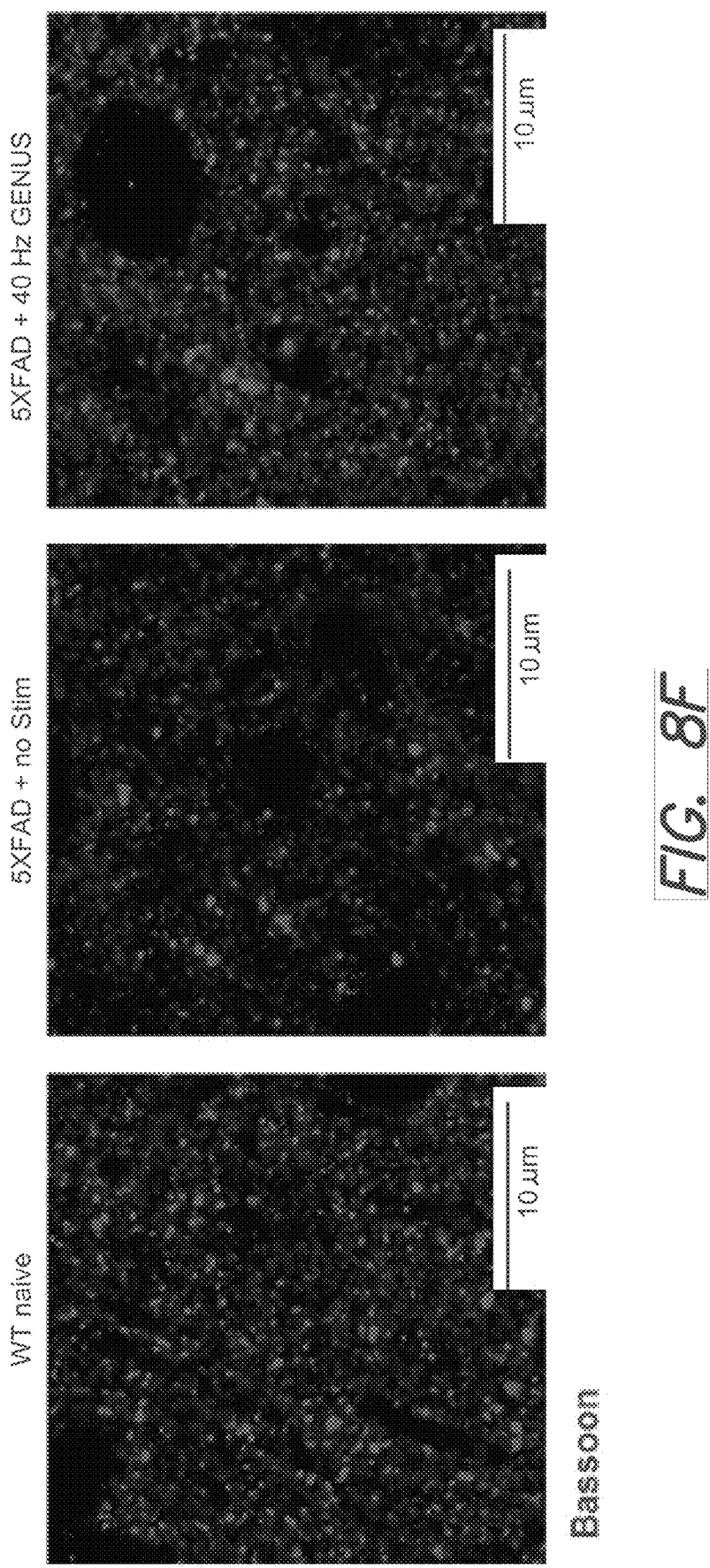
Figure 8G:
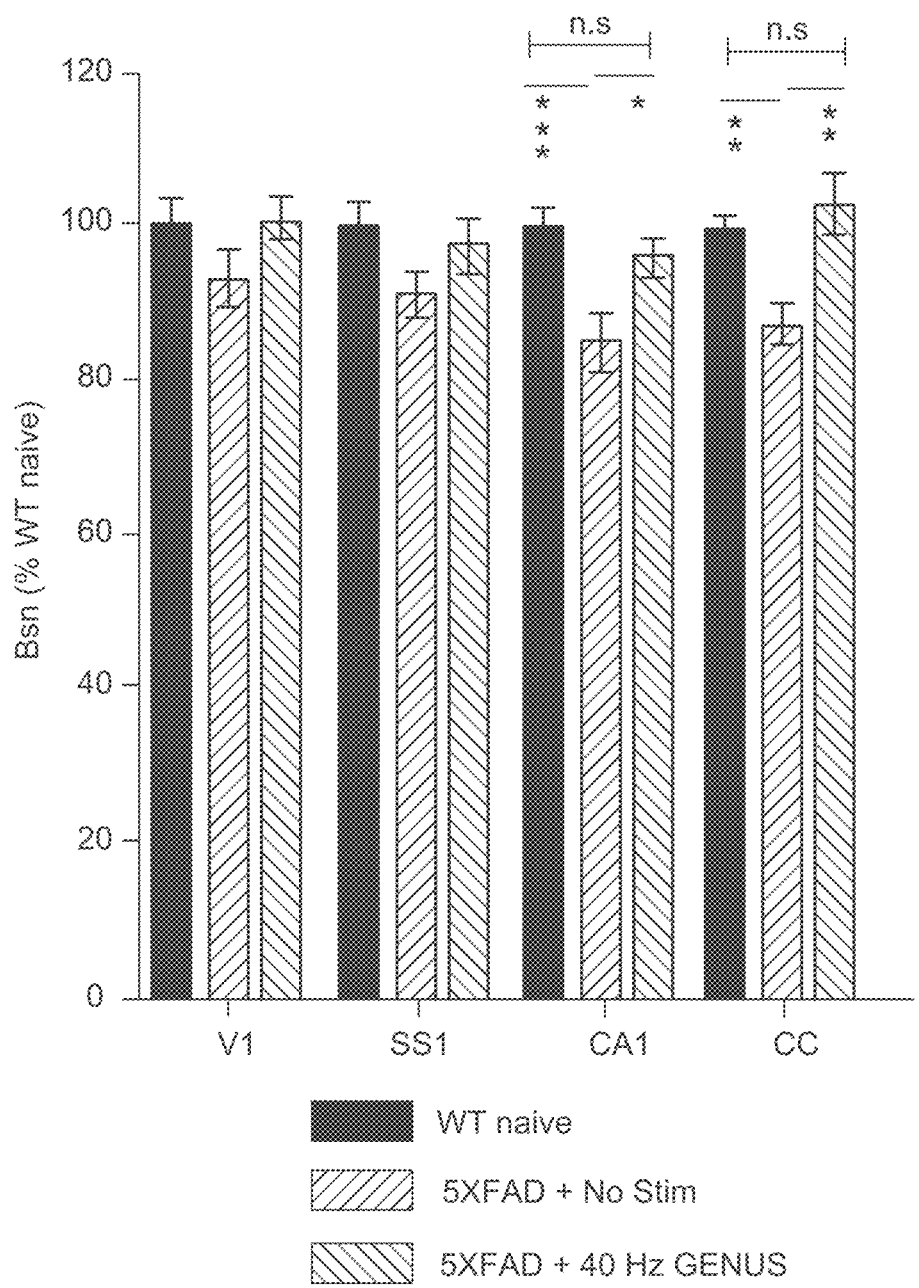
Figure 81:
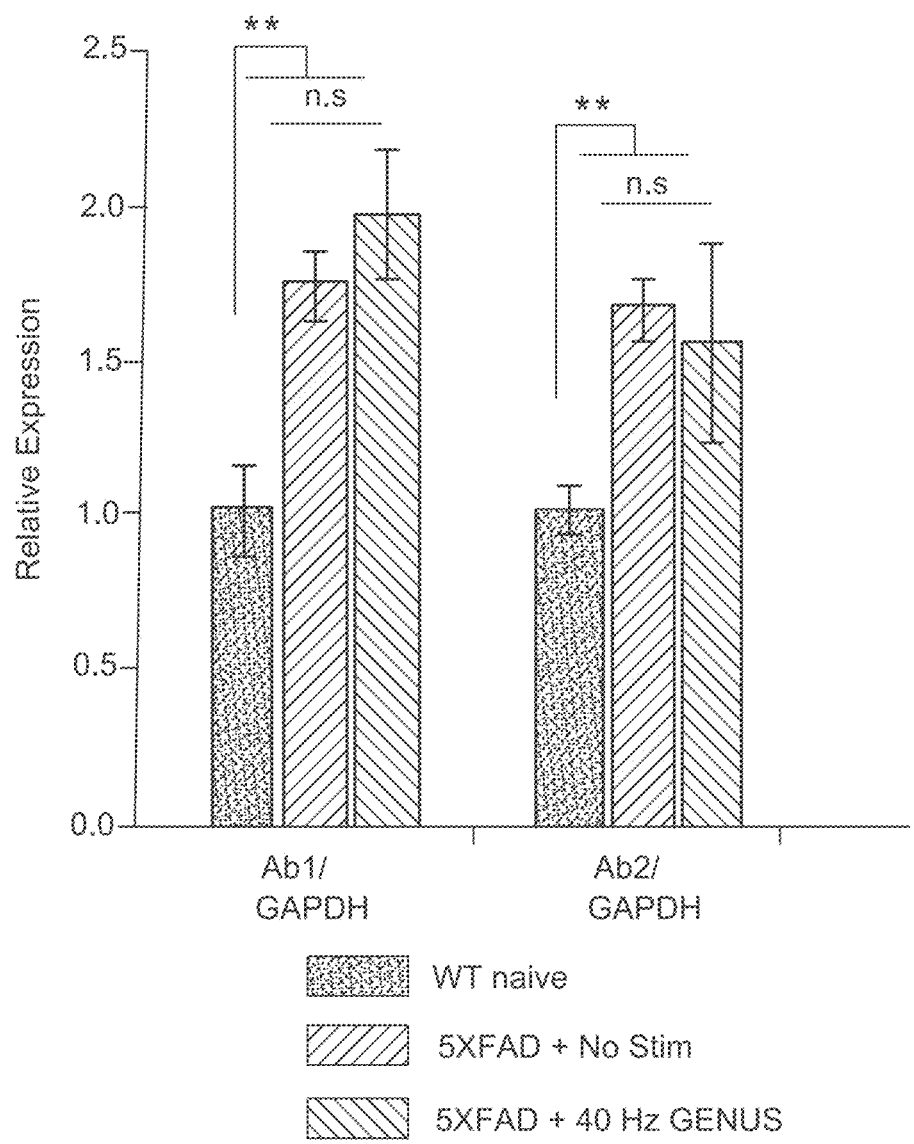

FIG. 8D shows that the number of plaques in GENUS stimulated 5XFAD mice was significantly lower than non-stimulated 5XFAD mice in V1, SS1, CA1 and CC. Related to main FIG. 2C-2D. N=6 mice per condition. Two-way ANOVA between groups effect F (1, 40)=30.01, P<0.0001. *P<0.001, P<0.01, *P<0.05.

In FIG. 8E, 9 month old non-stimulated 5XFAD mice showed significant reductions in neuronal density in CA1 and CC compare to the age matched WT littermates. GENUS significantly reduced neuronal loss in 5XFAD mice in CC. N=9 WT naïve, 6 5XFAD+No stim, and 6 5XFAD+GENUS mice. Two way ANOVA between groups effect F (2, 72)=14.93, P<0.0001. Bonferroni's multiple comparisons test, *P<0.001, P<0.01, *P<0.05.

In FIG. 8F, 10 month old 5XFAD mice underwent no stimulation or GENUS 1h per day for 22 days. Representative images show synaptic marker bassoon. Scale bar 10 μm.

In FIG. 8G, 5XFAD mice exhibited significant reductions in synaptic marker bassoon staining in CA1 and CC, which was significantly reduced by 40 Hz GENUS. N=9 WT naïve, 6 5XFAD+No stim, and 6 5XFAD+GENUS mice. Two way ANOVA between groups effect F (2, 72)=16.18, P<0.0001. Bonferroni's multiple comparisons test, *P<0.001, P<0.01, *P<0.05.

FIG. 8H provides full length immunoblots showing the expression levels of full length APP protein and endogenous GAPDH control. N=5 WT naïve mice, 3 non-stimulated 5XFAD mice and 4 GENUS stimulated 5XFAD mice.

FIG. 8I shows that APP protein expression was significantly higher in 5XFAD mice compared to WT naïve control. Between non-stimulated and GENUS stimulated 5XFAD mice it did not differ. Note that we did not measure the C/N fragments of APP proteins. C-terminal specific APP antibody, one way ANOVA F (2, 9)=4.436, P=0.046. N-terminal specific APP antibody, one way ANOVA F (2, 9)=13.194, P=0.002. Bonferroni's multiple comparisons test, **P<0.01.

FIGS. 9A through 9G illustrate that chronic visual stimulation ameliorates AD-associated pathology in P301S and CK-p25 mice, according to the inventive concepts disclosed.

FIG. 9A provides full length immunoblots showing the expression levels of total tau protein and GAPDH from visual cortex of non-stimulated, GENUS stimulated P301S tau mice, and age matched WT naïve littermates. Right: Total tau expression in P301S tau mice was increased compared to WT naïve mice, however; tau levels did not differ between non-stimulated and GENUS stimulated P301S mice. N=3 WT naïve, 3 non-stimulated and 4 GENUS stimulated P301S mice. ANOVA F (2, 7)=173.275, P<0.0001. Bonferroni's multiple comparisons test, ***P<0.001.

FIG. 9B shows that brains did not differ in weight among WT naive, non-stimulated P301S and GENUS stimulated P301S mice. There was a tendency towards an aberrant expansion of lateral ventricles in P301S tau mice compared to WT naïve mice. ANOVA F(2,19)=2.761, P=0.079.

FIG. 9C provides full length immunoblots showing the expression levels of p25+GFP (fusion protein), p25, p35 and GAPDH from visual cortex of CK naïve, non-stimulated and GENUS stimulated CK-p25 mice. Right: There was a significant increase in p25+GFP protein in CK-p25 mice compared to age matched CK naïve mice (one way ANOVA, F (2,12)=13.065, P=0.002), however; non-stimulated and GENUS stimulated CK-p25 did not differ in p25+GFP expression. Similarly, p25 expression level was significantly higher in CK-p25 mice compared to CK naïve mice but did not differ between non-stimulated and GENUS stimulated CK-p25 mice (one way ANOVA, F (2, 12)=3.581, P=0.025). Bonferroni's multiple comparisons test, *P<0.001, P<0.01, *P<0.05.

FIG. 9D provides representative images showing the thickness of visual cortex in CK naïve, non-stimulated CK-p25 and GENUS stimulated CK-p25 mice. Nuclear stain Hoechst is shown in blue and neuronal marker NeuN in red. Right: Bar chart shows the difference in visual cortex thickness among groups. Two-way ANOVA between group effect F (2, 36)=12.93, P<0.0001. Bonferroni's multiple comparisons test, *P<0.001, P<0.01, *P<0.05.

FIG. 9E provides representative images showing the qualitative differences among CK naïve, non-stimulated and GENUS stimulated CK-p25 mice detailing changes in hippocampal volume, cortical thickness and ventricle size. Related to main FIG. 3F-3H.

FIG. 9F shows that GENUS did not alter the p25+GFP fusion protein expression level (number of p25: GFP expressing neurons) compared to non-stimulated CK-p25 mice, across all brain regions tested, independent samples t-test between groups, P>0.05.

FIG. 9G provides representative images showing expression of the DNA double stranded break marker γH2Ax from CA1 in CK naïve, non-stimulated and GENUS stimulated CK-p25 mice. No γH2Ax positive nuclei were evident in CK naïve mice, therefore comparisons were made between non-stimulated and GENUS stimulated CK-p25 mice. N=6 mice per condition. Scale bar 100 μm. Right: GENUS significantly reduced γH2Ax positive nuclei in V1 (independent samples t-test; T=4.418, P=0.0006), SS1 (T=2.944, P=0.013), CA1 (T=2.664, P=0.0143) and CC (T=1.883, P=0.055).

FIGS. 10A through 10N illustrate that chronic visual stimulation modifies microglia, improves intracellular transport and synaptic transmission in neurons, according to the inventive concepts disclosed.

FIG. 10A shows microglia separation profile in FACS from representative CK naïve, non-stimulated and GENUS stimulated CK-p25 mice. Related main FIG. 4A 4C.

FIG. 10B shows microglia separation profile in FACS from representative WT naïve, non-stimulated and GENUS stimulated P301S tau mice.

In FIG. 10C, differentially expressed genes (DEGs) are shown in volcano plots. Group comparisons are shown to the right. Top: DEGs between WT naïve and non-stimulated P301S, N=5 mice per group. Middle top: DEGs between non-stimulated and GENUS stimulated P301S mice, N=5 mice per group.

FIG. 10D shows the top 7 processed gene ontology (GO) terms for biological processes associated with the identified DEGs. Group comparisons are shown to the top.

FIG. 10E provides representative images showing Iba1 in green and CD40 in red. Merged images presented in main FIG. 4D were separated for clarity.

FIG. 10F shows neuronal nuclei separation profile in FACS from representative CK naïve, non-stimulated and GENUS stimulated CK-p25 mice is shown. Group mean and SEM of % NeuN compare to total nuclei: CK naïve, 50±1.48; non-stimulated CK-p25, 40.98±0.719; GENUS stimulated CK-p25 mice, 45.08±1.691. ANOVA F (2, 12)=11.55, P=0.0016. Bonferroni's post hoc test, CK naïve Vs non-stimulated CK-p25, P=0.001' CK naïve Vs GENUS stimulated CK-p25 P=0.0609. GENUS reduced the loss of neuronal nuclei in CK-p25 mice.

Figure 10G:
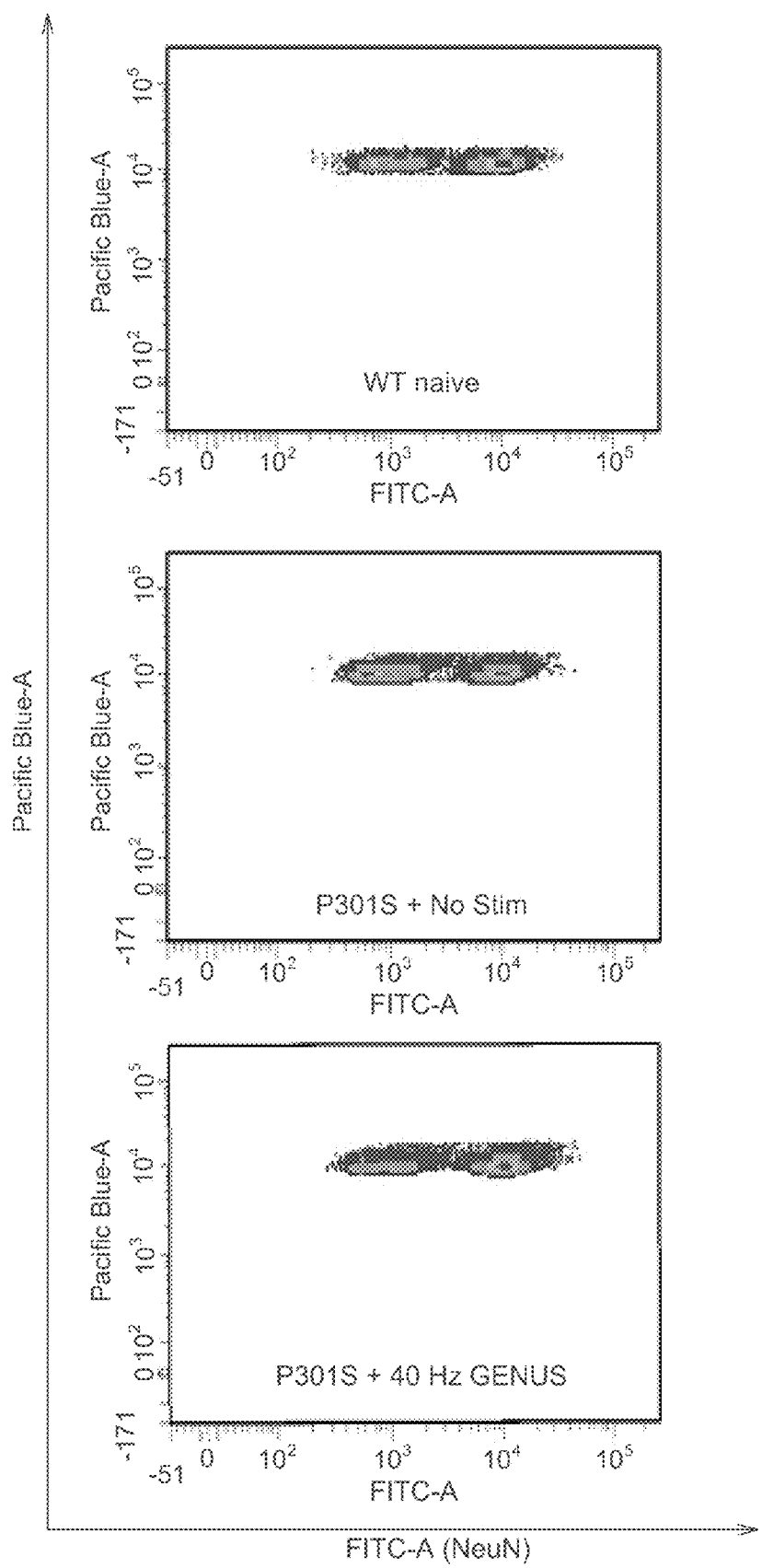
Figure 10I:
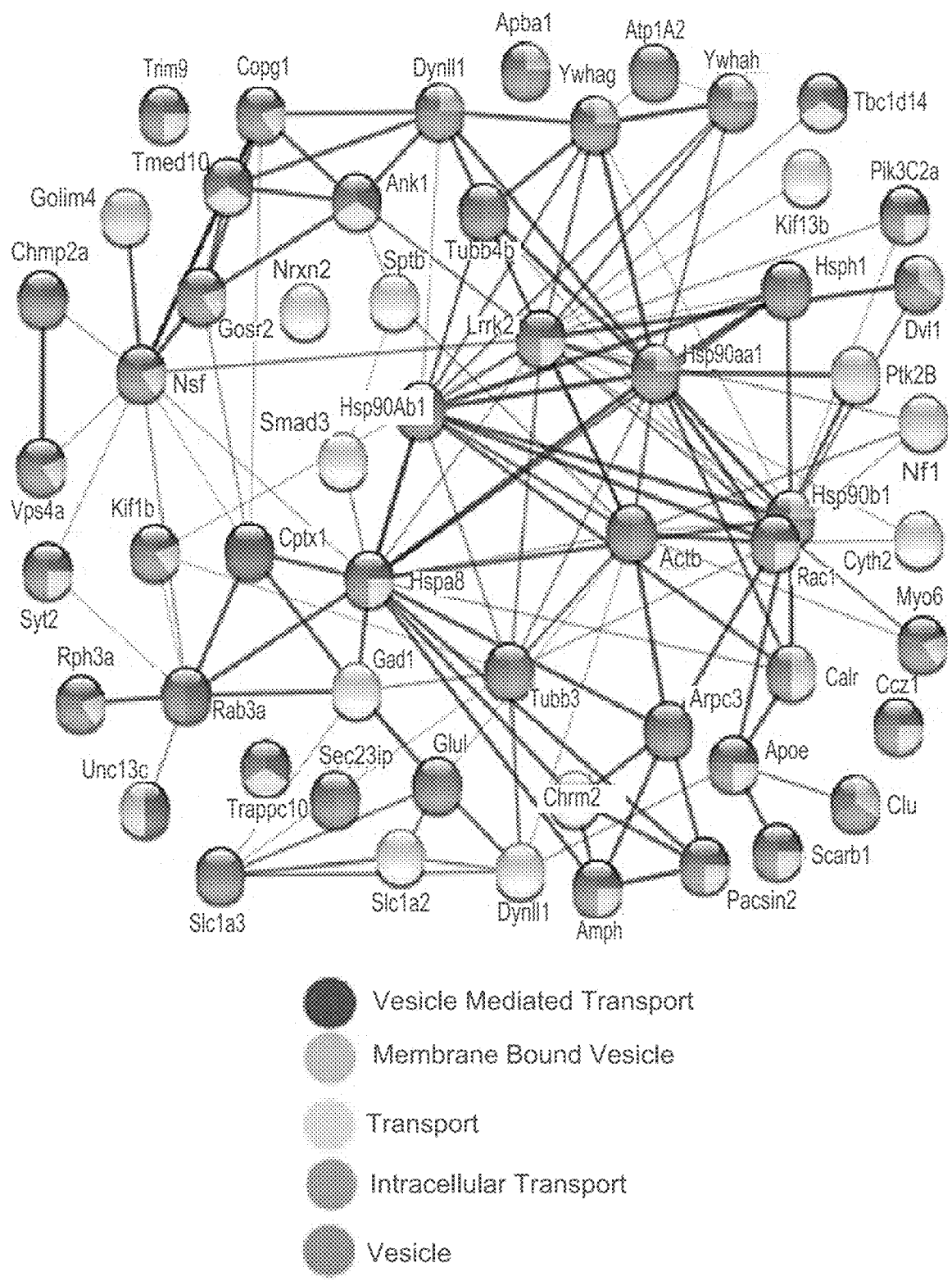

FIG. 10G shows neuronal nuclei separation profile in FACS from representative WT naïve, non-stimulated P301S and GENUS stimulated P301S mice is shown. Group mean and standard error of the mean (SEM) of percentage of NeuN positive nuclei found compare to total Hoechst positive nuclei: WT naïve, 52.45±2.03; non-stimulated P301S, 45.17±1.18; GENUS stimulated P301S, 50.38±2.09. ANOVA F (2,18)=4.97, P=0.0191. Bonferroni's post hoc test, WT naïve Vs non-stimulated P301S, P=0.028; WT naïve Vs GENUS stimulated P301S mice, P=0.99. GENUS reduced the loss of neuronal nuclei in P301S tau mice.

FIG. 10H provides bar graphs showing the percentage of total neurons (NeuN) positive nuclei compare to total nuclei as in FIGS. 10F and 10G. Top: Bar graph comparing WT naïve, non-stimulated and GENUS stimulated P301S mice. N=7 mice per group. ANOVA F (2, 18)=4.971, P=0.0191.

Bottom: Bar graph comparing CK naïve, non-stimulated and GENUS stimulated CK-p25 mice. N=5 mice for each group. ANOVA F (2, 12)=7.72, P=0.0070.

In FIG. 10I upregulated genes in P301S tau mice and CK-p25 mice after chronic GENUS were selected based on neurotransmitter transport and vesicle mediated transport clusters with 60 genes. Note that these genes were upregulated only in CK-p25, P301S or in both mice after GENUS compared to non-stimulated mice (analyzed by metascape). Protein-protein interaction network map (Analyzed with Cytoscape V3.6.1 followed by Strings; enrichment P value, 6.66E-15) is shown with tightly linked further functional enrichment GO terms.

Figure 10J:
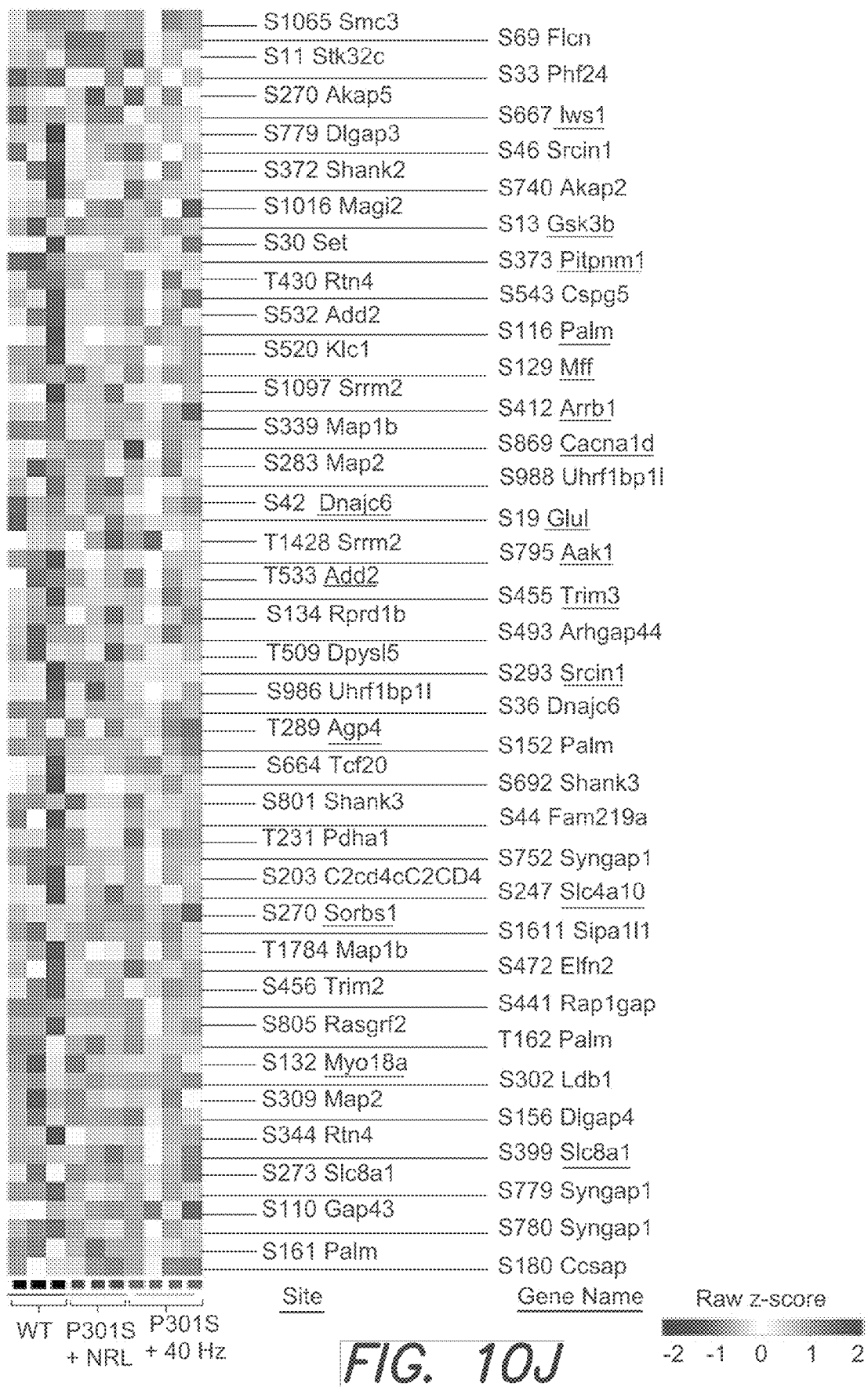

In FIG. 10J, the visual cortex from non-stimulated P301S tau-tg mice and GENUS stimulated 1 h/d for 22 days were subjected to S/T phosphoproteomics analysis. Heat-map shows the differentially phosphorylated proteins between non-stimulated and GENUS stimulated P301S mice that are involved in synaptic transmission and intracellular transport.

Figure 10K:
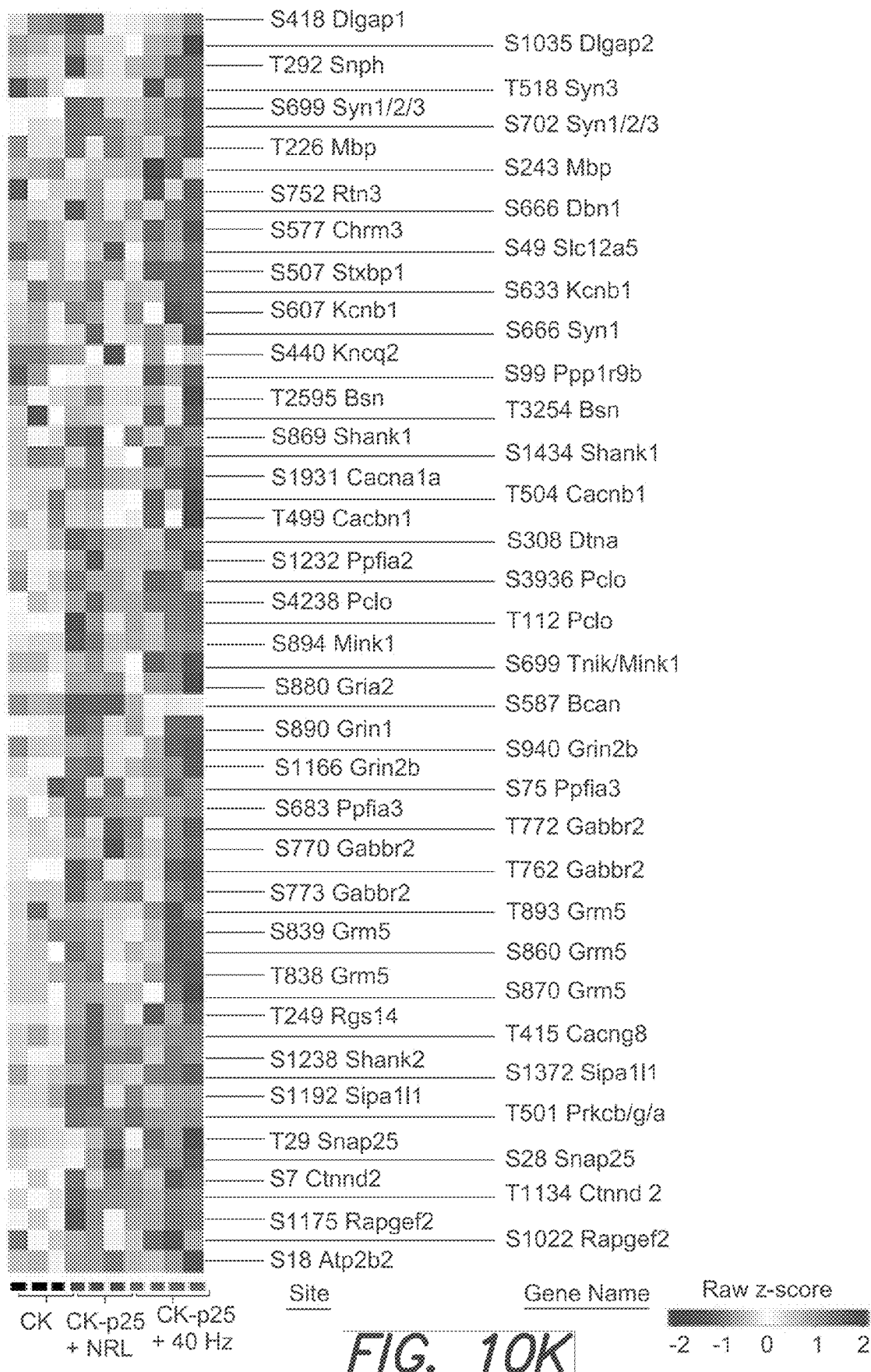

In FIG. 10K, a heat-map shows the differentially phosphorylated proteins involved in synaptic transmission (chemical synaptic transmission, trans-synaptic signaling) between non-stimulated and GENUS stimulated CK-p25 mice. Genes (corresponding proteins) names and the specific phospho-sites are shown.

Figure 10L:
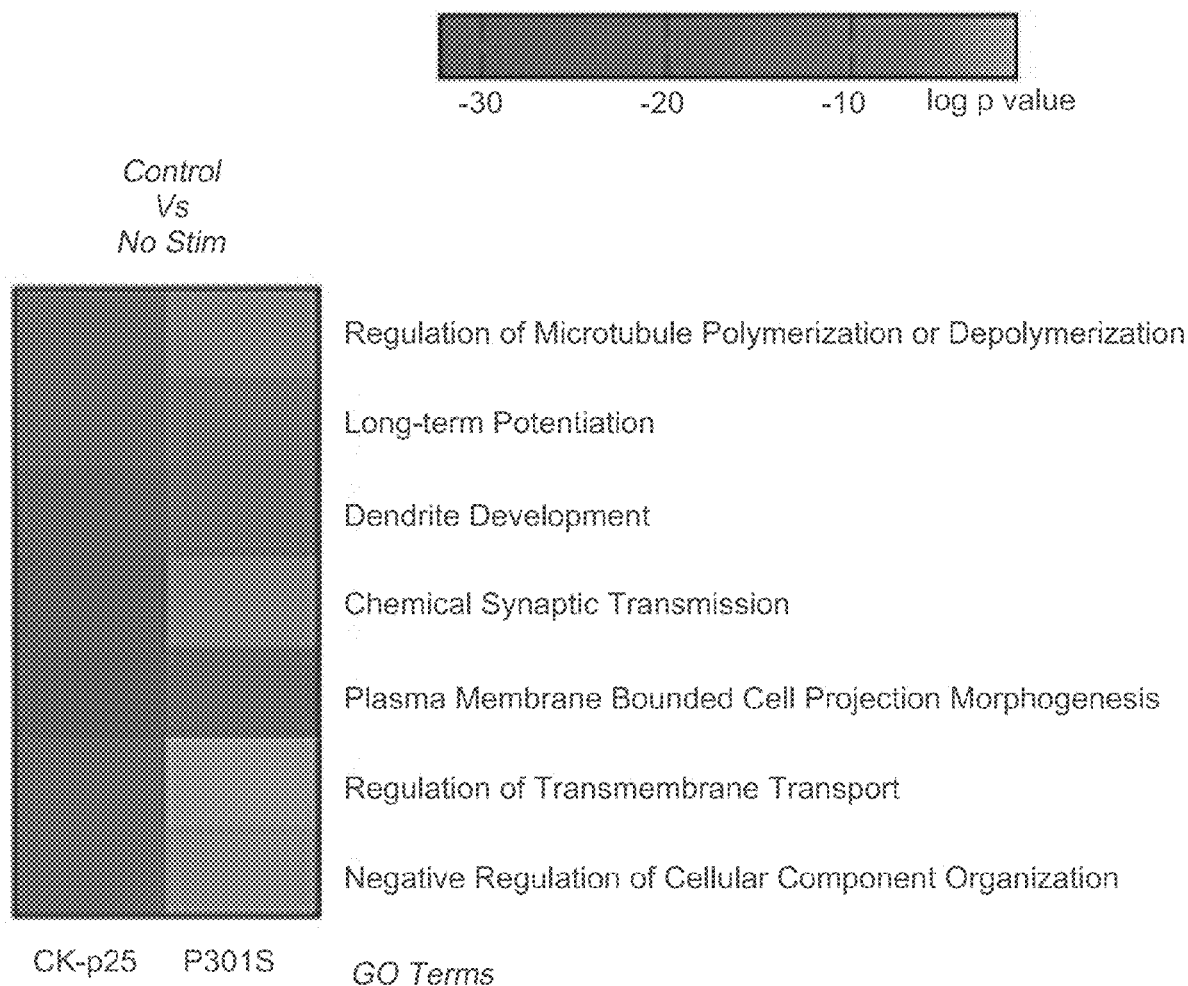

In FIG. 10L, P301S tau mice were subjected to no stimulation or GENUS stimulation for 22 days. Total protein expressions and S/T phosphorylated proteins analysis was performed on visual cortex tissue using tandem mass tag (TMT) 10-plex kit (see methods) and mass spectrometry (LC-MS/MS). N=3 WT naïve, 3 non-stimulated P301S and 4 GENUS stimulated P301S mice. Phosphorylated proteins with fold change of ±0.2 and adjusted P value of <0.05 were considered statistically significant. GO terms of biological processes associated with the differentially S/T phosphorylated proteins in CK-p25 and P301S tau mice compared to their respective control mice.

FIG. 10M—Top: Western blots show pS774 DNM-1, DNM-1, DNM-3 and GAPDH from CK naïve, non-stimulated and 40 Hz GENUS stimulated CK-p25 mice. pS774DNM-1 level was significantly higher in CK-p25 mice compare to CK naïve mice, whereas 40 Hz GENUS significantly reduced pS774DNM-1 in CK-p25 mice. N=4 CK naïve mice, 5 non-stimulated CK-p25 mice and 4 40 Hz GENUS stimulated CK-p25 mice (ANOVA F (2,12)=5.836, P=0.021). Bottom: Bar chart shows the group difference. Please note that this is an independent verification. Related to main FIG. 5F.

FIG. 10N—Top: Western blots show pS774 DNM-1, total DNM-1, DNM-3 and GAPDH from WT naïve, non-stimulated and 40 Hz GENUS stimulated P301S mice. Please note that this is an independent verification. *P<0.05. Related to main FIG. 5F.

FIGS. 11A through 11J illustrate behavioral characterization of the effect on a subject of acute and chronic visual stimulation according to the inventive concepts disclosed.

FIG. 11A—Top: Heat-maps of C57B16/J mice occupancy in 10 minute bins is shown, either with or without GENUS. No difference was evident in exploratory behavior during the first 10 min pre-stimulation baseline period. N=6 mice per group. T-test, T=0.3173, P=0.7576. Similarly, no systematic changes in velocity throughout the 40 Hz stimulation period were detectable when compared to the no-stimulation group. Bottom: Plot shows the velocity every minute, for the 30 minutes. Two-way repeated measures ANOVA: Exploration over 30 min time, F (29, 290)=6.747, P<0.0001; interaction between non-stimulated and GENUS stimulated WT mice, F (29, 290)=0.9354, P=0.5652.

In FIG. 11B, C57B16/J mice (4months old) was subjected to no stimulation or 40 Hz light flicker stimulation for 1 h and immediately afterwards were injected with picrotoxin and placed in an OF. Left: Distance travelled after picrotoxin injection, revealed no difference between GENUS and non-stimulation groups. N=4 mice per group. Repeated measures ANOVA F=0.527, P=0.717. Right: Racine scores. Score 0, normal behavior; score 1, immobility and rigidity; score 2, head bobbing; score 3, forelimb clonus and rearing; score 4, continuous rearing and falling; score 5, clonic-tonic seizure; score 6, death. No difference in seizure susceptibility was evident between the non-stimulated and GENUS groups. Repeated measures ANOVA F=0.429, P=0.994.

In FIG. 11C, following 3 days of habituation to a novel object, WT mice were tested for NOR. Left: Time spent exploring familiar and novel objects every minute for 30 min duration. Novel object discrimination in percentage is superimposed. Middle: histogram shows the cumulative (entire 30 min) exploration of familiar and novel objects. Both non-stimulated and GENUS stimulated mice spent significantly more time exploring the novel object compared to familiar object. There was no difference between groups, suggesting that acute 40 Hz light flicker exposure did not affect the ability of mice to discriminate novel objects. N=6 mice per group. Cumulative novel object preference compared to familiar object: No stim, T (6)=−13.055, P=0.00004; GENUS T (5)=−20.818, P=0.000004. Novel object preference between groups, t-test T=−0.314, P=0.760. Right: histogram of total distance travelled, showing GENUS does not alter locomotor behavior in WT mice. Total distance moved, t-test T=0.5096, P=0.6214.

In FIG. 11D, C57B16/J mice underwent no stimulation or GENUS 1 h per day for 7 days. The body weight of mice was measured 1 h before the stimulation paradigm every day for 7 days and 1-day post stimulation regimen. N=14 non-stimulated and 12 GENUS stimulated mice. Bar chart show the body weight across 7 days. There was an overall increase in body weight across days in both groups (F (6,144)=2.889, P=0.011), however; there was no difference in body weight between non-stimulated and GENUS stimulated group (F (6, 144)=1.327, P=0.249).

FIG. 11E shows that there was significant difference in the body weight between WT naïve and P301S tau mice (two-way ANOVA effects between groups F (2, 72)=8.947, P=0.0003), however; chronic GENUS (1 h/day for 22 days) did not affect the body weight of P301S compared to non-stimulated P301S tau mice. N=13 WT naïve, 14 non-stimulated and 12 GENUS stimulated P301S mice.

FIG. 11F shows that chronic GENUS did not affect body weight of CK-p25 mice compared to non-stimulated CK-p25 mice (two-way ANOVA effects between groups F (2, 122)=2.487, P=0.0874). N=25 CK naïve, 21 non-stimulated and 18 GENUS stimulated CK-p25 mice.

Figure 11G:
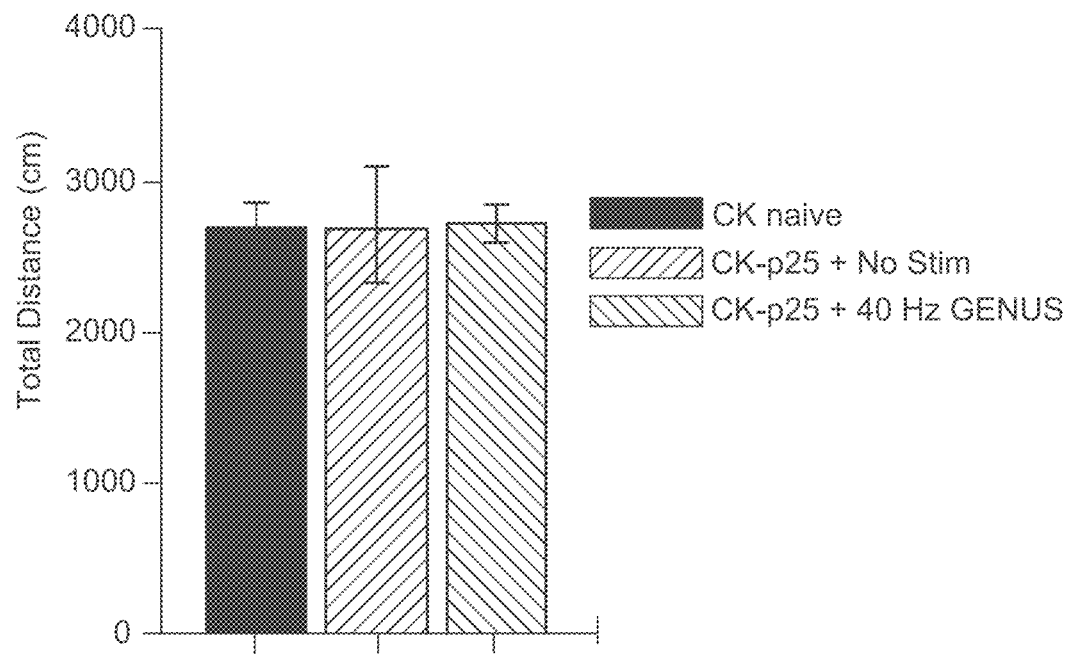

FIG. 11G is related to main FIG. 6F. N=same as in FIG. 6F. Total distance travelled in open field test was significant between groups. ANOVA F (2, 36)=10.27, P=0.0003. However, GENUS stimulated P301S mice did not differ compared to non-stimulated P301S (P>0.99).

Figure 11H:
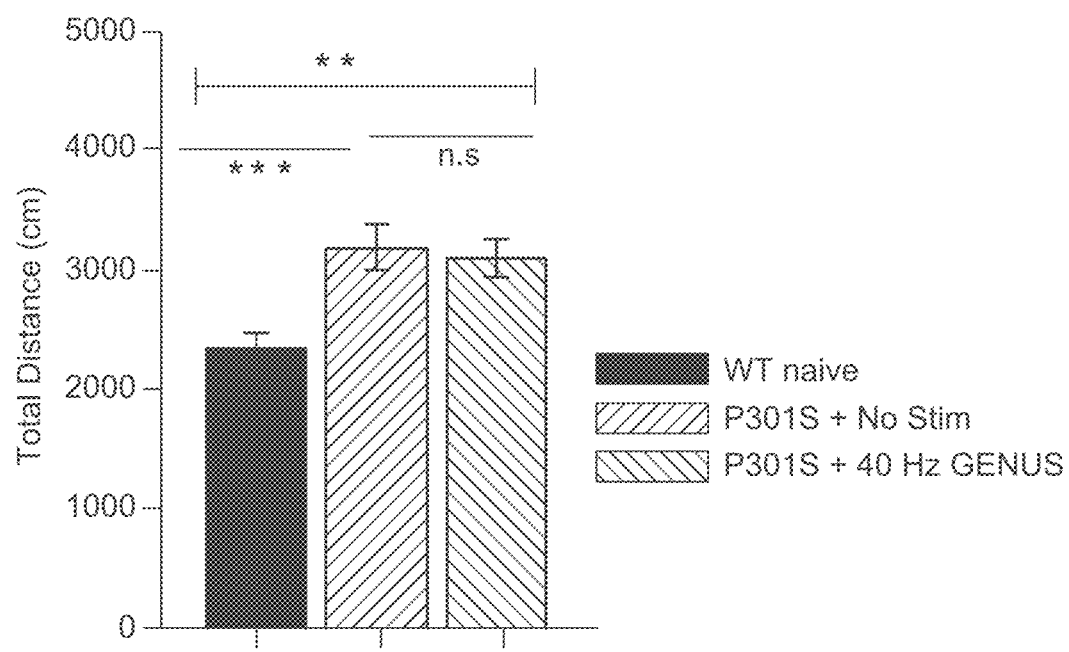
Figure 11I:
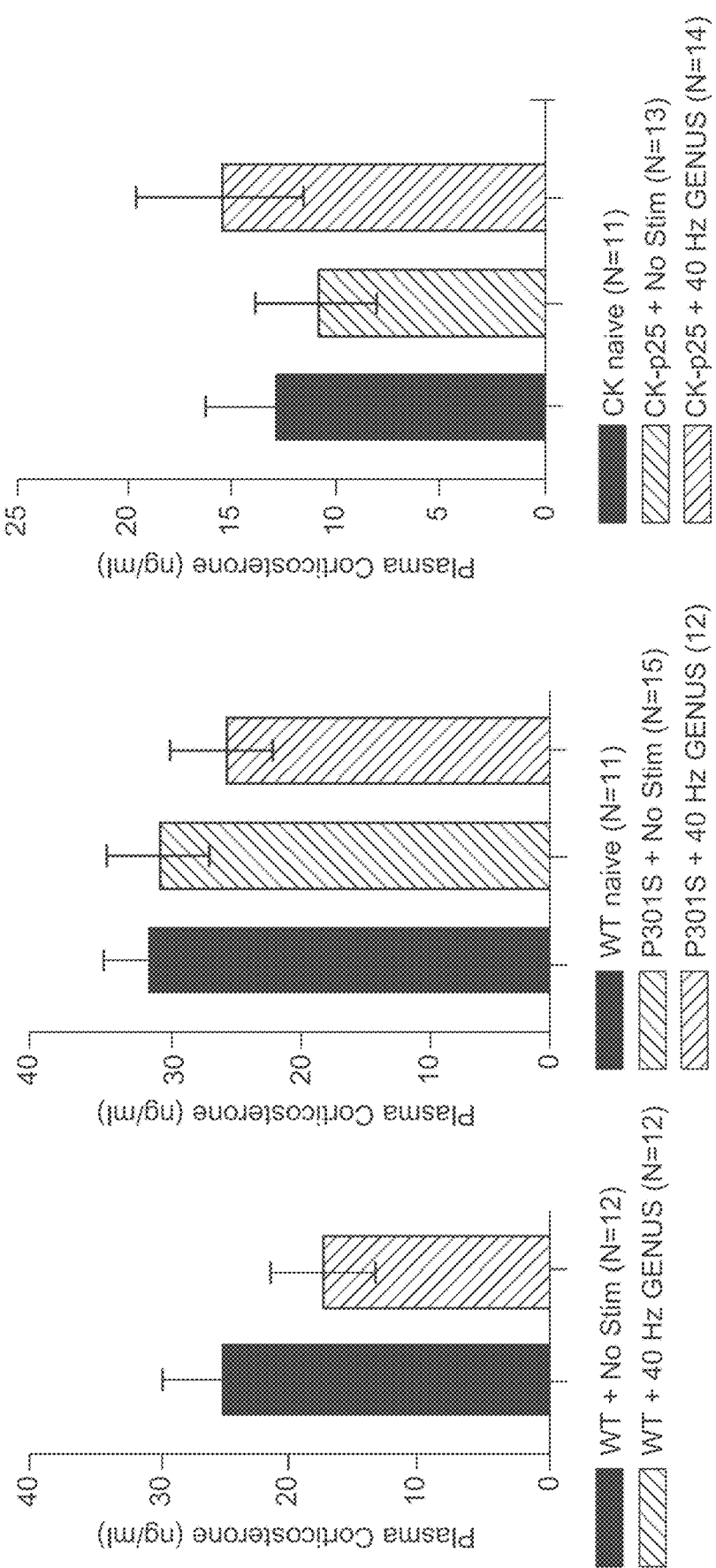
Figure 11J:
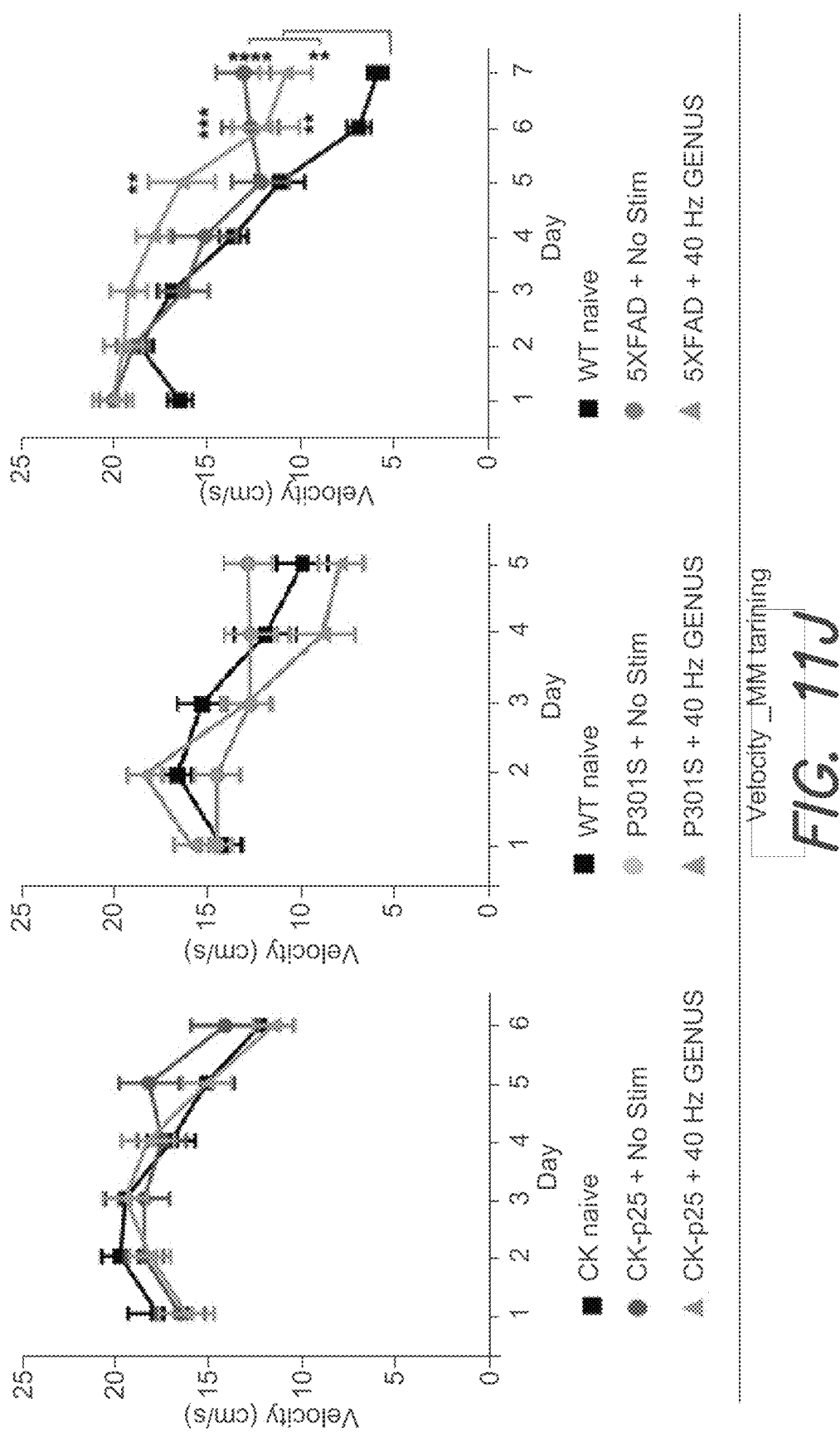

FIG. 11H is related to main FIG. 6B. N=same as in FIG. 6B. Total distance travelled in open field test is shown. There was no difference in total distance travelled during the open field test in non-stimulated and GENUS stimulated CK-p25 mice. ANOVA F (2, 49)=0.01552, P=0.9846.

FIG. 11I—Left: Plasma corticosterone levels did not differ between non-stimulated and 7 days GENUS stimulated WT mice. N=12 mice per group. T=1.17, P=0.255. Middle: Mice underwent no stimulation or GENUS 1 h per day for 42 days while p25 was induced in CK-p25 mice. Number of mice per group is indicated in the chart. Plasma corticosterone levels did not differ between CK naïve, non-stimulated and GENUS stimulated CK-p25 mice (F (2, 35)=0.4871, P=0.6185). Right: Plasma corticosterone in P301S tau mice (22 days stimulation) was also comparable between WT naïve, non-stimulated P301S and 22 days GENUS stimulated P301S mice (F (2, 35)=0.6874, P=0.5096). Number of mice in each group is presented in the figure accordingly.

FIG. 11J is related to main FIG. 7. The mean speed with which mice swam in the Morris water maze test from all the experiments. Left: No differences between any groups across all 6 days of training in CK-p25 mice were evident (FIG. 7D). Two-way ANOVA between groups effect F (2, 252)=0.3832, P=0.6821. Middle: There was no difference between groups across all 5 days of training in P301S tau mice (FIG. 7H). Two-way ANOVA between groups effect F (2, 225)=0.5726, P=0.5651. Right: There was a significant difference in 5XFAD mice cohort in swimming velocity (FIG. 7I). Two-way ANOVA between groups effect F (2, 273)=24.24, P<0.0001. Multiple comparison with Bonferroni's correction. There was no difference from Day 1 through D4. Day 5: WT naive vs. 5XFAD+No Stim, P>0.9999. WT naive vs. 5XFAD+40 Hz GENUS, P=0.0022. 5XFAD+No Stim vs. 5XFAD+40 Hz GENUS, P=0.0483. Day6: WT naive vs. 5XFAD+No Stim, P=0.0005. WT naive vs. 5XFAD+40 Hz GENUS, P=0.0037. 5XFAD+No Stim vs. 5XFAD+40 Hz GENUS, P>0.9999. Day 7: WT naive vs. 5XFAD+No Stim, P<0.0001. WT naive vs. 5XFAD+40 Hz GENUS, P=0.0043. 5XFAD+No Stim vs. 5XFAD+40 Hz GENUS, P=0.5716.

Figure 12A:
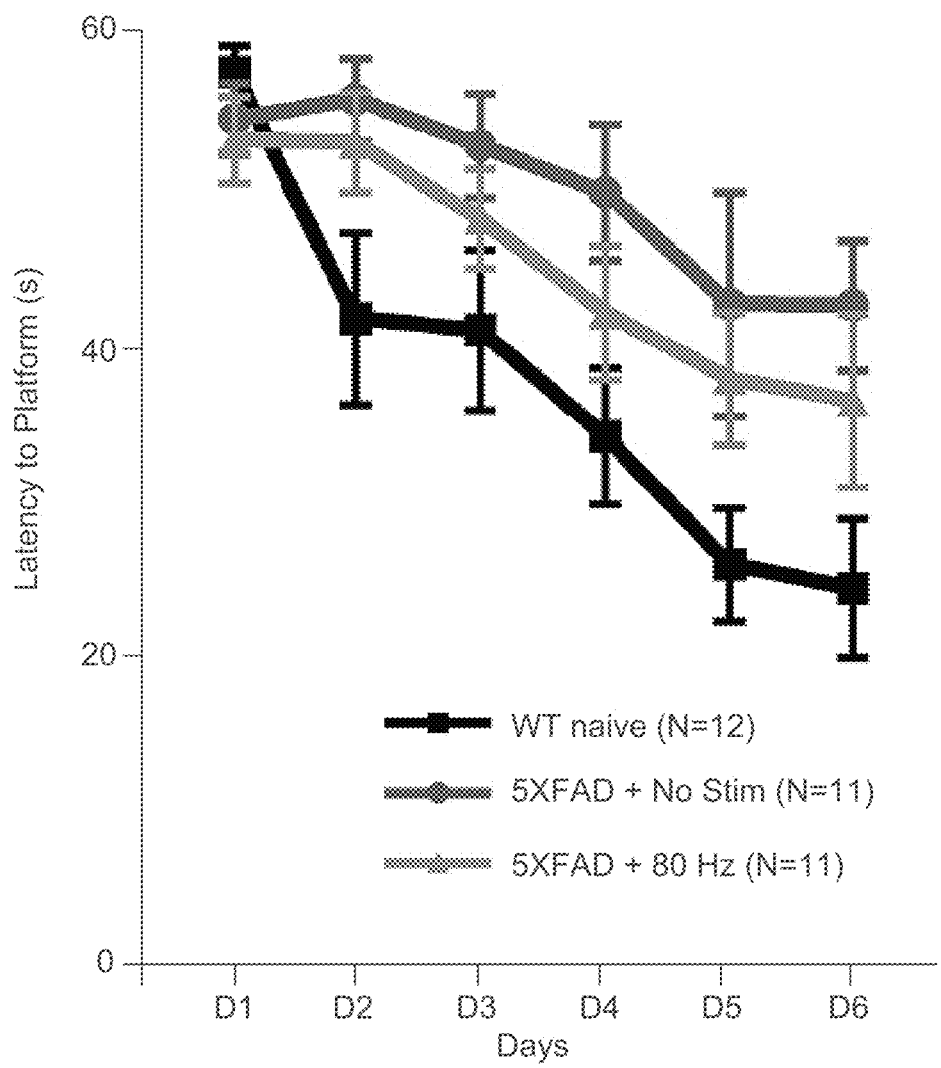
FIGS. 12A through 12C illustrate that chronic visual stimulation at 80 Hz did not affect Morris water maze in 5XFAD mice, according to the inventive concepts disclosed.
Figure 12B:
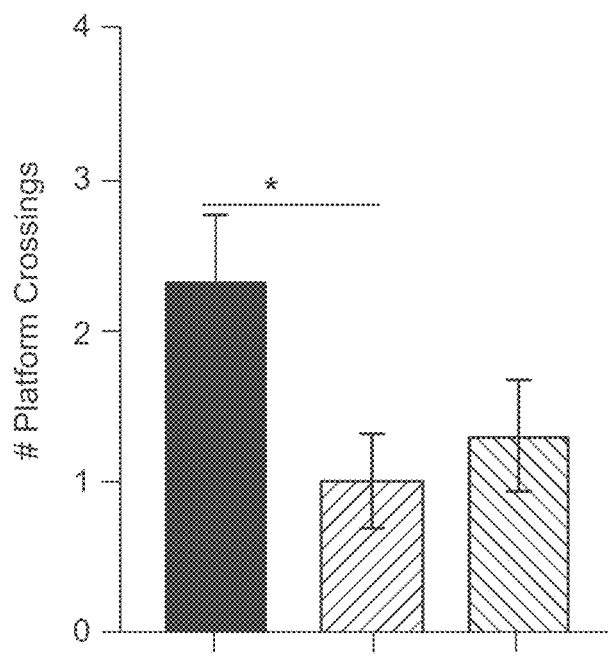
Figure 12C:
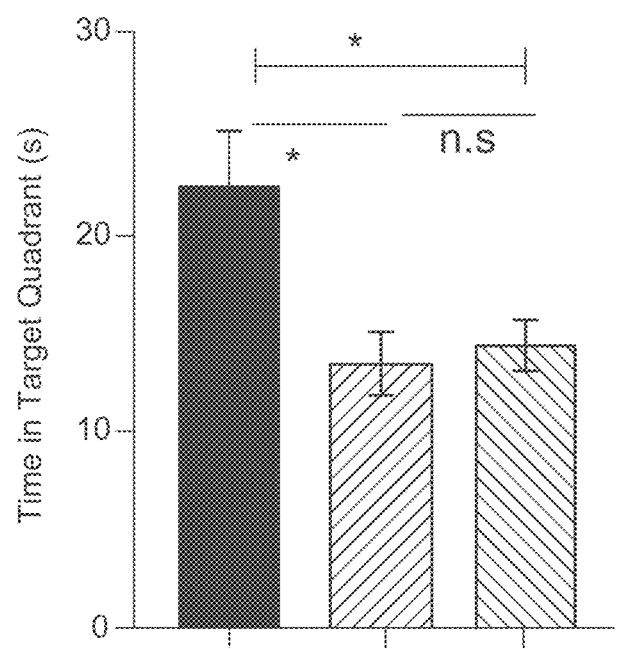

FIGS. 12A through 12C illustrate that chronic visual stimulation at 80 Hz did not affect Morris water maze in 5XFAD mice, according to the inventive concepts disclosed.

FIG. 12A shows performance in the MWM of 5XFAD mice exposed to 80 Hz stimulation for 1 h per day for 22 days. Number of mice per group is indicated in the line chart legends. Latency to find the platform during the training did not differ between non-stimulated and 80 Hz stimulated 5XFAD groups (Two-way ANOVA F (2, 180)=13.33, P<0.0001), however; both these groups required more time to find the platform compared to WT naïve mice.

FIG. 12B indicates the number of platform crossings during the probe test. F (2, 30)=3.622, P=0.0390. Multiple comparison with Bonferroni's correction. *P<0.05.

FIG. 12C shows time spent in the target quadrant during the probe test was significantly less in the non-stimulated and 80 Hz stimulated 5XFAD mice compared to WT naïve mice. F (2, 30)=5.643, P=0.0083. Multiple comparison with Bonferroni's correction, compared to WT naïve mice, on-stimulated—P=0.014, 80 Hz—P=0.0371. *P<0.05.

Experiment and Analysis Particulars
Star Methods

| REAGENT or RESOURCE | SOURCE | IDENTIFIER |
|---|---|---|
| Antibodies | | |
| Bassoon (1:500, dilution) | Abcam | Cat# ab82958, SAP7F407 |
| vGlut1 (1:1000) | Synaptic Systems | Cat# 135 303 |
| NeuN (1:2000) | Synaptic Systems | Cat# 266 004 |
| IBA1 (1:500) | Wako Chemicals | Cat# 019-19741 |
| GFAP (1:500) | Abcam | Cat# ab53554 |
| Ser202/T205 Tau (1:500) | Thermo Fisher Scientific | Cat# MN1020 |
| Total tau (1:1000) | Santa Cruz Biotechnology | Cat# sc-5587, H-150 |
| β-Amyloid (1:500) | Cell Signaling Technology | Cat# 8243, D54D2 |
| C1q (1:500) | Abcam | Cat# ab182451 |
| CD40 (1:200) | Thermo Fisher Scientific | Cat# MA5-17852 |
| γH2Ax (1:500) | Millipore | Cat# 05-636 |
| GFP (1:1000) | Thermo Fisher Scientific | Cat# A-11122 |
| DNM-1 (1:1000) | Thermo Fisher Scientific | Cat# MA5-15285, 3G4B6 |
| Ser774-DNM-1 (1:1000) | Thermo Fisher Scientific | Cat# PA5-38112 |
| DNM-3 (1:1000) | Thermo Fisher Scientific | Cat# PA1-662 |
| N-terminal APP (1:1000) | Millipore | Cat# MAB348, 22C11 |
| C-terminal APP (1:1000) | Thermo Fisher Scientific | Cat# 51-2700 |
| GAD65 (1:500) | Abcam | Cat# ab26113, GAD-6 |
| p35/p25 (1:1000) | In house made | N/A |
| GAPDH (1:2000) | Santa Cruz Biotechnology | Cat# sc-32233, 6C5 |
| β-Actin (1:3000) | Abcam | Cat# ab9485 |
| NFH (1:1000) | Cell Signaling Technology | Cat# 2836S, RMdO 20 |
| c-Fos (1:500) | Santa Cruz Biotechnology | Cat# sc-52 |
| Donkey anti-Rabbit, Alexa Fluor 488 | Invitrogen | Cat# A21206 |
| Donkey anti-Mouse, Alexa Fluor 488 | Invitrogen | Cat# A21202 |
| Donkey anti-Rabbit, Alexa Fluor 555 | Invitrogen | Cat# A-31572 |
| Donkey anti-Rabbit, Alexa Fluor 594 | Invitrogen | Cat# A11037 |
| Donkey anti-Goat, Alexa Fluor 594 | Invitrogen | Cat# A11058 |
| Donkey anti-Mouse, Alexa Fluor 594 | Invitrogen | Cat# A11032 |
| Donkey anti-Guinea pig, Alexa Fluor 647 | Invitrogen | Cat# A21450 |
| Donkey anti-Goat, Alexa Fluor 647 | Invitrogen | Cat# A21447 |
| Donkey anti-Mouse, Alexa Fluor 647 | Invitrogen | Cat# A31571 |
| Donkey anti-Rabbit, Alexa Fluor 647 | Invitrogen | Cat# A31573 |
| Experimental Models: Organisms/Strains | | |
| Mouse: wild type C57BL/6J | Jackson Laboratory | JAX: 000664 |
| B6; CBA-Tg(Camk2a-tTA)1Mmay/J | Jackson Laboratory | Stock No: 003010 |
| C57BL/6-Tg(tetO-CDK5R1/GFP)337Lht/J | Jackson Laboratory | Stock No: 005706 |
| 5XFAD: B6SJL-Tg(APPSwFlLon, PSEN1*M146L*L286V)6799Vas/Mmjax | Jackson Laboratory | Stock No: 34840-JAX |
| P301S tau-tg: B6; C3-Tg(Prnp-MAPT*P301S)PS19Vle/J | Jackson Laboratory | Stock No: 008169 |
| B6.129(Cg)-Fostm1.1(cre/ERT2)Luo/J | Jackson Laboratory | Stock No: 021882 |
| Software and Algorithms | | |
| MATLAB | Mathworks | mathworks.com |
| IMARIS | Bitplane | bitplane.com |
| ImageJ | NIH | imagej.nih.gov/ij |
| EthoVision XT | Noldus | noldus.com |
| TSEsystem | TSE Systems | tse-systems.com |
| GraphPad Prism | GraphPad | graphpad.com |
| Proteome Discoverer version 1.4.1.14 | Thermofisher | tools.thermofisher.com |
| Ingenuity Pathway Analysis | Qiagen | qiagenbioinformatics.com |
| SPSS (version 24) | IBM Analytics | ibm.com |
| ZEN | Zeiss | zeiss.com |

Animal Models

All the experiments were approved by the Committee for Animal Care of the Division of Comparative Medicine at the Massachusetts Institute of Technology. C57BL6, Tg(Camk2a-tTA), Tg(APPSwFlLon, PSEN1*M146L*L286V), Tg(Prnp-MAPT*P301S)PS19, and Fos-tm1.1(cre/ERT2) were obtained from the Jackson laboratory. Tg(tetO-CDK5R1/GFP) was generated in our lab. All the transgenic mice were bred and maintained in our animal facility.

C57BL/6J mice used were 3, 10 or 17 months old. CK-control and CK-p25 (Camk2a-tTA bred with tetO-CDK5R1/GFP) mice were raised on a doxycycline containing food. Normal rodent diet was given to induce p25-GFP transgene expression. Typically, p25 expression was induced for 6 weeks. At the start of the experiments the age of P301S tau mice were 7 months and 5XFAD mice were 9 or 11 months. All mice were group housed (2-5 mice per cage) except those that were implanted with microdrives. All experiments were done using age matched littermates. Immunostaining and electrophysiological experiments were performed twice using mice to the total number as defined in figure legends. All behavioral experiments (except Morris water maze in young and aged WT mice and tau P301S mice) described in this paper were performed once, using the total number of animals as defined in figure legends. No statistical methods were used to pre-determine sample sizes, instead we opted to use group sizes of similar previously published studies from our lab settings (Iaccarino et al., 2016; Nott et al., 2016) to ensure variance was kept to a minimum between groups. Box plot in FIG. 1 represent median, and upper (75%) and lower (25%) quartile range. Unless noted, all plots in FIG. 2 to FIG. 6 with error bars are reported as mean±SEM and all samples are reported as number of mice (N).

40 Hz Light Flicker Stimulation

Light flicker stimulation was delivered as previously described (Iaccarino et al., 2016). Mice were transported from the holding room to the flicker treatment room, located on adjacent floors of the same building. Following habituation under dim light for 1 h before the start of the experiment, mice were introduced to the test cage (similar to the home cage, except without bedding and three of its sides covered with black sheeting). Mice were allowed to freely move inside the cage but did not have access to food or water during the 1 h light flicker. An array of light emitting diodes (LEDs) was present on the open side of the cage and was driven to flicker at a frequency of 40 Hz with a square wave current pattern using an Arduino system. After 1 h of 40 Hz light flicker exposure mice were returned to their home cage and allowed to rest for a further 30 minutes before being transported back to the holding room. Normal room light control mice were exposed to the similar cages with similar food and water restriction, however; they experienced only normal room light.

Tissue Preparation

Immunohistochemistry: Mice were transcardially perused with 40 ml of ice cold phosphate buffered saline (PBS) followed by 40 ml of 4% paraformaldehyde in PBS. Brains were removed and post-fixed in 4% PFA overnight at 4° C. and transferred to PBS prior to sectioning.

Western blotting: Visual cortex was dissected out and snap frozen in liquid nitrogen and stored in a −80° C. freezer until processing. Samples were homogenized using a glass homogenizer with RIPA (50 mM Tris HCl pH 8.0, 150 mM NaCl, 1% NP-40, 0.5% sodium deoxycholate, 0.1% SDS) buffer. The concentration of proteins in samples were quantified using a Bio-Rad protein assay. Equal concentrations of proteins were prepared and added with SDS-sample buffer.

Immunohistochemistry

Brains were mounted on a vibratome stage (Leica VT1000S) using superglue and 40 µm sections prepared. Slices were subsequently washed with PBS and blocked using 5% normal donkey serum prepared in PBS containing 0.3% Triton-X100 (PBST) for 2 h at room temperature. Blocking buffer was aspirated out and the slices were incubated with the appropriate primary antibody (prepared in fresh blocking buffer) overnight at 4° C. on a shaker. Slices then were washed three times (10 minutes each) with the blocking buffer and then incubated with the Alexa Fluor 488, 555, 594 or 647 conjugated secondary antibodies for 2 h at room temperature. Following three washes (15 minutes each) with blocking buffer and one final wash with PBS (10 minutes), slices were mounted with fluromount-G (Electron microscopic Sciences).

The following combination of secondary antibodies were used: (1) Alexa Fluor 488, 594 and 647, (2) Alexa Fluor 555 and 647, and (3) Alexa Fluor 594 and 647.

Imaging and Quantification

Images were acquired using either LSM 710 or LSM 880 confocal microscopes (Zeiss) with 5×, 10×, 20×, 40× or 63× objectives at identical settings for all conditions. Images were quantified using either ImageJ 1.42q or Imarisx64 8.1.2 (Bitplane, Zurich, Switzerland). For each experimental condition, two coronal sections from the indicated number of animals were used. The averaged values from the two images per mouse was further used for quantification. Quantification was performed by an experimenter blind to the genotype and treatment conditions wherever possible.

NeuN, c-Fos and GFP positive cell counting: All images were acquired in Z-stacks-10 per image and were quantified. An average of every two and sum of all the counts was computed using ImageJ. NeuN counting from P301S tau-tg and 5XFAD was done by an experimenter blind to the treatment condition.

γH2Ax positive cell counting: The multi-point tool in ImageJ was used to count cells.

vGlut1, bassoon puncta: LSM 880, with a 63× objective and further zoom of 3 times was used to acquire the images. The deep layers (primarily 4 and 5) from visual and somatosensory cortices, CA1 stratum radiatum and layer 5 of the ventral cingulate cortex were all targeted. A single plane image was acquired. The particle count plugin in ImageJ was used to quantify the number of vGlut1 puncta.

pS202/T205 tau intensities: Using a LSM 710 with a 40× objective z-stacks of the entire slice thickness 40 µm (40 images from each field) were acquired. All images were compressed/collapsed and the signal intensity was measured in ImageJ.

pS774-DNM1 intensities: An LSM 880 with a 63× objective and further 3× zoom, was used to obtain z-stacks of the entire slice thickness 40 µm (40 images from each field). All images were compressed/collapsed and the signal intensity of puncta was measured in ImageJ.

Plaques: The D54D2 antibody stained overall plaque intensity and the number of plaques was quantified by an experimenter blind to the genotype and treatment conditions. The entire 40 µm slice was z-stack imaged at 0.5 µm intervals, these were then merged and the signal intensity measured using ImageJ. Plaques were counted using the particle analysis tool in ImageJ with a threshold of 5 µm². All plaque intensities and plaque number counting were done by an experimenter blind to the treatment condition.

C1q intensities: Using a LSM 710 with a 40× objective z-stacks of the entire slice thickness 40 µm (40 images from each field) were acquired. All images were compressed/collapsed and the signal intensity was measured in ImageJ.

CD40: An LSM 880 with a 63× objective was used to obtain z-stacks of the entire slice thickness 40 µm (40 images from each field). All images were compressed/collapsed and the signal intensity was measured in ImageJ.

Lateral ventricles: LSM 710 microscope with a 5× objective was used to image complete coronal slices at −2.0 bregma (rostral to caudal). Outlines covering the entire area of the lateral ventricles were drawn using the freehand selection tool from ImageJ and the area of the LV was measured.

Microglia: Iba1 immunoreactive cells were considered microglia. Using a LSM 710 with a 40× objective z-stacks of the entire slice thickness 40 µm (40 images from each field) were acquired. Imaris was used for 3D rendering of images to quantify the total volume of soma and processes microglia. Iba1 aggregation analysis was performed in Image J 3D rendering plugin. Minimum distance between Iba1 was calculated for every microglia from the images. All images were compressed/collapsed and Image J was used to quantify the total number of Iba1 positive cells.

Cortical thickness: LSM 710 microscope with a 5× objective was used to image complete cortical columns. The distance between outer cortical boundary and cortical side of corpus callosum was measured using ImageJ.

Brain weight measurement: Mice were transcardially perfused with PBS followed by 4% PFA and the brain was post-fixed overnight in 4% PFA. Brains were washed in PBS and any excess removed before being weighed in a wet lab high precision scale (Mettler Toledo, accurate to 1 mg). Another cohort of mice were sacrificed, brain was flash frozen in liquid nitrogen and brain weight was measured. Brain weight was normalized to CK naïve brains in each of these two independent measures.

Western Blotting

Six to eight μg of protein was loaded onto either 6, 8, 10, or 15% polyacrylamide gels and electrophoresed. Protein was transferred from acrylamide gels to nitrocellulose membranes (Bio-Rad) at 100 V for 120 min. Membranes were blocked using milk (5% w/v) diluted in PBS containing 0.1% Tween-20 (PBSTw), then incubated in primary antibodies overnight at 4° C. The following day they were washed three times with PBSTw and incubated with horseradish peroxidase-linked secondary antibodies (GE Healthcare) at room temperature for 60 min. After three further washes with PBSTw, membranes were treated with chemiluminscence substrates and the films were developed. Signal intensities were quantified using ImageJ 1.46q and normalized to values of control proteins such as β-actin, GAPDH or total proteins of the corresponding phosphorylated proteins analyses.

Microdrive Implantation and in Vivo Electrophysiology

Tungsten wire electrode drives: Microdrives were custom built using a 3D printed drive base with perfluoroalkoxy coated tungsten wire electrodes (50 μm bare diameter, 101.6 coated diameter; A-M Systems) and Neuralynx electrode interface board (EIB-36). Polyimide tubes were used to protect electrodes and reduce electrical noise. Electrodes were arranged to target layer 3 or 4 of visual cortex (co-ordinates relative to bregma, anterior-posterior (AP), −3.0; medial-lateral (ML), +2.0), SS1 (AP, −2.0; ML, +2.3), CA1 region of the hippocampus (AP, −1.8; ML, +1.5) and cingulate area of the prefrontal cortex (AP, +1.0; ML, +0.2). Reference electrode was placed in the cerebellum.

Tetrode drives: Custom microdrives contain four nichrome tetrodes (14 mm; California Fine Wire Company), gold-plated (Neuralynx) to an impedance of 200 to 250 kU, arranged in one row (running along the CA3 to CA1 axis of the dorsal hippocampus) was implanted to dorsal CA1 (AP, −1.8). Reference electrode was placed in the fiber tract above the hippocampus.

Surgery: Mice were anaesthetized with avertin, restrained in a stereotactic apparatus and craniotomies were made exposing the visual, somatosensory, and prefrontal cortices. Microdrives were implanted and slowly lowered to the target depth. Mice were allowed to recover for a period of 4 days.

In vivo electrophysiology: Following a 2-3 day habitation period to the chamber, recordings commenced with the animal allowed to move freely in a small open field. Recording sessions were composed a 10-15 minute period in which the LED was flashing at 40 Hz but was completely occluded by a black acrylic polypropylene sheet, immediately followed by a further 10 minutes with the sheet removed and animals exposed to the flickering LED. Data were acquired using Neuralynx SX system (Neuralynx, Bozeman, Mont., USA) and signals were sampled at 32,556 Hz. Position of animals was tracked using red light emitting diodes affixed to the microdrive. At the conclusion of the experiment mice underwent terminal anesthesia and electrode positions were marked by electrolytic lesioning of brain tissue with 50-μA current for 10 s through each electrode individually, to confirm their anatomical location.

Spikes: Single units was manually isolated by drawing cluster boundaries around the 3D projection of the recorded spikes, presented in SpikeSort3D software (Neuralynx). Cells were considered pyramidal neurons if mean spike width exceeded 200 μs and had a complex spike index (CSI)≥5.

Data analyses: LFPs were first filtered to the Nyquist frequency of the target sampling rate then down sampled by a factor of 20 (to 1628 Hz). Power spectral analyses were performed using the pwelch function in Matlab using a 500 ms time window with a 50% overlap, only segments of LFP data where animal velocity remained >4 cm/s were included in the analyses. The weighted phase lag index (WPLI), a measure of coherence more suited to small rodent brains was used as previously described (Vinck et al., 2011), to negate any potential contamination of coherence by volume conducted signals. WPLI was calculated for pairs of electrodes in anatomically distinct regions, only for periods in which animal speed was >4 cm/s. All analyses were performed using Matlab.

Pyramidal Cell 40 Hz Modulation: The relationship between spike firing times and 40 Hz LFP phase was calculated as previously described (Middleton and McHugh, 2016), using the Circular Statistics Toolbox. Briefly, spikes were sorted and LFP traces were filtered using the continuous wavelet transform with a cmor 1.5-1 wavelet centered on 40 Hz, returning the instantaneous signal phase and amplitudes. Spike times were linearly interpolated to determine phase, with peaks and troughs of gamma defined as 0 and 180 degrees respectively. The resulting phase values were binned to generate firing probabilities, for each 20-degree interval. Cells were considered to be phase-locked only if they had a distribution significantly different from uniform (P<0.05 circular Rayleigh test), with the strength of phase locking calculated as the mean resultant length.

RNA Sequencing

Isolation of microglia: The visual cortex was rapidly dissected and placed in ice cold Hanks' balanced salt solution (HBSS) (Gibco by Life Technologies, catalogue number 14175-095). The tissue was enzymatically digested using the Neural Tissue Dissociation Kit (P) (Miltenyi Biotec, catalogue number 130-092-628) according to the manufacturer's protocol, with minor modifications. Specifically, the tissue was enzymatically digested at 37° C. for 15 min instead of 35 min and the resulting cell suspension was passed through a 40 μm cell strainer (Falcon Cell Strainers, Sterile, Corning, product 352340) instead of a MACS SmartStrainer, 70 μm. The resulting cell suspension was then stained using allophycocyanin (APC)-conjugated CD11b mouse clone M1/70.15.11.5 (Miltenyi Biotec, 130-098-088) and phycoerythrin (PE)-conjugated CD45 antibody (BD Pharmingen, 553081) according to the manufacturer's (Miltenyi Biotec) recommendations. FACS was then used to purify CD11b and CD45 positive microglial cells. Standard, strict side scatter width versus area and forward scatter width versus area criteria were used to discriminate doublets and gate only singlets. Viable cells were identified by staining with propidium iodide (PI) and gating only PI-negative cells. CD11b and CD45 double positive ells were sorted into 1.5 ml centrifuge tubes which contains 500 μl of RNA lysis buffer (QIAGEN, catalogue number 74134) with 1% β-mercaptoethanol (Sigma-Aldrich, catalogue number M6250). RNA was extracted using RNeasy Plus Mini Kit (QIAGEN, catalogue number 74134) according to the manufacturer's protocol. RNA was eluted and then stored at −80° C. until whole transcriptome amplification, library preparation and sequencing.

Isolation of neurons: Visual cortex was homogenized in 0.5 mL ice cold PBS with protease inhibitors and the suspension was centrifuged at 1600 g for 10 minutes. Pellet was resuspended in 5 mL NF-1 hypotonic buffer, incubated for 5 min, and then Dounce-homogenized (pestle A) with 30 strokes. 5 mL NF-1 buffer was added to the suspension, washed pestle with 10 ml NF-1 buffer, for a combined total of 20 mL. Collected all in a 50 conical tube and filtered homogenate with 40 μm mesh filter. Pelleted nuclei at 3,000 rpm (1,600×g) for 15 min. Resuspended in 30 mL NF-1 buffer and mixed well. Rocked homogenate at 4° C. for 1 hour. Washed pellet once with 20 mL NF-1 buffer, centrifuged at 3,000 rpm for 15 min, and resuspended in 2-5 mL PBS+1% BSA+protease inhibitors without disturbing the pellet, on ice for 20 min. Alexa flour 488 or Alexa flour 647 conjugated NeuN antibodies (1:500) were added to the tubes, and incubated for 20 minutes at 4° C. Unbound antibodies was washed out with suspending and centrifuging with PBS+1% BSA+protease inhibitors. Spun down nuclei at 3,000 rpm for 15 min and resuspended in 0.5 mL (PBS+protease inhibitors) and filter with 40 μm mesh filter for FACS sorting. Two drops of nucblue live ready probes reagent was added (Thermo Fischer Scientific; Cat. No. R37605) for nuclei gating. NeuN positive ells were sorted into 1.5 ml centrifuge tubes which contains 500 μl of RNA lysis buffer (QIAGEN, catalogue number 74134) with 1% β-mercaptoethanol (Sigma-Aldrich, catalogue number M6250). RNA was extracted using RNeasy Plus Mini Kit (QIAGEN, catalogue number 74134) according to the manufacturer's protocol. RNA was eluted and then stored at −80° C. until whole transcriptome amplification, library preparation and sequencing.

RNA library preparation: Extracted total RNA was subject to QC using an Advanced Analytical-fragment Analyzer before library preparation. SMARTer Stranded Total RNA-Seq Kit-Pico Input was used for the P301S neuronal, CK-p25 neuronal, and P301S microglial RNA-seq. SMART-Seq v4 Ultra Low Input RNA Kit was used for CK-p25 microglia specific RNA-seq. Libraries were prepared according to the manufacturer's instructions, and sequenced on the Illumina Nextseq 500 platform at the MIT BioMicro Center.

The raw fastq data of 40-bp paired-end sequencing reads were aligned to the mouse mm9 reference genome using STAR2.4. The total number of reads and the percentage of reads aligned are as follows: CK-p25 neurons-total reads 18094674.857±827050.464; percentage aligned 85.323±0.414. P301S neurons-total reads 22792713.18±6308817.636; percentage aligned 84.45±0.548. CK-p25 microglia-total reads 28694964.5±435841.6674; percentage aligned 89.43±0.25. [P301S microglia-total reads 18990369.2±1667316.196; percentage aligned 27.243±4.04. Due to this very low mapping rate, this experiment requires further consideration]. The mapped reads were processed by Cufflinks2.2 (Trapnell et al., 2012) using mm9 reference gene annotation to estimate transcript abundances with library-type as fr-secondstrand (for stranded neuron data). Gene differential expression test between groups was performed using Cuffdiff module with p-value<0.05 (for neuron data). Geometric method was chosen as the library normalization method for Cuffdiff. For microglia data, featureCounts tool was used to quantify gene exonic counts from the non-stranded RNA-Seq data, and DESeq2 was employed to calculate statistical significance. Color-coded scatter plots were used to visualize group FPKM values for differentially expressed genes and other genes.

Z-scores of replicate expression FPKM values for differentially expressed genes were visualized in heatmaps for different sample groups. Gene ontology for microglia specific DEGs was performed using Metascape tool, whereas for neuron specific DEGs was performed using TOPPGENE Proteomics and Phospho-Proteomics Sample preparation, reduction, alkylation, and tryptic digestion: Visual cortex was dissected out and snap frozen in liquid nitrogen and stored in a −80° C. freezer until further use. Samples were subsequently homogenized using a plastic hand-held motor driven homogenizer with freshly prepared 8 M urea solution. The concentration of proteins in samples was quantified using a Bio-Rad protein assay. Samples containing 1 mg of protein per 1 ml were prepared, aliquoted and stored at −80° C. freezer until further use. Proteins were reduced with 10 mM dithiothreitol (DTT) for 1 h at 56° C., alkylated with 50 mM iodoacetamide for 1 h at room temperature (RT) and diluted to less than 1M urea with 100 mM ammonium acetate at pH 8.9. Proteins were digested using sequencing grade trypsin (Promega; 1 μg trypsin per 50 μg protein) overnight at RT. Enzyme activity was quenched by acidification of the samples with acetic acid. The peptide mixture was desalted and concentrated on a C18 Sep-Pak Plus cartridge (Waters) and eluted with 50% acetonitrile, 0.1% formic acid and 0.1% acetic acid. Solvent was evaporated in a SpeedVac vacuum centrifuge. 400 μg aliquots of each sample were aliquoted and frozen in liquid nitrogen for 5 min, lyophilized and stored at −80° C.

TMT labeling: TMT labeling and phosphopeptide enrichment: Lyophilized peptides were labeled with TMT-10-plex Mass Tag Labeling Kits (Thermo). For each TMT multiplex, a pooled sample was included consisting of a combination of equal amounts of peptides from WT, non stimulated and 40 Hz entrained mouse model of neurodegeneration, allowing for relative quantification to a normalization channel. For TMT labeling, nine samples from 9 mice peptide aliquots and one normalization channel (400 μg peptide for each channel) were resuspended in 100 μL of 70% (vol/vol) ethanol, 30% (vol/vol) 0.5 M triethyl-ammonium bicarbonate at pH 8.5, and incubated with TMT reagent resuspended in 40 μL anhydrous acetonitrile at RT for 1 h. The samples were concentrated, combined, and concentrated to dryness using a SpeedVac vacuum centrifuge.

Peptide Fractionation: The TMT-labeled peptide pellet was fractioned via high-pH reverse phase HPLC. Peptides were resuspended in 100 uL buffer A (10 mM TEAB, pH8) and separated on a 4.6 mm×250 mm 300Extend-C18, 5 um column (Agilent) using an 90 minute gradient with buffer B (90% MeCN, 10 mM TEAB, pH8) at a flow rate of 1 ml/min. The gradient was as follows: 1-5% B (0-10 min), 5-35% B (10-70 min), 35-70% B (70-80 min), 70% B (80-90 min). Fractions were collected over 75 minutes at 1 minute intervals from 10 min to 85 min. The fractions were concatenated into 15 fractions non-contiguously (1+16+31+46+61, 2+17+32+47+62, etc). The fractions then underwent speed-vac (Thermo Scientific Savant) to near dryness.

Phosphopeptide enrichment: Phosphopeptides were enriched from each of the 15 fractions using the High-Select Fe-NTA phosphopeptide enrichment kit (Thermo) per manufacturer's instructions.

Liquid chromatography-tandem mass spectrometry (LC-MS/MS): Peptides were separated by reverse phase HPLC (Thermo Easy nLC1000) using a precolumn (made in house, 6 cm of 10 µm C18) and a self-pack 5 µm tip analytical column (12 cm of 5 µm C18, New Objective) over a 140 minutes' gradient before nanoelectrospray using a QExactive Plus mass spectrometer (Thermo). Solvent A was 0.1% formic acid and solvent B was 80% MeCN/0.1% formic acid. The gradient conditions were 0-10% B (0-5 min), 10-30% B (5-105 min), 30-40% B (105-119 min), 40-60% B (119-124 min), 60-100% B (124-126 min), 100% B (126-136 min), 100-0% B (136-138 min), 0% B (138-140 min), and the mass spectrometer was operated in a data-dependent mode. The parameters for the full scan MS were: resolution of 70,000 across 350-2000 m/z, AGC 3e6 and maximum IT 50 ms. The full MS scan was followed by MS/MS for the top 10 precursor ions in each cycle with a NCE of 34 and dynamic exclusion of 30 s. Raw mass spectral data files (.raw) were searched using Proteome Discoverer (Thermo) and Mascot version 2.4.1 (Matrix Science). Mascot search parameters were: 10 ppm mass tolerance for precursor ions; 15 mmu for fragment ion mass tolerance; 2 missed cleavages of trypsin; fixed modification were carbamidomethylation of cysteine and TMT 10 plex modification of lysines and peptide N-termini; variable modifications were methionine oxidation, tyrosine phosphorylation, and serine/threonine phosphorylation. TMT quantification was obtained using Proteome Discoverer and isotopically corrected per manufacturer's instructions and were normalized to the mean of each TMT channel. Only peptides with a Mascot score greater than or equal to 25 and an isolation interference less than or equal to 30 were included in the data analysis.

The washed pre column was connected in series with an in-house packed analytical capillary column [50 µm ID×12 cm packed with 5 µm C18 beads (YMC gel, ODSAQ, 12 nm, S-5 µm, AQ12S05)] with an integrated electrospray tip (~1 µm orifice). Peptides were eluted using a 140 min (phosphopeptides) or 90 min (total peptide) gradient from 9 to 70% acetonitrile in 0.2 M acetic acid at a flow rate of 0.2 ml/min, with a flow split of ~10,000:1, yielding a final electrospray flow rate of ~20 nL/min. A total of 15 fractions from each sample were collected. Phosphopeptides were analyzed using a Thermo Q Exactive Hybrid Quadrupole-Orbitrap Plus mass spectrometer with the following settings: spray voltage, 2 kV; no sheath or auxiliary gas flow, heated capillary temperature, 250° C.; S-lens radio frequency level of 50%. The Q Exactive was operated in data-dependent acquisition mode. Full-scan MS spectra [mass/charge ratio (m/z), 350 to 2000; resolution, 70,000 at m/z 200] were detected in the Orbitrap analyzer after accumulation of ions at 3e6 target value based on predictive AGC from the previous scan. For every full scan, the 15 most intense ions were isolated (isolation width of 0.4 m/z) and fragmented (collision energy (CE): 32%) by higher-energy collisional dissociation (HCD) with a maximum injection time of 300 ms and 35,000 resolutions. Total peptide analysis was performed on an LTQ Orbitrap XL mass spectrometer with the following settings: spray voltage, 2 kV; no sheath or auxiliary gas flow, heated capillary temperature, 250° C. Analysis was performed in a data-dependent acquisition mode; full-scan mass spectra (m/z range 400-2000, resolution 60,000) were detected in the Orbitrap analyzer (ion target value 5×105). For every full scan, the 10 most intense ions were isolated (isolation width 3 Da) and fragmented by HCD (CE: 75%) in the HCD cell followed by detection in the Orbitrap (ion target value 1×105) for iTRAQ marker ion quantification.

Mass spectrometry peptide mapping data analysis: Raw mass spectral data files were loaded into Proteome Discoverer version 1.4.1.14 (DBversion: 79) (Thermo) and searched against the mouse SwissProt database using Mascot version 2.4 (Matrix Science). TMT reporter quantification was extracted and isotope corrected in Proteome Discoverer. Tandem mass spectra were matched with an initial mass tolerance of 10 ppm on precursor masses and 15 mmu for fragment ions. Cysteine carbamidomethylation, TMT-labeled lysine and protein N-terminal were searched as fixed modifications. Oxidized methionine, and phosphorylation of serine, threonine, and tyrosine were searched as variable modifications. Minimal peptide length was seven amino acids. The data sets were filtered by ion score >20 for all peptides to ensure high confidence in peptide identification and phosphorylation localization and to achieve an (FDR) below 1% for peptides. Phosphopeptide quantification was normalized based on median relative peptide quantification obtained from the crude peptide analysis to correct for slight variations in sample amount among TMT-channels. For each phosphopeptide, relative quantification was represented as a ratio between TMT ion intensities from each analyzed sample and the included normalization channel.

Bioinformatics analysis: To identify differentially expressed and phosphorylated peptides with significantly regulated ratios, we chose an arbitrary cutoff of ±20% difference with an adjusted P value of <0.05. The non-regulated background pool consisted of peptides with ratios between 0.8-1.2. Thus, subsequent bioinformatics analyses included peptides with ratios <0.8 and >1.2 relative to their normalization channel deemed as downregulated and upregulated, respectively. The name of proteins from protein accession numbers were converted to gene list using Uniprot ID mapping retrieval tool. Protein networks were obtained by using the STRING database (version 10.5). All active interaction sources except text mining were included and to ensure high confidence, a confidence score over 0.9 was required. Gene ontology (GO) term enrichment analysis was first performed on terms related to biological processes using the STRING (http://string-db.org), TOPPGENE (toppgene.cchmc.org) and Metascape (http://metascape.org) bioinformatics resources, and later was manually filtered to look for commonly present terms from these three resources. GO terms obtained in TOPPGENE was reported. For each individual mouse line (C57BL6/J, CK-p25, P301S tau-tg and 5XFAD), the analysis included gene sets derived from each pool of differentially regulated total peptide or S/T phosphopeptides (up- and downregulated).

Behavior

Open field: Mice were introduced into an open field box (dimensions: length=460 mm, width=460 mm and height=400 mm; TSE-Systems) and were tracked using Noldus (Ethovision) for 5 minutes, with time spent in the center and peripheral area of the arena measured.

Elevated plus maze (EPM): Mice were introduced into the center area of the EPM (ANY-Maze dimensions: arm length=35 cm, width=5 cm) and were tracked using Noldus program for 10 minutes. Time spent in each arm and the center of EPM was calculated offline.

Novel object recognition in CK-p25 and P301S tau mice: Mice were introduced into the open field arena and the time spent in the center of an arena is calculated. The next day, mice were re-introduced into the same open field box which now contained an additional two familiar objects (novel objects but will be familiar in the next session) and were allowed to explore the objects for 10 minutes. Following this, they were returned to the same arena 10 minutes after the last exploration, with one of the two objects replaced with the new object. Mice behavior was monitored for 7 minutes. Time spent exploring both the familiar and novel objects was recorded using Noldus and computed offline.

Seizure susceptibility: Mice were injected with picrotoxin (i.p injection) and placed in an open field arena and recorded for 30 minutes using Noldus and also from a side mounted camera. Distance travelled was calculated offline in Noldus, with seizure severity scored manually.

Morris water maze: MWM is a test for assessing spatial learning. MWM relies on visual cues to navigate from start locations around the perimeter of an open swimming arena to locate a submerged escape platform. Apparatus consisted of a circular pool (122 cm in diameter), filled with a tap water (22° C.-24° C.) and a non-toxic white paint added to make the solution opaque. An escape platform (10 cm in diameter) with a blunt protruding edge for better grip was submerged 1 inch under the water level. The pool was divided into four equal quadrants labeled N (north), E (east), S (south) and W (west). Mice were introduced to the maze in a randomized order across trials, from the edge, for trials of 60 seconds. The time required to find the hidden platform (latency) was recorded. The probe test was conducted 24 h after the last training trial, with the submerged platform removed. All the training and probe test trials were recorded using Noldus.

CK-p25, P301S and 5XFAD mice were subjected to GENUS in the morning (until 12 pm) and tested in the MWM in the afternoon (3-7 pm) which limited behavioral testing time to only 4 hours per day. We ensured a minimum of two and a maximum of 4 trials per day were used during training allowing us to run all groups in the MWM while also maintaining a strict dark/light cycle. Despite differences in number of training days, all AD mice used in MWM performed a comparable number of total training trails.

Statistical Analyses

Statistical analysis was conducted in SPSS, Matlab or Prism. Samples size was not pre-determined. Statistical significance was calculated using independent samples t-test, Wilcoxon Rank-sum test, one-way ANOVA or two-way repeated measures ANOVA with a Bonferroni post-hoc analysis and Krushkal Wallis test. Statistical significance was set at 0.05.

Conclusion

Inventive aspects of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

As used herein, the terms "about" and "approximately," when used in conjunction with numerical values and/or ranges, generally refer to those numerical values and/or ranges near to a recited numerical value and/or range. In some instances, the terms "about" and "approximately" can mean within ±10% of the recited value (inclusive of the recited value itself). For example, in some instances, "about 100 [units]" can mean within ±10% of 100 (e.g., from 90 to 110). In other instances, the terms "about" and "approximately" can mean within ±5% of the recited value (inclusive of the recited value itself). In yet other instances, the terms "about" and "approximately" can mean within ±1% of the recited value (inclusive of the recited value itself). The terms "about" and "approximately" can be used interchangeably.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will see, e.g., the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for treating dementia or Alzheimer's disease in a subject in need thereof, the method comprising:
   A) non-invasively delivering chronic visual stimuli having a frequency of about 30 Hz to about 50 Hz and having a 50% duty cycle to the subject for at least 1 hour per day for at least 22 days to entrain synchronized gamma oscillations in multiple brain regions of the subject including at least the prefrontal cortex (PFC) and the hippocampus of the subject.

2. The method of claim 1, wherein in A), the chronic visual stimuli have a frequency of about 35 Hz to about 45 Hz.

3. The method of claim 2, wherein in A), the chronic visual stimuli have a frequency of about 40 Hz.

4. The method of claim 3, wherein A) comprises inducing local field potential (LFP) at about 40 Hz in at least the prefrontal cortex and the hippocampus of the subject.

5. The method of claim 2, wherein A) comprises driving an array of light emitting diodes (LEDs) with a square wave current signal to generate the chronic visual stimuli.

6. The method of claim 5, wherein:
   the square wave current signal has the 50% duty cycle; and
   a frequency of the square wave current signal is equal to or approximately 40 Hz.

7. The method of claim 6, wherein A) comprises inducing local field potential (LFP) at about 40 Hz in at least the prefrontal cortex and the hippocampus of the subject.

8. The method of claim 1, wherein A) comprises non-invasively delivering the chronic visual stimuli for at least 1 hour per day for at least 42 days.

9. The method of claim 8, wherein:
   A) comprises driving an array of light emitting diodes (LEDs) with a square wave current signal to generate the chronic visual stimuli;
   the square wave current signal has the 50% duty cycle; and
   a frequency of the square wave current signal is equal to or approximately 40 Hz.

10. The method of claim 9, wherein A) comprises inducing local field potential (LFP) at about 40 Hz in at least the prefrontal cortex and the hippocampus of the subject.

11. The method of claim 10, wherein the multiple brain regions of the subject include the visual cortex, the somatosensory cortex, the hippocampus and the prefrontal cortex of the subject.

12. The method of claim 1, wherein A) comprises:
   A1) non-invasively delivering the chronic visual stimuli having the frequency of about 30 Hz to about 50 Hz to the subject to concurrently entrain synchronized gamma oscillations in the multiple brain regions of the subject including at least the prefrontal cortex and the hippocampus of the subject.

13. The method of claim 12, wherein A1) comprises:
   significantly increasing gamma coherence having a frequency between 30 Hz to 50 Hz between the multiple brain regions of the subject including at least the prefrontal cortex and the hippocampus of the subject.

14. The method of claim 13, wherein the multiple brain regions of the subject include the visual cortex, the somatosensory cortex, the hippocampus and the prefrontal cortex of the subject.

15. The method of claim 14, wherein in A), the chronic visual stimuli have a frequency of about 35 Hz to about 45 Hz.

16. The method of claim 15, wherein in A), the chronic visual stimuli have a frequency of about 40 Hz.

17. The method of claim 13, wherein A) comprises non-invasively delivering the chronic visual stimuli for at least 1 hour per day for at least 42 days.

18. The method of claim 17, wherein:
   A) comprises driving an array of light emitting diodes (LEDs) with a square wave current signal to generate the chronic visual stimuli;
   the square wave current signal has the 50% duty cycle; and
   a frequency of the square wave current signal is equal to or approximately 40 Hz.

19. The method of claim 12, wherein A1) further comprises:
   A2) non-invasively delivering the chronic visual stimuli having the frequency of about 30 Hz to about 50 Hz to modulate neuronal activity between the multiple brain regions of the subject including at least the prefrontal cortex and the hippocampus of the subject.

20. The method of claim 19, wherein A2) further comprises:
   non-invasively delivering the chronic visual stimuli having the frequency of about 30 Hz to about 50 Hz to coordinate neuronal activity between the multiple brain regions of the subject including at least the prefrontal cortex and the hippocampus of the subject.

21. The method of claim 20, wherein the multiple brain regions of the subject include the visual cortex, the somatosensory cortex, the hippocampus and the prefrontal cortex of the subject.

22. The method of claim 21, wherein in A), the chronic visual stimuli have a frequency of about 35 Hz to about 45 Hz.

23. The method of claim 22, wherein in A), the chronic visual stimuli have a frequency of about 40 Hz.

24. The method of claim 19, wherein A) comprises non-invasively delivering the chronic visual stimuli for at least 1 hour per day for at least 42 days.

25. The method of claim 22, wherein:
   A) comprises driving an array of light emitting diodes (LEDs) with a square wave current signal to generate the chronic visual stimuli;
   the square wave current signal has the 50% duty cycle; and
   a frequency of the square wave current signal is equal to or approximately 40 Hz.

26. The method of claim 19, wherein A2) further comprises:
   A3) non-invasively delivering the chronic visual stimuli having the frequency of about 30 Hz to about 50 Hz to reduce neurodegeneration in the multiple brain regions of the subject including at least the prefrontal cortex and the hippocampus of the subject.

27. The method of claim 26, wherein A3) further comprises:
non-invasively delivering the chronic visual stimuli having the frequency of about 30 Hz to about 50 Hz to reduce amyloid plaques in the multiple brain regions of the subject including at least the prefrontal cortex and the hippocampus of the subject.

28. The method of claim 26, wherein A3) further comprises:
non-invasively delivering the chronic visual stimuli having the frequency of about 30 Hz to about 50 Hz to reduce tau hyper-phosphorylation in the multiple brain regions of the subject including at least the prefrontal cortex and the hippocampus of the subject.

29. The method of claim 26, wherein A3) further comprises:
non-invasively delivering the chronic visual stimuli having the frequency of about 30 Hz to about 50 Hz to reduce loss of neurons and synapses in the multiple brain regions of the subject including at least the prefrontal cortex and the hippocampus of the subject.

30. The method of claim 26, wherein A3) further comprises:
non-invasively delivering the chronic visual stimuli having the frequency of about 30 Hz to about 50 Hz to reduce brain atrophy in the multiple brain regions of the subject including at least the prefrontal cortex and the hippocampus of the subject.

31. The method of claim 26, wherein A3) further comprises:
non-invasively delivering the chronic visual stimuli having the frequency of about 30 Hz to about 50 Hz to reduce ventricle expansion in the multiple brain regions of the subject including at least the prefrontal cortex and the hippocampus of the subject.

32. The method of claim 26, wherein A) comprises non-invasively delivering the chronic visual stimuli for at least 1 hour per day for at least 42 days.

33. The method of claim 32, wherein:
A) comprises driving an array of light emitting diodes (LEDs) with a square wave current signal to generate the chronic visual stimuli;
the square wave current signal has the 50% duty cycle; and
a frequency of the square wave current signal is equal to or approximately 40 Hz.

34. The method of claim 27, wherein A) comprises non-invasively delivering the chronic visual stimuli for at least 1 hour per day for at least 42 days.

35. The method of claim 34, wherein:
A) comprises driving an array of light emitting diodes (LEDs) with a square wave current signal to generate the chronic visual stimuli;
the square wave current signal has the 50% duty cycle; and
a frequency of the square wave current signal is equal to or approximately 40 Hz.

36. The method of claim 19, wherein A2) further comprises:
A3) non-invasively delivering the chronic visual stimuli having the frequency of about 30 Hz to about 50 Hz to reduce neuroinflammation in the multiple brain regions of the subject including at least the prefrontal cortex and the hippocampus of the subject.

37. The method of claim 36, wherein A3) further comprises:
A4) non-invasively delivering the chronic visual stimuli having the frequency of about 30 Hz to about 50 Hz to reduce an immune response of at least some microglia in the multiple brain regions of the subject including at least the prefrontal cortex and the hippocampus of the subject.

38. The method of claim 37, wherein A4) further comprises:
non-invasively delivering the chronic visual stimuli having the frequency of about 30 Hz to about 50 Hz to morphologically transform the at least some microglia in the multiple brain regions of the subject including at least the prefrontal cortex and the hippocampus of the subject.

39. The method of claim 37, wherein A4) further comprises:
non-invasively delivering the chronic visual stimuli having the frequency of about 30 Hz to about 50 Hz to increase protein degradation in the at least some microglia in the multiple brain regions of the subject including at least the prefrontal cortex and the hippocampus of the subject.

40. The method of claim 37, wherein A) comprises non-invasively delivering the chronic visual stimuli for at least 1 hour per day for at least 42 days.

41. The method of claim 40, wherein:
A) comprises driving an array of light emitting diodes (LEDs) with a square wave current signal to generate the chronic visual stimuli;
the square wave current signal has the 50% duty cycle; and
a frequency of the square wave current signal is equal to or approximately 40 Hz.

42. The method of claim 19, wherein A2) further comprises:
non-invasively delivering the chronic visual stimuli having the frequency of about 30 Hz to about 50 Hz to ameliorate aberrantly modified genes and proteins involved in at least one of membrane trafficking, intracellular transport, synaptic function, neuroinflammation, apoptotic process, and DNA damage in the multiple brain regions of the subject including at least the prefrontal cortex and the hippocampus of the subject.

43. The method of claim 12, wherein A1) further comprises:
A2) non-invasively delivering the chronic visual stimuli having the frequency of about 30 Hz to about 50 Hz to enhance learning and memory of the subject.

44. The method of claim 43, wherein A) comprises non-invasively delivering the chronic visual stimuli for at least I hour per day for at least 42 days.

45. The method of claim 44, wherein:
A) comprises driving an array of light emitting diodes (LEDs) with a square wave current signal to generate the chronic visual stimuli;
the square wave current signal has the 50% duty cycle; and
a frequency of the square wave current signal is equal to or approximately 40 Hz.

46. A method for treating dementia or Alzheimer's disease in a subject in need thereof, the method comprising:
A) non-invasively delivering chronic visual stimuli having a frequency of about 30 Hz to about 50 Hz to the subject to entrain synchronized gamma oscillations in multiple brain regions of the subject including at least the prefrontal cortex (PFC) and the hippocampus of the subject, wherein A) comprises non-invasively delivering the chronic visual stimuli having the frequency of about 30 Hz to about 50 Hz to the subject to:

A1) concurrently entrain synchronized gamma oscillations in the multiple brain regions of the subject including at least the prefrontal cortex and the hippocampus of the subject;

A2) coordinate neuronal activity between the multiple brain regions of the subject including at least the prefrontal cortex and the hippocampus of the subject;

A3) reduce neurodegeneration in the multiple brain regions of the subject including at least the prefrontal cortex and the hippocampus of the subject;

A4) reduce neuroinflammation in the multiple brain regions of the subject including at least the prefrontal cortex and the hippocampus of the subject;

A5) ameliorate aberrantly modified genes and proteins involved in at least one of membrane trafficking, intracellular transport, synaptic function, neuroinflammation, apoptotic process, and DNA damage in the multiple brain regions of the subject including at least the prefrontal cortex and the hippocampus of the subject; and A6) enhance learning and memory of the subject.

47. The method of claim 46, wherein A) comprises inducing local field potential (LFP) at about 40 Hz in at least the prefrontal cortex and the hippocampus of the subject.

48. The method of claim 47, wherein A) comprises non-invasively delivering the chronic visual stimuli for at least 1 hour per day for at least 22 days.

49. The method of claim 48, wherein A) comprises non-invasively delivering the chronic visual stimuli for at least 1 hour per day for at least 42 days.

50. The method of claim 48, wherein:
A) comprises driving an array of light emitting diodes (LEDs) with a square wave current signal to generate the chronic visual stimuli;
the square wave current signal has a 50% duty cycle; and
a frequency of the square wave current signal is equal to or approximately 40 Hz.

51. The method of claim 46, wherein:
A) comprises driving an array of light emitting diodes (LEDs) with a square wave current signal to generate the chronic visual stimuli;
the square wave current signal has a 50% duty cycle; and
a frequency of the square wave current signal is equal to or approximately 40 Hz.

* * * * *